US012570691B2

(12) United States Patent
Zhu et al.

(10) Patent No.: US 12,570,691 B2
(45) Date of Patent: \*Mar. 10, 2026

(54) PURIFICATION OF CHIMERIC FVIII MOLECULES

(71) Applicant: Bioverativ Therapeutics Inc., Waltham, MA (US)

(72) Inventors: Lily Zhu, Belmont, MA (US); Anxhela Kole, Quincy, MA (US); John Kulman, Belmont, MA (US); Marisol Acosta, Worcester, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 295 days.

This patent is subject to a terminal disclaimer.

(21) Appl. No.: 17/155,935

(22) Filed: Jan. 22, 2021

(65) Prior Publication Data

US 2021/0261607 A1 Aug. 26, 2021

Related U.S. Application Data

(63) Continuation of application No. 14/910,555, filed as application No. PCT/US2014/050411 on Aug. 8, 2014, now Pat. No. 10,947,269.

(60) Provisional application No. 61/863,810, filed on Aug. 8, 2013.

(51) Int. Cl.
*C07K 1/36* (2006.01)
*C07K 14/755* (2006.01)

(52) U.S. Cl.
CPC .............. *C07K 1/36* (2013.01); *C07K 14/755* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,215,051 A | 7/1980 | Palmer et al. |
| 4,683,195 A | 7/1987 | Mullis et al. |
| 4,683,202 A | 7/1987 | Mullis |
| 4,713,339 A | 12/1987 | Levinson et al. |
| 4,757,006 A | 7/1988 | Toole, Jr. et al. |
| 4,800,159 A | 1/1989 | Mullis et al. |
| 4,868,112 A | 9/1989 | Toole, Jr. |
| 4,965,188 A | 10/1990 | Mullis et al. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Doyen et al. |
| 5,364,771 A | 11/1994 | Lollar et al. |
| 5,543,502 A | 8/1996 | Nordfang et al. |
| 5,595,886 A | 1/1997 | Chapman et al. |
| 5,610,278 A | 3/1997 | Nordfang et al. |
| 5,648,260 A | 7/1997 | Winter et al. |
| 5,658,570 A | 8/1997 | Newman et al. |
| 5,739,277 A | 4/1998 | Presta et al. |
| 5,789,203 A | 8/1998 | Chapman et al. |
| 5,834,250 A | 11/1998 | Wells et al. |
| 5,859,204 A | 1/1999 | Lollar |
| 5,869,046 A | 2/1999 | Presta et al. |
| 5,972,885 A | 10/1999 | Spira et al. |
| 5,981,216 A | 11/1999 | Kenten et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,346,513 B1 | 2/2002 | Van Doyen et al. |
| 6,376,463 B1 | 4/2002 | Lollar |
| 6,458,563 B1 | 10/2002 | Lollar |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,737,056 B1 | 5/2004 | Presta |
| 6,821,505 B2 | 11/2004 | Ward |
| 6,998,253 B1 | 2/2006 | Presta et al. |

(Continued)

FOREIGN PATENT DOCUMENTS

| | | | |
|---|---|---|---|
| EP | 0295597 A2 | 12/1988 |
| WO | WO 1987/004187 A1 | 7/1987 |

(Continued)

OTHER PUBLICATIONS

GE Healthcare 2009 Data File 28-9662-37AB VIIISelect: 2 pages. (Year: 2009).*

Armour, K.L., et al., "Recombinant Human IgG Molecules Lacking Fc Gamma Receptor I Binding and Monocyte Triggering Activities," European Journal of Immunology 29(8):2613-2624, Wiley-VCH, Germany (1999).

Arnau, J., et al., "Current strategies for the Use of Affinity Tags and Tag Removal for the Purification of Recombinant Proteins," Protein Expression and Purification 48(1):1-13, Elsevier Inc., United States (2006).

Benhar, I. and Pastan, I., "Cloning, Expression and Characterization of the Fv Fragments of the Anti-Carbohydrate mAbs B1 and B5 as Single-Chain Immunotoxins," Protein Engineering Design and Selection 7(11):1509-1515, Oxford University Press, England (1994).

(Continued)

*Primary Examiner* — Marsha Tsay

(74) *Attorney, Agent, or Firm* — LATHROP GPM LLP; James H. Velema, Esq.

(57) ABSTRACT

The invention is directed to methods of purifying a chimeric protein comprising subjecting the chimeric protein to a factor VIII-specific affinity chromatography, and subjecting the chimeric protein to an AEX chromatography; wherein the chimeric protein comprises a factor VIII protein or a fragment thereof. The chimeric protein purified by the present methods shows improved factor VIII activity.

37 Claims, 9 Drawing Sheets

Specification includes a Sequence Listing.

(56) References Cited

U.S. PATENT DOCUMENTS

| | | | |
|---|---|---|---|
| 7,041,635 B2 | 5/2006 | Kim et al. | |
| 7,083,784 B2 | 8/2006 | Dall'acqua et al. | |
| 7,317,091 B2 | 1/2008 | Lazar et al. | |
| 7,348,004 B2 | 3/2008 | Peters et al. | |
| 7,404,956 B2 | 7/2008 | Peters et al. | |
| 7,862,820 B2 | 1/2011 | Peters et al. | |
| 7,884,075 B2 * | 2/2011 | Scheiflinger | C07K 14/755 |
| | | | 514/14.1 |
| 2003/0235536 A1 | 12/2003 | Blumberg | |
| 2004/0101740 A1 | 5/2004 | Sanders | |
| 2005/0100990 A1 | 5/2005 | Saenko et al. | |
| 2005/0165221 A1 | 7/2005 | Booth et al. | |
| 2006/0074199 A1 | 4/2006 | Hirata et al. | |
| 2007/0231329 A1 | 10/2007 | Lazar et al. | |
| 2007/0237765 A1 | 10/2007 | Lazar et al. | |
| 2007/0237766 A1 | 10/2007 | Lazar et al. | |
| 2007/0237767 A1 | 10/2007 | Lazar et al. | |
| 2007/0243188 A1 | 10/2007 | Lazar et al. | |
| 2007/0248603 A1 | 10/2007 | Lazar et al. | |
| 2007/0286859 A1 | 12/2007 | Lazar et al. | |
| 2008/0057056 A1 | 3/2008 | Lazar et al. | |
| 2009/0088370 A1 | 4/2009 | Winge | |
| 2010/0239554 A1 | 9/2010 | Schellenberger et al. | |
| 2010/0323956 A1 | 12/2010 | Schellenberger et al. | |
| 2011/0046060 A1 | 2/2011 | Schellenberger et al. | |
| 2011/0046061 A1 | 2/2011 | Schellenberger et al. | |
| 2011/0077199 A1 | 3/2011 | Schellenberger et al. | |
| 2011/0160435 A1 | 6/2011 | Borgvall et al. | |
| 2011/0172146 A1 | 7/2011 | Schellenberger et al. | |
| 2012/0289468 A1 | 11/2012 | Barnett | |
| 2016/0200794 A1 | 7/2016 | Metzner | |

FOREIGN PATENT DOCUMENTS

| | | | |
|---|---|---|---|
| WO | WO 1988/000831 A1 | 2/1988 | |
| WO | WO 1988/003558 A1 | 5/1988 | |
| WO | WO 1988/007089 A1 | 9/1988 | |
| WO | WO 1988/008035 A1 | 10/1988 | |
| WO | WO 1991/009122 A1 | 6/1991 | |
| WO | WO 1993/020093 A1 | 10/1993 | |
| WO | WO 1994/011503 A2 | 5/1994 | |
| WO | WO 1996/014339 A1 | 5/1996 | |
| WO | WO 1998/005787 A1 | 2/1998 | |
| WO | WO 1998/023289 A1 | 6/1998 | |
| WO | WO 1999/051642 A1 | 10/1999 | |
| WO | WO 1999/058572 A1 | 11/1999 | |
| WO | WO 2000/009560 A2 | 2/2000 | |
| WO | WO 2000/032767 A1 | 6/2000 | |
| WO | WO 2000/042072 A2 | 7/2000 | |
| WO | WO 2002/044215 A2 | 6/2002 | |
| WO | WO 2002/060919 A2 | 8/2002 | |
| WO | WO 2003/074569 A2 | 9/2003 | |
| WO | WO 2003/077834 A2 | 9/2003 | |
| WO | WO 2004/016750 A2 | 2/2004 | |
| WO | WO 2004/029207 A2 | 4/2004 | |
| WO | WO 2004/035752 A2 | 4/2004 | |
| WO | WO 2004/044859 A1 | 5/2004 | |
| WO | WO 2004/063351 A2 | 7/2004 | |
| WO | WO 2004/074455 A2 | 9/2004 | |
| WO | WO 2004/099249 A2 | 11/2004 | |
| WO | WO 2005/040217 A2 | 5/2005 | |
| WO | WO 2005/047327 A2 | 5/2005 | |
| WO | WO 2005/070963 A1 | 8/2005 | |
| WO | WO 2005/077981 A2 | 8/2005 | |
| WO | WO 2005/092925 A2 | 10/2005 | |
| WO | WO 2005/123780 A2 | 12/2005 | |
| WO | WO 2006/019447 A1 | 2/2006 | |
| WO | WO 2006/047350 A2 | 5/2006 | |
| WO | WO 2006/085967 A2 | 8/2006 | |
| WO | WO 2010/091122 A1 | 8/2010 | |
| WO | WO 2010/144502 A2 | 12/2010 | |
| WO | WO 2010/144508 A1 | 12/2010 | |
| WO | WO 2011/028228 A1 | 3/2011 | |
| WO | WO 2011/028229 A1 | 3/2011 | |
| WO | WO 2011/028344 A2 | 3/2011 | |
| WO | WO 2012/006623 A1 | 1/2012 | |
| WO | WO 2012/006635 A1 | 1/2012 | |
| WO | WO 2013/106787 A1 | 7/2013 | |
| WO | WO-2014011819 A2 * | 1/2014 | ............. A61K 38/36 |
| WO | WO 2015/021423 A2 | 2/2015 | |

OTHER PUBLICATIONS

Burmeister, W.P., et al., "Crystal Structure of the Complex of Rat Neonatal Fc Receptor with Fc," Nature 372(6504):379-383, Nature Publishing Group, England (1994).

Cameron, C., et al., "The Canine Factor VIII cDNA and 5' Flanking Sequence," Thrombosis and Haemostasis 79(2):317-322, Schattauer, Germany (1998).

Capon, D.J., et al., "Designing CD4 Immunoadhesins for AIDS Therapy," Nature 337(6207):525-531, Nature Publishing Group, England (1989).

Chhabra, E., S., et al., "Engineering a Novel rFVIII-VWF D'D3 Fusion Protein to Enhance Stability and Improve Pharmacokinetic Properties of FVIII," Journal of Thrombosis and Haemostasis 11(Suppl. 2):170, abstract OC 37.5, International Society on Thrombosis and Haemostasis, United States (Jul. 1, 2013).

Eaton, D.L., et al., "Construction and Characterization of an Active Factor VIII Variant Lacking the Central One-Third of the Molecule," Biochemistry 25(26):8343-8347, American Chemical Society, United States (1986).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).

GE Healthcare, Data File 28-9662-37 AA, Custom Designed Media, VIII Select, 2008, 2 pages.

GE Healthcare, Application Instructions 71-7100-00 AC, Ion Exchange, DEAE Sephacel, 2006, $N^1 1^{13}$-$1^{17}$, 8 pages (2006).

GE Healthcare III 2008 Ion Exchange Columns and Media 18-1127-31 AH, 8 pages (2008).

Genbank, "*Homo sapiens* von Willebrand factor (WWF), mRNA" NCBI Reference Sequence: NM_000552.3, accessed at http://www.ncbinlm.nih.gov/nuccore/NM_000552.3, accessed on Mar. 29, 2016, 10 pages.

Genbank, "Von Willebrand factor preproprotein [*Homo sapiens*]," NCBI Reference Sequence: NP_000543.2, accessed at http://www.ncbinlm.nih.gov/protein/NP_000543.2, accessed on Mar. 29, 2016, 6 pages.

Gitschier, J., et al., "Characterization of the Human Factor VIII Gene," Nature 312(5992):326-330, Nature Publishing Group, England (1984).

Graw, J., et al., "Haemophilia A: From Mutation Analysis to New Therapies," Nature Reviews. Genetics 6(6):488-501, Nature Publishing Group, England (2005).

Healey, J.F., et al., "The cDNA and Derived Amino Acid Sequence of Porcine Factor VIII," Blood 88(11):4209-4214, The American Society of Hematology, United States (1996).

Ho, S.N., et al., "Site-Directed Mutagenesis by Overlap Extension Using the Polymerase Chain Reaction," Gene 77(1):51-59, Elsevier Science Publishers B.V., Netherlands (1989).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

Horton, R.M., et al., "Gene Splicing by Overlap Extension," Methods in Enzymology 217:270-279, Academic Press, United States (1993).

International Search Report and Written Opinion for International Application No. PCT/US2014/050411, ISA/US, Alexandria, Virginia, United States, mailed on Nov. 13, 2014, 4 pages.

Israel, E.J., et al., "Expression of the neonatal Fc receptor, FcRn, on human intestinal epithelial cells," Immunology 92(1):69-74, Blackwell Sciences, England (1997).

(56) References Cited

OTHER PUBLICATIONS

Kasuda, S., et al., "Establishment of Embryonic Stem Cells Secreting Human Factor VIII for Cell-Based Treatment of Hemophilia A," Journal of Thrombosis and Haemostasis 6(8):1352-1359, International Society on Thrombosis and Haemostasis, England (2008).

Kobayashi, N., et al., "FcRn-Mediated Transcytosis of Immunoglobulin Gin Human Renal Proximal Tubular Epithelial Cells," American Journal of Physiology 282(2):F358-F365, American Physiological Society, United States (2002).

Langner, K-D., et al., "Synthesis of Biologically Active Deletion Mutants of Human Factor VIII:C," Behring Institute Mitteilungen 82:16-25, Behringwerke AG, Germany (1988).

Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (1989).

Lenting, P.J., et al., "Clearance Mechanisms of Von Willebrand Factor and Factor VIII," Journal of Thrombosis and Haemostasis 5(7):1353-1360, International Society on Thrombosis and Haemostasis, England (2007).

Lenting, P.J., et al., "The Life Cycle of Coagulation Factor VIII in View of its Structure and Function," Blood, 92(11):3983-3996, American Society of Hematology, United States (1998).

Liu, T., et al., "A New Class of Coagulation Factor VIII Molecules that Achieved Four-fold Longer Half-life than Recombinant FVIII in Hemophilia A Mice," Journal of Thrombosis and Haemostasis 11(Suppl. 2):71, abstract AS45.1, International Society on Thrombosis and Haemostasis, United States (Jul. 1, 2013).

Logan, J., et al., "Adenovirus Tripartite Leader Sequence Enhances Translation of mRNAs Late After Infection," Proceedings of the National Academy of Sciences USA 81(12):3655-3659, National Academy of Sciences, United States (1984).

Mackett, M., et al., "General Method for Production and Selection of Infectious Vaccinia Virus Recombinants Expressing Foreign Genes," Journal of Virology 49(3):857-864, American Society for Microbiology, United States (1984).

Mackett, M., et al., "Vaccinia Virus: A Selectable Eulcaryotic Cloning and Expression Vector," Proceedings of the National Academy of Sciences USA 79(23):7415-7419, National Academy of Sciences, United States (1982).

Mccue, J.T., et al., "Application of a Novel Affinity Adsorbent for the Capture and Purification of Recombinant Factor VIII Compounds," Journal of Chromatography A 1216(45):7824-7830, Elsevier, Netherlands (2009).

Mei, B., et al., "Expression of Human Coagulation Factor VIII in a Human Hybrid Cell Line, HKB11," Molecular Biotechnology 34(2):165-178, Humana Press Inc., United States (2006).

Meulien, P., et al., "A New Recombinant Procoagulant Protein Derived from the cDNA Encoding Human Factor VIII," Protein Engineering 2(4):301-306, IRL Press Ltd., England (1988).

Miao, H.Z., et al., "Bioengineering of Coagulation Factor VIII for Improved Secretion," Blood 103(9):3412-3419, The American Society of Hematology, United States (2004).

Mount, J.D., et al., "Sustained Phenotypic Correction of Hemophilia B dogs with a Factor IX Null Mutation by Liver-Directed Gene Therapy," Blood 99(8):2670-2676, The American Society of Hematology, United States (2002).

Neumann, E., et al., "Gene Transfer into Mouse Lyoma Cells By Electroporation in High Electric Fields," The EMBO Journal 1(7):841-845, IRL Press Limited, England (1982).

Panicali, D., et al., "Construction of Poxviruses as Cloning Vectors: Insertion of the Thymidine Kinase Gene from Herpes Simplex Virus into the DNA of Infectious Vaccinia Virus," Proceedings of the National Academy of Sciences of the United States of America 79(16):4927-4931, The National Academy of Sciences of the United States (1982).

Pipe, S.W., et al., "Functional Factor VIII made with Von Willebrand Factor at High Levels in Transgenic Milk," Journal of Thrombosis and Haemostasis 9(11):2235- 2242, International Society on Thrombosis and Haemostasis, England (2011).

Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (1995).

Ruberti, F., et al., "The Use of the RACE Method to Clone Hybridoma cDNA When V Region Primers Fail," Journal of Immunological Methods 173(1):33-39, Elsevier, United States (1994).

Ruther, U. and Muller-Hill, B., "Easy Identification of cDNA Clones," The EMBO Journal 2(10):1791-1794, IRL Press Ltd, England (1983).

Sarver, N., et al., "Stable Expression of Recombinant Factor VIII Molecules Using a Bovine Papillomavirus Vector," DNA 6(6):553-564, Maly Ann Liebert, Inc., United States (1987).

Schellenberger, V., et al., "A Recombinant Polypeptide Extends the in Vivo Half-Life of Peptides and Proteins in a Tunable Manner," Nature Biotechnology 27(12):1186-1190, Nature America, Inc., United States (2009).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma. R," The Journal of Biological Chemistry 276(9):6591-6604, American Society for Biochemistry and Molecular Biology, United States (2001).

Simonsen, C.C., et al., "Isolation and Expression of an Altered Mouse Dihydrofolate Reductase cDNA," Proceedings of the National Academy of Sciences 80(9):2495-2499, National Academy of Sciences, United States (1983).

Smith, G.E., et al., "Molecular Engineering of the Autographa Californica Nuclear Polyhedrosis Virus Genome: Deletion Mutations Within the Polyhedrin Gene," Journal of Virology 46(2):584-593, American Society for Microbiology, United States (1983).

Smith, T.F. and Waterman, M.S., "Comparison of Biosequences," Advances in Applied Mathematics 2(4):482-489, Academic Press, Inc., United States (1981).

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).

Toole, J.J., et al., "A Large Region (z95 kDa) of Human Factor VIII is Dispensable for in vitro Procoagulant Activity," Proceedings of the National Academy of Sciences USA 83(16):5939-5942, National Academy of Sciences, United States (1986).

Toole, J.J., et al., "Molecular Cloning of a cDNA Encoding Human Antihaemophilic Factor," Nature 312(5992):342-347, Nature Publishing Group, England (1984).

Vehar, G.A., et al., "Structure of Human Factor VIII," Nature 312(5992):337-342, Nature Publishing Group, England (1984).

Ward, E.S. and Ghetie, V., "The Effector Functions of Immunoglobulins: Implications for Therapy," Therapeutic Immunology 2(2):77-94, Blackwell Science Ltd., England (1995).

Wigler, M., et al., "Biochemical Transfer of Single-Copy Eucaryotic Genes Using Total Cellular DNA as Donor," Cell 14(3):725-731, Cell Press, United States (1978).

Wood, W.I., et al., "Expression of Active Human Factor VIII from Recombinant DNA Clones," Nature 312(5992):330-337, Nature Publishing Group, England (1984).

Zhou Y.F., et al., "Sequence and Structure Relationships within Von Willebrand Factor," Blood 120(2):449-458, American Society of Hematology, United States (Jul. 12, 2012).

* cited by examiner

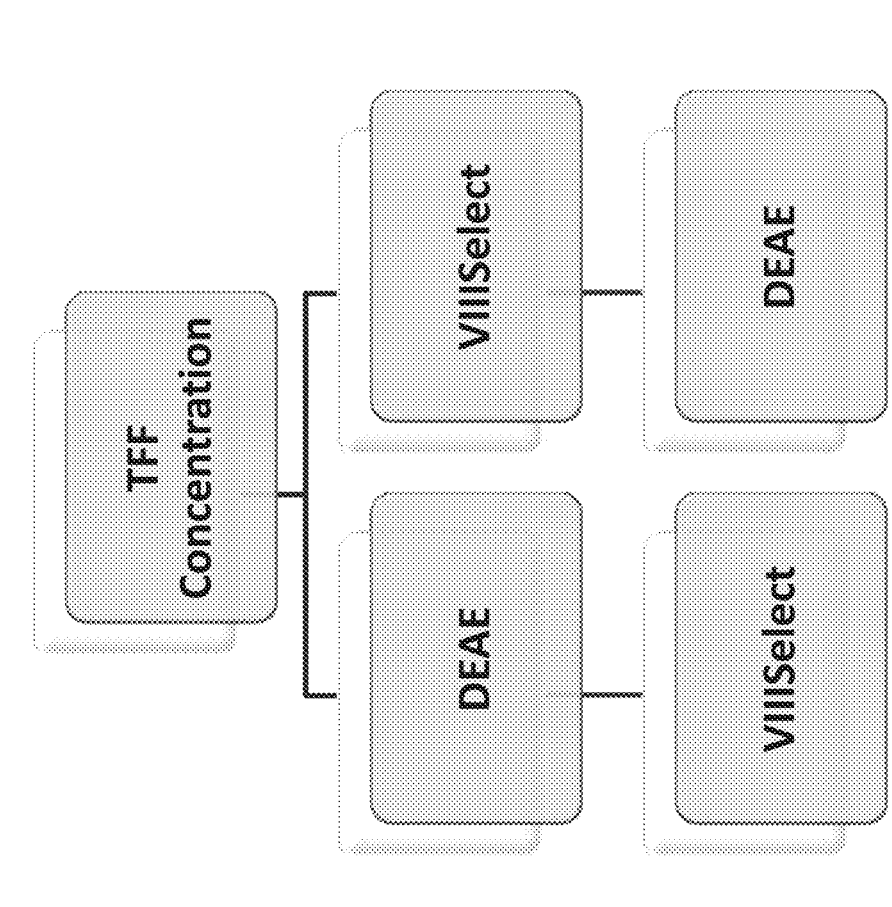
Figure 1: Summary flow-chart of chimeric protein purification method

Figure 2: Chromatogram of VIII-169/VWF-57 in a DEAE Column

Figure 3: FVIII-169/VWF-57 DEAE Capture Step – Stain-Free Gels
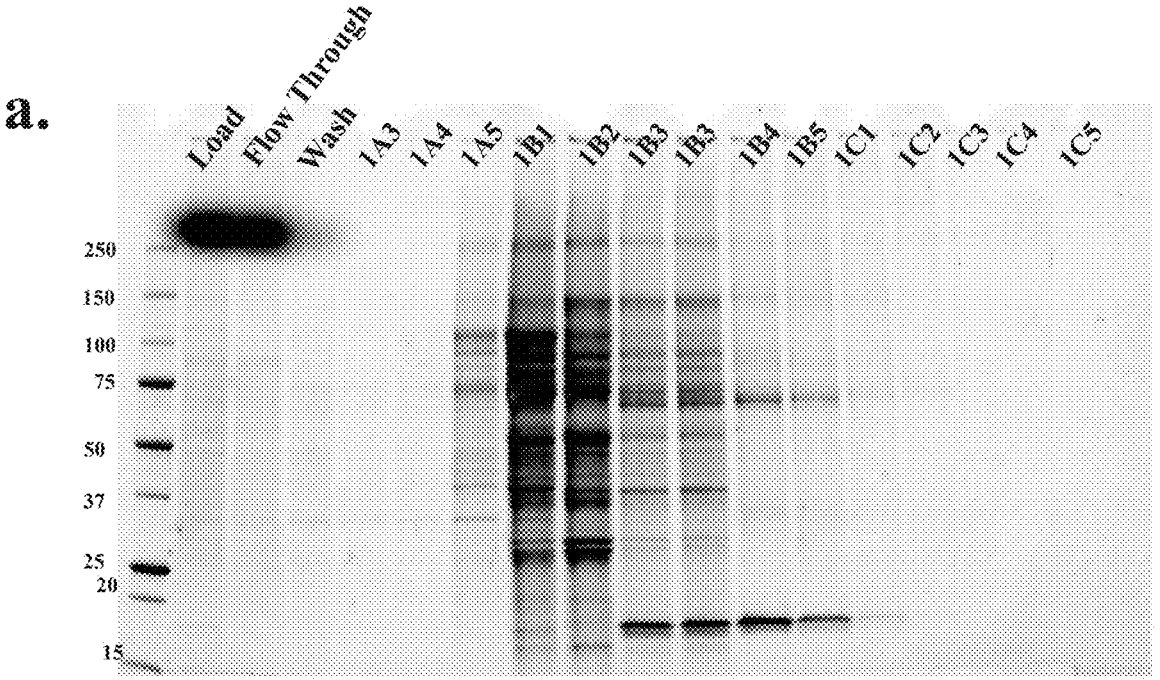
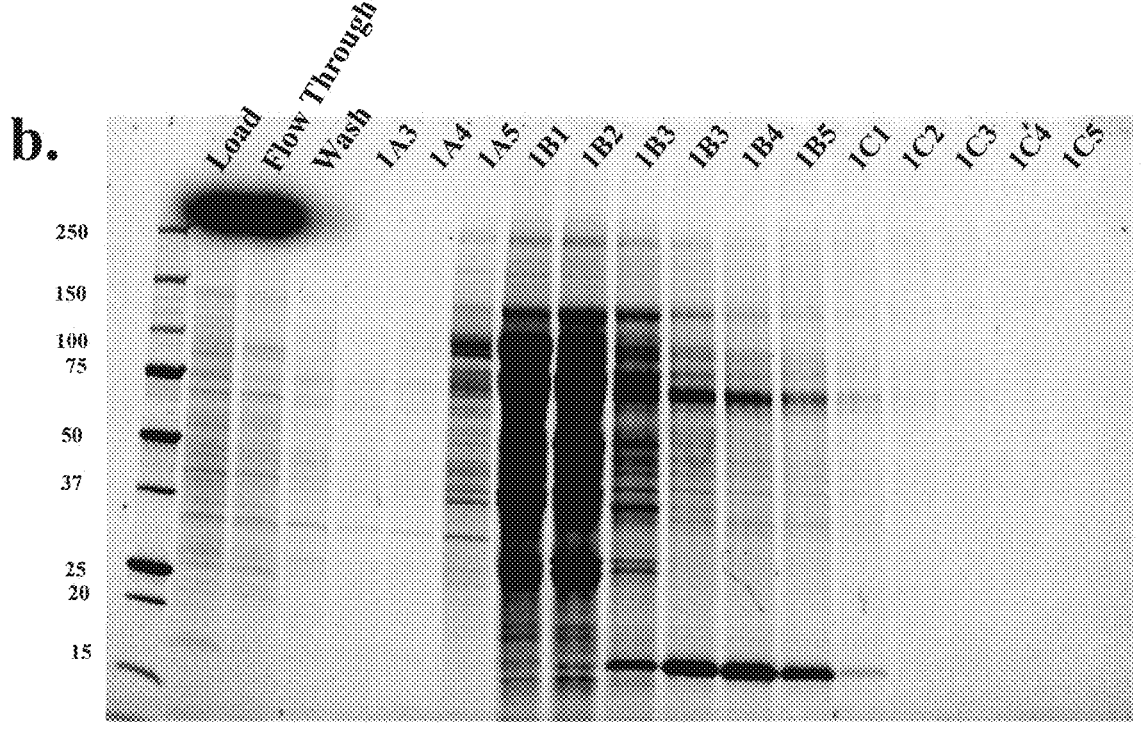

Figure 4: FVIII-169/VWF-57 DEAE Capture Step – Chromogenic Assay

Research Assay Sample Results

| Sample submission date | | 7/8/2014 | | | | |
|---|---|---|---|---|---|---|
| Assay type | | | | | | |
| FVIII 169 VWF 57 | | | | | | |
| Sample ID | Sample description | Volume (µL) | Est. Conc (IU/mL) | Buffer | Results IU/mL |
| 8 | DEAE Load | 100 ul | 5-15 | | 6.11 |
| 9 | DEAE Flow Through | 100 ul | 0-2 | | 4.36 |
| 10 | DEAE Wash | 100 ul | 0-2 | | 0.88 |
| 11 | 1A3 | 100 ul | 25-200 | | 5.64 |
| 12 | 1A4 | 100 ul | 25-200 | | 17.89 |
| 13 | 1A5 | 100 ul | 25-200 | | 24.15 |
| 14 | 1B1 | 100 ul | 25-200 | | 17.10 |
| 15 | 1B2 | 100 ul | 25-200 | | 10.86 |
| 16 | 1B3 | 100 ul | 25-200 | | 7.62 |
| 17 | 1B4 | 100 ul | 25-200 | | 4.98 |
| 18 | 1B5 | 100 ul | 25-200 | | 1.91 |

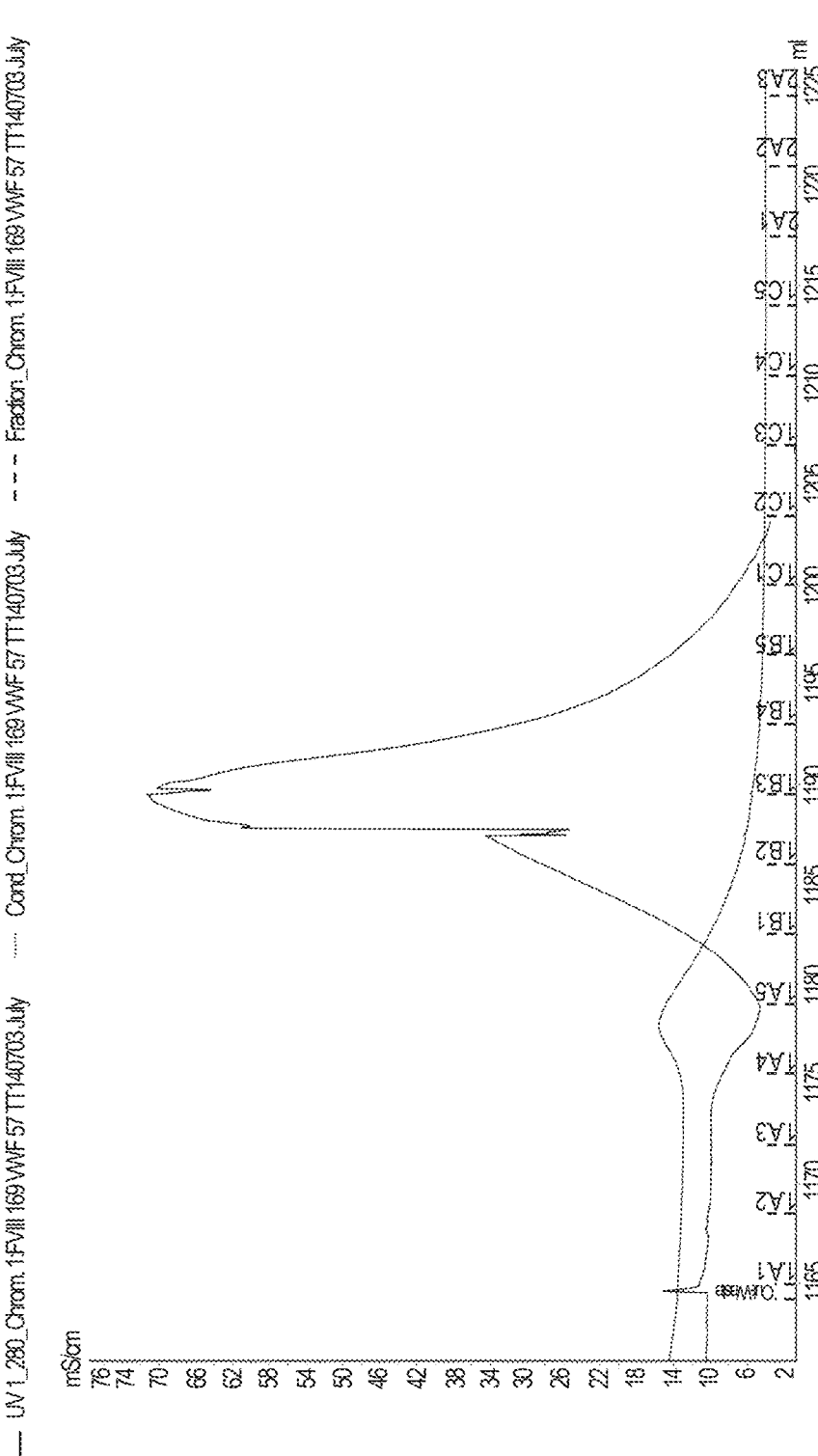
Figure 5: Chromatogram of VIII-169/VWF-57 in a VIIISelect Column

Figure 6: FVIII-169/VWF-57 VIIISelect Capture Step – Chromogenic Assay

| | | Research Assay Sample Results | | | | |
|---|---|---|---|---|---|---|
| Assay type | Sample submission date | | | 7/8/2014 | | |
| Sample ID | Sample description | | Volume (μL) | Est. Conc (IU/mL) | Buffer | Results IU/mL |
| | FVIII 169 VWF 57 TT140703 | | | | | |
| 1 | Harvest TT140703 | | 500 ul | 1–3 | | 0.87 |
| 2 | TFF (FT) | | 500 ul | 0–2 | | BLD |
| 3 | FVIIISelect Load | | 500 ul | 5–15 | | 6.68 |
| 4 | FVIII Select Flow Through | | 500 ul | 0–3 | | 1.31 |
| 5 | FVIII Select Wash | | 200 ul | 0–2 | | 0.24 |
| 6 | VIII Select Pool | | 100 ul | 25–150 | | 167.63 |
| 7 | FVIII Select Pool Post Desalting | | 100 ul | 25–150 | | 76.66 |

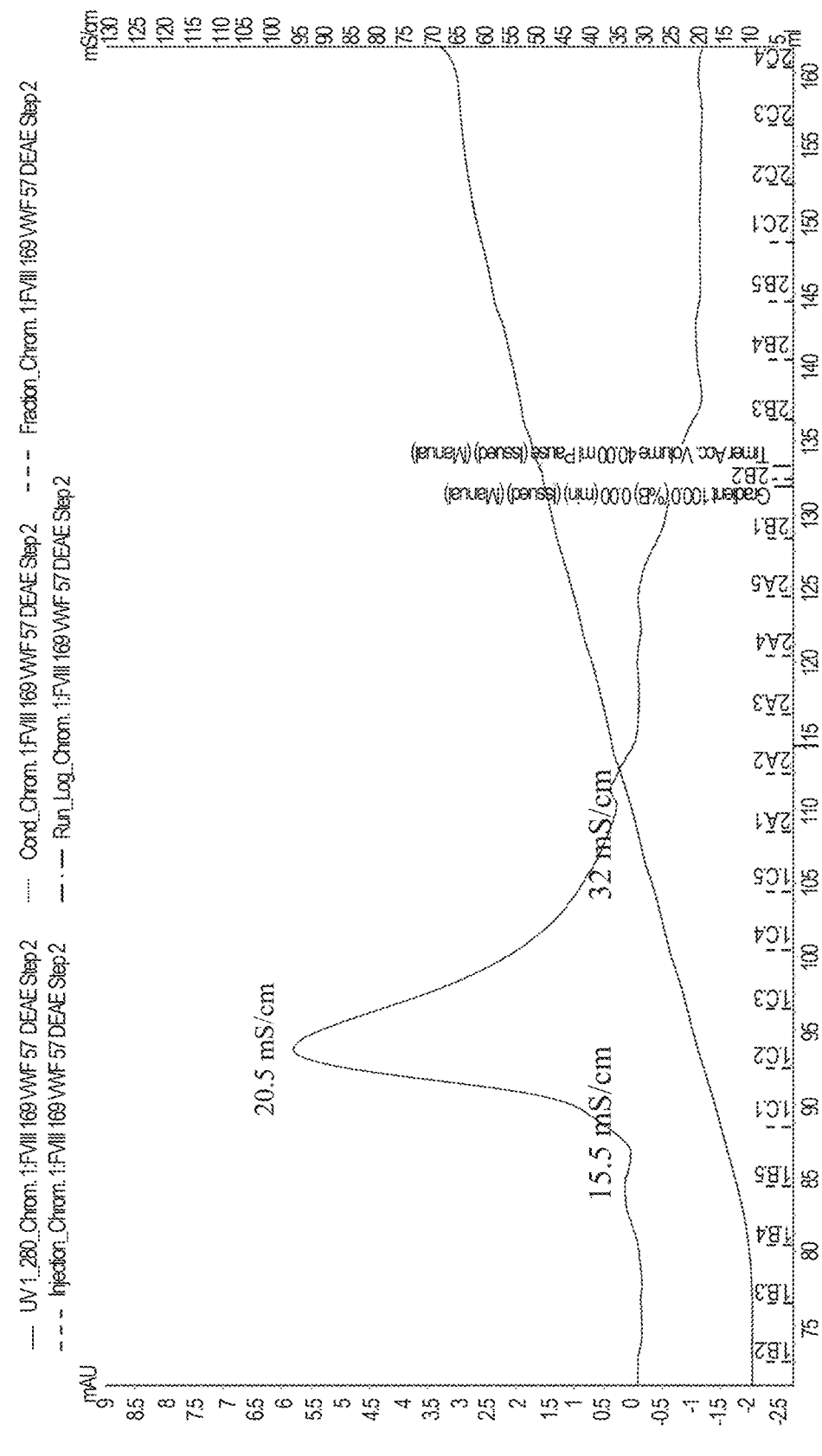
Figure 7: Chromatogram of VIII-169/VWF-57 in a DEAE Column – Post VIIISelect Polishing Step

Figure 8: FVIII-169/VWF-57 DEAE Capture Step (Post VIIISelect) – Stain-Free Gels
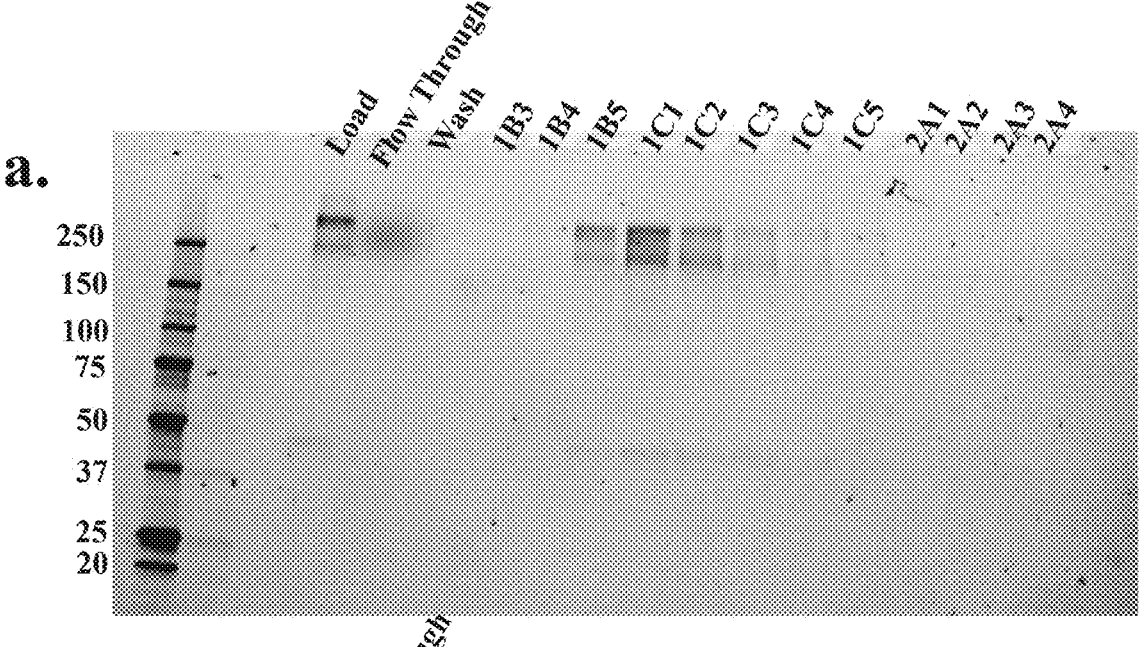
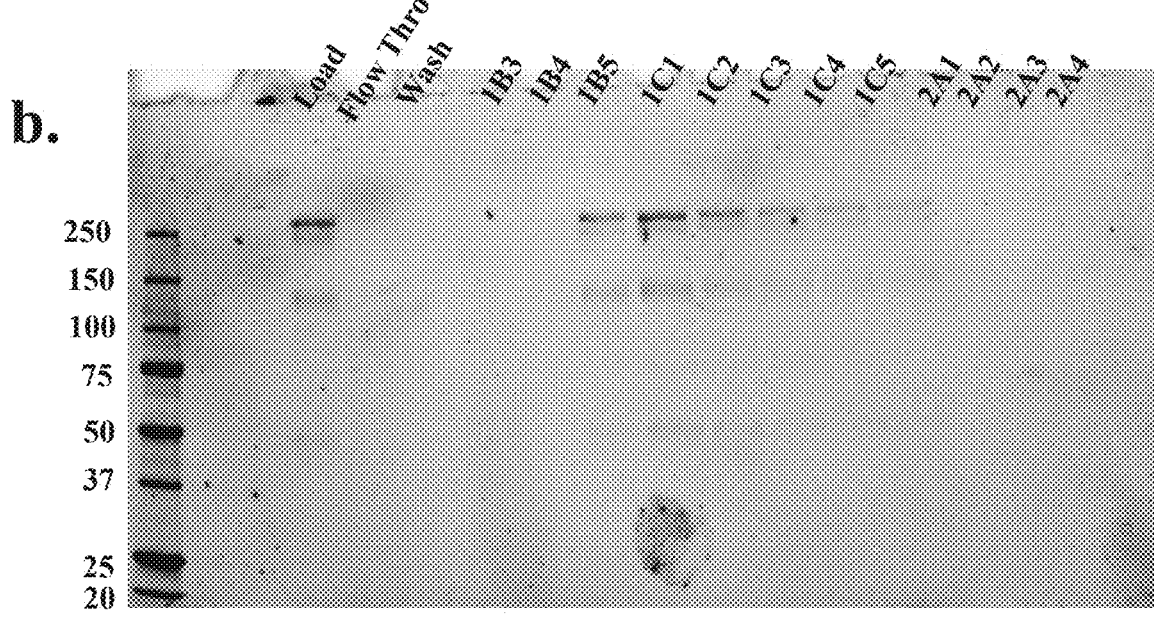

Figure 9: FVIII-169/VWF-57 DEAE Capture Step (Post VIIISelect Polishing Step) – Chromogenic Assay

Research Assay Sample Results

| Sample submission date | | 7/1/2014 | | | | |
|---|---|---|---|---|---|---|
| Assay type | | | | | | |
| | FVIII 169 VWF 57 TT140703 (Marisol FVIII Select to DEAE) | | | | | |
| Sample ID | Sample description | Volume (µL) | Est. Conc (IU/mL) | Buffer | | Results IU/mL |
| 1 | Load DEAE (20 ML) | 60 ul | 50-100 | | | 75.93 |
| 2 | Flow Through | 60 ul | 0-2 | | | 0.11 |
| 3 | Wash | 60 ul | 0-2 | | | BLD |
| 4 | 1B4 | 60 ul | 5--30 | | | BLD |
| 5 | 1B5 | 60 ul | 5--30 | | | 2.38 |
| 6 | 1C1 | 60 ul | 5--30 | | | 44.51 |
| 7 | 1C2 | 60 ul | 5--30 | | | ALD(87.48) |
| 8 | 1C3 | 60 ul | 5--30 | | | 68.22 |
| 9 | 1C4 | 60 ul | 5--30 | | | 41.31 |
| 10 | 1C5 | 60 ul | 5--30 | | | 25.53 |
| 11 | 2A1 | 60 ul | 5--30 | | | 15.75 |

PURIFICATION OF CHIMERIC FVIII MOLECULES

RELATED APPLICATIONS

This application is a continuation of U.S. patent application Ser. No. 14/910,555, filed Feb. 5, 2016, which is a 35 U.S.C. § 371 filing of International Patent Application No. PCT/US2014/050411, filed Aug. 8, 2014, which claims priority to U.S. Provisional Patent Application Ser. No. 61/863,810, filed Aug. 8, 2013, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Sep. 26, 2025, is named 714384_SA9-442USCON_ST25.txt and is 177,005 bytes in size.

BACKGROUND OF THE INVENTION

Haemophilia A is a bleeding disorder caused by defects in the gene encoding coagulation factor VIII (FVIII) and affects 1-2 in 10,000 male births. Graw et al., *Nat. Rev. Genet.* 6(6): 488-501 (2005). Patients affected with hemophilia A can be treated with infusion of purified or recombinantly produced FVIII.

In plasma, 95-98% of FVIII circulates in a tight non-covalent complex with full-length von Willebrand Factor (VWF). The formation of this complex is important for the maintenance of appropriate plasma levels of FVIII in vivo. Lenting et al., *Blood.* 92(11): 3983-96 (1998); Lenting et al., *J. Thromb. Haemost.* 5(7): 1353-60 (2007). The full-length wild-type FVIII is mostly present as a heterodimer having a heavy chain (MW 200 kD) and a light chain (MW 73 kD). When FVIII is activated due to proteolysis at positions 372 and 740 in the heavy chain and at position 1689 in the light chain, the VWF bound to FVIII is removed from the activated FVIII. The activated FVIII, together with activated factor IX, calcium, and phospholipid ("tenase complex"), induces the activation of factor X, generating large amounts of thrombin. Thrombin, in turn, then cleaves fibrinogen to form soluble fibrin monomers, which then spontaneously polymerize to form the soluble fibrin polymer. Thrombin also activates factor XIII, which, together with calcium, serves to crosslink and stabilize the soluble fibrin polymer, forming cross-linked (insoluble) fibrin. The activated FVIII is cleared fast from the circulation by proteolysis.

Though great advances have been made in the production of recombinant FVIII and variants thereof, purification remains a challenge. The purification of recombinant FVIII is challenging due to the characteristically low expression level of FVIII in transiently transfected cells and the sensitivity of FVIII to modest changes in pH and temperature. Thus, there remains a need for improved methods of purifying recombinant FVIII, and the present invention provides a novel purification method that yields highly active recombinant FVIII.

BRIEF DESCRIPTION OF THE DRAWINGS/FIGURES

FIG. 1 shows a flow-chart summarizing exemplary purification methods. "TFF" refers to tangential flow filtration. "DEAE" refers to diethylaminoethyl, a component of a particular anion exchange chromatography resin. "VIIISelect" refers to a factor VIII-specific affinity chromatography matrix, marketed by GE Healthcare.

FIG. 2 shows a chromatogram of the separation of FVIII-169/VWF-57 protein in an anion exchange chromatography column comprising DEAE. Conductivity and UV absorbance traces are indicated by arrows. A280 indicates the protein concentration in the collected fractions. The conductivity is indicated by text in different parts of the A280 peak (11 mS/cm at the start of elution to 23 mS/cm in the elution tail).

FIG. 3 shows 4-20% SDS PAGE gels of elution fractions under the peak, as shown in FIG. 2, and purification intermediates. The gels are stain-free. FIG. 3A shows a gel run under the non-reducing conditions, and FIG. 3B shows a gel run under the reducing conditions.

FIG. 4 shows the results of a FVIII chromogenic assay of elution fractions under the peak 1A3-1B5 of the chromatogram shown in FIG. 2. Protein activity is expressed as IU/mL.

FIG. 5 shows a chromatogram of the separation of FVIII-169/VWF-57 protein on a VIIISelect affinity column. Conductivity and UV absorbance traces are indicated by arrows. A280 indicates the protein concentration in the collected fractions, shown above the x-axis.

FIG. 6 shows the results of a FVIII chromogenic assay of elution fractions under the peak 1B1-1C1 of the chromatogram shown in FIG. 5. Elution fractions 1B1-1C1 under the peak (FIG. 5) were pooled and tested by FVIII chromogenic assay before and after buffer exchange. The starting material as well as intermediates (flow through and wash) were also tested. Protein activity is expressed as IU/mL.

FIG. 7 shows a chromatogram of the separation of FVIII-169/VWF-57 protein in an anion exchange chromatography column comprising DEAE, wherein the FVIII-169/VWF-57 protein was previously subjected to and eluted from a VIIISelect affinity chromatography matrix column. Conductivity and UV absorbance traces are indicated by arrows. A280 indicates the protein concentration in the collected fractions, shown below the x-axis. The conductivity is indicated in text in different parts of the A280 peak (15.5 mS/cm at the start of elution to 20.5 mS/cm elution peak, 32 mS/cm in the elution tail; ~150-320 mM NaCl concentration).

FIG. 8 shows 4-20% SDS PAGE gels of elution fractions under the peak, as shown in the chromatogram in FIG. 7, and purification intermediates. The gels are stain-free. FIG. 8a shows a gel run under the non-reducing conditions, and FIG. 8b shows a gel run under the reducing conditions.

FIG. 9 shows the results of a FVIII chromogenic assay of elution fractions under the peak 1B4-2A1 of the chromatogram in FIG. 7. Elution fractions 1B4-2A1 under the peak (FIG. 7) were tested by FVIII chromogenic assay. The starting material as well as intermediates (flow through and wash) were also tested. Protein activity is expressed as IU/mL.

DETAILED DESCRIPTION OF THE INVENTION

Described herein are methods of purifying chimeric proteins using a combination of protein-specific affinity chromatography and anion exchange (AEX) chromatography. This method is useful in purifying any chimeric proteins described herein, in particular chimeric proteins comprising a FVIII protein. When a FVIII chimeric protein is desired, it is found that subjecting the FVIII chimeric protein to a FVIII-specific affinity chromatography, such as VIIISelect (GE Healthcare), followed by subjecting the FVIII chimeric protein to AEX chromatography yields highly active FVIII chimeric protein. This represents a vast improvement over the existing FVIII purification methods.

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

As used herein, the term "about" allows for the degree of variation inherent in the methods and in the instrumentation used for measurement or quantitation. For example, depending on the level of precision of the instrumentation used, standard error based on the number of samples measured, and rounding error, the term "about" includes, without limitation, +10%.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo, or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, micro-injection, transduction, cell fusion, DEAE dextran, calcium phosphate precipitation, lipofection (lysosome fusion), use of a gene gun, or a DNA vector transporter.

"Culture," "to culture," and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, WI 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

As used herein, an "amino acid corresponding to" or an "equivalent amino acid" in a VWF sequence or a FVIII protein sequence is identified by alignment to maximize the identity or similarity between a first VWF or FVIII sequence and a second VWF or FVIII sequence. The number used to identify an equivalent amino acid in a second VWF or FVIII sequence is based on the number used to identify the corresponding amino acid in the first VWF or FVIII sequence.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number being the number of the amino acid in mature native FVIII (SEQ ID NO:4) to which the insertion site corresponds, which is immediately N-terminal to the position of the insertion. For example, the phrase "a3 comprises an XTEN at an insertion site which corresponds to amino acid 1656 of SEQ ID NO: 4" indicates that the heterologous moiety is located between two amino acids corresponding to amino acid 1656 and amino acid 1657 of SEQ ID NO: 4.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which an XTEN or any other polypeptide is inserted between two adjacent amino acids. Thus, the phrases "inserted immediately downstream of an amino acid" and "inserted between two amino acids of an insertion site" are used synonymously with "inserted at an insertion site."

The terms "inserted," "is inserted," "inserted into" or grammatically related terms, as used herein refers to the position of an XTEN in a chimeric polypeptide relative to the analogous position in native mature human FVIII. As used herein the terms refer to the characteristics of the recombinant FVIII polypeptide relative to native mature human FVIII, and do not indicate, imply or infer any methods or process by which the chimeric polypeptide was made. For example, in reference to a chimeric polypeptide provided herein, the phrase "an XTEN is inserted into immediately downstream of residue 745 of the FVIII polypeptide" means that the chimeric polypeptide comprises an XTEN immediately downstream of an amino acid which corresponds to amino acid 745 in native mature human FVIII, e.g., bounded by amino acids corresponding to amino acids 745 and 746 of native mature human FVIII.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein is created, for example, by chemical synthesis, or by creating and translating a poly-nucleotide in which the peptide regions are encoded in the desired relationship. A chimeric protein can further com-prises a second amino acid sequence associated with the first amino acid sequence by a covalent, non-peptide bond or a non-covalent bond.

As used herein, the term "half-life" refers to a biological half-life of a particular polypeptide in vivo. Half-life may be represented by the time required for half the quantity admin-istered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodi-ments, the term half-life as used herein refers to the half-life of the polypeptide in the β-phase. The typical § phase half-life of a human antibody in humans is 21 days.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alterna-tively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucle-otide chains). The term "linked" is also indicated by a hyphen (-).

As used herein the term "associated with" refers to a covalent or non-covalent bond formed between a first amino acid chain and a second amino acid chain. In one embodi-ment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or sym-metric hydrogen bond), van der Walls force, London dis-persion force, a mechanical bond, a halogen bond, aurophi-licity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or con-sists of a second Fc region without the clotting factor. The monomer-dimer hybrid construct thus is a hybrid compris-ing a monomer aspect having only one clotting factor and a dimer aspect having two Fc regions.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, Factor XIa or Factor Xa. Exemplary FXIa cleavage sites include, e.g, TQSFNDFTR (SEQ ID NO: 22) and SVSQTSKLTR (SEQ ID NO: 23). Exemplary thrombin cleavage sites include, e.g., DFLAEGGGVR (SEQ ID NO: 24), TTKIKPR (SEQ ID NO: 25), LVPRG (SEQ ID NO: 26) and ALRPR (amino acids 1 to 5 of SEQ ID NO: 27). Other enzymatic cleavage sites are known in the art.

As used herein, the term "processing site" or "intracellular processing site" refers to a type of enzymatic cleavage site in a polypeptide which is a target for enzymes that function after translation of the polypeptide. In one embodiment, such enzymes function during transport from the Golgi lumen to the trans-Golgi compartment. Intracellular process-ing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any resi-due]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

The term "Furin" refers to the enzymes corresponding to EC No. 3.4.21.75. Furin is subtilisin-like proprotein convertase, which is also known as PACE (Paired basic Amino acid Cleaving Enzyme). Furin deletes sections of inactive precursor proteins to convert them into biologically active proteins. During its intracellular transport, pro-peptide of VWF can be cleaved from mature VWF molecule by a Furin enzyme. In some embodiments, Furin cleaves the D1D2 from the D'D3 of VWF. In other embodiments, a nucleotide sequence encoding Furin can be expressed together with the nucleotide sequence encoding a VWF fragment so that D1D2 domains can be cleaved off intracellularly by Furin.

In constructs that include more than one processing or cleavage site, it will be understood that such sites may be the same or different.

A "processable linker" as used herein refers to a linker comprising at least one intracellular processing site, which are described elsewhere herein.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., Von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The chimeric protein of the invention is also used for on-demand treatment. The term "on-demand treatment" refers to the administration of a chimeric molecule in response to symptoms of a bleeding episode or before an activity that may cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a chimeric protein or a VWF fragment of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Many buffers are known in the art for use in buffer solutions and include, but are not limited to, histidine, citrate, phosphate, succinate, tris(hydroxymethyl)aminomethane (Tris), acetate, glycine, aconitate, maleate, phthalate, cacodylate, barbitol, 2-(N-morpholino)ethanesulfonic acid (MES), bis (2-hydroxyethyl)imino-tris-(hydroxymethyl)methane (Bistris), N-(2-Acetamido)iminodiacetic acid (ADA), piperazine-N,N'-bis(2-ethanesulfonic acid) (PIPES), 1,3-bis[tris (hydroxymethyl)-methylamino]propane (Bistrispropane), N-(Acetamido)-2-aminoethanesulfonic acid (ACES), 3-(N-morpholino)propanesulfonic acid (MOPS), N,N'-bis(2-hydroxyethyl)-2-amino-ethanesulfonic acid (BES), N-tris(hydroxymethyl)methyl-2-amino-ethanesulfonic acid (TES), N-2-hydroxyethylpiperazine-N'-ethanesulfonic acid (HEPES), N-2-hydroxyethylpiperazine-N'-propanesulfonic acid (HEPPS), N-tris(hydroxymethyl)methylglycine (Tricine), N,N-bis(2-hydroxyethyl)glycine (Bicine), glycylglycine, N-tris(hydroxymethyl)methyl-3-amino-propanesulfonic acid (TAPS), 1,3-bis[tris(hydroxymethyl)-methylamino] propane (Bistrispropane), as well as combinations of these.

The term "loading buffer" refers to the buffer, in which the polypeptide being purified is applied to a purification device, e.g., a chromatography column or a filter cartridge. Typically, the loading buffer is selected so that separation of the polypeptide of interest from unwanted impurities can be accomplished.

The terms "wash solution" and "wash buffer" are used interchangeably herein and refer to the buffer used to remove contaminant(s), such as process-related impurities, from the polypeptide-bound purification device (e.g., a chromatography matrix) without removing significant amounts of the polypeptide of interest. The wash solution can comprise a salt, a detergent, a solvent, a polymer, or any combinations thereof.

The terms "elution solution" and "elution buffer" are used interchangeably herein and refer to the buffer, which is typically used to remove (elute) the polypeptide of interest from the purification device (e.g., a chromatographic column or filter cartridge) to which it was applied earlier. Typically, the elution solution is selected so that separation of the polypeptide of interest from unwanted impurities can be accomplished. Often, the concentration of a particular ingredient, such as a particular salt (e.g., NaCl) in the elution is varied during the elution procedure (gradient). The gradient can be continuous or stepwise (interrupted by hold periods). In certain embodiments, low pH, such as a pH value below 4.5, is used in an elution solution.

The term "chromatography" refers to the process by which a solute of interest, typically a polypeptide, in a mixture is separated from other solutes in a mixture as a result of differences in rates at which the individual solutes of the mixture migrate through a stationary medium under the influence of a moving phase, or in bind and elute processes. The chromatography steps of the present invention can employ any type of chromatographic method. For example, such methods include without limitation: gas chromatography, liquid chromatography (e.g., high performance liquid chromatography); affinity chromatography (such as Protein-A or antibody-antigen affinity chromatography); supercritical fluid chromatography; ion exchange chromatography (such as anion or cation exchange chromatography); size-exclusion chromatography; reversed phase chromatography; two-dimensional chromatography; simulated moving bed chromatography, pyrolysis gas chromatography, fast protein (FPLC) chromatography; countercurrent chromatography; chiral chromatography; aqueous normal phase (ANP) chromatography; mixed mode chromatography; and, pseudo-affinity chromatography.

Any or all chromatographic steps of the invention can be carried out by any mechanical means. Chromatography can be carried out in a column. The column can be run with or without pressure and from top to bottom or bottom to top. The direction of the flow of fluid in the column can be reversed during the chromatography process. Chromatography can also be carried out using a batch process in which the solid support is separated from the liquid used to load, wash, and elute the sample by any suitable means, including gravity, centrifugation, or filtration. Chromatography can also be carried out by contacting the sample with a filter that absorbs or retains some molecules in the sample more strongly than others.

The term "affinity chromatography" refers to a protein separation technique in which a chimeric protein is reversibly and specifically bound to a biospecific ligand, e.g. FVIIISelect. In one embodiment, the biospecific ligand, e.g., FVIIISelect, is covalently attached to a chromatographic solid phase material and is accessible to the polypeptide of interest (e.g., a chimeric protein) in solution as the solution contacts the chromatographic solid phase material. The polypeptide of interest (e.g., chimeric FVIII protein) retains its specific binding affinity for the biospecific ligand (e.g., FVIIISelect) during the chromatographic steps, while other solutes and/or proteins in the mixture do not bind appreciably or specifically to the ligand. Binding of the chimeric protein to the immobilized ligand allows contaminating proteins or protein impurities to be passed through the chromatographic medium while the chimeric protein remains specifically bound to the immobilized ligand on the solid phase material. The specifically bound chimeric FVIII protein is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody or peptide binding to FVIII. In one embodiment, a ligand for the chimeric FVIII protein is FVIIISelect from GE Healthcare.

The terms "anion exchange resin," "anion exchange adsorbent," or "anion exchange matrix" are used herein to refer to a solid phase which is positively charged, e.g., having one or more positively charged ligands, such as quaternary amino groups, attached thereto. Commercially available anion exchange resins include DEAE SEPHAROSE™ Fast Flow, Q SEPHAROSE™ Fast Flow, Q SEPHAROSE™ High Performance, Q SEPHAROSE™ XL, CAPTO™ DEAE, CAPTO™ Q, and CAPTO™ Q ImpRes from GE Healthcare Life Sciences, or FRACTOGEL® EMD TMAE HiCap, FRACTOGEL® EMD DEAE, and ESHMUNO® Q from EMD Millipore, or UNOSPHERE™ Q and NUVIA™ Q from Bio-Rad.

The terms "cation exchange resin," "cation exchange adsorbent," or "cation exchange matrix" refer to a solid phase which is negatively charged, and which thus has free cations for exchange with cations in an aqueous solution passed over or through the solid phase. A negatively charged ligand attached to the solid phase to form the cation exchange resin can, e.g., be a carboxylate or sulfonate. Commercially available cation exchange resins include carboxy-methyl-cellulose, sulphopropyl (SP) immobilized on agarose (e.g., SP SEPHAROSE™ XL, SP-SEPHAROSE™ Fast Flow, SP SEPHAROSE™ High Performance, CM SEPHAROSE™ Fast Flow, CM SEPHAROSE™ High Performance, CAPTO™ S, and CAPTO™ SP ImpRes from GE Healthcare Life Sciences, or FRACTOGEL® EMD SE HiCap, FRACTOGEL® EMD SO3-, FRACTOGEL® EMD COO—, ESHMUNO® S, and ESHMUNO® CPX from EMD Millipore, or UNOSPHERE™ S and NUVIA™ S from Bio-Rad).

As used herein, the terms "percent recovery" and "percent purity," are intended to mean the recovery or purity achieved when a target compound (e.g., a chimeric FVIII protein) is conveyed through a purification step or procedure, compared to the quantity or purity of the target compound in the sample prior to the purification step or procedure. Achieving an increase in percent purity entails obtaining a product with reduced levels of contaminants (in proportion to the target compound) when a sample is compared before and after a purification step or procedure. Preferred percentages within the meaning of percent recovery and percent purity as defined above include, without limitation, at least about 50%, at least about 60%, at least about 70%, at least about 80%, at least about 90%, at least about 95%, at least about 98%, and at least about 99%.

Methods for the determination of yield or purity of a polypeptide are known to those of skill in the art. Yield or purity of a polypeptide can be determined by any suitable, art-recognized method of analysis (e.g., band intensity on a silver stained gel, polyacrylamide gel electrophoresis, ELISA, HPLC and the like). An exemplary method is size-exclusion chromatography (SEC) or high-performance liquid chromatography (HPLC), described herein below.

Purity can be determined using relative "area under the curve" (AUC) values, which can typically be obtained for peaks in a chromatogram, such as an HPLC chromatogram. Optionally, purities are determined by chromatographic or other means using a standard curve generated using a reference material of known purity. Purity can also be determined on a weight-by-weight basis.

The term "polymer" refers to a molecule formed by covalent linkage of two or more monomers, where the monomers are not amino acids. Non-limiting examples of polymers include polyethyl glycol, polypropyl glycol, and copolymers of ethylene and propylene glycol.

The term "detergent" refers to nonionic or zwitterionic surfactants such as polysorbates (e.g., polysorbates 20 or 80); poloxamers (e.g., poloxamer 188); octylphenol ethylene oxide condensate (also known as Octoxynol-9, t-octylphe-noxypolyethoxyethanol, TRITON™, or TRITON™ X-100); 3-[(3-cholamidopropyl)dimethylammonio]-1-propane-sulfonate (CHAPS); 3-[(3-cholamidopropyl)dimethylam-monio]-2-hydroxy-1-propanesulfonate (CHAPSO); sodium dodecyl sulfate (SDS), sodium laurel sulfate, sodium octyl glycoside; lauryl-, myristyl-, linoleyl- or stearyl-sulfo-betaine; lauryl-, myristyl-, linoleyl- or stearyl-sarcosine; linoleyl-, myristyl-, or cetyl-betaine, lauroamidopropyl-, cocamidopropyl-, linoleamidopropyl-, myristamidopropyl-, palmidopropyl-, or isostearamidopropyl-betaine (e.g. lau-roamidopropyl); myristamidopropyl-, palmidopropyl-, or isostearamidopropyl-dimethylamine; sodium methyl cocoyl-, or disodium methyl oleyl-taurate; and 1-ethyl-1-(2-hydroxyethyl)-2-isoheptadecylimidazolinium ethylsulfate (e.g., the MONAQUAT™ series, Mona Industries, Inc., Paterson, New Jersey). Non-limiting examples of commer-cial products comprising compounds similar to TRITON™ X-100 include CONCO™ NI, DOWFAX™ 9N, IGEPAL™ CO, MAKON™, NEUTRONYX® 600's, NONIPOL™ NO, POLYTERGENT® B, RENEX™ 600's, SOLAR™ NO, STEROX™, SERFONIC™ N, T-DET-N™, TERGI-TOL™ NP, TRITON™ N, TWEEN-20®, and TWEEN-80®.

The term "TFF" or "tangential flow filtration" as used herein refers to a method of concentrating biomolecules in a sample, including the concentration of proteins in a media.

Methods of Purifying Chimeric Proteins

The present invention is directed to methods of purifying chimeric proteins. The disclosed method can be applied to any FVIII protein disclosed herein, e.g., a chimeric protein comprising a FVIII protein linked to an Fc region and a VWF protein linked to a second Fc region, wherein the VWF protein comprises, consisting essentially of, or consisting of D'D3 domain of VWF, e.g., Factor VIII-169/VWF-57. How-ever, one of ordinary skill in the art would recognize that the disclosed methods are amendable for use with any protein comprising a FVIII protein or a fragment thereof.

A chimeric protein disclosed herein can be produced by recombinant methods. In one embodiment, a chimeric pro-tein can be expressed by host cells in media, wherein the expressed protein is released by the cells into the surround-ing media, which can be collected as conditioned media. The conditioned media, which comprise the chimeric protein, can then be subjected to one or more purification methods. After the media are collected, the media can be concentrated to improve the downstream purification process. In one embodiment, the collected media are concentrated using filtration, centrifugation, or any other known methods. In another embodiment, the collected media are concentrated by tangential flow filtration (TFF). In other embodiments, the conditioned media is concentrated by at least about 2, at least about 3, at least about 4, at least about 5, at least about 6, at least about 7, at least about 8, at least about 9, at least about 10, at least about 15, at least about 20, at least about 50, or at least 100 fold.

One aspect of the methods of the invention includes subjecting a chimeric protein to an affinity chromatography prior to subjecting the chromatography to an anion exchange chromatography. Subjecting the chimeric protein to an affin-ity chromatography prior to the anion exchange chromatog-raphy can increase the overall protein yield, maintain high protein activity, and/or improve protein stability compared to the method of subjecting the chimeric protein to an anion exchange chromatography without the affinity chromatog-raphy. In certain embodiments, some or all of the condi-tioned media comprising the chimeric protein is contacted with or subjected to a protein-specific affinity chromatogra-phy matrix. The conditioned media can be in a crude or concentrated form. In one embodiment, a factor VIII-spe-cific affinity chromatography matrix comprising a low molecular weight ligand that binds factor VIII is used as the protein-specific affinity chromatography. One such example of a low molecular weight ligand that binds factor VIII is VIIISelect (GE Healthcare), though any low molecular weight ligand that is capable of binding factor VIII can be used. The factor VIII-specific affinity chromatography matrix can be equilibrated prior to use.

In one embodiment, a FVIII-specific affinity chromatog-raphy matrix is FVIIISelect. VIIISelect is based on highly cross-linked agarose base matrix, which enables rapid pro-cessing of large sample volumes. The ligand, a 13 kD recombinant protein, is attached to the porous base matrix via a hydrophilic spacer arm making it easily available for binding to recombinant b domain-depleted factor VIII. The main characteristics of VIIISelect are shown in Table 1:

TABLE 1

| Main Characteristics of VIIISelect | |
| --- | --- |
| Matrix | highly cross-linked agarose |
| Average particle size | 75 μm |
| Ligand | Recombinant protein (M, 13 000) produced in *S. cerevisiae*. |
| Capacity | Typically 20,000 IU/ml gel |
| Recommended flow rate | Up to 300 cm/h at 30 cm bed height |
| Maximum back pressure | 0.3 MPa, 3 bar |
| pH stability | |
| Long term | 3-10 |
| Short term | 2-12 |

Recombinant chimeric FVIII proteins can be applied directly to the VIIISelect column from clarified cell lysates or supernatants. A typical protocol for using VIIISelect, with recommended buffers, is described in Table 2:

TABLE 2

| FVIIISelect Protocol | |
| --- | --- |
| Equilibration/ loading buffer: | 10 mM histidine, 20 mM calcium chloride, 300 mM sodium chloride, and 0.02% TWEEN 80 ® at pH 7.0 |
| Washing buffer 1 | 20 mM histidine, 20 mM calcium chloride, 300 mM sodium chloride, and0.02% TWEEN 80 ®at pH 6.5 |
| Washing buffer 2 | 20 mM histidine, 20 mM calcium chloride, 1.0M sodium chloride, and 0.02% TWEEN 80 ® at pH 6.5. |
| Elution buffer | 20 mM histidine, 20 mM calcium chloride, 1.5M sodium chloride, and 0.02% TWEEN 80 ® dissolved in 50% ethylene glycol at pH 6.5 |

A chimeric FVIII protein can be purified by (1) packing the column with VIIISelect, (2) equilibrating with 10 CV (column volumes) of equilibration buffer, (3) loading the sample in loading buffer, (4) washing with 5 CV of washing buffer 1, and (5) washing with 5 CV of washing buffer 2, and (6) eluting with 5-10 CV of elution buffer.

In one embodiment, buffers contain Ca2+ ions in order to promote formation of the active conformation of factor VIII. In another embodiment, a surfactant is added to inhibit surface-induced denaturation. In other embodiments, neutral pH buffers and histidine are used for binding, washing, and elution for maintaining the specific factor VIII activity. Depending on the nature of the applied material to VIIISelect, regeneration can be applied after each cycle, followed by re-equilibration in equilibration/loading buffer.

The chimeric protein purified by the present methods can have increased factor VIII activity compared to the chimeric protein purified by the factor VIII specific affinity chromatography without a DEAE affinity chromatography. In one embodiment, the factor VIII activity of a chimeric protein purified by the present methods is increased at least 1.5 fold, at least two fold, at least three fold, at least four fold, at least five fold, at least six fold, at least seven fold, at least eight fold, at least nine fold, or at least ten fold compared to the factor VIII activity of the chimeric protein purified by the factor VIII specific affinity chromatography without a DEAE affinity chromatography. In another embodiment, the factor VIII activity of a chimeric protein purified by the present methods is at least about 5 IU/mL, at least about 7 IU/mL, at least about 9 IU/mL, at least about 10 IU/mL, at least about 12 IU/mL, at least about 14 IU/mL, at least about 16 IU/mL, at least about 18 IU/mL, at least about 20 IU/mL, at least about 22 IU/mL, at least about 24 IU/mL, at least about 26 IU/mL, at least about 28 IU/mL, or at least about 30 IU/mL.

The presently described purification methods can further entail various washes and/or elutions. For example, the factor VIII-specific affinity chromatography matrix and/or the AEX chromatography resin can be washed before or after the chimeric protein is introduced using buffers and methods provided herein. Further, the chimeric protein can be eluted from the factor VIII-specific affinity chromatography matrix and/or the AEX chromatography resin using specific buffers and methods provided herein. In some embodiments, the method further comprises eluting the chimeric protein from the AEX chromatography resin. The present disclosure provides for the use of various buffers including but not limited to equilibration buffers, wash buffers, and elution buffers.

The presently disclosed method involves the use of several individually described equilibration buffers. As used herein, an equilibration buffer can include a factor VIII-specific affinity chromatography equilibration buffer, an AEX equilibration buffer, a DEAE buffer, or any equivalent thereof. Additionally, several wash buffers are used in the present method. As used herein, a wash buffer can include a factor VIII-specific affinity chromatography wash buffer, an AEX wash buffer, a DEAE buffer, or any equivalent thereof. Further, several elution buffers are described in the present invention, including a factor VIII-specific affinity chromatography elution buffer, an AEX chromatography elution buffer, a DEAE elution buffer, or any equivalents thereof.

In at least one embodiment, the chimeric protein is subjected to a factor VIII-specific affinity chromatography matrix. The chimeric protein can be eluted from the factor VIII-specific affinity chromatography matrix. In some embodiments, the method comprises collecting the chimeric protein eluted from the factor VIII-specific affinity chromatography matrix. In other embodiments, the eluted chimeric protein can then be subjected and/or bound to an anion exchange (AEX) chromatography resin, e.g., comprising diethylaminoethyl (DEAE). In one embodiment, the method of purifying a chimeric protein comprises: (i) subjecting the chimeric protein to a factor VIII-specific affinity chromatography matrix, e.g., FVIIISelect; and (ii) binding the chimeric protein to an anion exchange (AEX) chromatography resin. In certain embodiments, the chimeric protein can be eluted from the factor VIII-specific affinity chromatography and/or the AEX chromatography. The eluted chimeric protein can then be collected or subjected to further purification, e.g., the chimeric protein eluted from the factor VIII-specific affinity chromatography can be subjected to an AEX chromatography.

In other embodiments, all or some of the conditioned media comprising the chimeric protein is subjected to an AEX chromatography resin. The chimeric protein can then optionally be eluted from the AEX chromatography resin and collected or subjected to further purification. In some embodiments, the chimeric protein eluted from the AEX chromatography resin is subjected to a factor VIII-specific affinity chromatography, such as VIIISelect (GE Healthcare). The chimeric protein can then optionally be eluted from the factor VIII-specific affinity chromatography and optionally collected. In one particular embodiment, the method of purifying a chimeric protein comprises: (i) subjecting the chimeric protein to an anion exchange (AEX) chromatography resin; and (ii) subjecting all or some of the eluted chimeric protein to a factor VIII-specific affinity chromatography matrix.

The chromatography mediums used in the present invention can optionally be pretreated prior to their use. For example, the factor VIII-specific affinity chromatography matrix can be equilibrated prior to the addition of the conditioned media or prior to the addition of protein eluted from an AEX chromatography. In some embodiments, the factor VIII-specific affinity chromatography matrix is equilibrated using a factor VIII-specific affinity chromatography matrix buffer.

In some embodiments, the factor VIII-specific affinity chromatography equilibration buffer comprises one or more salts. The salts that can be used in the buffer can include, but are not limited to, calcium salts, sodium salts, potassium salts, magnesium salts, or any combination thereof. In certain embodiments, the equilibration buffer comprises at least 100 mM or a salt. In some embodiments, the salt is a sodium salt, e.g., NaCl, and/or a calcium salt, e.g., $CaCl_2$.

In some embodiments, the factor VIII-specific affinity chromatography equilibration buffer comprises from about 10 mM to about 500 mM, from about 10 mM to about 150 mM, from about 30 mM to about 140 mM, from about 50 mM to about 130 mM, from about 70 mM to about 120 mM, from about 50 mM to about 150 mM, from about 50 mM to about 100 mM, or from about 100 mM to 150 mM NaCl. In other embodiments, the factor VIII-specific affinity chromatography equilibration buffer comprises at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, or at least about 150 mM NaCl. In one embodiment, the factor VIII-specific affinity chromatography equilibration buffer comprises at least about 100 mM NaCl.

In some embodiments, the factor VIII-specific affinity chromatography equilibration buffer comprises from about 1 mM to about 100 mM, from about 1 mM to about 10 mM, from about 2 mM to about 9 mM, from about 3 mM to about 7 mM, from about 6 mM to about 6 mM, from about 1 mM to about 5 mM, or from about 5 mM to about 10 mM CaCl$_2$. In other embodiments, the factor VIII-specific affinity chromatography equilibration buffer comprises at least about 1 mM, at least about 2 mM, at least about 3 mM, at least about 4 mM, at least about 5 mM, at least about 6 mM, at least about 7 mM, at least about 8 mM, at least about 9 mM, or at least about 10 mM CaCl$_2$. In one embodiment, the factor VIII-specific affinity chromatography equilibration buffer comprises at least about 5 mM CaCl$_2$.

The factor VIII-specific affinity chromatography equilibration buffer can comprise one or more of the buffers described herein, including but not limited to HEPES, tris-(hydroxymethyl)aminoethane, and phosphate. In some embodiments, the factor VIII-specific affinity chromatography equilibration buffer comprises from about 1 mM to about 100 mM, from about 1 mM to about 15 mM, from about 3 mM to about 14 mM, from about 5 mM to about 13 mM, from about 7 mM to about 12 mM, from about 5 mM to about 15 mM, from about 5 mM to about 10 mM, or from about 10 mM to 15 mM HEPES. In other embodiments, the factor VIII-specific affinity chromatography equilibration buffer comprises at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, or at least about 20 mM HEPES. In one embodiment, the factor VIII-specific affinity chromatography equilibration buffer comprises at least about 10 mM HEPES.

Further, the factor VIII-specific affinity chromatography equilibration buffer can comprise a detergent. The detergent can include but not be limited to any such example provided in the present disclosure, including polysorbate 20 (TWEEN-20®), polysorbate 80 (TWEEN-80®), polyethylene glycol p-(1,1,3,3-tetramethylbutyl)-phenyl ether, octylphenoxypolyethoxyethanol (IGEPAL®), octylphenoxypolyeth-oxyethanol (Nonidet P-40®), CHAPS, or CHAPSO.

In some embodiments, the factor VIII-specific affinity chromatography equilibration buffer comprises from about 0.005% to about 0.5%, from about 0.01% to about 0.5%, from about 0.05% to 0.5%, from about 0.05% to 0.4%, from about 0.05% to 0.3%, from about 0.05% to 0.2%, from about 0.05% to 0.15%, from about 0.05% to 0.1%, from about 0.1% to 0.5%, from about 0.1% to 0.4%, from about 0.1% to 0.3%, or from about 0.1% to 0.2% polysorbate 20. In other embodiments, the factor VIII-specific affinity chromatography equilibration buffer comprises at least about 0.005%, at least about 0.006%, at least about 0.007%, at least about 0.008%, at least about 0.009%, at least about 0.01%, at least about 0.02%, at least about 0.03%, at least about 0.04%, at least about 0.05%, at least about 0.06%, at least about 0.07%, at least about 0.08%, at least about 0.09%, or at least about 0.1% polysorbate 20. In one embodiment, the factor VIII-specific affinity chromatography equilibration buffer comprises at least about 0.01% polysorbate 20. In some embodiments, the polysorbate 20 is TWEEN-20®.

In some embodiments, the factor VIII-specific affinity chromatography equilibration buffer has a pH of from about 5.0 to about 9.0, from about 5.5 to about 8.5, from about 6.0 to about 8.0, from about 6.5 to about 8.0, from about 7.0 to 8.0, or from about 7.2 to 7.6. In another embodiment, the factor VIII-specific affinity chromatography matrix equilibration buffer has a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, or 8.0. In still other embodiments, the factor VIII-specific affinity chromatography matrix equilibration buffer has a pH of 7.4.

In one embodiment, the factor VIII-specific affinity chromatography equilibration buffer comprises 10 mM HEPES, 100 mM NaCl, 0.01% polysorbate 20, and 5 mM CaCl$_2$, and the factor VIII-specific affinity chromatography matrix equilibration buffer has a pH of 7.4.

As noted above, the presently disclosed method of purifying a chimeric protein can further comprise washing the factor VIII-specific affinity chromatography after the addition of the conditioned media comprising the chimeric protein. The use of successive washes increases protein purity by washing away unbound materials. While various buffers known in the art may be used to wash the factor VIII-specific affinity chromatography, in some embodiments, the factor VIII-specific affinity chromatography matrix is washed with the factor VIII-specific affinity chromatography equilibration buffer, described above, and/or a factor VIII-specific affinity chromatography wash buffer.

The number of times a chromatography is washed can be optimized to reach the desired level of purity. In the present invention, the factor VIII-specific affinity chromatography can be washed with 1 or more column volume of one or more selected buffers. For example, the factor VIII-specific affinity chromatography can be washed one or more column volumes of a first buffer followed by one or more column volumes of a second buffer, and so forth. As used herein, 1 column volume is equivalent to an amount of buffer sufficient to fill the chromatography apparatus or column. In some embodiments, the factor VIII-specific affinity chromatography is washed with at least 1, at least 2, at least 3, at least 4, at least 5, at least 6, at least 7, at least 8, at least 9, at least 10 column volumes of the factor VIII-specific affinity chromatography wash buffer. In other embodiments, the factor VIII-specific affinity chromatography is washed with at least 1, at least 2, at least 3, at least 4, at least 5, at least 6, at least 7, at least 8, at least 9, at least 10 column volumes of the factor VIII-specific affinity chromatography equilibration buffer. In one embodiment, the factor VIII-specific affinity chromatography is washed with about 5 column volumes of the factor VIII-specific affinity chromatography equilibration buffer, then optionally about 10 column volumes of factor VIII-specific affinity chromatography wash buffer, and then optionally about 10 column volumes of the factor VIII-specific affinity chromatography equilibration buffer. The flow through from each wash can be collected for analysis, e.g., to optimize the number of washes needed until the flow through is relatively devoid of non-target proteins or to monitor the effectiveness of the chromatography to bind and hold target protein.

The factor VIII-specific affinity chromatography wash buffer can comprise one or more salts. The salts useful in the wash buffer include, but are not limited to, calcium salts, sodium salts, potassium salts, magnesium salts, or any combination thereof. In some embodiments, the wash buffer comprises at least 0.8M salt. In other embodiments, the salt is a sodium salt, e.g., NaCl, and/or a calcium salt, e.g., CaCl$_2$.

In some embodiments, the factor VIII-specific affinity chromatography wash buffer comprises from about 0.1M to about 5.0M, from about 0.1M to about 4.0M, from about 0.1M to about 3.0M, from about 0.1M to about 2.0M, from about 0.1M to about 1.0M, from about 0.5M to about 5.0M, from about 0.5M to about 4.0M, from about 0.5M to about 3.0M, from about 0.5M to about 2.0M, from about 0.5M to about 1.0M, from about 0.1M to about 1.0M, from about 0.2M to about 1.0M, from about 0.3M to about 1.0M, from about 0.4M to about 1.0M, from about 0.6M to about 1.0M, from about 0.7M to about 1.0M, or from about 0.8M to about 1.0M NaCl. In other embodiments, the factor VIII-specific affinity chromatography wash buffer comprises at least about 0.1M, at least about 0.2M, at least about 0.3M, at least about 0.4M, at least about 0.5M, at least about 0.6M, at least about 0.7M, at least about 0.8M, at least about 0.9M, at least about 1.0M, at least about 1.1M, at least about 1.2M, at least about 1.3M, at least about 1.4M, or at least about 1.5M NaCl. In one embodiment, the factor VIII-specific affinity chromatography wash buffer comprises at least about 0.8M NaCl.

In some embodiments, the factor VIII-specific affinity chromatography wash buffer comprises from about 0.05M to about 5M, from about 0.05M to about 4M, from about 0.05M to about 3M, from about 0.05M to about 2M, from about 0.05M to about 1M, from about 0.05M to about 0.5M, from about 0.1M to about 0.5M, from about 0.1M to about 0.4M, from about 0.1M to about 0.3M, from about 0.1M to about 0.2M, from about 0.2M to about 1M, or from about 0.2M to about 0.5M. In other embodiments, the factor VIII-specific affinity chromatography wash buffer comprises at least about 0.05M, at least about 0.1M, at least about 0.15M, at least about 0.2M, at least about 0.3M, at least about 0.4M, at least about 0.5M, at least about 0.6M, at least about 0.7M, at least about 0.8M, at least about 0.9M, or at least about 1.0M $CaCl_2$. In one embodiment, the factor VIII-specific affinity chromatography matrix wash buffer comprises at least about 0.2M $CaCl_2$.

The factor VIII-specific affinity chromatography wash buffer can comprise one or more of the buffers described herein, including but not limited to HEPES, tris-(hydroxymethyl)aminoethane, or phosphate. In some embodiments, the factor VIII-specific affinity chromatography wash buffer comprises from about 1 mM to about 100 mM, from about 1 mM to about 15 mM, from about 3 mM to about 14 mM, from about 5 mM to about 13 mM, from about 7 mM to about 12 mM, from about 5 mM to about 15 mM, from about 5 mM to about 10 mM, or from about 10 mM to 15 mM HEPES. In other embodiments, the factor VIII-specific affinity chromatography wash buffer comprises at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, or at least about 20 mM HEPES. In one embodiment, the factor VIII-specific affinity chromatography wash buffer comprises at least about 10 mM HEPES.

Additionally, the factor VIII-specific affinity chromatography wash buffer can comprise a detergent. The detergent can include but not be limited to any such detergent provided in the present disclosure, including polysorbate 20 (TWEEN-20®), polysorbate 80 (TWEEN-80®), polyethylene glycol p-(1,1,3,3-tetramethylbutyl)-phenyl ether, octylphenoxypolyethoxyethanol (IGEPAL®), octylphenoxypolyeth-oxyethanol (Nonidet P-40®), CHAPS, or CHAPSO. In some embodiments, the factor VIII-specific affinity chromatography equilibration buffer comprises from about 0.005% to about 0.5%, from about 0.01% to about 0.5%, from about 0.05% to 0.5%, from about 0.05% to 0.4%, from about 0.05% to 0.3%, from about 0.05% to 0.2%, from about 0.05% to 0.15%, from about 0.05% to 0.1%, from about 0.1% to 0.5%, or from about 0.1% to 0.4%, from about 0.1% to 0.3%, or from about 0.1% to 0.2% polysorbate 20. In other embodiments, the factor VIII-specific affinity chromatography wash buffer comprises at least about 0.005%, at least about 0.006%, at least about 0.007%, at least about 0.008%, at least about 0.009%, at least about 0.01%, at least about 0.02%, at least about 0.03%, at least about 0.04%, at least about 0.05%, at least about 0.06%, at least about 0.07%, at least about 0.08%, at least about 0.09%, or at least about 0.1% polysorbate 20. In one embodiment, the factor VIII-specific affinity chromatography wash buffer comprises at least about 0.01% polysorbate 20. In some embodiments, the polysorbate 20 is TWEEN-20®.

In some embodiments, the factor VIII-specific affinity chromatography wash buffer has a pH of from about 5.0 to about 9.0, from about 5.5 to about 8.5, from about 6.0 to about 8.0, from about 6.5 to about 7.5, or from about 7.0 to 7.5. In other embodiments, the factor VIII-specific affinity chromatography wash buffer has a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, or 8.0. In one embodiment, the factor VIII-specific affinity chromatography matrix wash buffer has a pH of 7.2.

In one particular embodiment, the factor VIII-specific affinity chromatography matrix wash buffer comprises 0.8M NaCl, 0.2M $CaCl_2$, 10 mM HEPES, 0.01% polysorbate 20, and the factor VIII-specific affinity chromatography matrix wash buffer has a pH of 7.2.

As discussed above, the chimeric protein can optionally be eluted from the factor VIII-specific affinity chromatography using a factor VIII-specific affinity chromatography elution buffer. The chimeric protein can be eluted using at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 column volumes of the factor VIII-specific affinity chromatography elution buffer. In certain embodiments, the chimeric protein is eluted from the factor VIII-specific affinity chromatography matrix using 20 column volumes of the factor VIII-specific affinity chromatography elution buffer.

The factor VIII-specific affinity chromatography elution buffer can comprise one or more salts. The salts useful in the elution buffer include, but are not limited to, calcium salts, sodium salts, potassium salts, magnesium salts, or any combination thereof. In certain embodiments, the wash buffer comprises a salt concentration of at least 50 mM. In other embodiments, the salt is a sodium salt, e.g., NaCl, and/or a calcium salt, e.g., $CaCl_2$.

In some embodiments, the factor VIII-specific affinity chromatography elution buffer comprises from about 5 mM to about 500 mM, from about 10 mM to about 400 mM, from about 10 mM to about 300 mM, from about 10 mM to about 200 mM, from about 10 mM to about 100 mM, from about 5 mM to about 50 mM, from about 5 mM to about 100 mM, from about 10 mM to about 90 mM, from about 20 mM to about 80 mM, from about 30 mM to about 70 mM, from about 40 mM to about 60 mM, from about 5 mM to about 50 mM, or from about 50 mM to about 100 mM $CaCl_2$. In other embodiments, the factor VIII-specific affinity chromatography elution buffer comprises at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, at least about 85 mM, at least about 90 mM, at least about 95 mM, or at least about 100 mM CaCl$_2$. In one embodiment, the factor VIII-specific affinity chromatography elution buffer comprises at least about 50 mM CaCl$_2$.

The factor VIII-specific affinity chromatography elution buffer can comprise one or more amino acids. In certain embodiments, the one or more amino acids are selected from histidine, arginine, leucine, isoleucine, threonine, glutamate, glutamic acid, glycine, asparagine, aspartic acid, lysine, and any combination thereof. In another embodiment, the one or more amino acids are selected from histidine, arginine, and a combination of both.

In some embodiments, the factor VIII-specific affinity chromatography elution buffer comprises from about 5 mM to about 500 mM, from about 10 mM to about 400 mM, from about 10 mM to about 300 mM, from about 10 mM to about 200 mM, from about 10 mM to about 100 mM, from about 5 mM to about 50 mM, from about 5 mM to about 100 mM, from about 10 mM to about 90 mM, from about 20 mM to about 80 mM, from about 30 mM to about 70 mM, from about 40 mM to about 60 mM, from about 5 mM to about 50 mM, or from about 50 mM to about 100 mM histidine. In other embodiments, the factor VIII-specific affinity chromatography elution buffer comprises at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, at least about 85 mM, at least about 90 mM, at least about 95 mM, or at least about 100 mM histidine. In one embodiment, the factor VIII-specific affinity chromatography elution buffer comprises at least about 50 mM histidine.

In some embodiments, the factor VIII-specific affinity chromatography elution buffer comprises from about 0.1 mM to about 5 mM, from about 0.1 mM to about 4 mM, from about 0.1 mM to about 3 mM, from about 0.1 mM to about 2 mM, from about 0.1 mM to about 1 mM, from about 0.1 mM to about 0.9 mM, from about 0.2 mM to about 1.0 mM, from about 0.2 mM to about 1.0 mM, from about 0.3 mM to about 1.0 mM, from about 0.4 mM to about 1.0 mM, from about 0.5 mM to about 1.0 mM, from about 0.6 mM to about 1.0 mM, from about 0.7 mM to about 1.0 mM, from about 0.8 mM to about 1.0 mM, from about 0.9 mM to about 1.0 mM, from about 0.9 mM to about 1.5 mM, from about 0.9 mM to about 2.0 mM, from about 0.9 mM to about 2.5 mM, or from about 0.9 mM to about 5.0 mM arginine. In other embodiments, the factor VIII-specific affinity chromatography elution buffer comprises at least about 0.1 mM, at least about 0.2 mM, at least about 0.3 mM, at least about 0.4 mM, at least about 0.5 mM, at least about 0.6 mM, at least about 0.7 mM, at least about 0.8 mM, at least about 0.9 mM, at least about 1.0 mM, at least about 1.1 mM, at least about 1.2 mM, at least about 1.3 mM, at least about 1.4 mM, at least about 1.5 mM arginine. In one embodiment, the factor VIII-specific affinity chromatography elution buffer comprises at least about 0.9M arginine. In some embodiments, the arginine is in the form of arginine-HCl.

The factor VIII-specific affinity chromatography elution buffer can comprise a co-solvent selected from propylene glycol, polypropylene glycol, ethylene glycol, polyethylene glycol, dimethyl sulfoxide (DMSO), and any combination thereof, as these water-miscible organic solvents are known to disrupt the hydrated structure of macromolecular solutes and thereby promote the replacement of interfacial water molecules that contribute to the hydrogen bonding network of macromolecular complexes. In some embodiments, factor VIII-specific affinity chromatography elution buffer comprises from about 10% to about 60%, from about 20% to about 60%, from about 30% to about 60%, from about 40% to about 50%, from about 10% to about 50%, from about 20% to about 50%, or from about 30% to about 50% propylene glycol. In other embodiments, the factor VIII-specific affinity chromatography elution buffer comprises at least about 10%, at least about 20%, at least about 30%, at least about 35%, at least about 40%, at least about 41%, at least about 42%, at least about 43%, at least about 44%, at least about 45%, at least about 46%, at least about 47%, at least about 48%, at least about 49%, at least about 50%, at least about 55%, or at least about 60% propylene glycol. In one embodiment, the factor VIII-specific affinity chromatography elution buffer comprises at least about 45% propylene glycol.

The factor VIII-specific affinity chromatography elution buffer can comprise a detergent. The detergent can include but not be limited to any such detergent provided in the present disclosure, including polysorbate 20 (TWEEN-20®), polysorbate 80 (TWEEN-80®), polyethylene glycol p-(1,1,3,3-tetramethylbutyl)-phenyl ether, octylphenoxy-polyethoxyethanol (IGEPAL®), octylphenoxypolyeth-oxy-ethanol (Nonidet P-40®), CHAPS, or CHAPSO. In some embodiments, the factor VIII-specific affinity chromatography elution buffer comprises from about 0.01% to about 0.2%, from about 0.02% to about 0.2%, from about 0.03% to about 0.2%, from about 0.04% to about 0.2%, from about 0.05% to about 0.2%, from about 0.02% to about 0.15%, from about 0.02% to about 0.1%, from about 0.02% to about 0.09%, from about 0.02% to about 0.08%, from about 0.02% to about 0.07%, from about 0.02% to about 0.06%, from about 0.03% to about 0.08%, from about 0.04% to about 0.07%, or from about 0.05% to about 0.1% polysorbate 20. In other embodiments, the factor VIII-specific affinity chromatography elution buffer comprises at least about 0.01%, at least about 0.02%, at least about 0.03%, at least about 0.04%, at least about 0.05%, at least about 0.06%, at least about 0.07%, at least about 0.08%, at least about 0.09%, at least about 0.1%, at least about 0.15%, or at least about 0.2% polysorbate 20. In one embodiment, the factor VIII-specific affinity chromatography elution buffer comprises at least about 0.05% polysorbate 20. In some embodiments, the polysorbate 20 is TWEEN-20®.

In some embodiments, the factor VIII-specific affinity chromatography elution buffer has a pH of from about 5.0 to about 9.0, from about 5.5 to about 8.5, from about 6.0 to about 8.0, from about 6.5 to about 7.5, or from about 7.0 to 7.5. In some embodiments, the factor VIII-specific affinity chromatography elution buffer has a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, or 8.0. In some embodiments, the factor VIII-specific affinity chromatography elution buffer has a pH of 7.2.

In one particular embodiment, the factor VIII-specific affinity chromatography elution buffer comprises 50 mM histidine, 0.9M arginine-HCl, 50 mM CaCl$_2$, 45% propylene glycol, and 0.05% polysorbate 20, and the factor VIII-specific affinity chromatography elution buffer has a pH of 7.2.

As discussed above, some embodiments of the disclosed method involve the use of an AEX chromatography. In certain embodiments, the crude conditioned media, filtered and concentrated conditioned media, and/or the chimeric protein eluted from the factor VIII-specific affinity chromatography can be contacted with an AEX chromatography. This can be an initial purification step when crude or concentrated conditioned media are used, or this can be an additional purification when eluted chimeric protein is used. The latter option can be referred to herein as a "polishing step."

The AEX chromatography can optionally be pre-equilibrated prior to addition of either the conditioned media or the chimeric protein. In some embodiments, the AEX chromatography resin is pre-equilibrated using a DEAE buffer. The DEAE buffer can comprise one or more salt. The salts that can be used in the DEAE buffer include, but are not limited to, calcium salts, sodium salts, potassium salts, magnesium salts, or any combination thereof. In some embodiments, the DEAE buffer comprises a salt concentration of at least 100 mM. In certain embodiments, the salt is a sodium salt, e.g., NaCl, and/or a calcium salt, e.g., $CaCl_2$.

In some embodiments, the DEAE buffer comprises from about 10 mM to about 500 mM, from about 10 mM to about 150 mM, from about 30 mM to about 140 mM, from about 50 mM to about 130 mM, from about 70 mM to about 120 mM, from about 50 mM to about 150 mM, from about 50 mM to about 100 mM, or from about 100 mM to 150 mM NaCl. In other embodiments, the DEAE buffer comprises at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, or at least about 150 mM NaCl. In one embodiment, the DEAE buffer comprises at least about 100 mM NaCl.

In some embodiments, the DEAE buffer comprises from about 1 mM to about 100 mM, from about 1 mM to about 10 mM, from about 2 mM to about 9 mM, from about 3 mM to about 7 mM, from about 6 mM to about 6 mM, from about 1 mM to about 5 mM, or from about 5 mM to about 10 mM $CaCl_2$. In other embodiments, the DEAE buffer comprises at least about 1 mM, at least about 2 mM, at least about 3 mM, at least about 4 mM, at least about 5 mM, at least about 6 mM, at least about 7 mM, at least about 8 mM, at least about 9 mM, or at least about 10 mM $CaCl_2$. In one embodiment, the DEAE buffer comprises at least about 5 mM $CaCl_2$.

The DEAE buffer can comprise one or more of the buffers described herein, including but not limited to HEPES, tris-(hydroxymethyl)aminoethane, or phosphate. In some embodiments, the DEAE buffer comprises from about 1 mM to about 100 mM, from about 1 mM to about 15 mM, from about 3 mM to about 14 mM, from about 5 mM to about 13 mM, from about 7 mM to about 12 mM, from about 5 mM to about 15 mM, from about 5 mM to about 10 mM, or from about 10 mM to 15 mM HEPES. In other embodiments, the DEAE buffer comprises at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, or at least about 20 mM HEPES. In one embodiment, the DEAE buffer comprises at least about 10 mM HEPES.

The DEAE buffer can comprise a detergent. The detergent can include but not be limited to any such detergent provided in the present disclosure, including polysorbate 20 (TWEEN-20®), polysorbate 80 (TWEEN-80®), polyethylene glycol p-(1,1,3,3-tetramethylbutyl)-phenyl ether, octylphenoxypolyethoxyethanol (IGEPAL®), octylphenoxypolyeth-oxyethanol (Nonidet P-40®), CHAPS, or CHAPSO. In some embodiments, the DEAE buffer comprises from about 0.005% to about 0.5%, from about 0.01% to about 0.5%, from about 0.05% to 0.5%, from about 0.05% to 0.4%, from about 0.05% to 0.3%, from about 0.05% to 0.2%, from about 0.05% to 0.15%, from about 0.05% to 0.1%, from about 0.1% to 0.5%, from about 0.1% to 0.4%, from about 0.1% to 0.3%, or from about 0.1% to 0.2% polysorbate 80. In other embodiments, the DEAE buffer comprises at least about 0.005%, at least about 0.006%, at least about 0.007%, at least about 0.008%, at least about 0.009%, at least about 0.01%, at least about 0.02%, at least about 0.03%, at least about 0.04%, at least about 0.05%, at least about 0.06%, at least about 0.07%, at least about 0.08%, at least about 0.09%, or at least about 0.1% polysorbate 80. In one embodiment, the DEAE buffer comprises at least about 0.01% polysorbate 80. In some embodiments, the polysorbate 80 is TWEEN-80®.

In some embodiments, the DEAE buffer has a pH of from about 5.0 to about 9.0, from about 5.5 to about 8.5, from about 6.0 to about 8.0, from about 6.5 to about 7.5, or from about 7.0 to 7.5. In some embodiments, the DEAE buffer has a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, or 8.0. In some embodiments, the DEAE buffer has a pH of 7.2.

In one particular embodiment, the DEAE buffer comprises 10 mM HEPES, 100 mM NaCl, 5 mM $CaCl_2$, and 0.01% polysorbate 80, and the DEAE buffer has a pH of 7.2.

As discussed above, the presently disclosed method can further comprise washing the AEX chromatography following addition of either the conditioned media or the chimeric protein eluted from the factor VIII-specific affinity chromatography. The AEX chromatography can be washed with any suitable buffer known in the art or disclosed herein, including but not limited to the DEAE buffer. In certain embodiments, the AEX chromatography is washed with at least 1, at least 2, at least 3, at least 4, at least 5, at least 6, at least 7, at least 8, at least 9, at least 10, at least 15, or at least 20 column volumes of DEAE buffer.

The method can further comprise eluting the chimeric protein from the AEX chromatography. The chimeric protein can be eluted from the AEX chromatography using an AEX chromatography elution buffer. In certain embodiments, the chimeric protein is eluted from the AEX chromatography resin using a 0-100% AEX chromatography elution buffer gradient over at least 1, at least 2, at least 3, at least 4, at least 5, at least 6, at least 7, at least 8, at least 9, at least 10, at least 15, or at least 20 column volumes of AEX chromatography elution buffer. In other embodiments, the chimeric protein is eluted by serially washing the AEX chromatography resin with increasing concentrations of the AEX chromatography elution buffer. In one particular embodiment, the chimeric protein is eluted from the AEX chromatography resin using a 0-100% AEX chromatography elution buffer gradient over about 5 column volumes.

In some embodiments the AEX chromatography elution buffer comprises one or more salts. Examples of salts include, but are not limited to, calcium salts, sodium salts, potassium salts, magnesium salts, or any combination thereof. In some embodiments, the AEX chromatography elution buffer comprises a salt concentration of at least 250 mM to 300 mM, at least 300 mM, at least 300 mM to 350 mM, at least 350 mM to 400 mM, least 250 mM to 350 mM, at least 300 mM to 400 mM, or at least 250 mM to 400 mM. In other embodiments, the AEX chromatography elution buffer comprises a salt concentration of at least 0.8M. In other embodiments, the salt is a sodium salt, e.g., NaCl, and/or a calcium salt, e.g., $CaCl_2$.

In some embodiments, the AEX chromatography elution buffer comprises from about 0.1M to about 5.0M, from about 0.1M to about 4.0M, from about 0.1M to about 3.0M, from about 0.1M to about 2.0M, from about 0.1M to about 1.0M, from about 0.5M to about 5.0M, from about 0.5M to about 4.0M, from about 0.5M to about 3.0M, from about 0.5M to about 2.0M, from about 0.5M to about 1.0M, from about 0.1M to about 1.0M, from about 0.2M to about 1.0M, from about 0.3M to about 1.0M, from about 0.4M to about 1.0M, from about 0.6M to about 1.0M, from about 0.7M to about 1.0M, or from about 0.8M to about 1.0M NaCl. In other embodiments, the AEX chromatography elution buffer comprises at least about 0.1M, at least about 0.2M, at least about 0.3M, at least about 0.4M, at least about 0.5M, at least about 0.6M, at least about 0.7M, at least about 0.8M, at least about 0.9M, at least about 1.0M, at least about 1.1M, at least about 1.2M, at least about 1.3M, at least about 1.4M, or at least about 1.5M NaCl. In one embodiment, the AEX chromatography elution buffer comprises at least about 0.8M NaCl.

In some embodiments, the AEX chromatography elution buffer comprises from about 1 mM to about 100 mM, from about 1 mM to about 10 mM, from about 2 mM to about 9 mM, from about 3 mM to about 7 mM, from about 6 mM to about 6 mM, from about 1 mM to about 5 mM, or from about 5 mM to about 10 mM $CaCl_2$. In other embodiments, the AEX chromatography elution buffer comprises at least about 1 mM, at least about 2 mM, at least about 3 mM, at least about 4 mM, at least about 5 mM, at least about 6 mM, at least about 7 mM, at least about 8 mM, at least about 9 mM, or at least about 10 mM $CaCl_2$. In one embodiment, the AEX chromatography elution buffer comprises at least about 5 mM $CaCl_2$.

The AEX chromatography elution buffer can comprise one or more of the buffers described herein, including but not limited to HEPES, tris-(hydroxymethyl)aminoethane, or phosphate. In some embodiments, the AEX chromatography elution buffer comprises from about 1 mM to about 100 mM, from about 1 mM to about 15 mM, from about 3 mM to about 14 mM, from about 5 mM to about 13 mM, from about 7 mM to about 12 mM, from about 5 mM to about 11 mM, from about 5 mM to about 10 mM, or from about 10 mM to 15 mM HEPES. In other embodiments, the AEX chromatography elution buffer comprises at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, or at least about 20 mM HEPES. In one embodiment, the AEX chromatography elution buffer comprises at least about 10 mM HEPES.

The AEX chromatography elution buffer can comprise a detergent. The detergent can include but not be limited to any such detergent provided in the present disclosure, including polysorbate 20 (TWEEN-20®), polysorbate 80 (TWEEN-80®), polyethylene glycol p-(1,1,3,3-tetramethyl-butyl)-phenyl ether, octylphenoxypolyethoxyethanol (IG-EPAL®), octylphenoxypolyeth-oxyethanol (Nonidet P-40®), CHAPS, or CHAPSO. In some embodiments, the AEX chromatography elution buffer comprises from about 0.005% to about 0.5%, from about 0.01% to about 0.5%, from about 0.05% to 0.5%, from about 0.05% to 0.4%, from about 0.05% to 0.3%, from about 0.05% to 0.2%, from about 0.05% to 0.15%, from about 0.05% to 0.1%, from about 0.1% to 0.5%, from about 0.1% to 0.4%, from about 0.1% to 0.3%, or from about 0.1% to 0.2% polysorbate 80. In other embodiments, the AEX chromatography elution buffer comprises at least about 0.005%, at least about 0.006%, at least about 0.007%, at least about 0.008%, at least about 0.009%, at least about 0.01%, at least about 0.02%, at least about 0.03%, at least about 0.04%, at least about 0.05%, at least about 0.06%, at least about 0.07%, at least about 0.08%, at least about 0.09%, or at least about 0.1% poly-sorbate 80. In one embodiment, the AEX chromatography elution buffer comprises at least about 0.01% polysorbate 80. In some embodiments, the polysorbate 80 is TWEEN-80®.

In some embodiments, the AEX chromatography elution buffer has a pH of from about 5.0 to about 9.0, from about 5.5 to about 8.5, from about 6.0 to about 8.0, from about 6.5 to about 7.5, or from about 7.0 to 7.5. In some embodiments, the AEX chromatography elution buffer has a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.8, 7.9, or 8.0. In some embodiments, the AEX chromatography elution buffer has a pH of 7.2.

In one particular embodiment, the AEX chromatography elution buffer comprises 10 mM HEPES, 0.8M NaCl, 5 mM $CaCl_2$, and 0.01% polysorbate 80, and the AEX chromatography elution buffer has a pH of 7.2.

The purification method described herein can be expanded to include additional purification steps including but not limited to subjecting the eluted chimeric protein from either the factor VIII-specific affinity chromatography matrix or the AEX chromatography matrix to an Fc receptor (FcRn affinity chromatography matrix). As noted above, the chimeric protein can optionally comprise a factor VIII protein or fragment thereof linked to a first Fc region and, optionally, a VWF protein or fragment thereof linked to a second Fc region. Subsequent exposure of the eluted chimeric protein to FcRn affinity chromatography could enhance the purity of the chimeric protein. In certain embodiments, the method of purifying a chimeric protein comprises: (i) binding the chimeric protein to an anion exchange (AEX) chromatography resin; (ii) eluting the chimeric protein with an AEX chromatography elution buffer; and (iii) subjecting the eluted product to an Fc receptor (FcRn) affinity chromatography. In some embodiments, the elution buffer comprises a salt concentration of at least 250 mM. Examples of the salt include, but are not limited to, calcium salts, sodium salts, potassium salts, magnesium salts, or any combination thereof. In another embodiment, the method of purifying a chimeric protein comprises: (i) subjecting the chimeric protein to a factor VIII-specific affinity chromatography; (ii) subjecting the chimeric protein to an AEX chromatography; and (iii) subjecting the chimeric protein to an Fc receptor (FcRn) affinity chromatography. In certain embodiments, the chimeric protein is eluted from one or more of the factor VIII-specific affinity chromatography, AEX chromatography, and Fc receptor (FcRn) affinity chromatography.

FcRn affinity chromatography can comprise the use of one or more of (a) an equilibration buffer, (b) a wash buffer; and (c) an elution buffer. In certain embodiments, one or more of the FcRn affinity chromatography equilibration, wash, and elution buffer comprise a salt concentration of at least 100 mM. In some embodiments, one or more of the FcRn affinity chromatography equilibration and wash buffer comprise a salt concentration of about 100 mM. In other embodiments, the FcRn affinity chromatography elution buffer comprises a salt concentration of about 250 mM.

In some embodiments, the method of purifying a chimeric protein comprises the steps of: (i) subjecting the chimeric protein to a tangential flow filtration (TFF) step; (ii) subjecting the chimeric protein to a VIIISelect affinity chromatography matrix; (iii) binding the chimeric protein to an anion exchange (AEX) chromatography resin; and (iv) eluting the chimeric protein with an AEX chromatography elution buffer. In some embodiments, the AEX chromatography elution buffer comprises one or more salts, e.g., calcium salts, sodium salts, potassium salts, magnesium salts, or any combination thereof. In some embodiments, the AEX chromatography elution buffer comprises a salt concentration of at least 250 mM. In some embodiments, the chimeric protein comprises a factor VIII protein linked to a first Fc region, and a von Willebrand Factor (VWF) protein linked to a second Fc region. In some embodiments, the VWF comprises the D' domain and the D3 domain of VWF. In some embodiments, the VIIISelect affinity chromatography equilibration buffer comprises a salt concentration of about 100 mM. In some embodiments, the VIIISelect affinity chromatography wash buffer comprises the salt concentration of at least 250 mM-300 mM, at least 300 mM, at least 300 mM to 350 mM, at least 350 mM to 400 mM, at least 250 mM to 350 mM, at least 300 mM to 400 mM, or at least 250 mM to 400 mM. In some embodiments, the AEX chromatography elution buffer comprises the salt concentration of at least 250 mM to 300 mM, at least 300 mM, at least 300 mM to 350 mM, at least 350 mM to 400 mM, at least 250 mM to 350 mM, at least 300 mM to 400 mM, or at least 250 mM to 400 mM. In some embodiments, the salt is a sodium salt, such as sodium chloride. In some embodiments, the salt is a calcium salt, such as calcium chloride.

Additional purification steps that may be conducted following the above disclosed methods are not limited to FcRn affinity chromatography. The disclosed methods may be combined with one or more known purification, separation, isolation, concentration, steps. In some embodiments, the method can further comprise subjecting the eluted chimeric protein to one or more additional purification and/or separation steps. In some embodiments, the one or more additional purification and/or separation steps are selected from, but not limited to, cation exchange chromatography, hydrophobic interaction chromatography, size exclusion chromatography, filtration, viral inactivation, precipitation, gel filtration, multimodal chromatography, reversed phase chromatography, precipitation, and chromatofocusing. Additionally, the chimeric protein can be collected at any point during the method or subsequent to the disclosed method and analyzed using any analytical techniques disclosed herein or known to one of ordinary skill in the art.

Chimeric Proteins

The chimeric protein that can be purified by the present purification methods includes a FVIII protein with a half-life longer than wild-type Factor VIII. The chimeric protein for the present invention includes a chimeric Factor VIII protein with extended half-life, which comprises a VWF fragment and an XTEN sequence, which prevents or inhibits a FVIII half-life limiting factor, i.e., endogenous VWF, from associating with the FVIII protein. Endogenous VWF associates with about 95% to about 98% of FVIII in non-covalent complexes. While endogenous VWF is a FVIII half-life limiting factor, endogenous VWF bound to a FVIII protein is also known to protect FVIII in various ways. For example, full length VWF (as a multimer having about 250 kDa) can protect FVIII from protease cleavage and FVIII activation, stabilize the FVIII heavy chain and/or light chain, and prevent clearance of FVIII by scavenger receptors. But, at the same time, endogenous VWF limits the FVIII half-life by preventing pinocytosis and by clearing FVIII-VWF complex from the system through the VWF clearance pathway. It is believed, while not bound by a theory, that endogenous VWF is a half-life limiting factor that prevents the half-life of a FVIII protein fused to a half-life extender from being longer than about two-fold of wild-type FVIII. Therefore, the present invention is directed to preventing or inhibiting interaction between endogenous VWF and a FVIII protein using a VWF fragment, thereby increasing a half-life of the FVIII protein by using an XTEN sequence alone or an XTEN sequence in combination with an Ig constant region or a portion thereof. The XTEN sequence can be linked to the FVIII protein or the VWF fragment. The FVIII protein associated with the VWF fragment is thus cleared from the circulation more slowly by one or more VWF clearance receptors and then can have the full half-life extension of the XTEN sequence or the XTEN sequence in combination of the Ig constant region, as compared to wild type FVIII or a FVIII protein without the VWF fragment.

In one embodiment, a VWF fragment is associated (or linked) with the FVIII protein by a covalent or a non-covalent bond. In some instances, however, the physical blockage or chemical association (e.g., non-covalent bonding) between the VWF fragment and the FVIII protein may not be strong enough to provide a stable complex comprising the FVIII protein and the VWF fragment in the presence of endogenous VWF. For example, a VWF fragment forming a non-covalent bond with a FVIII protein without any other connections may readily be dissociated in vivo from the FVIII protein in the presence of endogenous VWF, replacing the VWF fragment (e.g., recombinant VWF, i.e., rVWF) with endogenous VWF. Therefore, the FVIII protein non-covalently bound to endogenous VWF would undergo the VWF clearance pathway and be readily cleared from the system. In order to prevent the dissociation of the VWF fragment with the FVIII protein, in some embodiments, the association or linkage between the FVIII protein and the VWF fragment is a covalent bond, e.g., a peptide bond, one or more amino acids, or a disulfide bond. In certain embodiments, the association (i.e., linkage) between the adjunct moiety and the FVIII protein is a peptide bond or a linker between the FVIII protein and the VWF fragment ("FVIII/VWF linker"). Non-limiting examples of the linker is described elsewhere herein. In some embodiments, the VWF fragment is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. Non-limiting examples of the VWF fragment are described elsewhere herein.

In certain embodiments, the VWF fragment chemically (e.g., non-covalently) binds to or physically blocks one or more VWF binding sites on a FVIII protein. The VWF binding site on a FVIII protein is located within the A3 domain or the C2 domain of the FVIII protein. In still other embodiments, the VWF binding site on a FVIII protein is located within the A3 domain and C2 domain. For example, the VWF binding site on a FVIII protein can correspond to amino acids 1669 to 1689 and/or 2303 to 2332 of SEQ ID NO: 4 [full-length mature FVIII].

The invention also provides a chimeric protein (comprising a FVIII protein and a VWF fragment) further comprising one or more XTEN sequences, which provide additional half-life extension properties. The one or more XTEN sequences can be inserted within the FVIII protein or the VWF fragment or linked to the N-terminus or the C-terminus of the FVIII protein or the VWF fragment. The invention also includes a FVIII protein linked to an XTEN sequence (a first half-life extending moiety) and an Ig constant region or a portion thereof (a second half-life extending moiety) so that the two half-life extending moieties extend a half-life of the FVIII protein through two different mechanisms.

In some embodiments, a chimeric protein comprises a FVIII protein linked to a first Ig constant region or a portion thereof (e.g., a first FcRn binding partner), a VWF fragment linked to a second Ig constant region or a portion thereof (e.g., a second FcRn binding partner), and one or more XTEN sequences inserted or linked to the FVIII protein or the VWF fragment, wherein the VWF fragment prevents the FVIII half-life limiting factor (e.g., endogenous VWF) from binding to the FVIII protein, wherein the first and second Ig constant regions or portions thereof forms a covalent bond, e.g., a disulfide bond, and the one or more XTEN sequences extends the half-life of the FVIII protein.

In certain embodiments, a chimeric protein of the invention comprises a FVIII protein linked to a VWF fragment by an optional linker (i.e., FVIII/VWF linker) and one or more XTEN sequences inserted or linked to the FVIII protein or the VWF fragment, wherein the VWF fragment prevents the FVIII half-life limiting factor (e.g., endogenous VWF) from binding to the FVIII protein and the one or more XTEN sequences extends the half-life of the FVIII protein. In one aspect, the optional linker (FVIII/VWF linker) comprises a sortase recognition motif. In another aspect, the optional linker (FVIII/VWF linker) comprises a cleavable site. Examples of the cleavage linker (i.e., linker containing one or more cleavage site) are described elsewhere herein.

The chimeric protein of the present invention includes, but is not limited to:

(1) a VWF fragment comprising a D' domain and a D3 domain, an XTEN sequence, and FVIII, wherein the XTEN sequence is linked to the VWF fragment;

(2) a FVIII protein, an XTEN sequence, and an Ig constant region or a portion thereof, wherein the FVIII protein is linked to an XTEN sequence and the Ig constant region or a portion thereof, or (3) a FVIII protein, an XTEN sequence, and a VWF fragment, wherein the XTEN sequence is linked to the FVIII protein at the C-terminus or N-terminus or inserted immediately downstream of one or more amino acids (e.g., one or more XTEN insertion sites) of FVIII, and the VWF fragment and the FVIII protein are associated with each other.

(1) Von Willebrand Factor (VWF) Fragment Linked to XTEN, and FVIII

The present invention is directed to a chimeric protein comprising (i) a VWF fragment comprising a D' domain and a D3 domain of VWF, (ii) an XTEN sequence, and (iii) a FVIII protein, wherein (i), (ii), and (iii) are linked to or associated with each other. The VWF fragment linked to the XTEN sequence, as a part of a chimeric protein in the present invention, associates with the FVIII protein, thus preventing or inhibiting interaction between endogenous VWF and the FVIII protein. In certain embodiment, the VWF fragment, which is capable of preventing or inhibiting binding of the FVIII protein with endogenous VWF, can at the same time has at least one VWF-like FVIII protecting property. Examples of the VWF-like FVIII protecting properties include, but are not limited to, protecting FVIII from protease cleavage and FVIII activation, stabilizing the FVIII heavy chain and/or light chain, and preventing clearance of FVIII by scavenger receptors. As a result, the VWF fragment can prevent clearance of the FVIII protein through the VWF clearance pathway, thus reducing clearance of FVIII from the system. In some embodiments, the VWF fragments of the present invention bind to or are associated with a FVIII protein and/or physically or chemically block the VWF binding site on the FVIII protein. The FVIII protein associated with the VWF fragment is thus cleared from the circulation more slowly, as compared to wild type FVIII or FVIII not associated with the VWF fragment.

In one embodiment, the invention is directed to a chimeric protein comprising (i) a VWF fragment comprising the D' domain and the D3 domain of VWF, (ii) an XTEN sequence, and (iii) a FVIII protein, wherein the XTEN sequence is linked to the VWF fragment (e.g., (a1) V-X or (a2) X-V, wherein V comprises a VWF fragment and X comprises an XTEN sequence), and the VWF fragment is linked to or associated with the FVIII protein. In another embodiment, the VWF fragment and the XTEN sequence can be linked by a linker (e.g., (a3) V-L-X or (a4) X-L-V) or a peptide bond. The linker can be a cleavable linker, e.g., a thrombin cleavable linker, which can be cleaved at the site of coagulation. In other embodiments, the VWF fragment, the XTEN sequence, and the FVIII protein are placed in a single polypeptide chain. In still other embodiments, the chimeric protein comprises two polypeptide chains, a first chain comprising the VWF fragment and the XTEN sequence and the second chain comprises the FVIII protein. In still other embodiments, the XTEN sequence can be linked to the N-terminus or the C-terminus of the VWF fragment or inserted immediately downstream of one or more amino acids in the VWF fragment.

In certain embodiments, a chimeric protein of the invention comprises a formula comprising:

(a) V-X-FVIII, (b) FVIII-X-V, (c) V-X:FVIII, (d) X-V:FVIII, (e) FVIII:V-X, (f) FVIII:X-V, or (a-5) X-V-FVIII, wherein V comprises a VWF fragment, X comprises one or more XTEN sequences, FVIII comprises a FVIII protein;

(-) represents a peptide bond or one or more amino acids; and (:) is a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula V-X-FVIII means formula NH2-V-X-FVIII-COOH. In one embodiment, the formulas described herein can comprise any additional sequences between the two moieties. For example, formula V-X-FVIII can further comprise any sequences at the N-terminus of V between V and X, between X and FVIII, or at the C-terminus of FVIII unless otherwise specified. In another embodiment, the hyphen (-) indicates a peptide bond.

In other embodiments, a chimeric protein of the invention comprises a formula comprising:

(a) V(X1)-X2-FVIII, (b) FVIII-X2-V(X1), (c) V(X1):FVIII, (d) FVIII:V(X1), (a5) X2-V(X1)-FVIII, wherein V(XI) comprises a VWF fragment and a first XTEN sequence (XI), wherein the XTEN sequence is inserted immediately downstream of one or more amino acids in the VWF fragment, X2 comprises one or more optional XTEN sequences, FVIII comprises a FVIII protein;

(-) is a peptide bond or one or more amino acids; and (:) is a chemical association or a physical association.

In some embodiments, a chimeric protein comprises (i) a VWF fragment comprising a D' domain and a D3 domain of VWF, (ii) an XTEN sequence, (iii) a FVIII protein, (iv) a first optional linker, and (v) a second optional linker, wherein the XTEN sequence is linked to the VWF fragment and/or to the FVIII protein by the linker. In certain embodiments, a chimeric protein comprises a formula comprising:

(b1) V-L1-X-L2-FVIII, (b2) FVIII-L2-X-L1-V, (b3) V-Li-X:FVIII, (b4) X-Li-V:FVIII, (b5) FVIII:V-L1-X, (b6) FVIII:X-Li-V, (b7) X-L1-V-L2-FVIII, (b8) FVIII-L2-V-L1-X, wherein V comprises a VWF fragment, X comprises one or more XTEN sequences, FVIII comprises a FVIII protein, L1 comprises a first optional linker, e.g., a first cleavable linker, L2 comprises a second optional linker, e.g., a second cleavable linker or an optional processable linker;

(-) is a peptide bond or one or amino acids; and (:) is a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula (b1) V-L1-X-L2-FVIII means formula NH2-V-L1-X-L2-FVIII-COOH. In one embodiment, the formulas described herein can comprise any additional sequences between the two moieties. In another embodiment, the hyphen (-) indicates a peptide bond.

Another aspect of the present invention is to provide a FVIII chimeric protein not interacting with a FVIII half-life limiting factor, e.g., endogenous VWF, and at the same time maximizing the half-life of the FVIII protein using an XTEN sequence (a first half-life extender) in combination with a second half-life extender or a moiety providing a covalent bond between the FVIII protein and the VWF fragment, e.g., an Ig constant region or a portion thereof. In one embodiment, a chimeric protein of the invention comprises (i) a VWF fragment comprising a D' domain and a D3 domain of VWF, (ii) an XTEN sequence, (iii) a FVIII protein, and (iv) an Ig constant region or a portion thereof (also referred to herein as F), wherein (1) the VWF fragment is linked to the XTEN sequence by an optional linker, e.g., a cleavable linker, (2) the VWF fragment is associated with or linked to the FVIII protein by an additional optional linker, e.g., a cleavable linker, and (3) the Ig constant region or a portion thereof is linked to the VWF fragment, the XTEN sequence, or the FVIII protein. In another embodiment, a chimeric protein of the invention comprises (i) a VWF fragment comprising a D' domain and a D3 domain of VWF, (ii) an XTEN sequence, (iii) a FVIII protein, (iv) an Ig constant region or a portion thereof (F1 or a first Ig constant region or a portion thereof), and (v) an additional Ig constant region or a portion thereof (F2 or a second Ig constant region or a portion thereof), wherein (1) the VWF fragment is linked to the XTEN sequence by an optional linker, e.g., a cleavable linker, (2) the XTEN sequence or the VWF fragment is linked to the Ig constant region or a portion thereof, (3) the FVIII is linked to the additional Ig constant region or a portion thereof, and (4) the Ig constant region or a portion thereof is associated with or linked to the additional Ig constant region or a portion thereof. In one embodiment, the association or linkage between the two Ig constant regions or a portion thereof is a covalent bond, e.g., a disulfide bond. In another embodiment, the association or linkage between the two Ig constant regions or a portion thereof is a processable linker, wherein the processible linker is intracellularly processed by a protease. For example, the chimeric protein comprises a formula comprising:

(g) V-L2-X-L1-F1: FVIII-L3-F2;

(h) V-L2-X-L1-F1:F2-L3-FVIII;

(i) F-L1-X-L2-V: FVIII-L3-F2;

(j) F-L1-X-L2-V:F2-L3-FVIII;

(k) V-L2-X-L1-F1-L4-FVIII-L3-F2;

(l) F2-L3-FVIII-L4-F1-L1-X-L2-V;

(m) FVIII-L2-F2-L4-V-L2-X-L1-F1; and (n) F1-L1-X-L2-V-L4-F2-L2-FVIII, wherein V comprises a VWF fragment, Each of L1 and L3 comprises an optional linker, L2 comprises an optional linker, e.g., a cleavable linker, L4 is an optional linker, e.g., a processable linker, FVIII comprises a FVIII protein, X comprises one or more XTEN sequences, F1 comprises an optional Ig constant region or a portion thereof, F2 comprises an optional additional Ig constant region or a portion thereof;

(-) is a peptide bond or one or more amino acids; and (:) is a chemical association or a physical association.

In some embodiments, the FVIII protein in any constructs or formulas disclosed herein can further comprises at least one, at least two, at least three, at least four, at least five, or at least six XTEN sequences, each of the XTEN sequences inserted immediately downstream of one or more amino acids in the FVIII protein or linked to the N-terminus or the C-terminus of the FVIII protein. Non-limiting examples of the XTEN insertion sites are disclosed elsewhere herein.

In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula (n) F1-L1-X-L2-V-L4-F2-L2-FVIII means formula NH2-F1-L1-X-L2-V-L4-F2-L2-FVIII-COOH. In one embodiment, the formulas described herein can comprise any additional sequences between the two moieties. In another embodiment, the hyphen (-) indicates a peptide bond.

In one embodiment, either or both of the Ig constant region or a portion thereof (sometimes indicated herein by "F" or "F1") and the additional Ig constant region or a portion thereof (sometimes indicated herein by "F2") linked to the VWF fragment or the FVIII protein can extend the half-life of the VWF fragment, the FVIII protein, or both. In another embodiment, a pair of the Ig constant region or a portion thereof (sometimes indicated herein by "F" or "F1") and the additional Ig constant region or a portion thereof (sometimes indicated herein by "F2"), each of which are linked to the VWF fragment and the FVIII protein, provides a bond stronger than the non-covalent bond between the FVIII protein and the VWF fragment, i.e., a covalent bond, e.g., a disulfide bond, thereby preventing endogenous VWF from replacing the VWF fragment in vivo. F1 or F2 can comprise an Fc region or an FcRn binding partner. In other embodiments, either or both of F1 and F2 linked to the VWF fragment and/or the FVIII protein form a covalent bond (e.g., a disulfide bond) between F1 and F2, thereby placing the VWF fragment and the FVIII protein in close proximity to prevent interaction of the FVIII protein with the VWF fragment. In some embodiments, F1 and F2 are identical or different. Non-limiting examples of F1 and F2 can be selected from the group consisting of a CH1 domain, a CH2 domain, a CH3 domain, a CH4 domain, a hinge domain, any functional fragments, derivatives, or analogs thereof, and two or more combinations thereof. In one embodiment, F1, F2, or both comprise at least one CH1 domain, at least one CH2 domain, at least one CH3 domain, at least one CH4 domain, or the functional fragments, derivatives, or analogs thereof. In another embodiment, F1, F2, or both comprise at least one hinge domain or portion thereof and at least one CH2 domain or portion thereof (e.g., in the hinge-CH2 orientation). In other embodiments, F1, F2, or both comprise at least one CH2 domain or portion thereof and at least one CH3 domain or portion thereof (e.g., in the CH2-CH3 orientation.) Examples of the combination include, but are not limited to, a CH2 domain, a CH3 domain, and a hinge domain, which are also known as an Fc region (or Fc domain), e.g., a first Fc region or a first FcRn binding partner for F1 and a second Fc region or a second FcRn binding partner for F2. In other embodiments, F1 is linked to the VWF fragment by a linker, and/or F2 is linked to the FVIII protein by a linker. In some embodiments, F1 and/or F2 comprises, consisting essentially of, or consisting of a hinge region. Additional non-limiting examples of the Fc regions or the FcRn binding partners are described elsewhere herein.

In certain embodiments, a chimeric protein of the invention comprises two polypeptide chains, a first polypeptide chain comprising, consisting essentially of, or consisting of a VWF fragment comprising a D' domain and a D3 domain, an XTEN sequence, a first Ig constant region or a portion thereof (e.g., a first Fc region), and an optional linker between the VWF fragment and the XTEN sequence or the XTEN sequence or the first Ig constant region or a portion thereof and a second polypeptide chain comprising, consisting essentially of, or consisting of a FVIII protein and a second Ig constant region or a portion thereof (e.g., a second Fc region). The linker between the VWF fragment and the first Ig constant region or a portion thereof can be a cleavable linker, e.g., a thrombin cleavable linker, which can be cleaved at the site of coagulation. In some embodiments, the first polypeptide chain and the second polypeptide chain are associated with each other. The association between the first chain and the second chain prevents replacement of the first chain comprising the VWF fragment with endogenous VWF in vivo. In one embodiment, the association between the first chain and the second chain can be a covalent bond. In a particular embodiment, the covalent bond is a disulfide bond. In some embodiments, the FVIII protein in the second chain further comprises one or more XTEN sequences linked to the C-terminus or N-terminus of the FVIII protein or inserted immediately downstream of one or more amino acids (e.g., at least one insertion site disclosed herein) in the FVIII protein. Non-limiting examples of the insertion sites are described elsewhere herein.

In other embodiments, a chimeric protein of the invention comprises three polypeptide chains, wherein a first polypeptide chain comprises, consists essentially of, or consists of a heavy chain of a FVIII protein, a second polypeptide chain comprises, consists essentially of, or consists of a light chain of a FVIII protein fused to a first Ig constant region or a portion thereof (e.g., a first Fc region), and a third polypeptide chain comprises, consists essentially of, or consists of a VWF fragment comprising a D' domain and a D3 domain, an XTEN sequence, a second Ig constant region or a portion thereof (e.g, a second Fc region), and an optional linker between the XTEN sequence and the second Ig constant region or a portion thereof or the VWF fragment and the XTEN sequence. The linker in the third chain can be a cleavable linker, which is cleaved at the site of coagulation, e.g., a thrombin cleavage site. In some embodiments, the heavy chain FVIII or the light chain FVIII is linked to one or more XTEN sequences, which can be linked to the N-terminus, the C-terminus, or inserted within one or more insertion sites within the FVIII sequence. Non-limiting examples of the insertion sites are disclosed elsewhere herein In yet other embodiments, a chimeric protein of the invention comprises two polypeptide chains, a first polypeptide chain comprising, consisting essentially of, or consisting of a heavy chain of a FVIII protein and a second polypeptide chain comprising, consisting essentially of, or consisting of a light chain of a FVIII protein, a first Ig constant region or a portion thereof (e.g., a first Fc region), a first linker (e.g., a processable linker, which contains one or more protease cleavage sites comprising one or more intracellular processing sites), a VWF fragment, a second linker (e.g., a thrombin cleavable linker), an XTEN sequence, and a second Ig constant region or a portion thereof (e.g., a second Fc region), wherein the light chain of the FVIII protein is linked to the first Ig constant region or a portion thereof (e.g., the first Fc region), which is further linked to the VWF fragment by the first linker, and wherein the VWF fragment is linked to the XTEN sequence, which is further linked to the second Ig constant region or a portion thereof by the second linker. In certain embodiments, the first linker is a processable linker, and the second linker is a cleavable linker. Upon expression, the chimeric protein can be processed by an intracellular processing enzyme, which cleaves the processable linker, and thus the chimeric protein can comprise, consists essentially of, or consists of three polypeptide chains. In addition, the VWF fragment can be cleaved off at the site of coagulation due to the cleavable linker.

In certain embodiments, a chimeric protein of the invention comprises one polypeptide chain, which comprises a single chain FVIII protein, a first Ig constant region or a portion thereof (e.g., a first Fc region), a first linker (e.g., a processable linker), a VWF fragment, an XTEN sequence, a second linker (e.g., a thrombin cleavable linker), and a second Ig constant region or a portion thereof (e.g., a second Fc region), wherein the single chain FVIII protein is linked to the first Ig constant region or a portion thereof, which is also linked to the VWF fragment by the first linker, and the VWF fragment is linked to the XTEN sequence, which is further linked to the second Ig constant region or a portion thereof. In one embodiment, the VWF fragment and the XTEN sequence are linked by the second linker. In another embodiment, the XTEN sequence and the second Ig constant region or a portion thereof are linked by the second linker. In other embodiments, the second chain further comprises a third linker. The single polypeptide chain can thus comprise the VWF fragment linked to the XTEN sequence by the second linker and the XTEN linked to the second Ig constant region or a portion thereof by the third linker. The second linker and the third linker can be identical or different. In one embodiment, the first linker is a processable linker. In another embodiment, the second linker or the third linker is a cleavable linker comprising one or two cleavable sites. In a specific embodiment, the second linker is a thrombin cleavable linker. The linkers useful in the invention are described elsewhere herein.
(2) FVIII, XTEN, and Fc A chimeric protein of the invention also comprises (i) a FVIII protein, (ii) an XTEN sequence (a first half-life extender), and (iii) an Ig constant region or a portion thereof (a second half-life extender), in which the XTEN sequence is linked to the FVIII protein by an optional linker and the Ig constant region or a portion thereof by an additional optional linker. The XTEN sequence and the Ig constant region or a portion thereof can be used together to extend half-life of the FVIII protein. In one embodiment, the chimeric protein is a monomer. In another embodiment, the chimeric protein is a dimer (a homodimer or a heterodimer).

The present invention is also directed to a chimeric protein comprising (i) a FVIII protein, (ii) an XTEN sequence, (iii) an Ig constant region or a portion thereof (i.e., a first Ig constant region or a portion thereof, "F," or "F1"), and (iv) an additional Ig constant region or a portion thereof (i.e., a second Ig constant region or a portion thereof or "F2"). In one embodiment, the XTEN sequence is linked to the FVIII protein at the C-terminus or the N-terminus or inserted immediately downstream of one or more amino acids in the FVIII protein (e.g., one or more XTEN insertion sites), the FVIII protein is linked to the first Ig constant region or a portion thereof, and the first Ig constant region or a portion thereof and the second Ig constant region or a portion thereof are associated with or linked to each other by an optional linker. In certain aspects, the chimeric protein is a monomer-dimer hybrid, which comprises a first polypeptide chain and a second polypeptide chain, wherein the first polypeptide chain comprises a FVIII protein, an XTEN sequence, and a first Ig constant region or a portion thereof, and the second polypeptide chain comprises, consists essentially of, or consists of a second Ig constant region or a portion thereof without the FVIII protein and wherein the first chain and the second chain are associated with each other. The association between the Ig constant region or a portion thereof (e.g., the first Fc region) and the additional Ig constant region or a portion thereof (e.g., a second Fc region) is a chemical association or a physical association. In certain embodiments, the chemical association is a covalent bond. In other embodiments, the chemical association is a non-covalent interaction, e.g., an ionic interaction, a hydrophobic interaction, a hydrophilic interaction, a Van der Waals interaction, or a hydrogen bond. In other embodiments, the association is a non-peptide covalent bond. In still other embodiments, the association is a peptide bond.

In other aspects, the chimeric protein is a single polypeptide chain comprising a FVIII protein, an XTEN sequence, a first Ig constant region or a portion thereof, a linker, e.g., a processable linker, and a second Ig constant region or a portion thereof, wherein the single polypeptide chain is processed after expression by an intracellular enzyme and becomes two polypeptide chains.

In one embodiment, the Ig constant region or a portion thereof (sometimes indicated herein by "F" or "F1") linked to the FVIII protein can extend the half-life of the FVIII protein together with the XTEN sequence. In another embodiment, the Ig constant region or a portion thereof ("F" or "F1") is an Fc region or an FcRn binding partner described elsewhere herein.

In other embodiments, the additional Ig constant region or a portion thereof (sometimes indicated herein by "F2" or a second Ig constant region or a portion thereof) associated with or linked to the first Ig constant region or a portion thereof can also extend the half-life of the FVIII protein. In other embodiments, the second Ig constant region or a portion thereof ("F2") together with the first Ig constant region or a portion thereof and the XTEN sequence can extend the half-life of the FVIII protein. The additional Ig constant region or a portion thereof can be an Fc region or an FcRn binding partner described elsewhere herein.

In certain embodiments, the second Ig constant region or a portion thereof associated with the first Ig constant region or a portion thereof is further linked to a VWF fragment described elsewhere herein and an optional XTEN sequence.

In some embodiments, either or both of the Ig constant region or a portion thereof ("F" or "F1" or a first Ig constant region or a portion thereof) and an additional Ig constant region or a portion thereof (i.e., a second Ig constant region or a portion thereof or "F2") (indicated in this paragraph as "the Ig constant regions or portion thereof") can include, but not limited to, a CH1 domain, a CH2 domain, a CH3 domain, a CH4 domain, a hinge domain, any functional fragments, derivatives, or analogs thereof or two or more combinations thereof. In one embodiment, the Ig constant region or a portion thereof comprises at least one CH1 domain, at least one CH2 domain, at least one CH3 domain, at least one CH4 domain, or the functional fragments, derivatives, or analogues thereof. In another embodiment, the Ig constant region or a portion thereof comprises at least one hinge domain or portion thereof and at least one CH2 domain or portion thereof (e.g., in the hinge-CH2 orientation). In other embodiments, the Ig constant domain or portion thereof comprises at least one CH2 domain or portion thereof and at least one CH3 domain or portion thereof (e.g., in the CF2-CH3 orientation.) Examples of the combination include, but are not limited to, a CH2 domain, a CH3 domain, and a hinge domain, which are also known as an Fc region (or Fc domain), e.g., first Fc region. Additional examples of the Ig constant regions or portion thereof are described elsewhere herein.

The chimeric protein of the invention can have an extended half-life of the FVIII protein compared to wild-type FVIII. In one embodiment, the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of the FVIII protein is at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, or at least about 108 hours.

(3) FVIII, XTEN, and VWF

In one aspect, a chimeric protein of the present invention comprises (i) a FVIII protein, (ii) an XTEN sequence, and (iii) a VWF fragment comprising a D' domain and a D3 domain of VWF, wherein the FVIII protein is linked to the XTEN sequence and wherein the FVIII protein is associated with or linked to the VWF fragment. In one embodiment, the VWF fragment of the chimeric protein described herein is not capable of binding to a VWF clearance receptor. In another embodiment, the VWF fragment is capable of protecting the FVIII protein from one or more protease cleavages, protecting the FVIII protein from activation, stabilizing the heavy chain and/or the light chain of the FVIII protein, or preventing clearance of the FVIII protein by one or more scavenger receptors. In other embodiments, the VWF fragment prevents or inhibits binding of endogenous VWF to the VWF binding site in the FVIII protein. The VWF binding site can be located in the A3 domain or the C2 domain of the FVIII protein or both the A3 domain and the C2 domain. In a specific embodiment, the VWF binding site comprises the amino acid sequence corresponding to amino acids 1669 to 1689 and/or amino acids 2303 to 2332 of SEQ ID NO: 2.

In another aspect, a chimeric protein comprises (i) a FVIII protein, (ii) an XTEN sequence, (iii) a VWF fragment, which comprises a D' domain and a D3 domain of VWF, and (iv) an Ig constant region or a portion thereof, wherein the XTEN sequence is linked to the FVIII protein at the C-terminus or the N-terminus or inserted immediately downstream of one or more amino acids (e.g., one or more XTEN insertion sites disclosed herein) in the FVIII protein, the VWF fragment is linked to or associated with the FVIII protein or the XTEN sequence, and the Ig constant region or a portion thereof is linked to the FVIII protein, the XTEN sequence, the VWF fragment, or any combinations thereof.

The Ig constant region or a portion thereof useful for chimeric proteins of the invention is described elsewhere herein. In one embodiment, the Ig constant region or a portion thereof is capable of extending a half-life of a FVIII protein. In another embodiment, the Ig constant region or a portion thereof comprises a first Fc region or a first FcRn binding partner. In yet other embodiments, the Ig constant region or a portion thereof is linked to the FVIII protein by an optional linker. In still other embodiments, the linker comprises a cleavable linker. The chimeric protein can be a single polypeptide chain, i.e., a monomer (i.e., a single chain), containing (i), (ii), (iii), and (iv) or two chains containing a first chain comprising (i) and (ii) and a second chain comprising (iii) and (iv). In other aspects, the chimeric protein is a dimer (e.g., a homodimer or a heterodimer). In one embodiment, the chimeric protein comprises two chains, each comprising (i), (ii), (iii), and (iv).

In certain embodiments, a chimeric protein comprises (i) a FVIII protein, (ii) an XTEN sequence, (iii) a VWF fragment, which comprises a D' domain and a D3 domain of VWF, (iv) an Ig constant region or a portion thereof (sometimes also indicated as "F," "a first Ig constant region or a portion thereof", or "F2"), and (v) an additional Ig constant region or a portion thereof (sometimes also indicated as "F2" or "a second Ig constant region or a portion thereof"), wherein (1) the FVIII protein is linked to the XTEN sequence at the C-terminus or N-terminus of the FVIII protein or inserted immediately downstream of one or more amino acids (e.g., one or more XTEN insertion sites disclosed herein) in the FVIII protein, (2) either the XTEN sequence or the FVIII protein is linked to the Ig constant region or a portion thereof, (3) the VWF fragment is linked to the second Ig constant region or a portion thereof, and (4) the Ig constant region or a portion thereof is associated with the second Ig constant region or a portion thereof. In one embodiment, the Ig constant region or a portion thereof linked to the FVIII protein or the XTEN sequence is further linked to the VWF fragment by a linker, e.g., a processable linker. In another embodiment, the additional Ig constant region or a portion thereof useful for chimeric proteins of the invention can further be linked to the FVIII protein or the Ig constant region or a portion thereof by an optional linker, e.g., a processable linker. In some embodiments, a pair of the Ig constant region or a portion thereof and the additional Ig constant region or a portion thereof, each of which are linked to the VWF fragment and the FVIII protein, provides a bond stronger than the non-covalent bond between the FVIII protein and the VWF fragment, i.e., a covalent bond, e.g., a disulfide bond, thereby preventing endogenous VWF from replacing the VWF fragment in vivo. In other embodiments, either or both of the Ig constant region or a portion thereof and the additional Ig constant region or a portion thereof are capable of extending a half-life of the FVIII protein or the VWF fragment. In other embodiments, the additional Ig constant region or a portion thereof comprises a second Fc region or an FcRn binding partner. The Ig constant region or a portion thereof and the additional Ig constant region or a portion thereof in the chimeric proteins are identical or different.

In certain embodiments, the Ig constant region or a portion thereof and the additional Ig constant region or a portion thereof are associated by a chemical association or a physical association. In one embodiment, the chemical association, i.e., (:), is at least one non-peptide bond. In certain embodiments, the chemical association, i.e., (:), is a covalent bond. In other embodiments, the chemical association, i.e., (:), is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety. In some embodiments, the association between the Ig constant region or a portion thereof and the additional Ig constant region or a portion thereof can be a covalent bond, e.g., a disulfide bond, which prevents replacement the VWF fragment or the polypeptide containing the VWF fragment with endogenous VWF. Therefore, preventing interaction between the FVIII protein and endogenous VWF eliminates the half-life limiting factor for the FVIII protein, and thus a half-life of the FVIII protein is extended compared to a FVIII protein without the VWF protein or wild-type FVIII.

In other aspects, a chimeric protein comprises a formula comprising:

(1) FVIII(X1)-L1-F1:V-L2-X2-L3-F2;
(2) FVIII(X1)-L1-F1:F2-L3-X2-L2-V;
(3) F1-L1-FVIII(X1): V-L2-X2-L3-F2;
(4) F1-L1-FVIII(X1); F2-L3-X2-L2-V;
(5) FVIII(X1)-L1-F1-L4-V-L2-X2-L3-F2;
(6) FVIII(X1)-L1-F1-L4-F2-L3-X2-L2-V;
(7) F1-L1-FVIII(X1)-L4-V-L2-X2-L3-F2, or
(8) F1-L1-FVIII(X1)-L4-F2-L3-X2-L2-V, wherein FVIII(X1) comprises a FVIII protein and one or more XTEN sequences, wherein the one or more XTEN sequence are linked to the N-terminus or C-terminus of the FVIII protein or inserted immediately downstream of one or more amino acids (e.g., one or more XTEN insertion sites disclosed herein) in the FVIII protein;

each of L1, L2, or L3 comprises an optional linker, e.g., a cleavable linker;

L4 is a linker, e.g., a processable linker;

X2 comprises one or more optional XTEN sequences;

F1 comprises an Ig constant region or a portion thereof;

F2 comprises an optional additional Ig constant region or a portion thereof, and V comprises a VWF fragment;

(-) is a peptide bond or one or more amino acids; and (:) comprises a chemical association or a physical association. In one embodiment, (:) represents a chemical association, e.g., at least one non-peptide bond. In another embodiment, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, or a hydrogen bond. In other embodiments, (:) is a non-peptide covalent bond. In still other embodiments, (:) is a peptide bond. In yet other embodiments, (:) represents a physical association between two sequences, wherein a portion of a first sequence is in close proximity to a second sequence such that the first sequence shields or blocks a portion of the second sequence from interacting with another moiety, and further that this physical association is maintained without allowing the second sequence to interact with other moieties. The orientation of the polypeptide formulas herein is listed from N-terminus (left) to C-terminus (right). For example, formula V-X-FVIII means formula NH2-V-X-FVIII-COOH. In one embodiment, the formulas described herein can comprise any additional sequences between the two moieties. For example, formula V-X-FVIII can further comprise any sequences at the N-terminus of V between V and X, between X and FVIII, or at the C-terminus of FVIII unless otherwise specified. In another embodiment, the hyphen (-) indicates a peptide bond.

In one aspect, the chimeric protein comprises two polypeptide chains, (A) a first chain comprising (i) a single chain FVIII protein (ii) an XTEN sequence, and (iii) a first Ig constant region or a portion thereof, e.g., a first Fc region or FcRn binding partner, wherein the XTEN sequence is linked to the FVIII protein at the N-terminus or C-terminus or inserted immediately downstream of one or more amino acids of the FVIII protein (e.g., one or more XTEN insertion sites disclosed herein) and the first Ig constant region or a portion thereof is linked to the XTEN sequence when the XTEN sequence is linked to the FVIII protein at the N-terminus or the C-terminus or the FVIII protein when the XTEN sequence is inserted within the FVIII protein, and (B) a second chain comprising (iv) a VWF fragment comprising a D' domain and a D3 domain, (v) a linker, and (vi) a second Ig constant region or a portion thereof, e.g., a second Fc region or a second FcRn binding partner, wherein the VWF fragment is linked to the linker, e.g., a cleavable linker, which is further linked to the second Ig constant region or a portion thereof, and wherein the first polypeptide chain and the second polypeptide chain are associated with each other, e.g., a covalent bond, e.g., a disulfide bond. In one embodiment, the linker is a cleavable linker described elsewhere herein, e.g., a thrombin cleavable linker. In some embodiments, the second chain comprises one or more XTEN sequences between (iv) and (v) or (v) and (vi).

In other aspects, the chimeric protein comprises one polypeptide chain comprising (i) a single chain FVIII protein (ii) an XTEN sequence, (iii) a first Ig constant region or a portion thereof, e.g., a first Fc region or a first FcRn binding partner, (iv) a first linker, (v) a VWF fragment comprising a D' domain and a D3 domain, (vi) a second linker, and (vii) a second Ig constant region or a portion thereof, e.g., a second Fc region or a second FcRn binding partner, wherein (i) to (vii) are linked in the order or in any orders. In one embodiment, the first linker is a processable linker, which can be intracellularly processed or cleaved after expression and makes the single polypeptide chain into two polypeptide chains. In another embodiment, the second linker is a cleavable linker described herein, e.g., a thrombin cleavable linker. The XTEN sequence used herein can be linked to the FVIII protein by an optional linker at the N-terminus or the C terminus of the FVIII protein or inserted immediately downstream of one or more amino acids (e.g., one or more XTEN insertion sites) in the FVIII protein.

In certain aspects, a chimeric protein comprises three polypeptide chains, (A) a first polypeptide chain comprising (i) a heavy chain of a FVIII protein and (ii) an XTEN sequence, which are linked to each other and (B) a second polypeptide chain comprising (iii) a light chain of the FVIII protein and (iv) a first Ig constant region or a portion thereof, e.g., a first Fc region or a first FcRn binding partner, which are linked to each other, and (C) a third polypeptide chain comprising (v) a VWF fragment comprising a D' domain and a D3 domain, (vi) a linker, and (vii) a second Ig constant region or a portion thereof, e.g., a second Fc region or a second FcRn binding partner, wherein the second chain is associated with the first chain and the third chain. In one embodiment, the association between the first chain and the second chain is a chemical association or a physical association. For example, the association between the first chain and the second chain can be a metal bond. In another embodiment, the association between the second chain and the third chain is also a chemical association or a physical association, e.g., a covalent bond or a non-covalent bond. In certain embodiments, the association between the second chain and the third chain is through the two Ig constant regions or a portion thereof and is a disulfide bond. The bonding between the second chain and the third chain prevents or inhibits binding of the FVIII protein with endogenous VWF, thus preventing the FVIII protein being cleared by the VWF clearance pathway. In some embodiments, the linker is a processable linker, which is intracellularly cleaved after expression in a host cell. The XTEN sequence used herein is linked to the FVIII protein by an optional linker at the N-terminus or C terminus of the FVIII protein or inserted immediately downstream of one or more amino acids (e.g., one or more XTEN insertion sites) in the FVIII protein.

In certain embodiments, the VWF fragment is directly linked to the FVIII protein, which comprises one or more XTENs, by a peptide bond or a linker. As one way of linking the VWF fragment and the FVIII protein, in which one or more XTENs are inserted or linked, through a direct link (e.g. a peptide bond) or a linker, an enzymatic ligation (e.g., sortase) can be employed. For example, sortase refers to a group of prokaryotic enzymes that modify surface proteins by recognizing and cleaving a carboxyl-terminal sorting signal. For most substrates of sortase enzymes, the recognition signal consists of the motif LPXTG (Leu-Pro-any-Thr-Gly (SEQ ID NO: 28), then a highly hydrophobic transmembrane sequence, then a cluster of basic residues such as arginine. Cleavage occurs between the Thr and Gly, with transient attachment through the Thr residue to the active site Cys residue of a ligation partner, followed by transpeptidation that attaches the protein covalently to the cell wall. In some embodiments, the ligation partner contains Gly(n). In other embodiments, the chimeric protein further comprises a sortase recognition motif. In some embodiments, the VWF fragment is attached to FVIII comprising one or more XTENs inserted within or linked to using sortase mediated in vitro protein ligation.

In one embodiment, a VWF fragment linked to a sortase recognition motif by an optional linker can be fused to a FVIII protein linked to Gly(n) by a sortase, wherein n can be any integer and wherein one or more XTENs are inserted within or linked to the FVIII protein. A ligation construct comprises the VWF fragment (N-terminal portion of the construct) and the FVIII protein, in which one or more XTENs are inserted or linked (C-terminal portion of the construct), wherein the sortase recognition motif is inserted in between. Another ligation construct comprises the VWF fragment (N-terminal portion of the construct, the linker, the sortase recognition motif, and the FVIII protein, in which one or more XTENs are inserted or linked (C-terminal portion of the construct). In another embodiment, a FVIII protein linked to a sortase recognition motif by an optional linker can be fused to a VWF fragment linked to Gly(n) by a sortase, wherein n is any integer. A resulting ligation construct comprises the FVIII protein (N-terminal portion of the construct), in which one or more XTENs are inserted or linked, and the VWF fragment (C-terminal portion of the construct), wherein the sortase recognition motif is inserted in between. Another resulting ligation construct comprises the FVIII protein (N-terminal portion of the construct), in which one or more XTENs are inserted or linked, the linker, the sortase recognition motif, and the VWF fragment (C-terminal portion of the construct). In other embodiments, a VWF fragment linked to a sortase recognition motif by a first optional linker can be fused to a heterologous moiety, e.g., an immunoglobulin constant region or a portion thereof, e.g., an Fc region, linked to a thrombin cleavage site by a second optional linker. A resulting construct can comprise the VWF fragment (N-terminal portion), the first linker, the sortase recognition motif, the protease cleavage site, the second optional linker, and the heterologous moiety.

In some embodiments, the VWF fragment is associated with the FVIII protein. The association between the VWF fragment and the FVIII protein can be a chemical association or a physical association. The chemical association can be a non-covalent interaction, e.g., an ionic interaction, a hydrophobic interaction, a hydrophilic interaction, a Van der Waals interaction, or a hydrogen bond. In yet other embodiments, the association between the FVIII protein and the VWF fragment is a physical association between two sequences, e.g., due to an additional association between the sequence having the FVIII protein and the sequence having the VWF fragment, wherein a portion of a first sequence is in close proximity to a second sequence such that the first sequence shields or blocks a portion of the second sequence from interacting with another moiety.

As a result of preventing or inhibiting endogenous VWF interaction with the FVIII protein by the VWF fragment, the chimeric protein described herein have an extended half-life compared to wild-type FVIII or the corresponding chimeric protein without the VWF fragment. In one embodiment, the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than a FVIII protein without the VWF fragment. In another embodiment, the half-life of the FVIII protein is at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, or at least about 108 hours. In a particular embodiment, the half-life of the FVIII protein is extended at least 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, or at least about 27 hours in HemA mice.

In some embodiments, the chimeric protein is a chimeric heterodimer of FVIII-169 and VWF-57, hereinafter referred to as FVIII-169/VWF-57. The FVIII-169 construct comprises a B domain deleted FVIII protein with R1648A substitution fused to an Fc region, wherein an XTEN sequence (e.g., AE288) is inserted at amino acid 745 corresponding to mature full length FVIII (A1-a1-A2-a2-288XTEN-a3-A3-C1-C2-Fc). VWF-57 is a VWF-Fc fusion construct that comprises D'D3 domain of the VWF protein (with two amino acid substitutions in D'D3 domain, i.e., C336A and C379A) linked to the Fc region via a VWF linker, which comprises LVPR thrombin site ("LVPR") and GS linker ("GS"), wherein an XTEN sequence (i.e., 144XTEN) is inserted between D'D3 domain and the VWF linker (D'D3-144XTEN-GS+LVPR-Fc). The sequences of FVIII-169 and VWF057 are disclosed elsewhere herein.

A) Von Willebrand Factor (VWF) Fragments

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D'/D3 domain (which binds to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

The term "a VWF fragment" as used herein includes, but is not limited to, functional VWF fragments comprising a D' domain and a D3 domain, which are capable of inhibiting binding of endogenous VWF to FVIII. In one embodiment, the VWF fragment binds to the FVIII protein. In another embodiment, the VWF fragment blocks the VWF binding site on the FVIII protein, thereby inhibiting interaction of the FVIII protein with endogenous. The VWF fragments include derivatives, variants, mutants, or analogues that retain these activities of VWF.

The 2813 monomer amino acid sequence for human VWF is reported as Accession Number_NP_000543.2_in Genbank. The nucleotide sequence encoding the human VWF is reported as Accession Number_NM_000552.3_in Genbank. The nucleotide sequence of human VWF is designated as SEQ ID NO: 1. SEQ ID NO: 2 is the amino acid sequence encoded by SEQ ID NO: 1. Each domain of VWF is listed in Table 3.

TABLE 3

VWF Sequences

| VWF domains | | Amino acid Sequence | | | |
|---|---|---|---|---|---|
| VWF Signal Peptide (Amino acids 1 to 22 of SEQ ID NO: 2) | 1 | MI PARFAGVL LALALILPGT LC 22 | | | |
| VWF DID2 region (Amino acids 23 to 763 of SEQ ID NO: 2) | 23 | | | AEGTRGRS | STARCSLEGS |
| | | DFVNTFDGSM | | | |
| | 51 | YSFAGYCSYL FFDIHLFVNG | LAGGCQKRSF | SIIGDFQNGK | RVSLSVYLGE |
| | 101 | TVTQGDQRVS DGSGNFQVLL | MPYASKGLYL | ETEAGYYKLS | GEAYGFVARI |
| | 151 | SDRYENKTCG WALSSGEQWC | LCGNENIFAE | DDEMTQEGTL | TSDPYDFANS |
| | 201 | ERASPPSSSC VDPEPFVALC | NISSGEMQKG | LWEQCQLLKS | TSVFARCHPL |
| | 251 | EKTLCECAGG CSPVCPAGME | LECACPALLE | YARTCAQEGM | VLYGWTDHSA |
| | 301 | YRQCVSPCAR LCVESTECPC | TCQSLHINEM | CQERCVDGCS | CPEGQLLDEG |
| | 351 | VHSGKRYPPG TGQSHFKSFD | TSLSRDCNTC | ICRNSQWICS | NEECPGECLV |
| | 401 | NRYFTFSGIC TRSVTVRLPG | QYLLARDCQD | HSFSIVIETV | QCADDRDAVC |
| | 451 | LHNSLVKLKH RLSYGEDLQM | GAGVAMDGQD | IQLPLLKGDL | RIQHTVTASV |
| | 501 | DWDGRGRLLV LAEPRVEDFG NAWKLHGDCQ TFEACHRAVS | KLSPVYAGKT DLQKQHSDPC | CGLCGNYNGN ALNPRMTRFS | QGDDELTPSG EEACAVLTSP |
| | 601 | PLPYLRNCRY AWREPGRCEL | DVCSCSDGRE | CLCGALASYA | AACAGRGVRV |
| | 651 | NCPKGQVYLQ PGLYMDERGD | | | |
| | 701 | CVPKAQCPCY SGVPGSLLPD | YDGEIFQPED | IFSDHHTMCY | CEDGFMHCTM |
| | 751 | AVLSSPLSHR SKR | | | 763 |
| VWF D' Domain | 764 | | SLSCRPP | MVKLVCPADN | LRAEGLECTK |
| | | TCQNYDLECM | | | |
| | 801 | SMGCVSGCLC TVKIGCNTCV | PPGMVRHENR | CVALERCPCF | HQGKEYAPGE |
| | 851 | CRDRKWNCTD | HVCDAT | | 866 |
| VWF D3 Domain | 867 | | CSTI | GMAHYLTFDG | LKYLFPGECQ |
| | | YVLVQDYCGS | | | |
| | 901 | | | | |
| | | VNVKRPMKDE | | | |
| | 951 | THFEVVESGR KVCGLCGNED | YIILLLGKAL | SVVWDRHLSI | SVVLKQTYQE |

TABLE 3-continued

| VWF Sequences | |
| --- | --- |
| VWF domains | Amino acid Sequence |

|  |  |
| --- | --- |
| | 1001 GIQNNDLTSS NLQVEEDPVD EGNSWKVSSQ CADTRKVPLD |
| |       SSPATCHNNI |
| | 1051 MKQTMVDSSC RILTSDVFQD CNKLVDPEPY LDVCLYDTCS |
| |       CESIGDCACF |
| | 1101 CDTIAAYAHV CAQHGKVVTW RTATLCPQSC EERNLRENGY |
| |       ECEWRYNSCA |
| | 1151 PACQVTCQHP EPLACPVQCV EGCHAHCPPG KILDELLQTC |
| |       VDPEDCPVCE |
| | 1201 VAGRRFASGK KVTLNPSDPE HCQICHCDVV NLTCEACQEP |
| | 1240 |
| | |
| VWF A1 Domain | 1241 GGLVVPPTDA |
| | 1251 PVSPTTLYVE DISEPPLHDF YCSRLLDLVF LLDGSSRLSE |
| |       AEFEVLKAFV |
| | 1301 VDMMERLRIS QKWVRVAVVE YHDGSHAYIG LKDRKRPSEL |
| |       RRIASQVKYA |
| | 1351 GSQVASTSEV LKYTLFQIFS KIDRPEASRI ALLLMASQEP |
| |       QRMSRNFVRY |
| | 1401 VQGLKKKKVI VIPVGIGPHA NLKQIRLIEK QAPENKAFVL |
| |       SSVDELEQQR |
| | 1451 DEIVSYLCDL APEAPPPTLP PDMAQVTVG       1479 |
| | |
| | 1480                         P GLLGVSTLGP KRNSMVLDVA |
| | 1501 FVLEGSDKIG EADENRSKEF MEEVIQRMDV GQDSIHVTVL |
| |       QYSYMVTVEY |
| | 1551 PFSEAQSKGD ILQRVREIRY QGGNRTNTGL ALRYLSDHSF |
| |       LVSQGDREQA 1600 |
| | 1601 PNLVYMVTGN PASDEIKRLP GDIQVVPIGV GPNANVQELE |
| |       RIGWPNAPIL |
| | 1651 IQDFETLPRE APDLVLQRCC SGEGLQIPTL SPAPDCSQPL |
| |       DVILLLDGSS |
| | 1701 SFPASYFDEM KSFAKAFISK ANIGPRLTQV SVLQYGSITT |
| |       IDVPWNVVPE |
| | 1751 KAHLLSLVDV MQREGGPSQI GDALGFAVRY LTSEMHGARP |
| |       GASKAVVILV |
| | 1801 TDVSVDSVDA AADAARSNRV TVFPIGIGDR YDAAQLRILA |
| |       GPAGDSNVVK |
| | 1851 LQRIEDLPTM VTLGNSFLHK LCSGFVRICM DEDGNEKRPG |
| |       DVWT LP DQCH |
| | 1901 TVTCQPDGQT LLKSHRVNCD RGLRPSCPNS QSPVKVEETC |
| |       GCRWTCPCVC |
| | 1951 TGSSTRHIVT FDGQNFKLTG SCSYVLFQNK EQDLEVILHN |
| |       GACS PGARQG |
| | 2001 CMKSIEVKHS ALSVEXHSDM EVTVNGRLVS VPYVGGNMEV |
| |       NVYGAIMHEV |
| | 2051 RFNHLGHIFT FTPQNNEFQL QLSPKTFASK TYGLCGICDE |
| |       NGANDEMLRD |
| | 2101 GTVTTDWKTL VQEWTVQRPG QTCQPILEEQ CLVPDSSHCQ |
| |       VLLLPLFAEC |
| | 2151 HKVLAPATFY AICQQDSCHQ EQVCEVIASY AHLCRTNGVC |
| |       VDWRTPDFCA |
| | 2201 MSCPPSLVYN HCEHGCPRHC DGNVSSCGDH PSEGCFCPPD |
| |       KVMLEGSCVP |
| | 2251 EEACTQCIGE DGVQHQFLEA WVPDHQPCQI CTCLSGRKVN |
| |       CTTQPCPTAK |
| | 2301 APTCGLCEVA RLRQNADQCC PEYECVCDPV SCDLPPVPHC |
| |       ERGLQPTLTN |
| | 2351 PGECRPNFTC ACRKEECKRV SPPSCPPHRL PTLRKTQCCD |
| |       EYECACNCVN |
| | 2401 STVSCPLGYL ASTATNDCGC TTTTCLPDKV CVHRSTIYPV |
| |       GQFWEEGCDV |
| | 2451 CTCTDMEDAV MGLRVAQCSQ KPCEDSCRSG FTYVLHEGEC |
| |       CGRCLPSACE |
| | 2501 VVTGSPRGDS QSSWKSVGSQ WASPENPCLI NECVRVKEEV |
| |       FIQQRNVSCP |
| | 2551 QLEVPVCPSG FQLSCKTSAC CPSCRCERME ACMLNGTVIG |
| |       PGKTVMIDVC |
| | 2601 TTCRCMVQVG VISGFKLECR KTTCNPCPLG YKEENNTGEC |
| |       CGRCLPTACT |
| | 2651 IQLRGGQIMT LKRDETLQDG CDTHFCKVNE RGEYFWEKRV |
| |       TGCPPFDEHK |

TABLE 3-continued

| VWF Sequences |
|---|

| VWF domains | Amino acid Sequence |
|---|---|

2701 CLAEGGKIMK IPGTCCDTCE EPECNDITAR LQYVKVGSCK
     SEVEVDIHYC
2751 QGKCASKAMY SIDINDVQDQ CSCCSPTRTE PMQVALHCTN
     GSVVYHEVLN
2801 AMECKCSPRK CSK

Nucleotide Sequence (SEQ ID NO: 1)

| Full-length VWF | |
|---|---|

1 ATGATTCCTG CCAGATTTGC CGGGGTGCTG
     CTTGCTCTGG CCCTCATTTT
  51 GCCAGGGACC CTTTGTGCAG AAGGAACTCG
     CGGCAGGTCA TCCACGGCCC
 101 GATGCAGCCT TTTCGGAAGT GACTTCGTCA
     ACACCTTTGA TGGGAGCATG
 151 TACAGCTTTG CGGGATACTG CAGTTACCTC
     CTGGCAGGGG GCTGCCAGAA
 201 ACGCTCCTTC TCGATTATTG GGGACTTCCA
     GAATGGCAAG AGAGTGAGCC
 251 TCTCCGTGTA TCTTGGGGAA TTTTTTGACA
     TCCATTTGTT TGTCAATGGT
 301 ACCGTGACAC AGGGGGACCA AAGAGTCTCC
     ATGCCCTATG CCTCCAAAGG
 351 GCTGTATCTA GAAACTGAGG CTGGGTACTA
     CAAGCTGTCC GGTGAGGCCT
 401 ATGGCTTTGT GGCCAGGATC GATGGCAGCG
     GCAACTTTCA AGTCCTGCTG
 451 TCAGACAGAT ACTTCAACAA GACCTGCGGG
     CTGTGTGGCA ACTTTAACAT
 501 CTTTGCTGAA GATGACTTTA TGACCCAAGA
     AGGGACCTTG ACCTCGGACC
 551 CTTATGACTT TGCCAACTCA TGGGCTCTGA
     GCAGTGGAGA ACAGTGGTGT
 601 GAACGGGCAT CTCCTCCCAG CAGCTCATGC
     AACATCTCCT CTGGGGAAAT
 651 GCAGAAGGGC CTGTGGGAGC AGTGCCAGCT
     TCTGAAGAGC ACCTCGGTGT
 701 TTGCCCGCTG CCACCCTCTG GTGGACCCCG
     AGCCTTTTGT GGCCCTGTGT
 751 GAGAAGACTT TGTGTGAGTG TGCTGGGGGG
     CTGGAGTGCG CCTGCCCTGC
 801 CCTCCTGGAG TACGCCCGGA CCTGTGCCCA
     GGAGGGAATG GTGCTGTACG
 851 GCTGGACCGA CCACAGCGCG TGCAGCCCAG
     TGTGCCCTGC TGGTATGGAG
 901 TATAGGCAGT GTGTGTCCCC TTGCGCCAGG
     ACCTGCCAGA GCCTGCACAT
 951 CAATGAAATG TGTCAGGAGC GATGCGTGGA
     TGGCTGCAGC TGCCCTGAGG
1001 GACAGCTCCT GGATGAAGGC CTCTGCGTGG
     AGAGCACCGA GTGTCCCTGC
1051 GTGCATTCCG GAAAGCGCTA CCCTCCCGGC
     ACCTCCCTCT CTCGAGACTG
1101 CAACACCTGC ATTTGCCGAA ACAGCCAGTG
     GATCTGCAGC AATGAAGAAT
1151 GTCCAGGGGA GTGCCTTGTC ACTGGTCAAT
     CCCACTTCAA GAGCTTTGAC
1201 AACAGATACT TCACCTTCAG TGGGATCTGC
     CAGTACCTGC TGGCCCGGGA
1251 TTGCCAGGAC CACTCCTTCT CCATTGTCAT
     TGAGACTGTC CAGTGTGCTG
1301 ATGACCGCGA CGCTGTGTGC ACCCGCTCCG
     TCACCGTCCG GCTGCCTGGC
1351 CTGCACAACA GCCTTGTGAA ACTGAAGCAT
     GGGGCAGGAG TTGCCATGGA
1401 TGGCCAGGAC ATCCAGCTCC CCCTCCTGAA
     AGGTGACCTC CGCATCCAGC
1451 ATACAGTGAC GGCCTCCGTG CGCCTCAGCT
     ACGGGGAGGA CCTGCAGATG
1501 GACTGGGATG GCCGCGGGAG GCTGCTGGTG
     AAGCTGTCCC CCGTCTATGC
1551 CGGGAAGACC TGCGGCCTGT GTGGGAATTA
     CAATGGCAAC CAGGGCGACG
1601 ACTTCCTTAC CCCCTCTGGG CTGGCRGAGC
     CCCGGGTGGA GGACTTCGGG
1651 AACGCCTGGA AGCTGCACGG GGACTGCCAG
     GACCTGCAGA AGCAGCACAG

TABLE 3-continued

| VWF Sequences | |
|---|---|
| VWF domains | Amino acid Sequence |

```
1701 CGATCCCTGC GCCCTCAACC CGCGCATGAC
     CAGGTTCTCC GAGGAGGCGT
1751 GCGCGGTCCT GACGTCCCCC ACATTCGAGG
     CCTGCCATCG TGCCGTCAGC
1801 CCGCTGCCCT ACCTGCGGAA CTGCCGCTAC
     GACGTGTGCT CCTGCTCGGA
1851 CGGCCGCGAG TGCCTGTGCG GCGCCCTGGC
     CAGCTATGCC GCGGCCTGCG
1901 CGGGGAGAGG CGTGCGCGTC GCGTGGCGCG
     AGCCAGGCCG CTGTGAGCTG
1951 AACTGCCCGA AAGGCCAGGT GTACCTGCAG
     TGCGGGACCC CCTGCAACCT
2001 GACCTGCCGC TCTCTCTCTT ACCCGGATGA
     GGAATGCAAT GAGGCCTGCC
2051 TGGAGGGCTG CTTCTGCCCC CCAGGGCTCT
     ACATGGATGA GAGGGGGGAC
2101 TGCGTGCCCA AGGCCCAGTG CCCCTGTTAC
     TATGACGGTG AGATCTTCCA
2151 GCCAGAAGAC ATCTTCTCAG ACCATCACAC
     CATGTGCTAC TGTGAGGATG
2201 GCTTCATGCA CTGTACCATG AGTGGAGTCC
     CCGGAAGCTT GCTGCCTGAC
2251 GCTGTCCTCA GCAGTCCCCT GTCTCATCGC
     AGCAAAAGGA GCCTATCCTG
2301 TCGGCCCCCC ATGGTCAAGC TGGTGTGTCC
     CGCTGACAAC CTGCGGGCTG
2351 AAGGGCTCGA GTGTACCAAA ACGTGCCAGA
     ACTATGACCT GGAGTGCATG
2401 AGCATGGGCT GTGTCTCTGG CTGCCTCTGC
     CCCCCGGGCA TGGTCCGGCA
2451 TGAGAACAGA TGTGTGGCCC TGGAAAGGTG
     TCCCTGCTTC CATCAGGGCA
2501 AGGAGTATGC CCCTGGAGAA ACAGTGAAGA
     TTGGCTGCAA CACTTGTGTC
2551 TGTCGGGACC GGAAGTGGAA CTGCACAGAC
     CATGTGTGTG ATGCCACGTG
2601 CTCCACGATC GGCATGGCCC ACTACCTCAC
     CTTCGACGGG CTCAAATACC
2651 TGTTCCCCGG GGAGTGCCAG TACGTTCTGG
     TGCAGGATTA CTGCGGCAGT
2701 AACCCTGGGA CCTTTCGGAT CCTAGTGGGG
     AATAAGGGAT GCAGCCACCC
2751 CTCAGTGAAA TGCAAGAAAC GGGTCACCAT
     CCTGGTGGAG GGAGGAGAGA
2801 TTGAGCTGTT TGACGGGGAG GTGAATGTGA
     AGAGGCCCAT GAAGGATGAG
2851 ACTCACTTTG AGGTGGTGGA GTCTGGCCGG
     TACATCATTC TGCTGCTGGG
2901 CAAAGCCCTC TCCGTGGTCT GGGACCGCCA
     CCTGAGCATC TCCGTGGTCC
2951 TGAAGCAGAC ATACCAGGAG AAAGTGTGTG
     GCCTGTGTGG GAATTTTGAT
3001 GGCATCCAGA ACAATGACCT CACCAGCAGC
     AACCTCCAAG TGGAGGAAGA
3051 CCCTGTGGAC TTTGGGAACT CCTGGAAAGT
     GAGCTCGCAG TGTGCTGACA
3101 CCAGAAAAGT GCCTCTGGAC TCATCCCCTG
     CCACCTGCCA TAACAACATC
3151 ATGAAGCAGA CGATGGTGGA TTCCTCCTGT
     AGAATCCTTA CCAGTGACGT
3201 CTTCCAGGAC TGCAACAAGC TGGTGGACCC
     CGAGCCATAT CTGGATGTCT
3251 GCATTTACGA CACCTGCTCC TGTGAGTCCA
     TTGGGGACTG CGCCTGCTTC
3301 TGCGACACCA TTGCTGCCTA TGCCCACGTG
     TGTGCCCAGC ATGGCAAGGT
3351 GGTGACCTGG AGGACGGCCA CATTGTGCCC
     CCAGAGCTGC GAGGAGAGGA
3401 ATCTCCGGGA GAACGGGTAT GAGTGTGAGT
     GGCGCTATAA CAGCTGTGCA
3451 CCTGCCTGTC AAGTCACGTG TCAGCACCCT
     GAGCCACTGG CCTGCCCTGT
3501 GCAGTGTGTG GAGGGCTGCC ATGCCCACTG
     CCCTCCAGGG AAAATCCTGG
3551 ATGAGCTTTT GCAGACCTGC GTTGACCCTG
     AAGACTGTCC AGTGTGTGAG
```

TABLE 3-continued

| VWF Sequences | |
| --- | --- |
| VWF domains | Amino acid Sequence |
| | 3601 GTGGCTGGCC GGCGTTTTGC CTCAGGAAAG
AAAGTCACCT TGAATCCCAG |
| | 3651 TGACCCTGAG CACTGCCAGA TTTGCCACTG
TGATGTTGTC AACCTCACCT |
| | 3701 GTGAAGCCTG CCAGGAGCCG GGAGGCCTGG
TGGTGCCTCC CACAGATGCC |
| | 3751 CCGGTGAGCC CCACCACTCT GTATGTGGAG
GACATCTCGG AACCGCCGTT |
| | 3801 GCACGATTTC TACTGCAGCA GGCTACTGGA
CCTGGTCTTC CTGCTGGATG |
| | 3851 GCTCCTCCAG GCTGTCCGAG GCTGAGTTTG
AAGTGCTGAA GGCCTTTGTG |
| | 3901 GTGGACATGA TGGAGCGGCT GCGCATCTCC
CAGAAGTGGG TCCGCGTGGC |
| | 3951 CGTGGTGGAG TACCACGACG GCTCCCACGC
CTACATCGGG CTCAAGGACC |
| | 4001 GGAAGCGACC GTCAGAGCTG CGGCGCATTG
CCAGCCAGGT GAAGTATGCG |
| | 4051 GGCAGCCAGG TGGCCTCCAC CAGCGAGGTC
TTGAAATACA CACTGTTCCA |
| | 4101 AATCTTCAGC AAGATCGACC GCCCTGAAGC
CTCCCGCATC GCCCTGCTCC |
| | 4151 TGATGGCCAG CCAGGAGCCC AACGGGATGT
CCCGGAACTT TGTCCGCTAC |
| | 4201 GTCCAGGGCC TGAAGAAGAA GAAGGTCATT
GTGATCCCGG TGGGCATTGG |
| | 4251 GCCCCATGCC AACCTCAAGC AGATCCGCCT
CATCGAGAAG CAGGCCCCTG |
| | 4301 AGAACAAGGC CTTCGTGCTG AGCAGTGTGG
ATGAGCTGGA GCAGCAAAGG |
| | 4351 GACGAGATCG TTAGCTACCT CTGTGACCTT
GCCCCTGAAG CCCCTCCTCC |
| | 4401 TACTCTGCCC CCCGACATGG CACAAGTCAC
TGTGGGCCCG GGGCTCTTGG |
| | 4451 GGGTTTCGAC CCTGGGGCCC AAGAGGAACT
CCATGGTTCT GGATGTGGCG |
| | 4501 TTCGTCCTGG AAGGATCGGA CAAAATTGGT
GAAGCCGACT TCAACAGGAG |
| | 4551 CAAGGAGTTC ATGGAGGAGG TGATTCAGCG
GATGGATGTG GGCCAGGACA |
| | 4601 GCATCCACGT CACGGTGCTG CAGTACTCCT
ACATGGTGAC CGTGGAGTAC |
| | 4651 CCCTTCAGCG AGGCACAGTC CAAAGGGGAC
ATCCTGCAGC GGGTGCGAGA |
| | 4701 GATCCGCTAC CAGGGCGGCA ACAGGACCAA
CACTGGGCTG GCCCTGCGGT |
| | 4751 ACCTCTCTGA CCACAGCTTC TTGGTCAGCC
AGGGTGACCG GGAGCAGGCG |
| | 4801 CCCAACCTGG TCTACATGGT CACCGGAAAT
CCTGCCTCTG ATGAGATCAA |
| | 4851 GAGGCTGCCT GGAGACATCC AGGTGGTGCC
CATTGGAGTG GGCCCTAATG |
| | 4901 CCAACGTGCA GGAGCTGGAG AGGATTGGCT
GGCCCAATGC CCCTATCCTC |
| | 4951 ATCCAGGACT TTGAGACGCT CCCCCGAGAG
GCTCCTGACC TGGTGCTGCA |
| | 5001 GAGGTGCTGC TCCGGAGAGG GGCTGCAGAT
CCCCACCCTC TCCCCTGCAC |
| | 5051 CTGACTGCAG CCAGCCCCTG GACGTGATCC
TTCTCCTGGA TGGCTCCTCC |
| | 5101 AGTTTCCCAG CTTCTTATTT TGATGAAATG
AAGAGTTTCG CCAAGGCTTT |
| | 5151 CATTTCAAAA GCCAATATAG GGCCTCGTCT
CACTCAGGTG TCAGTGCTGC |
| | 5201 AGTATGGAAG CATCACCACC ATTGACGTGC
CATGGAACGT GGTCCCGGAG |
| | 5251 AAAGCCCATT TGCTGAGCCT TGTGGACGTC
ATGCAGCGGG AGGGAGGCCC |
| | 5301 CAGCCAAATC GGGGATGCCT TGGGCTTTGC
TGTGCGATAC TTGACTTCAG |
| | 5351 AAATGCATGG TGCCAGGCCG GGAGCCTCAA
AGGCGGTGGT CATCCTGGTC |
| | 5401 ACGGACGTCT CTGTGGATTC AGTGGATGCA
GCAGCTGATG CCGCCAGGTC |
| | 5451 CAACAGAGTG ACAGTGTTCC CTATTGGAAT
TGGAGATCGC TACGATGCAG |

TABLE 3-continued

| VWF Sequences | |
| --- | --- |
| VWF domains | Amino acid Sequence |

```
5501 CCCAGCTACG GATCTTGGCA GGCCCAGCAG
     GCGACTCCAA CGTGGTGAAG
5551 CTCCAGCGAA TCGAAGACCT CCCTACCATG
     GTCACCTTGG GCAATTCCTT
5601 CCTCCACAAA CTGTGCTCTG GATTTGTTAG
     GATTTGCATG GATGAGGATG
5651 GGAATGAGAA GAGGCCCGGG GACGTCTGGA
     CCTTGCCAGA CCAGTGCCAC
5701 ACCGTGACTT GCCAGCCAGA TGGCCAGACC
     TTGCTGAAGA GTCATCGGGT
5751 CAACTGTGAC CGGGGGCTGA GGCCTTCGTG
     CCCTAACAGC CAGTCCCCTG
5801 TTAAAGTGGA AGAGACCTGT GGCTGCCGCT
     GGACCTGCCC CTGYGTGTGC
5851 ACAGGCAGCT CCACTCGGCA CATCGTGACC
     TTTGATGGGC AGAATTTCAA
5901 GCTGACTGGC AGCTGTTCTT ATGTCCTATT
     TCAAAACAAG GAGCAGGACC
5951 TGGAGGTGAT TCTCCATAAT GGTGCCTGCA
     GCCCTGGAGC AAGGCAGGGC
6001 TGCATGAAAT CCATCGAGGT GAAGCACAGT
     GCCCTCTCCG TCGAGSTGCA
6051 CAGTGACATG GAGGTGACGG TGAATGGGAG
     ACTGGTCTCT GTTCCTTACG
6101 TGGGTGGGAA CATGGAAGTC AACGTTTATG
     GTGCCATCAT GCATGAGGTC
6151 AGATTCAATC ACCTTGGTCA CATCTTCACA
     TTCACTCCAC AAAACAATGA
6201 GTTCCAACTG CAGCTCAGCC CCAAGACTTT
     TGCTTCAAAG ACGTATGGTC
6251 TGTGTGGGAT CTGTGATGAG AACGGAGCCA
     ATGACTTCAT GCTGAGGGAT
6301 GGCACAGTCA CCACAGACTG GAAAACACTT
     GTTCAGGAAT GGACTGTGCA
6351 GCGGCCAGGG CAGACGTGCC AGCCCATCCT
     GGAGGAGCAG TGTCTTGTCC
6401 CCGACAGCTC CCACTGCCAG GTCCTCCTCT
     TACCACTGTT TGCTGAATGC
6451 CACAAGGTCC TGGCTCCAGC CACATTCTAT
     GCCATCTGCC AGCAGGACAG
6501 TTGCCACCAG GAGCAAGTGT GTGAGGTGAT
     CGCCTCTTAT GCCCACCTCT
6551 GTCGGACCAA CGGGGTCTGC GTTGACTGGA
     GGACACCTGA TTTCTGTGCT
6601 ATGTCATGCC CACCATCTCT GGTCTACAAC
     CACTGTGAGC ATGGCTGTCC
6651 CCGGCACTGT GATGGCAACG TGAGCTCCTG
     TGGGGACCAT CCCTCCGAAG
6701 GCTGTTTCTG CCCTCCAGAT AAAGTCATGT
     TGGAAGGCAG CTGTGTCCCT
6751 GAAGAGGCCT GCACTCAGTG CATTGGTGAG
     GATGGAGTCC AGCACCAGTT
6801 CCTGGAAGCC TGGGTCCCGG ACCACCAGCC
     CTGTCAGATC TGCACATGCC
6851 TCAGCGGGCG GAAGGTCAAC TGCACAACGC
     AGCCCTGCCC CACGGCCAAA
6901 GCTCCCACGT GTGGCCTGTG TGAAGTAGCC
     CGCCTCCGCC AGAATGCAGA
6951 CCAGTGCTGC CCCGAGTATG AGTGTGTGTG
     TGACCCAGTG AGCTGTGACC
7001 TGCCCCCAGT GCCTCACTGT GAACGTGGCC
     TCCAGCCCAC ACTGACCAAC
7051 CCTGGCGAGT GCAGACCCAA CTTCACCTGC
     GCCTGCAGGA AGGAGGAGTG
7101 CAAAAGAGTG TCCCCACCCT CCTGCCCCCC
     GCACCGTTTG CCCACCCTTC
7151 GGAAGACCCA GTGCTGTGAT GAGTATGAGT
     GTGCCTGCAA CTGTGTCAAC
7201 TCCACAGTGA GCTGTCCCCT TGGGTACTTG
     GCCTCAACCG CCACCAATGA
7251 CTGTGGCTGT ACCACAACCA CCTGCCTTCC
     CGACAAGGTG TGTGTCCACC
7301 GAAGCACCAT CTACCCTGTG GGCCAGTTCT
     GGGAGGAGGG CTGCGATGTG
7351 TGCACCTGCA CCGACATGGA GGATGCCGTG
     ATGGGCCTCC GCGTGGCCCA
```

TABLE 3-continued

| VWF Sequences | |
|---|---|
| VWF domains | Amino acid Sequence |
| | 7401 GTGCTCCCAG AAGCCCTGTG AGGACAGCTG<br>TCGGTCGGGC TTCACTTACG |
| | 7451 TTCTGCATGA AGGCGAGTGC TGTGGAAGGT<br>GCCTGCCATC TGCCTGTGAG |
| | 7501 GTGGTGACTG GCTCACCGCG GGGGGACTCC<br>CAGTCTTCCT GGAAGAGTGT |
| | 7551 CGGCTCCCAG TGGGCCTCCC CGGAGAACCC<br>CTGCCTCATC AATGAGTGTG |
| | 7601 TCCGAGTGAA GGAGGAGGTC TTTATACAAC<br>AAAGGAACGT CTCCTGCCCC |
| | 7651 CAGCTGGAGG TCCCTGTCTG CCCCTCGGGC<br>TTTCAGCTGA GCTGTAAGAC |
| | 7701 CTCAGCGTGC TGCCCAAGCT GTCGCTGTGA<br>GCGCATGGAG GCCTGCATGC |
| | 7751 TCAATGGCAC TGTCATTGGG CCCGGGAAGA<br>CTGTGATGAT CGATGTGTGC |
| | 7801 ACGACCTGCC GCTGCATGGT GCAGGTGGGG<br>GTCATCTCTG GATTCAAGCT |
| | 7851 GGAGTGCAGG AAGACCACCT GCAACCCCTG<br>CCCCCTGGGT TACAAGGAAG |
| | 7901 AAAATAACAC AGGTGAATGT TGTGGGAGAT<br>GTTTGCCTAC GGCTTGCACC |
| | 7951 ATTCAGCTAA GAGGAGGACA GATCATGACA<br>CTGAAGCGTG ATGAGACGCT |
| | 8001 CCAGGATGGC TGTGATACTC ACTTCTGCAA<br>GGTCAATGAG AGAGGAGAGT |
| | 8051 ACTTCTGGGA GAAGAGGGTC ACAGGCTGCC<br>CACCCTTTGA TGAACACAAG |
| | 8101 TGTCTTGCTG AGGGAGGTAA AATTATGAAA<br>ATTCCAGGCA CCTGCTGTGA |
| | 8151 CACATGTGAG GAGCCTGAGT GCAACGACAT<br>CACTGCCAGG CTGCAGTATG |
| | 8201 TCAAGGTGGG AAGCTGTAAG TCTGAAGTAG<br>AGGTGGATAT CCACTACTGC |
| | 8251 CAGGGCAAAT GTGCCAGCAA AGCCATGTAC<br>TCCATTGACA TCAACGATGT |
| | 8301 GCAGGACCAG TGCTCCTGCT GCTCTCCGAC<br>ACGGACGGAG CCCATGCAGG |
| | 8351 TGGCCCTGCA CTGCACCAAT GGCTCTGTTG<br>TGTACCATGA GGTTCTCAAT |
| | 8401 GCCATGGAGT GCAAATGCTC CCCCAGGAAG<br>TGCAGCAAGT GA |

The VWF fragment as used herein can be a VWF fragment comprising a D' domain and a D3 domain of VWF, wherein the VWF fragment binds to Factor VIII (FVIII) and inhibits binding of endogenous VWF (full-length VWF) to FVIII. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. In one embodiment, a VWF fragment comprises, consists essentially of, or consists of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof. The VWF fragment described herein does not contain a site binding to a VWF clearance receptor. In another embodiment, the VWF fragment described herein is not amino acids 764 to 1274 of SEQ ID NO: 2. The VWF fragment of the present invention can comprise any other sequences linked to or fused to the VWF fragment. For example, a VWF fragment described herein can further comprise a signal peptide.

In one embodiment, the VWF fragment binds to or is associated with a FVIII protein. By binding to or associating with a FVIII protein, a VWF fragment of the invention protects FVIII from protease cleavage and FVIII activation, stabilizes the heavy chain and light chain of FVIII, and prevents clearance of FVIII by scavenger receptors. In another embodiment, the VWF fragment binds to or associates with a FVIII protein and blocks or prevents binding of the FVIII protein to phospholipid and activated Protein C. By preventing or inhibiting binding of the FVIII protein with endogenous, full-length VWF, the VWF fragment of the invention reduces the clearance of FVIII by VWF clearance receptors and thus extends half-life of the FVIII protein. The half-life extension of a FVIII protein is thus due to the binding of or associating with the VWF fragment lacking a VWF clearance receptor binding site to the FVIII protein and shielding or protecting of the FVIII protein by the VWF fragment from endogenous VWF which contains the VWF clearance receptor binding site. The FVIII protein bound to or protected by the VWF fragment can also allow recycling of a FVIII protein. By eliminating the VWF clearance pathway receptor binding sites contained in the full length VWF molecule, the FVIII/VWF heterodimers of the invention are shielded from the VWF clearance pathway, further extending FVIII half-life.

In one embodiment, a VWF fragment of the present invention comprises the D' domain and the D3 domain of VWF, wherein the D' domain is at least 60%, 70%, 80%, 85%, 90%, 95%, 96%, 97%, 98%, 99%, or 100% identical to amino acids 764 to 866 of SEQ ID NO: 2, wherein the VWF fragment prevents binding of endogenous VWF to FVIII. In another embodiment, a VWF fragment comprises the D' domain and the D3 domain of VWF, wherein the D3 domain is at least 60%, 70%, 80%, 85%, 90%, 95%, 96%, 97%, 98%, 99%, or 100% identical to amino acids 867 to 1240 of SEQ ID NO: 2, wherein the VWF fragment prevents binding of endogenous VWF to FVIII. In some embodiments, a VWF fragment described herein comprises, consists essentially of, or consists of the D' domain and D3 domain of VWF, which are at least 60%, 70%, 80%, 85%, 90%, 95%, 96%, 97%, 98%, 99%, or 100% identical to amino acids 764 to 1240 of SEQ ID NO: 2, wherein the VWF fragment prevents binding of endogenous VWF to FVIII. In other embodiments, a VWF fragment comprises, consists essentially of, or consists of the D1, D2, D', and D3 domains at least 60%, 70%, 80%, 85%, 90%, 95%, 96%, 97%, 98%, 99%, or 100% identical to amino acids 23 to 1240 of SEQ ID NO: 2, wherein the VWF fragment prevents binding of endogenous VWF to FVIII. In still other embodiments, the VWF fragment further comprises a signal peptide operably linked thereto.

In some embodiments, a VWF fragment of the invention consists essentially of or consists of (1) the D'D3 domain, the D1D'D3 domain, D2D'D3 domain, or D1D2D'D3 domain and (2) an additional VWF sequence up to about 10 amino acids (e.g., any sequences from amino acids 764 to 1240 of SEQ ID NO: 2 to amino acids 764 to 1250 of SEQ ID NO: 2), up to about 15 amino acids (e.g., any sequences from amino acids 764 to 1240 of SEQ ID NO: 2 to amino acids 764 to 1255 of SEQ ID NO: 2), up to about 20 amino acids (e.g., any sequences from amino acids 764 to 1240 of SEQ ID NO: 2 to amino acids 764 to 1260 of SEQ ID NO: 2), up to about 25 amino acids (e.g., any sequences from amino acids 764 to 1240 of SEQ ID NO: 2 to amino acids 764 to 1265 of SEQ ID NO: 2), or up to about 30 amino acids (e.g., any sequences from amino acids 764 to 1240 of SEQ ID NO: 2 to amino acids 764 to 1260 of SEQ ID NO: 2). In a particular embodiment, the VWF fragment comprising or consisting essentially of the D' domain and the D3 domain is neither amino acids 764 to 1274 of SEQ ID NO: 2 nor the full-length mature VWF. In some embodiments, the D1D2 domain is expressed in trans with the D'D3 domain. In some embodiments, the D1D2 domain is expressed in cis with the D'D3 domain.

In other embodiments, the VWF fragment comprising the D'D3 domains linked to the D1D2 domains further comprises an intracellular cleavage site, e.g., (a cleavage site by PACE (furin) or PC5), allowing cleavage of the D1D2 domains from the D'D3 domains upon expression. Non-limiting examples of the intracellular cleavage site are disclosed elsewhere herein.

In yet other embodiments, a VWF fragment comprises the D' domain and the D3 domain, but does not comprise an amino acid sequence selected from the group consisting of (1) amino acids 1241 to 2813 of SEQ ID NO: 2, (2) amino acids 1270 to amino acids 2813 of SEQ ID NO: 2, (3) amino acids 1271 to amino acids 2813 of SEQ ID NO: 2, (4) amino acids 1272 to amino acids 2813 of SEQ ID NO: 2, (5) amino acids 1273 to amino acids 2813 of SEQ ID NO: 2, (6) amino acids 1274 to amino acids 2813 of SEQ ID NO: 2, and any combinations thereof.

In still other embodiments, a VWF fragment of the present invention comprises, consists essentially of, or consists of an amino acid sequence corresponding to the D' domain, D3 domain, and A1 domain, wherein the amino acid sequence is at least 60%, 70%, 75%, 80%, 85%, 90%, 95%, 96%, 97%, 98%, 99%, or 100% identical to amino acid 764 to 1479 of SEQ ID NO: 2, wherein the VWF fragment prevents binding of endogenous VWF to FVIII. In a particular embodiment, the VWF fragment is not amino acids 764 to 1274 of SEQ ID NO: 2.

In some embodiments, a VWF fragment of the invention comprises the D' domain and the D3 domain, but does not comprise at least one VWF domain selected from the group consisting of (1) an A1 domain, (2) an A2 domain, (3) an A3 domain, (4) a D4 domain, (5) a B1 domain, (6) a B2 domain, (7) a B3 domain, (8) a C1 domain, (9) a C2 domain, (10) a CK domain, (11) a CK domain and C2 domain, (12) a CK domain, a C2 domain, and a C1 domain, (13) a CK domain, a C2 domain, a C1 domain, a B3 domain, (14) a CK domain, a C2 domain, a C1 domain, a B3 domain, a B2 domain, (15) a CK domain, a C2 domain, a C1 domain, a B3 domain, a B2 domain, and a B1 domain, (16) a CK domain, a C2 domain, a C1 domain, a B3 domain, a B2 domain, a B1 domain, and a D4 domain, (17) a CK domain, a C2 domain, a C1 domain, a B3 domain, a B2 domain, a B1 domain, a D4 domain, and an A3 domain, (18) a CK domain, a C2 domain, a C1 domain, a B3 domain, a B2 domain, a B1 domain, a D4 domain, an A3 domain, and an A2 domain, (19) a CK domain, a C2 domain, a C1 domain, a B3 domain, a B2 domain, a B1 domain, a D4 domain, an A3 domain, an A2 domain, and an A1 domain, and (20) any combinations thereof.

In yet other embodiments, the VWF fragment comprises the D'D3 domains and one or more domains or modules. Examples of such domains or modules include, but are not limited to, the domains and modules disclosed in Zhour et al., Blood published online Apr. 6, 2012: DOI 10.1182/blood-2012-01-405134. For example, the VWF fragment can comprise the D'D3 domain and one or more domains or modules selected from the group consisting of A1 domain, A2 domain, A3 domain, D4N module, VWD4 module, C8-4 module, TIL-4 module, C1 module, C2 module, C3 module, C4 module, C5 module, C5 module, C6 module, and any combinations thereof.

In still other embodiments, the VWF fragment is linked to a heterologous moiety, wherein the heterologous moiety is linked to the N-terminus or the C-terminus of the VWF fragment or inserted immediately downstream of one or more amino acids (e.g., one or more XTEN insertion sites) in the FVIII protein in the VWF fragment. For example, the insertion sites for the heterologous moiety in the VWF fragment can be in the D' domain, the D3 domain, or both. The heterologous moiety can be a half-life extender.

In certain embodiments, a VWF fragment of the invention forms a multimer, e.g., dimer, trimer, tetramer, pentamer, hexamer, heptamer, or the higher order multimers. In other embodiments, the VWF fragment is a monomer having only one VWF fragment. In some embodiments, the VWF fragment of the present invention can have one or more amino acid substitutions, deletions, additions, or modifications. In one embodiment, the VWF fragment can include amino acid substitutions, deletions, additions, or modifications such that the VWF fragment is not capable of forming a disulfide bond or forming a dimer or a multimer. In another embodiment, the amino acid substitution is within the D' domain and the D3 domain. In a particular embodiment, a VWF fragment of the invention contains at least one amino acid substitution at a residue corresponding to residue 1099, residue 1142, or both residues 1099 and 1142 of SEQ ID NO: 2. The at least one amino acid substitution can be any amino acids that are not occurring naturally in the wild type VWF. For example, the amino acid substitution can be any amino acids other than cysteine, e.g., Isoleucine, Alanine, Leucine, Asparagine, Lysine, Aspartic acid, Methionine, Phenylalanine, Glutamic acid, Threonine, Glutamine, Tryptophan, Glycine, Valine, Proline, Serine, Tyrosine, Arginine, or Histidine. In another example, the amino acid substitution has one or more amino acids that prevent or inhibit the VWF fragments from forming multimers.

In certain embodiments, the VWF fragment useful herein can be further modified to improve its interaction with FVIII, e.g., to improve binding affinity to FVIII. As a non-limiting example, the VWF fragment comprises a serine residue at the residue corresponding to amino acid 764 of SEQ ID NO: 2 and a lysine residue at the residue corresponding to amino acid 773 of SEQ ID NO: 2. Residues 764 and/or 773 can contribute to the binding affinity of the VWF fragments to FVIII. In other embodiments, The VWF fragments useful for the invention can have other modifications, e.g., the protein can be pegylated, glycosylated, hesylated, or polysialylated.

B) XTEN Sequences

As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties when linked to a VWF fragment or a FVIII sequence of the invention to create a chimeric protein. Such desirable properties include but are not limited to enhanced pharmacokinetic parameters and solubility characteristics. As used herein, "XTEN" specifically excludes antibodies or antibody fragments such as single-chain antibodies or Fc fragments of a light chain or a heavy chain.

In some embodiments, the XTEN sequence of the invention is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

The XTEN sequence of the invention can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 4A, resulting in a family sequence. As used herein, "family" means that the XTEN has motifs selected only from a single motif category from Table 4A; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII or VWF. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 4A. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 4A

| XTEN Sequence Motifs of 12 Amino Acids and Motif Families | | |
| --- | --- | --- |
| Motif Family* | MOTIF SEQUENCE | SEQ ID NO. |
| AD | GESPGGSSGSES | 69 |
| AD | GSEGSSGPGESS | 70 |
| AD | GSSESGSSEGGP | 71 |
| AD | GSGGEPSESGSS | 72 |
| AE, AM | GSPAGSPTSTEE | 73 |
| AE, AM, AQ | GSEPATSGSETP | 74 |
| AE, AM, AQ | GTSESATPESGP | 75 |
| AE, AM, AQ | GTSTEPSEGSAP | 76 |
| AF, AM | GSTSESPSGTAP | 77 |
| AF, AM | GTSTPESGSASP | 78 |
| AF, AM | GTSPSGESSTAP | 79 |
| AF, AM | GSTSSTAESPGP | 80 |
| AG, AM | GTPGSGTASSSP | 81 |
| AG, AM | GSSTPSGATGSP | 82 |
| AG, AM | GSSPSASTGTGP | 83 |
| AG, AM | GASPGTSSTGSP | 84 |
| AQ | GEPAGSPTSTSE | 85 |
| AQ | GTGEPSSTPASE | 86 |
| AQ | GSGPSTESAPTE | 87 |
| AQ | GSETPSGPSETA | 88 |
| AQ | GPSETSTSEPGA | 89 |
| AQ | GSPSEPTEGTSA | 90 |
| BC | GSGASEPTSTEP | 91 |
| BC | GSEPATSGTEPS | 92 |
| BC | GTSEPSTSEPGA | 93 |
| BC | GTSTEPSEPGSA | 94 |
| BD | GSTAGSETSTEA | 95 |
| BD | GSETATSGSETA | 96 |
| BD | GTSESATSESGA | 97 |
| BD | GTSTEASEGSAS | 98 |

*Denotes individual motif sequences that, when used together in various permutations, results in a "family sequence"

XTEN can have varying lengths for insertion into or linkage to FVIII or VWF. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN include short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to FVIII or VWF can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length. The precise length of an XTEN inserted into or linked to FVIII or VWF can vary without adversely affecting the activity of the FVIII or VWF. In one embodiment, one or more of the XTEN used herein has 36 amino acids, 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the XTEN sequence used in the invention is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, and AG2004. See US 2010-0239554 A1.

In one embodiment, the XTEN sequence is at least 60%, 70%, 80%, 90%, 95%, 96%, 97%, 98%, 99% or 100% identical to an amino acid sequence selected from the group consisting of AE42, AE864, AE576, AE288, AE144, AG864, AG576, AG288, AG144, and any combinations thereof. In another embodiment, the XTEN sequence is selected from the group consisting of AE42, AE864, AE576, AE288, AE144, AG864, AG576, AG288, AG144, and any combinations thereof. In a specific embodiment, the XTEN sequence is AE288. The amino acid sequences for certain XTEN sequences of the invention are shown in Table 4B.

TABLE 4B

XTEN Sequences

| XTEN | Amino Acid Sequence |
|---|---|
| AE42 SEQ ID NO: 12 | GAPGSPAGSPTSTEEGTSESATPESGPGS EPATSGSETPASS |

TABLE 4B-continued

XTEN Sequences

| XTEN | Amino Acid Sequence |
|---|---|
| AE72 SEQ ID NO: 13 | GAP TSESATPESG PGSEPATSGS ETPGTSESAT PESGPGSEPA TSGSETPGTS ESATPESGPG TSTEPSEGSA PGASS |
| AE144 SEQ ID NO: 14 | GSEPATSGSETPGTSESATPESGPGSEPA TSGSETPGSPAGSPTSTEEGTSTEPSEGS APGSEPATSGSETPGSEPATSGSETPGSE PATSGEETPGTETEPEEGEAPGTEEEAPE SGPGSEPATSGSETPGTSTEPSEGSAP |
| AG144 SEQ ID NO: 15 | GTPGSGTASSSPGSSTPSGATGSPGSSPS ASTGTGPGSSPSASTGTGPGASPGTSSTG SPGASPGTSSTGSPGSSTPSGATGSPGSS PSASTGTGPGASPGTSSTGSPGSSPSAST GTGPGTPGSGTASSSPGSSTPSGATGSP |
| AE288 SEQ ID NO: 16 | GTEESATPESGPGSEPATSGSETTGTSES ATPESGPGSEPATSGSETPGTSESATPES GPGTSTEPSEGSAPGSPAGSPTSTEEGTS ESATPESGPGSEPATSGSETPGTSESATP ESGPGSPAGSPTSTEEGSPAGSPTSTEEG TSTEPSEGSAPGTSESATPESGPGTSESA TPESGPGTSESATPESGPGSEPATSGSET PGSEPATSGSETPGSPAGSPTSTEEGTST EPSEGSAPGTSTEPSEGSAPGSEPATSGS ETPGTSESATPESGPGTSTEPSEGSAP |
| AG288 SEQ ID NO: 17 | PGASPGTSSTGSIJGASPGTSSTGSPGTP GSGTASSSPGSSTPSGATGSPGTPGSGTA SSPGSSTPSGATGSPGTPGSGTASSSPGS STPSGATGSPGSSTPSGATGSPGSSPSAS TGTGPGSSPSASTGTGPGASPGTSSTGSP GTPGSGTASSSPGSSTPSGATGSPGSSPS ASTGTGPGSSPSASTGTGPGASPGTSSTG SPGASPGTSSTGSPGSSTPSGATGSPGSS PSASTGTGPGASPGTSSTGSPGSSPSAST GTGPGTPGSGTASSSPGSSTPSGATGS |
| AE576 SEQ ID NO: 18 | GSPAGSPTSTEEGTSESATPESGPGTSTE PSEGSAPGSPAGSPTSTEEGTSTEPSEGS APGTSTEPSEGSAPGTSESATPESGPGSE PATSGSETPGSEPATSGSETPGSPAGSPT STEEGTSESATPESGPGTSTEPSEGSAPG TSTEPSEGSAPGSPAGSPTSTEEGTSTEP SEGSAPGTSTEPSEGSAPGTSESATPESG PGTSTEPSEGSAPGTSESATPESGPGSEP ATSGSETPGTSTEPSEGSAPGTSTEPSEG SAPGTSESATPESGPGTSESATPESGPGS PAGSPTSTEEGTSESATPESGPGSEPATS GSETPGTSESATPESGPGTSTEPSEGSAP GTSTEPSEGSAPGTSTEPSEGSAPGTSTE PSEGSAPGTSTEPSEGSAPGTSTEPSEGS APGSPAGSPTSTEEGTSTEPSEGSAPGTS ESATPESGPGSEPATSGSETPGTSESATP ESGPGSEPATSGSETPGTSESATPESGPG TSTEPSEGSAPGTSESATPESGPGSPAGS PTSTEEGSPAGSPTSTEEGSPAGSPTSTE EGTSESATPESGPGTSTEPSEGSAP |
| AG576 SEQ ID NO: 19 | PGTPGSGTASSSPGSSTPSGATGSPGSSP SASTGTGPGSSPSASTGTGPGSSTPSGAT GSPGSSTPSGATGSPGASPGTSSTGSPGA SPGTSSTGSPGASPGTSSTGSPGTPGSGT ASSSPGASPGTSSTGSPGASPGTSSTGSP GASPGTSSTGSPGSSPSASTGTGPGTPGS GTASSSPGASPGTSSTGSPGASPGTSSTG SPGASPGTSSTGSPGSSTPSGATGSPGSS TPSGATGSPGASPGTSSTGSPGTPGSGTA SSSPGSSTPSGATGSPGSSTPSGATGSPG SSTPSGATGSPGSSPSASTGTGPGASPGT SSTGSPGASPGTSSTGSPGTPGSGTASSS PGASPGTSSTGSPGASPGTSSTGSPGASP GTSSTGSPGASPGTSSTGSPGTPGSGTAS SSPGSSTPSGATGSPGTPGSGTASSSPGS STPSGATGSPGTPGSGTASSSPGSSTPSG |

TABLE 4B-continued

XTEN Sequences

| XTEN | Amino Acid Sequence |
|---|---|
| | ATGSPGSSTPSGATGSPGSSPSASTGTGP GSSSASTGTGPGASPGTSSTGSPGTPGSG TASSSPGSSTPSGATGSPGSSPSASTGTG PGSSPSASTGTGPGASPGTSSTGS |
| AE864<br>SEQ ID NO: 20 | GSPAGSPTSTEEGTSESATPESGPGTSTE PSEGSAPGSPAGSPTSTEEGTSTEPSEGS APGTSTEPSEGSAPGTSESATPESGPGSE PATSGSETPGSEPATSGSETPGSPAGSPT STEEGTSESATPESGPGTSTEPSEGSAPG TSTEPSEGSAPGSPAGSPTSTEEGTSTEP SEGSAPGTSTEPSEGSAPGTSESATPESG PGTSTEPSEGSAPGTSESATPESGPGSEP ATSGSETPGTSTEPSEGSAPGTSTEPSEG SAPGTSESATPESGPGTSESATPESGPGS PAGSPTSTEEGTSESATPESGPGSEPATS GSETPGTSESATPESGPGTSTEPSEGSAP GTSTEPSEGSAPGTSTEPSEGSAPGTSTE PSEGSAPGTSTEPSEGSAPGTSTEPSEGS APGSPAGSPTSTEEGTSTEPSEGSAPGTS ESATPESGPGSEPATSGSETPGTSESATP ESGPGSEPATSGSETPGTSESATPESGPG TSTEPSEGSAPGTSESATPESGPGSPAGS PTSTEEGSPAGSPTSTEEGSPAGSPTSTE EGTSESATPESGPGTSTEPSEGSAPGTSE SATPESGPGSEPATSGSETPGTSESATPE SGPGSEPATSGSETPGTSESATPESGPGT STEPSEGSAPGSPAGSPTSTEEGTSESAT PESGPGSEPATSGSETPGTSESATPESGP GSPAGSPTSTEEGSPAGSPTSTEEGTSTE PSEGSAPGTSESATPESGPGTSESATPES GPGTSESATPESGPGSEPATSGSETPGSE PATSGSETPGSPAGSPTSTEEGTSTEPSE GSAPGTSTEPSEGSAPGSEPATSGSETPG TSESATPESGPGTSTEPSEGSAP |
| AG864<br>SEQ ID NO: 21 | GASPGTSSTGSPGSSPSASTGTGPGSSPS ASTGTGPGTPGSGTASSSPGSSTPSGATG SPGSSPSASTGTGPGASPGTSSTGSPGTP GSGTASSSPGSSTPSGATGSPGTPGSGTA SSSPGASPGTSSTGSPGASPGTSSTGSPG TPGSGTASSSPGSSTPSGATGSPGASPGT SSTGSPGTPGSGTASSSPGSSTPSGATGS PGSSPSASTGTGPGSSPSASTGTGPGSST PSGATGSPGSSTPSGATGSPGASPGTSST GSPGASPGTSSTGSPGASPGTSSTGSPGT PGSGTASSSPGASPGTSSTGSPGASPGTS STGSPGASPGTSSTGSPGSSPSASTGTGP GTPGSGTASSSPGASPGTSSTGSPGASPG TSSTGSPGASPGTSSTGSPGSSTPSGATG SPGSSTPSGATGSPGASPGTSSTGSPGTP GSGTASSSPGSSTPSGATGSPGSSTPSGA TGSPGSSTPSGATGSPGSSPSASTGTGPG ASPGTSSTGSPGASPGTSSTGSPGTPGSG TASSSPGASPGTSSTGSPGASPGTSSTGS PGASPGTSSTGSPGASPGTSSTGSPGTPG SGTASSSPGSSTPSGATGSPGTPGSGTAS SSPGSSTPSGATGSPGTPGSGTASSSPGS STPSGATGSPGASPGTSSTGSPGSSPSAS TGTGPGSSPSASTGTGPGASPGTSSTGSP GTPGSGTASSSPGSSTPSGATGSPGSSPS ASTGTGPGSSPSASTGTGPGASPGTSSTG SPGASPGTSSTGSPGSSTPSGATGSPGSS PSASTGTGPGASPGTSSTGSPGSSPSAST GTGPGTPGSGTASSSPGSSTPSGATGSPG SSTPSGATGSPGASPGTSSTGSP |

In further embodiments, the XTEN sequence used in the invention affects the physical or chemical property, e.g., pharmacokinetics, of the chimeric protein of the present invention. The XTEN sequence used in the present invention can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN sequence linked to a FVIII protein in this invention increases pharmacokinetic properties such as longer terminal half-life or increased area under the curve (AUC), so that the chimeric protein described herein stays in vivo for an increased period of time compared to wild type FVIII. In further embodiments, the XTEN sequence used in this invention increases pharmacokinetic properties such as longer terminal half-life or increased area under the curve (AUC), so that FVIII protein stays in vivo for an increased period of time compared to wild type FVIII.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2.

C) Factor VIII (FVIII) Protein

"A FVIII protein" as used herein means a functional FVIII polypeptide in its normal role in coagulation, unless otherwise specified. The term a FVIII protein includes a functional fragment, variant, analog, or derivative thereof that retains the function of full-length wild-type Factor VIII in the coagulation pathway. "A FVIII protein" is used interchangeably with FVIII polypeptide (or protein) or FVIII. Examples of the FVIII functions include, but not limited to, an ability to activate coagulation, an ability to act as a cofactor for factor IX, or an ability to form a tenase complex with factor IX in the presence of Ca2+ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632).

A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g. factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The FVIII polypeptide and polynucleotide sequences are known, as are many functional fragments, mutants and modified versions. Examples of human FVIII sequences (full-length) are shown below.

TABLE 5

| Amino Acid Sequence of Full-length Factor VIII (Full-length FVIII (FVIII signal peptide underlined; FVIII heavy chain is double underlined; B domain is italicized; and FVIII light chain is in plain text) |
|---|

Signal Peptide:

(SEQ ID NO: 3)

MQIELSTCFFLCLLRFCFS

Mature Factor VIII*

(SEQ ID NO: 4)

ATRRYYLGAVELSWDYMQSDLGELPVDARFPPRVPKSFPFNTSVVYKKTLFVEFTDHLFNIAKPRPPWMGLL

GPTIQAEVYDTVVITLKNMASHPVSLHAVGVSYWKASEGAEYDDQTSQREKEDDKVFPGGSHTYVWQVLKEN

GPMASDPLCLTYSYLSHVDLVKDLNSGLIGALLVCREGSLAKEKTQTLHKFILLFAVFDEGKSWHSETKNSL

MQDRDAASARAWPKMHTVNGYVNRSLPGLIGCHRKSVYWHVIGMGTTPEVHSIFLEGHTFLVRNHRQASLEI

SPITFLTAQTLLMDLGQFLLFCHISSHQHDGMEAYVKVDSCPEEPQLRMKNNEEAEDYDDDLTDSEMDVVRF

DDDNSPSFIQIRSVAKKHPKTWVHYIAAEEEDWDYAPLVLAPDDRSYKSQYLNNGPQRIGRKYKKVRFMAYT

DETFKTREAIQHESGILGPLLYGEVGDTLLIIFKNQASRPYNIYPHGITDVRPLYSRRLPKGVKHLKDFPIL

PGEIFKYKWTVTVEDGPTKSDPRCLTRYYSSFVNMERDLASGLIGPLLICYKESVDQRGNQIMSDKRNVILE

SVFDENRSWYLTENIQRFLPNPAGVQLEDPEFQASNIMHSINGYVFDSLQLSVCLHEVAYWYILSIGAQTDF

LSVFFSGYTFKHKMVYEDTLTLFPFSGETVFMSMENPGLWILGCHNSDFRNRGMTALLKVSSCDKNTGDYYE

DSYEDISAYLLSKNNAIEPR*SFSQNSRHPSTRQKQFNATTIPENDIEKTDPWFAHRTPMPKIQNVSSSDLLM*

*LLRQSPTPHGLSLSDLQEAKYETFSDDPSPGAIDSNNSLSEMTHFRPQLHHSGDMVFTPESGLQLRLNEKLG*

*TTAATELKKLDFKVSSTSNNLISTIPSDNLAAGTDNTSSLGPPSMPVHYDSQLDTTLFGKKSSPLTESGGPL*

*SLSEENNDSKLLESGLMNSQESSWGKNVSSTESGRLFKGKRAHGPALLTKDNALFKVSISLLKTNKTSNNSA*

*TNRKTHIDGPSLLIENSPSVWQNILESDTEFKKVTPLIHDRMLMDKNATALRLNHMSNKTTSSKNMEMVQQK*

*KEGPIPPADQNPDMSFFKMLFLPESARWIQRTHGKNSLNSGQGPSPKQLVSLGPEKSVEGQNFLSEKNKVVV*

*GKGEFTKDVGLKEMVFPSSRNLFLTNLDNLHENNTHNQEKKIQEEIEKKETLIQENVVLPQIHTVTGTKNFM*

*KNLFLLSTRQNVEGSYDGAYAPVLQDFRSLNDSTNRTKKHTAHFSKKGEEENLEGLGNQTKQIVEKYACTTR*

*ISPNTSQQNFVTQRSKRALKQFRLPLEETELEKRIIVDDTSTQWSKNMKHLTPSTLTQIDYNEKEKGAITQS*

*PLSDCLTRSHSIPQANRSPLPIAKVSSFPSIRPIYLTRVLFQDNSSHLPAASYRKKDSGVQESSHFLQGAKK*

*NNLSLAILTLEMTGDQREVGSLGTSATNSVTYKKVENTVLPKPDLPKTSGKVELLPKVHIYQKDLFPTETSN*

*GSPGHLDLVEGSLLQGTEGAIKWNEANRPGKVPFLRVATESSAKTPSKLLDPLAWDNHYGTQIPKEEWKSQE*

*KSPEKTAFKKKDTILSLNACESNHAIAAINEGQNKPEIEVTWAKQGRTERLCSQNPPVLKRHQREITRTTLQ*

SDQEEIDYDDTISVEMKKEDFDIYDEDENQSPRSFQKKTRHYFIAAVERLWDYGMSSSPHVLRNRAQSGSVP

QFKKVVFQEFTDGSFTQPLYRGELNEHLGLLGPYIRAEVEDNIMVTFRNQASRPYSFYSSLISYEEDQRQGA

EPRKNFVKPNETKTYFWKVQHHMAPTKDEFDCKAWAYFSDVDLEKDVHSGLIGPLLVCHTNTLNPAHGRQVT

VQEFALFFTIFDETKSWYFTENMERNCRAPCNIQMEDPTFKENYRFHAINGYIMDTLPGLVMAQDQRIRWYL

LSMGSNENIHSIHFSGHVFTVRKKEEYKMALYNLYPGVFETVEMLPSKAGIWRVECLIGEHLHAGMSTLFLV

YSNKCQTPLGMASGHIRDFQITASGQYGQWAPKLARLHYSGSINAWSTKEPFSWIKVDLLAPMIIHGIKTQG

ARQKFSSLYISQFIIMYSLDGKKWQTYRGNSTGTLMVFFGNVDSSGIKHNIFNPPIIARYIRLHPTHYSIRS

TABLE 5-continued

Amino Acid Sequence of Full-length Factor VIII
(Full-length FVIII (FVIII signal peptide underlined;
FVIII heavy chain is double underlined; B domain is
italicized; and FVIII light chain is in plain text)

TLRMELMGCDLNSCSMPLGMESKAISDAQITASSYFTNMFATWSPSKARLHLQGRSNAWRPQVNNPKEWLQV

DFQKTMKVTGVTTQGVKSLLTSMYVKEFLISSSQDGHQWTLFFQNGKVKVFQGNQDSFTPVVNSLDPPLLTR

YLRIHPQSWVHQIALRMEVLGCEAQDLY

TABLE 6

Nucleotide Sequence Encoding
Full-Length FVIII (SEQ ID NO: 5)*

| 661 | | | | | ATG CAAATAGAGC TCTCCACCTG |
|---|---|---|---|---|---|
| 721 | CTTCTTTCTG | TGCCTTTTGC | GATTCTGCTT | TAGTGCCACC | AGAAGATACT ACCTGGGTGC |
| 781 | AGTGGAACTG | TCATGGGACT | ATATGCAAAG | TGATCTCGGT | GAGCTGCCTG TGGACGCAAG |
| 841 | ATTTCCTCCT | AGAGTGCCAA | AATCTTTTCC | ATTCAACACC | TCAGTCGTGT ACAAAAAGAC |
| 901 | TCTGTTTGTA | GAATTCACGG | ATCACCTTTT | CAACATCGCT | AAGCCAAGGC CACCCTGGAT |
| 961 | GGGTCTGCTA | GGTCCTACCA | TCCAGGCTGA | GGTTTATGAT | ACAGTGGTCA TTACACTTAA |
| 1021 | GAACATGGCT | TCCCATCCTG | TCAGTCTTCA | TGCTGTTGGT | GTATCCTACT GGAAAGCTTC |
| 1083 | TGAGGGAGCT | GAATATGATG | ATCAGACCAG | TCAAAGGGAG | AAAGAAGATG ATAAAGTCTT |
| 1141 | CCCTGGTGGA | AGCCATACAT | ATGTCTGGCA | GGTCCTGAAA | GAGAATGGTC CAATGGCCTC |
| 1201 | TGACCCACTG | TGCCTTACCT | ACTCATATCT | TTCTCATGTG | GACCTGGTAA AAGACTTGAA |
| 1261 | TTCAGGCCTC | ATTGGAGCCC | TACTAGTATG | TAGAGAAGGG | AGTCTGGCCA AGGAAAAGAC |
| 1321 | ACAGACCTTG | CACAAATTTA | TACTACTTTT | TGCTGTATTT | GATGAAGGGA AAAGTTGGCA |
| 1381 | CTCAGAAACA | AAGAACTCCT | TGATGCAGGA | TAGGGATGCT | GCATCTGCTC GGGCCTGGCC |
| 1441 | TAAAATGCAC | ACAGTCAATG | GTTATGTAAA | CAGGTCTCTG | CCAGGTCTGA TTGGATGCCA |
| 1501 | CAGGAAATCA | GTCTATTGGC | ATGTGATTGG | AATGGGCACC | ACTCCTGAAG TGCACTCAAT |
| 1561 | ATTCCTCGAA | GGTCAGACAT | TTCTTGTGAG | GAACCATCGC | CAGGCGTGCT TGGAAATCTC |
| 1621 | GCCAATAACT | TTCCTTACTG | CTCAAACACT | CTTGATGGAC | CTTGGACAGT TTCTACTGTT |
| 1681 | TTGTCATATC | TCTTCCCACC | AACATGATGG | CATGGAAGCT | TATGTCAAAG TAGACAGCTG |
| 1741 | TCCAGAGGAA | CCCCAACTAC | GAATGAAAAA | TAATGAAGAA | GCGGAAGACT ATGATGATGA |
| 1801 | TCTTACTGAT | TCTGAAATGG | ATGTGGTCAG | GTTTGATGAT | GACAACTCTC CTTCCTTTAT |
| 1861 | CCAAATTCGC | TCAGTTGCCA | AGAAGCATCC | TAAAACTTGG | GTACATTACA TTGCTGCTGA |
| 1921 | AGAGGAGGAC | TGGGACTATG | CTCCCTTAGT | CCTCGCCCCC | GATGACAGAA GTTATAAAAG |
| 1981 | TCAATATTTG | AACAATGGCC | CTCAGCGGAT | TGGTAGGAAG | TACAAAAAAG TCCGATTTAT |
| 2041 | GGCATACACA | GATGAAACCT | TTAAGACTCG | TGAAGCTATT | CAGCATGAAT CAGGAATCTT |
| 2101 | GGGACCTTTA | CTTTATGGGG | AAGTTGGAGA | CACACTGTTG | ATTATATTTA AGAATCAAGC |
| 2161 | AAGCAGACCA | TATAACATCT | ACCCTCACGG | AATCACTGAT | GTCCGTCCTT TGTATTCAAG |
| 2221 | GAGATTACCA | AAAGGTGTAA | AACATTTGAA | GGATTTTCCA | ATTCTGCCAG GAGAAATATT |
| 2281 | CAAATATAAA | TGGACAGTGA | CTGTAGAAGA | TGGGCCAACT | AAATCAGATC CTCGGTGCCT |
| 2341 | GACCCGCTAT | TACTCTAGTT | TCGTTAATAT | GGAGAGAGAT | CTAGCTTCAG GACTCATTGG |
| 2401 | CCCTCTCCTC | ATCTGGTACA | AGAATCTGT | AGATCAAAGA | GGAAACCAGA TAATGTCAGA |

TABLE 6-continued

| Nucleotide Sequence Encoding |
| Full-Length FVIII (SEQ ID NO: 5)* |

```
2461   CAAGAGGAAT GTCATCCTGT TTTCTGTATT TGATGAGAAC CGAAGCTGGT ACCTCACAGA

2521   GAATATAGAA CGGTTTCTCC CCAATCCAGC TGGAGTGCAG CTTGAGGATC CAGAGTTCCA

2581   AGCCTCCAAC ATCATGCACA GCATGAATGG CTATGTTTTT GATAGTTTGC AGTTGTCAGT

2641   TTGTTTGCAT GAGGTGGCAT ACTGGTACAT TCTAAGCATT GGAGCACAGA CTGACTTCCT

2701   TTCTGTCTTC TTCTCTGGAT ATACCTTCAA ACACAAATG GTCTATGAAG ACACACTCAC

2761   CCTATTCCCA TTCTCAGGAG AAACTGTCTT CATGTCGATG GAAAACCCAG GTCTATGGAT

2821   TCTGGGGTGC CACAACTCAG ACTTTGGGAA CAGAGGCATG AGGGCGTTAC TGAAGGTTTC

2881   TAGTTGTGAC AAGAACACTG GTGATTATTA CGAGGACAGT TATGAAGATA TTTCAGCATA

2941   GTTGCTGAGT AAAAACAATG CCATTGAACC AAGAAGCTTC TCCCAGAATT CAAGACACCC

3001   TAGCACTAGG CAAAAGCAAT TTAATGCCAC CACAATTCCA GAAAATGACA TAGAGAAGAC

3061   TGACCCTTGG TTTGCACACA GAACACCTAT GCCTAAAATA CAAAATGTCT CCTCTAGTGA

3121   TTTGTTGATG CTCTTGCGAC AGAGTCCTAC TCCACATGGG CTATCCTTAT CTGATCTCCA

3181   AGAAGCCAAA TATGAGACTT TTTCTGATGA TCCATCACCT GGAGCAATAG ACAGTAATAA

3241   CAGCCTGTCT GAAATGACAC ACTTCAGGCC ACAGCTCCAT CACAGTGGGG ACATGGTATT

3301   TACCCCTGAG TCAGGCCTCC AATTAAGATT AAATGAGAAA CTGGGGACAA CTGCAGCAAC

3361   AGAGTTGAAG AAACTTGATT TCAAAGTTTC TAGTACATCA AATAATCTGA TTTCAACAAT

3421   TCCATCAGAC AATTTGGCAG CAGGTACTGA TAATACAAGT TCCTTAGGAC CCCCAAGTAT

3481   GCCAGTTCAT TATGATAGTC AATTAGATAC CACTCTATTT GGCAAAAAGT CATCTCCCCT

3541   TACTGAGTCT GGTGGACCTC TGAGCTTGAG TGAAGAAAAT AATGATTCAA AGTTGTTAGA

5601   ATCAGGTTTA ATGAATAGCC AAGAAAGTTC ATGGGGAAAA AATGTATCGT CAACAGAGAG

3661   TGGTAGGTTA TTTAAAGGGA AAAGAGCTCA TGGACCTGCT TTGTTGACTA AAGATAATGC

3721   CTTATTCAAA GTTAGCATCT CTTTGTTAAA GACAAACAAA ACTTCCAATA ATTCAGCAAC

3781   TAATAGAAAG ACTCACATTG ATGGCCCATC ATTATTAATT GAGAATAGTC CATCAGTCTG

3841   GCAAAATATA TTAGAAAGTG ACACTGAGTT TAAAAAAGTG ACACCTTTGA TTCATGACAG

3901   AATGCTTATG GACAAAAATG CTACAGCTTT GAGGCTAAAT CATATGTCAA ATAAAACTAC

3961   TTCATCAAAA AACATGGAAA TGGTCCAACA GAAAAAAGAG GGCCCCATTC CACCAGATGC

4021   ACAAAATCCA GATATGTCGT TCTTTAAGAT GCTATTCTTG CCAGAATCAG CAAGGTGGAT

4081   ACAAAGGACT CATGGAAAGA ACTCTCTGAA CTCTGGGCAA GGCCCCAGTC CAAAGCAATT

4141   AGTATCCTTA GGACCAGAAA AATCTGTGGA AGGTCAGAAT TTCTTGTCTG AGAAAAACAA

4201   AGTGGTAGTA GGAAAGGGTG AATTTACAAA GGACGTAGGA CTCAAAGAGA TGGTTTTTCC

4261   AAGCAGCAGA AACCTATTTC TTACTAACTT GGATAATTTA CATGAAAATA ATACACACAA

4321   TCAAGAAAAA AAAATTCAGG AAGAAATAGA AAAGAAGGAA ACATTAATCC AAGAGAATGT

4381   AGTTTTGCCT CAGATACATA CAGTGACTGG CACTAAGAAT TTCATGAAGA ACCTTTTCTT

4441   ACTGAGCACT AGGCAAAATG TAGAAGGTTC ATATGACGGG GCATATGCTC CAGTACTTCA

4501   AGATTTTAGG TCATTAAATG ATTCAACAAA TAGAACAAAG AAACACACAG CTCATTTCTC

4563   AAAAAAGGGG GAGGAAGAAA ACTTGGAAGG CTTGGGAAAT CAAACCAAGC AAATTGTAGA

4621   GAAATATGCA TGCACCACAA GGATATCTCC TAATACAAGC CAGCAGAATT TTGTCACGCA

4681   ACGTAGTAAG AGAGCTTTGA AACAATTCAG ACTCCCACTA GAAGAAACAA AACTTGAAAA

4741   AAGGATAATT GTGGATGACA CCTCAACCCA GTGGTCCAAA AACATGAAAC ATTTGACCCC
```

TABLE 6-continued

| Nucleotide Sequence Encoding |
| :---: |
| Full-Length FVIII (SEQ ID NO: 5)* |

```
4801  GAGCACCCTC ACACAGATAG ACTACAATGA GAAGGAGAAA GGGGCCATTA CTCAGTCTCC

4861  CTTATCAGAT TGCCTTACGA GGAGTCATAG CATCCCTCAA GCAAATAGAT CTCCATTACC

4921  CATTGCAAAG GTATCATCAT TTCCATCTAT TAGACCTATA TATCTGACCA GGGTCCTATT

4981  CCAAGACAAC TCTTCTCATC TTCCAGCAGC ATCTTATAGA AAGAAAGATT CTGGGGTCCA

5041  AGAAAGCAGT CATTTCTTAC AAGGAGCCAA AAAAAATAAC CTTTCTTTAG CCATTCTAAC

5101  CTTGGAGATG ACTGGTGATC AAAGAGAGGT TGGCTCCCTG GGGACAAGTG CCACAAATTC

5161  AGTCACATAC AAGAAAGTTG AGAACACTGT TCTCCCGAAA CCAGACTTGC CCAAAACATC

5221  TGGCAAAGTT GAATTGCTTC CAAAAGTTCA CATTTATCAG AAGGACCTAT TCCCTACGGA

5281  AACTAGCAAT GGGTCTCCTG GCCATCTGGA TCTCGTGGAA GGGAGCCTTC TTCAGGGAAC

5341  AGAGGGAGCG ATTAAGTGGA ATGAAGCAAA CAGACCTGGA AAAGTTCCCT TTCTGAGAGT

5401  AGCAACAGAA AGCTCTGCAA AGACTCCCTC CAAGCTATTG GATCCTCTTG CTTGGGATAA

5461  CCACTATGGT ACTCAGATAC CAAAAGAAGA GTGGAAATCC CAAGAGAAGT CACCAGAAAA

5521  AACAGCTTTT AAGAAAAAGG ATACCATTTT GTCCCTGAAC GCTTGTGAAA GCAATCATGC

5581  AATAGCAGCA ATAAATGAGG ACAAAATAA GCCCGAAATA GAAGTCACCT GGGCAAAGCA

5641  AGGTAGGACT GAAAGGCTGT GCTCTCAAAA CCCACCAGTC TTGAAACGCC ATCAACGGGA

5701  AATAACTCGT ACTACTCTTC AGTCAGATCA AGAGGAAATT GACTATGATG ATACCATATC

5761  AGTTGAAATG AAGAAGGAAG ATTTTGACAT TTATGATGAG GATGAAAATC AGAGCCCCCG

5621  CAGCTTTCAA AAGAAAACAC GACACTATTT TATTGCTGCA GTGGAGAGGC TCTGGGATTA

5881  TGGGATGAGT AGCTCCCCAC ATGTTCTAAG AAACAGGGCT CAGAGTGGCA GTGTCCCTCA

5941  GTTCAAGAAA GTTGTTTTCC AGGAATTTAC TGATGGCTCC TTTACTCAGC CCTTATACCG

6001  TGGAGAACTA AATGAACATT TGGGACTCCT GGGGCCATAT ATAAGAGCAG AAGTTGAAGA

6061  TAATATCATG GTAACTTTCA GAAATCAGGC CTCTCGTCCC TATTCCTTCT ATTCTAGCCT

6121  TATTTCTTAT GAGGAAGATC AGAGGCAAGG AGCAGAACCT AGAAAAAACT TTGTCAAGCC

6181  TAATGAAACC AAAACTTACT TTTGGAAAGT GCAACATCAT ATGGCACCCA CTAAAGATGA

6241  GTTTGACTGC AAAGCCTGGG CTTATTTCTC TGATGTTGAC CTGGAAAAAG ATGTGCACTC

6301  AGGCCTGATT GGACCCCTTC TGGTCTGCCA CACTAACACA CTGAACCCTG CTCATGGGAG

6361  ACAAGTGACA GTACAGGAAT TTGCTCTGTT TTTCACCATC TTTGATGAGA CCAAAAGCTG

6421  GTACTTCACT GAAAATATGG AAAGAAACTG CAGGGCTCCC TGCAATATCC AGATGGAAGA

6481  TCCCACTTTT AAAGAGAATT ATCGCTTCCA TGCAATCAAT GGCTACATAA TGGATACACT

6541  ACCTGGCTTA GTAATGGCTC AGGATCAAAG GATTCGATGG TATCTGCTCA GCATGGGCAG

6601  CAATGAAAAC ATCCATTCTA TTCATTTCAG TGGACATGTG TTCACTGTAC GAAAAAAAGA

6661  GGAGTATAAA ATGGCACTGT ACAATCTCTA TCCAGGTGTT TTTGAGACAG TGGAAATGTT

6721  ACCATCCAAA GCTGGAATTT GGCGGGTGGA ATGCCTTATT GGCGAGCATC TACATGCTGG

6781  GATGAGCACA CTTTTTCTGG TGTACAGCAA TAAGTGTCAG ACTCCCCTGG GAATGGCTTC

6841  TGGACACATT AGAGATTTTC AGATTACAGC TTCAGGACAA TATGGACAGT GGGCCCCAAA

6901  GCTGGCCAGA CTTCATTATT CCGGATCAAT CAATGCCTGG AGCACCAAGG AGCCCTTTTC

6961  TTGGATCAAG GTGGATCTGT TGGCACCAAT GATTATTCAC GGCATCAAGA CCCAGGGTGC

7021  CCGTCAGAAG TTCTCCAGCC TCTACATCTC TCAGTTTATC ATCATGTATA GTCTTGATGG
```

TABLE 6-continued

Nucleotide Sequence Encoding
Full-Length FVIII (SEQ ID NO: 5)*

```
7081   GAAGAAGTGG CAGACTTATC GAGGAAATTC CACTGGAACC TTAATGGTCT TCTTTGGCAA

7141   TGTGGATTCA TCTGGGATAA AACACAATAT TTTTAACCCT CCAATTATTG CTCGATACAT

7201   CCGTTTGCAC CCAACTCATT ATAGCATTCG CAGCACTCTT CGCATGGAGT TGATGGGCTG

7261   TGATTTAAAT AGTTGCAGCA TGCCATTGGG AATGGAGAGT AAAGCAATAT CAGATGCACA

7321   GATTACTGCT TCATCCTACT TTACCAATAT GTTTGCCACC TGGTCTCCTT CAAAAGCTCG

7381   ACTTCACCTC CAAGGGAGGA GTAATGCCTG GAGACCTCAG GTGAATAATC CAAAAGAGTG

7441   GCTGCAAGTG GACTTCCAGA AGACAATGAA AGTCACAGGA GTAACTACTC AGGGAGTAAA

7501   ATCTCTGCTT ACCAGCATGT ATGTGAAGGA GTTCCTCATC TCCAGCAGTC AAGATGGCCA

7561   TCAGTGGACT CTCTTTTTTC AGAATGGCAA AGTAAAGGTT TTTCAGGGAA ATCAAGACTC

7621   CTTCACACCT GTGGTGAACT CTCTAGACCC ACCGTTACTG ACTCGCTACC TTCGAATTCA

7681   CCCCCAGAGT TGGGTGCACC AGATTGCCCT GAGGATGGAG GTTCTGGGCT GCGAGGCACA

7741   GGACCTCTAC
```

*The underlined nucleic acids encode a signal peptide.

FVIII polypeptides include full-length FVIII, full-length FVIII minus Met at the N-terminus, mature FVIII (minus the signal sequence), mature FVIII with an additional Met at the N-terminus, and/or FVIII with a full or partial deletion of the B domain. In certain embodiments, FVIII variants include B domain deletions, whether partial or full deletions.

The sequence of native mature human FVIII is presented as SEQ ID NO: 4. A native FVIII protein has the following formula: A1-a1-A2-a2-B-a3-A3-C1-C2, where A1, A2, and A3 are the structurally-related "A domains," B is the "B domain," C1 and C2 are the structurally-related "C domains," and a1, a2 and a3 are acidic spacer regions. Referring to the primary amino acid sequence position in SEQ ID NO:4, the A1 domain of human FVIII extends from Alal to about Arg336, the a1 spacer region extends from about Met337 to about Val374, the A2 domain extends from about Ala375 to about Tyr719, the a2 spacer region extends from about Glu720 to about Arg740, the B domain extends from about Ser741 to about Arg 1648, the a3 spacer region extends from about Glu1649 to about Arg1689, the A3 domain extends from about Ser1690 to about Leu2025, the C1 domain extends from about Gly2026 to about Asn2072, and the C2 domain extends from about Ser2073 to Tyr2332. Other than specific proteolytic cleavage sites, designation of the locations of the boundaries between the domains and regions of FVIII can vary in different literature references. The boundaries noted herein are therefore designated as approximate by use of the term "about."

The human FVIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; and U.S. Pat. No. 4,757,006). The FVIII amino acid sequence was deduced from cDNA as shown in U.S. Pat. No. 4,965,199. In addition, partially or fully B-domain deleted FVIII is shown in U.S. Pat. Nos. 4,994,371 and 4,868,112. In some embodiments, the human FVIII B-domain is replaced with the human Factor V B-domain as shown in U.S. Pat. No. 5,004,803. The cDNA sequence encoding human Factor VIII and amino acid sequence are shown in SEQ ID NOs: 4 and 5, respectively, of US Application Publ. No. 2005/0100990.

The porcine FVIII sequence is published in Toole, J. J., et al., Proc. Natl. Acad. Sci. USA 83:5939-5942 (1986). Further, the complete porcine cDNA sequence obtained from PCR amplification of FVIII sequences from a pig spleen cDNA library has been reported in Healey, J. F., et al., Blood 88:4209-4214 (1996). Hybrid human/porcine FVIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503. U.S. Pat. No. 5,859,204, Lollar, J. S., also discloses the porcine cDNA and deduced amino acid sequences. U.S. Pat. No. 6,458,563 discloses a B-domain-deleted porcine FVIII.

U.S. Pat. No. 5,859,204 to Lollar, J. S. reports functional mutants of FVIII having reduced antigenicity and reduced immunoreactivity. U.S. Pat. No. 6,376,463 to Lollar, J. S. also reports mutants of FVIII having reduced immunoreactivity. US Appl. Publ. No. 2005/0100990 to Saenko et al. reports functional mutations in the A2 domain of FVIII.

In one embodiment, the FVIII (or FVIII portion of a chimeric protein) may be at least 50%, 60%, 70%, 80%, 90%, 95%, 96%, 97%, 98%, 99%, or 100% identical to a FVIII amino acid sequence of amino acids 1 to 1438 of SEQ ID NO: 6 or amino acids 1 to 2332 of SEQ ID NO: 4 (without a signal sequence) or a FVIII amino acid sequence of amino acids 1 to 19 of SEQ ID NO: 3 and 1 to 1438 of SEQ ID NO: 6 or amino acids 1 to 19 of SEQ ID NO: 3 and amino acids 1 to 2332 of SEQ ID NO: 4 (with a signal sequence), wherein the FVIII has a clotting activity, e.g., activates Factor IX as a cofactor to convert Factor X to activated Factor X. The FVIII (or FVIII portion of a chimeric protein) may be identical to a FVIII amino acid sequence of amino acids 1 to 1438 of SEQ ID NO: 6 or amino acids 1 to 2332 of SEQ ID NO: 4 (without a signal sequence). The FVIII may further comprise a signal sequence.

The "B-domain" of FVIII, as used herein, is the same as the B-domain known in the art that is defined by internal amino acid sequence identity and sites of proteolytic cleavage, e.g., residues Ser741-Arg1648 of full-length human FVIII. The other human FVIII domains are defined by the following amino acid residues: A1, residues Alal-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine FVIII are also known in the art. In one embodiment, the B domain of FVIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 7. (BDD FVIII heavy chain is double underlined; B domain is italicized; and BDD FVIII light chain is in plain text). A nucleotide sequence encoding Table 7 (SEQ ID NO: 7) is shown in Table 8.

TABLE 7

| Amino Acid Sequence of B-domain Deleted Factor VIII (BDD FVIII) |
|---|
| BDD FVIII |
| (SEQ ID NO: 6) |
| ATRRYYLGAVELSWDYMQSDLGELPVDARFPPRVPKSFPFNTSVVYKKTLFVEFTDHLFNIAKPRPPWMGLL |
| GPTIQAEVYDTVVITLKNMASHPVSLHAVGVSYWKASEGAEYDDQTSQREKEDDKVFPGGSHTYVWQVLKEN |
| GPMASDPLCLTYSYLSHVDLVKDLNSGLIGALLVCREGSLAKEKTGTLHKFILLFAVFDEGKSWHSETKNSL |
| MQDRDAASARAWPKMHTVNGYVNRSLPGLIGCHRKSVYWHVIGMGTTPEVHSIFLEGHTFLVRNHRQASLEI |
| SPITFLTAQTLLMDLGQFLLFCHISSHQHDGMEAYVKVDSCPEEPQLRMKNNEEAEDYDDDLTDSEMDVVRF |
| DDDNSPSFIQIRSVAKKHPKTWVHYIAAEEEDWDYAPLVLAPDDRSYKSQYLNNGPQRIGRKYKKVRFMAYT |
| DETFKTREAIQHESGILGPLLYGEVGDTLLIIFKNQASRPYNIYPHGITDVRPLYSRRLPKGVKHLKDFPIL |
| PGEIFKYKWTVTVEDGPTKSDPRCLTRYYSSFVNMERDLASGLIGPLLICYKESVDQRGNQIMSDKRNVILF |
| SVFDENRSWYLTENIQRFLPNPAGVQLEDPEFQASNIMHSINGYVFDSLQLSVCLHEVAYWYILSIGAQTDF |
| LSVFFSGYTFKHKMVYEDTLTLFPFSGETVFMSMENPGLWILGCHNSDFRNRGMTALLKVSSCDKNTGDYYE |
| DSYEDISAYLLSKNNAIEPR*SFSQNPPVLKRHQR*EITRTTLQSDQEEIDYDDTISVEMKKEDFDIYDEDENQ |
| SPRSFQKKTRHYFIAAVERLWDYGMSSSPHVLRNRAQSGSVPQFKKVVFQEFTDGSFTQPLYRGELNEHLGL |
| LGPYIRAEVEDNIMVTFRNQASRPYSFYSSLISYEEDQRQGAEPRKNFVKPNETKTYFWKVQHHMAPTKDEF |
| DCKAWAYFSDVDLEKDVHSGLIGPLLVCHTNTLNPAHGRQVTVQEFALFFTIFDETKSWYFTENMERNCRAP |
| CNIQMEDPTFKENYRFHAINGYIMDTLPGLVMAQDQRIRWYLLSMGSNENIHSIHFSGHVFTVRKKEEYKMA |
| LYNLYPGVFETVEMLPSKAGIWRVECLIGEHLHAGMSTLFLVYSNKCQTPLGMASGHIRDFQITASGQYGQW |
| APKLARLHYSGSINAWSTKEPFSWIKVDLLAPMIIHGIKTQGARQKFSSLYISQFIIMYSLDGKKWQTYRGN |
| STGTLMVFFGNVDSSGIKHNIFNPPIIARYIRLHPTHYSIRSTLRMELMGCDLNSCSMPLGMESKAISDAQI |
| TASSYFTNMFATWSPSKARLHLQGRSNAWRPQVNNPKEWLQVDFQKTMKVTGVTTQGVKSLLTSMYVKEFLI |
| SSSQDGHQWTLFFQNGKVKVFQGNQDSFTPVVNSLDPPLLTRYLRIHPQSWVHQIALRMEVLGCEAQDLY |

TABLE 8

| Nucleotide Sequence Encoding BDD FVIII (SEQ ID NO: 7)* | | | |
|---|---|---|---|
| 661 | A TGCAAATAGA | GCTCTCCACC | TGCTTCTTTC |
| 721 | TGTGCCTTTT GCGATTCTGC | TTTAGTGCCA | CCAGAAGATA CTACCTGGGT GCAGTGGAAC |
| 731 | TGTCATGGGA CTATATGCAA | AGTGATCTCG | GTGAGCTGCC TGTGGACGCA AGATTTCCTC |
| 841 | CTAGAGTGCC AAAATCTTTT | CCATTCAACA | CCTCAGTCGT GTACAAAAAG ACTCTGTTTG |
| 901 | TAGAATTCAC GGATCACOTT | TTCAACATCG | CTAAGCCAAG GCCACCCTGG ATGGGTCTGC |
| 961 | TAGGTCCTAC CATCCAGGCT | GAGGTTTATG | ATACAGTGGT CATTACACTT AAGAACATGG |
| 1021 | CTTCCCATCC TGTCAGTCTT | CATGCTGTTG | GTGTATCCTA CTGGAAAGCT TCTGAGGGAG |

TABLE 8-continued

| Nucleotide Sequence Encoding BDD FVIII (SEQ ID NO: 7)* |
| --- |

```
1081   CTGAATATGA TGATCAGACC AGTCAAAGGG AGAAAGAAGA TGATAAAGTC TTCCCTGGTG

1141   GAAGCCATAC ATATGTCTGG CAGGTCCTGA AAGAGAATGG TCCAATGGCC TCTGACCCAC

1201   TGTGCCTTAC CTACTCATAT CTTTCTCATG TGGACCTGGT AAAAGACTTG AATTCAGGCC

1261   TCATTGGAGC CCTACTAGTA TGTAGAGAAG GGAGTCTGGC CAAGGAAAAG ACACAGACCT

1321   TGCACAAATT TATACTACTT TTTGCTGTAT TTGATGAAGG GAAAAGTTGG CACTCAGAAA

1381   CAAAGAACTC CTTGATGCAG GATAGGGATG CTGCATCTGC TCGGGCCTGG CCTAAAATGC

1441   ACACAGTCAA TGGTTATGTA AACAGGTCTC TGCCAGGTCT GATTGGATGC CACAGGAAAT

1501   CAGTCTATTG GCATGTGATT GGAATGGGCA CCACTCCTGA AGTGCACTCA ATATTCCTCG

1561   AAGGTCACAC ATTTCTTGTG AGGAACCATC GCCAGGCGTC CTTGGAAATC TCGCCAATAA

1621   CTTTCCTTAC TGCTCAAACA CTCTTGATGG ACCTTGGACA GTTTCTACTG TTTTGTCATA

1681   TCTCTTCCCA CCAACATGAT GGCATGGAAG CTTATGTCAA AGTAGACAGC TGTCCAGAGG

1741   AACCCCAACT ACGAATGAAA AATAATGAAG AAGCGGAAGA CTATGATGAT GATCTTACTG

1801   ATTCTGAAAT GGATGTGGTC AGGTTTGATG ATGACAACTC TCCTTCCTTT ATCCAAATTC

1861   GCTCAGTTGC CAAGAAGCAT CCTAAAACTT GGGTACATTA CATTGCTGCT GAAGAGGAGG

1921   ACTGGGACTA TGCTCCCTTA GTCCTCGCCC CCGATGACAG AAGTTATAAA AGTCAATATT

1981   TGAACAATGG CCCTCAGCGG ATTGGTAGGA AGTACAAAAA AGTCCGATTT ATGGCATACA

2041   CAGATGAAAC CTTTAAGACT CGTGAAGCTA TTCAGCATGA ATCAGGAATC TTGGGACCTT

2101   TACTTTATGG GGAAGTTGGA GACACACTGT TGATTATATT TAAGAATCAA GCAAGCAGAC

2161   CATATAAaAT CTACCCTCAC GGAATCACTG ATGTCCGTCC TTTGTATTCA AGGAGATTAC

2221   CAAAAGGTGT AAAACATTTG AAGGATTTTC CAATTCTGCC AGGAGAAATA TTCAAATATA

2281   AATGGACAGT GACTGTAGAA GATGGGCCAA CTAAATCAGA TCCTCGGTGC CTGACCCGCT

2341   ATTACTCTAG TTTCGTTAAT ATGGAGAGAG ATCTAGCTTC AGGACTCATT GGCCCTCTCC

2401   TCATCTGCTA CAAAGAATCT GTAGATCAAA GAGGAAACCA GATAATGTCA GACAAGAGGA

2461   ATGTCATCCT GTTTTCTGTA TTTGATGAGA ACCGAAGCTG GTACCTCACA GAGAATATAC

2521   AACGCTTTCT CCCCAATCCA GCTGGAGTGC AGCTTGAGGA TCCAGAGTTC CAAGCCTCCA

2581   ACATCATGCA CAGCATCAAT GGCTATGTTT TTGATAGTTT GCAGTTGTCA GTTTGTTTGC

2641   ATGAGGTGGC ATACTGGTAC ATTCTAAGCA TTGGAGCACA GACTGACTTC CTTTCTGTCT

2701   TCTTCTCTGG ATATACCTTC AAACACAAAA TGGTCTATGA AGACACACTC ACCCTATTCC

2761   CATTCTCAGG AGAAACTGTC TTCATGTCGA TGGAAAACCC AGGTCTATGG ATTCTGGGGT

2821   GCCACAACTC AGACTTTCGG AACAGAGGCA TGACCGCCTT ACTGAAGGTT TCTAGTTGTG

2881   ACAAGAACAC TGGTGATTAT TACGAGGACA GTTATGAAGA TATTTCAGCA TACTTGCTGA

2941   GTAAAAACAA TGCCATTGAA CCAAGAAGCT TCTCTCAAAA CCCACCAGTC TTGAAACGCC

3001   ATCAACGGGA AATAACTCGT ACTACTCTTC AGTCAGATCA AGAGGAAATT GACTATGATG

3061   ATACCATATC AGTTGAAATG AAGAAGGAAG ATTTTGACAT TTATGATGAG GATGAAAATC

3121   AGAGCCCCCG CAGCTTTCAA AAGAAAACAC GACACTATTT TATTGCTGCA GTGGAGAGGC

3181   TCTGGGATTA TGGGATGAGT AGCTCCCCAC ATGTTCTAAG AAACAGGGCT CAGAGTGGCA

3241   GTGTCCCTCA GTTCAAGAAA GTTGTTTTCC AGGAATTTAC TGATGGCTCC TTTACTCAGC

3301   CCTTATACCG TGGAGAACTA AATGAACATT TGGGACTCCT GGGGCCATAT ATAAGAGCAG

3361   AAGTTGAAGA TAATATCATG GTAACTTTCA GAAATCAGGC CTCTCGTCCC TATTCCTTCT
```

TABLE 8-continued

Nucleotide Sequence Encoding
BDD FVIII (SEQ ID NO: 7)*

```
3421   ATTCTAGCCT TATTTCTTAT GAGGAAGATC AGAGGCAAGG AGCAGAACCT AGAAAAAACT

3481   TTGTCAAGCC TAATGAAACC AAAACTTACT TTTGGAAAGT GCAACATCAT ATGGCACCCA

3541   CTAAAGATGA GTTTGACTGC AAAGCCTGGG CTTATTTCTC TGATGTTGAC CTGGAAAAAG

3601   ATGTGCACTC AGGCCTGATT GGACCCCTTC TGGTCTGCCA CACTAACACA CTGAACCCTG

3661   CTCATGGGAG ACAAGTGACA GTACAGGAAT TTGCTCTGTT TTTCACCATC TTTGATGAGA

3721   CCAAAAGCTG GTACTTCACT GAAAATATGG AAAGAAACTG CAGGGCTCCC TGCAATATCC

3781   AGATGGAAGA TCCCACTTTT AAAGAGAATT ATCGCTTCCA TGCAATCAAT GGCTACATAA

3841   TGGATACACT ACCTGGCTTA GTAATGGCTC AGGATCAAAG GATTCGATGG TATCTGCTCA

3901   GCATGGGCAG CAATGAAAAC ATCCATTCTA TTCATTTCAG TGGACATGTG TTCACTGTAC

3961   GAAAAAAAGA GGAGTATAAA ATGGCACTGT ACAATCTCTA TCCAGGTGTT TTTGAGACAG

4021   TGGAAATGTT ACCATCCAAA GCTGGAATTT GGCGGGTGGA ATGCCTTATT GGCGAGCATC

4081   TACATGCTGG GATGAGCACA CTTTTTCTGG TGTACAGCAA TAAGTGTCAG ACTCCCCTGG

4141   GAATGGCTTC TGGACACATT AGAGATTTTC AGATTACAGC TTCAGGACAA TATGGACAGT

4201   GGGCCCCAAA GCTGGCCAGA CTTCATTATT CCGGATCAAT CAATGCCTGG AGCACCAAGG

4261   AGCCCTTTTC TTGGATCAAG GTGGATCTGT TGGCACCAAT GATTATTCAC GGCATCAAGA

4321   CCCAGGGTGC CCGTCAGAAG TTCTCCAGCC TCTACATCTC TCAGTTTATC ATCATGTATA

1381   GTCTTGATGG GAAGAAGTGG CAGACTTATC GAGGAAATTC CACTGGAACC TTAATGGTCT

4441   TCTTTGGCAA TGTGGATTCA TCTGGGATAA AACACAATAT TTTTAACCCT CCAATTATTG

4501   CTCGATACAT CCGTTTGCAC CCAACTCATT ATAGCATTCG CAGCACTCTT CGCATGGAGT

4561   TGATGGGCTG TGATTTAAAT AGTTGCAGCA TGCCATTGGG AATGGAGAGT AAAGCAATAT

4621   CAGATGCACA GATTACTGCT TCATCCTACT TTACCAATAT GTTTGCCACC TGGTCTCCTT

4681   CAAAAGCTCG ACTTCACCTC CAAGGGAGGA GTAATGCCTG GAGACCTCAG GTGAATAATC

4741   CAAAAGAGTG GCTGCAAGTG GACTTCCAGA AGACAATGAA AGTCACAGGA GTAACTACTC

4801   AGGGAGTAAA ATCTCTGCTT ACCAGCATGT ATGTGAAGGA GTTCCTCATC TCCAGCAGTC

4861   AGAATGGCAA TCAGTGGACT CTCTTTTTTC AGAATGGCAA AGTAAAGGTT TTTCAGGGAA

4921   ATCAAGACTC CTTCACACCT GTGGTGAACT CTCTAGACCC ACCGTTACTG ACTCGCTACC

4981   TTCGAATTCA CCCCCAGAGT TGGGTGCACC AGATTGCCCT GAGGATGGAG GTTCTGGGCT

5041   GCGAGGCACA GGACCTCTAC
```

*The underlined nucleic acids encode a signal peptide.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563. In some embodiments, a B-domain-deleted FVIII sequence of the present invention comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of SEQ ID NO: 4, i.e., SEQ ID NO: 6). In some embodiments, a B-domain-deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions may be made in any FVIII sequence.

In some embodiments, the FVIII has a partial B-domain. In some embodiments, the FVIII protein with a partial B-domain is FVIII198. FVIII198 is a partial B-domain containing single chain FVIIIFc molecule-226N6. 226 represents the N-terminus 226 amino acid of the FVIII B-domain, and N6 represents six N-glycosylation sites in the B-domain.

In one embodiment, FVIII is cleaved right after Arginine at amino acid 1648 (in full-length Factor VIII or SEQ ID NO: 4), amino acid 754 (in the 5743/Q1638 B-domain deleted Factor VIII or SEQ ID NO: 6), or the corresponding Arginine residue (in other variants), thereby resulting in a heavy chain and a light chain. In another embodiment, FVIII comprises a heavy chain and a light chain, which are linked or associated by a metal ion-mediated non-covalent bond.

In other embodiments, FVIII is a single chain FVIII that has not been cleaved right after Arginine at amino acid 1648 (in full-length FVIII or SEQ ID NO: 4), amino acid 754 (in the S743/Q1638 B-domain-deleted FVIII or SEQ ID NO: 6), or the corresponding Arginine residue (in other variants). A single chain FVIII may comprise one or more amino acid substitutions. In one embodiment, the amino acid substitution is at a residue corresponding to residue 1648, residue 1645, or both of full-length mature Factor VIII polypeptide (SEQ ID NO: 4) or residue 754, residue 751, or both of SQ BDD Factor VIII (SEQ ID NO: 6). The amino acid substitution can be any amino acids other than Arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine.

FVIII can further be cleaved by thrombin and then activated as FVIIIa, serving as a cofactor for activated Factor IX (FIXa). And the activated FIX together with activated FVIII forms a Xase complex and converts Factor X to activated Factor X (FXa). For activation, FVIII is cleaved by thrombin after three Arginine residues, at amino acids 372, 740, and 1689 (corresponding to amino acids 372, 740, and 795 in the B-domain deleted FVIII sequence), the cleavage generating FVIIIa having the 50 kDa A1, 43 kDa A2, and 73 kDa A3-C1-C2 chains. In one embodiment, the FVIII protein useful for the present invention is non-active FVIII. In another embodiment, the FVIII protein is an activated FVIII.

The protein having FVIII polypeptide linked to or associated with the VWF fragment can comprise a sequence at least 50%, 60%, 70%, 80%, 90%, 95%, 96%, 97%, 98%, 99%, or 100% identical to SEQ ID NO: 4 or 6, wherein the sequence has the FVIII clotting activity, e.g., activating Factor IX as a cofactor to convert Factor X to activated Factor X (FXa).

"Hybrid" or "chimeric" polypeptides and proteins, as used herein, includes a combination of a first polypeptide chain, e.g., the VWF fragment, optionally fused to a first Ig constant region or a portion thereof, with a second polypeptide chain, e.g., a FVIII protein linked to an XTEN sequence, optionally fused to a second Ig constant region or a portion thereof, thereby forming a heterodimer. In one embodiment, the first polypeptide and the second polypeptide in a hybrid are associated with each other via protein-protein interactions, such as charge-charge or hydrophobic interactions. In another embodiment, the first polypeptide and the second polypeptide in a hybrid are associated with each other via disulfide or other covalent bond(s). Hybrids are described, for example, in US 2004/101740 and US 2006/074199. The second polypeptide may be an identical copy of the first polypeptide or a non-identical polypeptide. In one embodiment, the first polypeptide is a FVIII protein(X)-Fc fusion protein, and the second polypeptide is a polypeptide comprising, consisting essentially of, or consisting of an Fc region, wherein the first polypeptide and the second polypeptide are associated with each other. In another embodiment, the first polypeptide comprises a VWF fragment-XTEN-Fc fusion protein, and the second polypeptide comprises FVIII-Fc fusion protein, making the hybrid a heterodimer. In other embodiments, the first polypeptide comprises a VWF fragment-Fc fusion protein, and the second polypeptide comprises FVIII(X)-Fc fusion protein, making the hybrid a heterodimer. In yet other embodiments, the first polypeptide comprises a VWF fragment-XTEN-Fc fusion protein, and the second polypeptide comprises FVIII (X)-Fc fusion protein. The first polypeptide and the second polypeptide can be associated through a covalent bond, e.g., a disulfide bond, between the first Fc region and the second Fc region. The first polypeptide and the second polypeptide can further be associated with each other by binding between the VWF fragment and the FVIII protein.

A FVIII protein useful in the present invention can include FVIII having one or more additional XTEN sequences, which do not affect the FVIII coagulation activity. Such XTEN sequences can be fused to the C-terminus or N-terminus of the FVIII protein or inserted between one or more of the two amino acid residues in the FVIII protein while the insertions do not affect the FVIII coagulation activity or FVIII function. In one embodiment, the insertions improve pharmacokinetic properties of the FVIII protein (e.g., half-life). In another embodiment, the insertions can be multiple insertions, e.g., more than two, three, four, five, six, seven, eight, nine, or ten insertions. Examples of the insertion sites include, but are not limited to, the sites listed in Tables 7, 8, 9, 10, 11, 12, 13, 14, 15 or any combinations thereof.

The FVIII protein linked to one or more XTEN sequences can be represented as FVIII(X), FVIII(X1), $\text{FVIII}_{(a \rightarrow b)}$-X-$\text{FVIII}_{(c \rightarrow d)}$, wherein $\text{FVIII}_{(a \rightarrow b)}$ comprises, consists essentially of, or consists of a first portion of a FVIII protein from amino acid residue "a" to amino acid residue "b"; X or X1 comprises, consists essentially of, or consists of one or more XTEN sequences, $\text{FVIII}_{(c \rightarrow d)}$ comprises, consists essentially of, or consists of a second portion of a FVIII protein from amino acid residue "c" to amino acid residue "d";

a is the N-terminal amino acid residue of the first portion of the FVIII protein, b is the C-terminal amino acid residue of the first portion of the FVIII protein but is also the N-terminal amino acid residue of the two amino acids of an insertion site in which the XTEN sequence is inserted, c is the N-terminal amino acid residue of the second portion of the FVIII protein but is also the C-terminal amino acid residue of the two amino acids of an insertion site in which the XTEN sequence is inserted, and d is the C-terminal amino acid residue of the FVIII protein, and wherein the first portion of the FVIII protein and the second portion of the FVIII protein are not identical to each other and are of sufficient length together such that the FVIII protein has a FVIII coagulation activity.

In one embodiment, the first portion of the FVIII protein and the second portion of the FVIII protein are fragments of SEQ ID NO: 4 [full length mature FVIII sequence] or SEQ ID NO: 6 [B-domain deleted FVIII], e.g., N-terminal portion and C-terminal portion, respectively. In certain embodiments, the first portion of the FVIII protein comprises the A1 domain and the A2 domain of the FVIII protein. The second portion of the FVIII protein comprises the A3 domain, the C1 domain, and optionally the C2 domain. In yet other embodiments, the first portion of the FVIII protein comprises the A1 domain and A2 domain, and the second portion of the FVIII protein comprises a portion of the B domain, the A3 domain, the C1 domain, and optionally the C2 domain. In still other embodiments, the first portion of the FVIII protein comprises the A1 domain, A2 domain, and a portion of the B domain of the FVIII protein, and the second portion of the FVIII protein comprises the A3 domain, the C1 domain, and optionally the C2 domain. In still other embodiments, the first portion of the FVIII protein comprises the A1 domain, A2 domain, and a first portion of the B domain of the FVIII protein. The second portion of the FVIII protein comprises a second portion of the B domain, the A3 domain, the C1 domain, and optionally the C2 domain. In some embodiments, the two amino acids ("b" and "c") can be any one or more of the amino acid residues insertion sites shown in Tables 7, 8, 9, 10, 11, 12, 13, 14, and 15. For example, "b" can be the amino acid residue immediately upstream of the site in which one or more XTEN sequences are inserted or linked, and "c" can be the amino acid residue immediately downstream of the site in which the one or more XTEN sequences are inserted or linked. In some embodiments, "a" is the first mature amino acid sequence of a FVIII protein, and "d" is the last amino acid sequence of a FVIII protein. For example, $\text{FVIII}_{(a \rightarrow b)}$ can be an amino acid sequence at least 70%, 80%, 90%, 95%, 96%, 97%, 98%, 99%, or 100% identical to amino acids 1 to 745 of SEQ ID NO: 6 [B domain deleted FVIII amino acid sequence] or SEQ ID NO: 4 [full length FVIII] and $\text{FVIII}_{(c \rightarrow d)}$ can be amino acids 746 to 1438 of SEQ ID NO: 6 or amino acids 1641 to 2332 of SEQ ID NO: 4, respectively.

In some aspects, the insertion site in the FVIII protein is located in one or more domains of the FVIII protein, which is the N-terminus, the A1 domain, the A2 domain, the A3 domain, the B domain, the C1 domain, the C2 domain, the C-terminus, or two or more combinations thereof or between two domains of the FVIII protein, which are the A1 domain and a1 acidic region, and the a1 acidic region and A2 domain, the A2 domain and a2 acidic region, the a2 acidic region and B domain, the B domain and A3 domain, and the A3 domain and C1 domain, the C1 domain and C2 domain, or any combinations thereof. For example, the insertion sites in which the XTEN sequence can be inserted are selected from the group consisting of the N-terminus and A1 domain, the N-terminus and A2 domain, the N-terminus and A3 domain, the N-terminus and B domain, the N-terminus and C1 domain, the N-terminus and C2 domain, the N-terminus and the C-terminus, the A1 and A2 domains, the A1 and A3 domains, the A1 and B domains, the A1 and C1 domains, the A1 and C2 domains, the A1 domain and the C-terminus, the A2 and A3 domains, the A2 and B domains, the A2 and C1 domains, the A2 and C2 domains, the A2 domain and the C-terminus, the A3 and B domains, the A3 and C1 domains, the A3 and C2 domains, the A3 domain and the C-terminus, the B and C1 domains, the B and C2 domains, the B domain and the C-terminus, the C1 and C2 domains, the C1 and the C-terminus, the C2 domain, and the C-terminus, and two or more combinations thereof. Non-limiting examples of the insertion sites are listed in Tables 7, 8, 9, 10, 11, 12, 13, 14, and 15.

The FVIII protein, in which the XTEN sequence is inserted immediately downstream of one or more amino acids (e.g., one or more XTEN insertion sites) in the FVIII protein or linked at the C-terminus or the N-terminus, retains the FVIII activity after linkage to or insertion by the XTEN sequence. The XTEN sequence can be inserted in the FVIII protein once or more than once, twice, three times, four times, five times, or six times such that the insertions do not affect the FVIII activity (i.e., the FVIII protein still retains the coagulation property).

The FVIII protein useful in the present invention can be linked to one or more XTEN polypeptides at the N-terminus or C-terminus of the FVIII protein by an optional linker or inserted immediately downstream of one or more amino acids (e.g., one or more XTEN insertion sites) in the FVIII protein by one or more optional linkers. In one embodiment, the two amino acid residues in which the XTEN sequence is inserted or the amino acid residue to which the XTEN sequence is linked correspond to the two or one amino acid residues of SEQ ID NO: 4 [full length mature FVIII] selected from the group consisting of the residues in Table 9, Table 10, Table 11, and Table 12 and any combinations thereof.

In other embodiments, at least one XTEN sequence is inserted in any one or more XTEN insertion sites disclosed herein or any combinations thereof. In one aspect, at least one XTEN sequence is inserted in one or more XTEN insertion sites disclosed in one or more amino acids disclosed in Table 9.

TABLE 9

Exemplary XTEN Insertion Sites

| No. | XTEN Insertion Point* | Insertion Residue | FVIII BDD Downstream Sequence | FVIII Domain |
|---|---|---|---|---|
| 1 | 0 | (N-terminus) | ATR | A1 |
| 2 | 3 | R | RYY | A1 |
| 3 | 17 | M | QSD | A1 |
| 4 | 18 | Q | SDL | A1 |
| 5 | 22 | G | ELP | A1 |
| 6 | 24 | L | PVD | A1 |
| 7 | 26 | V | DAR | A1 |
| 8 | 28 | A | RFP | A1 |
| 9 | 32 | P | RVP | A1 |
| 10 | 38 | F | PFN | A1 |
| 11 | 40 | F | NTS | A1 |
| 12 | 41 | N | TSV | A1 |
| 13 | 60 | N | IAK | A1 |
| 14 | 61 | I | AKP | A1 |
| 15 | 65 | R | PPW | A1 |
| 16 | 81 | Y | DTV | A1 |
| 17 | 111 | G | AEY | A1 |
| 18 | 116 | D | QTS | A1 |
| 19 | 119 | S | QRE | A1 |
| 20 | 120 | Q | REK | A1 |
| 21 | 128 | V | FPG | A1 |
| 22 | 129 | F | PGG | A1 |
| 23 | 130 | P | GGS | A1 |
| 24 | 182 | G | SLA | A1 |
| 25 | 185 | A | KEK | A1 |
| 26 | 188 | K | TQT | A1 |
| 27 | 205 | G | KSW | A1 |
| 28 | 210 | S | ETK | A1 |
| 29 | 211 | E | TKN | A1 |
| 30 | 216 | L | MQD | A1 |
| 31 | 220 | R | DAA | A1 |
| 32 | 222 | A | ASA | A1 |
| 33 | 223 | A | SAR | A1 |
| 34 | 224 | S | ARA | A1 |
| 35 | 230 | K | MHT | A1 |
| 36 | 243 | P | GLI | A1 |
| 37 | 244 | G | LIG | A1 |
| 38 | 250 | R | KSV | A1 |
| 39 | 318 | D | GME | A1 |
| 40 | 333 | P | QLR | A1 |
| 42 | 334 | Q | LRM | A1 |
| 43 | 336 | R | MKN | a1 |
| 44 | 339 | N | NEE | a1 |
| 45 | 345 | D | YDD | a1 |
| 46 | 357 | V | VRF | a1 |
| 47 | 367 | S | FIQ | a1 |
| 48 | 370 | S | RPY | a1 |
| 49 | 375 | A | KKH | A2 |
| 50 | 376 | K | KHP | A2 |
| 51 | 378 | H | PKT | A2 |
| 52 | 399 | V | LAP | A2 |
| 53 | 403 | D | DRS | A2 |
| 54 | 405 | R | SYK | A2 |
| 55 | 409 | S | QYL | A2 |
| 56 | 416 | P | QRI | A2 |
| 57 | 434 | E | TFK | A2 |
| 58 | 438 | T | REA | A2 |
| 59 | 441 | A | IQH | A2 |
| 60 | 442 | I | QHE | A2 |
| 61 | 463 | I | IFK | A2 |
| 62 | 487 | Y | SRR | A2 |
| 63 | 490 | R | LPK | A2 |
| 64 | 492 | P | KGV | A2 |
| 65 | 493 | K | GVK | A2 |
| 66 | 494 | G | VKH | A2 |
| 67 | 500 | D | FPI | A2 |
| 68 | 506 | G | EIF | A2 |
| 69 | 518 | E | DGP | A2 |
| 70 | 556 | K | ESV | A2 |

TABLE 9-continued

Exemplary XTEN Insertion Sites

| No. | XTEN Insertion Point* | Insertion Residue | FVIII BDD Downstream Sequence | FVIII Domain |
|---|---|---|---|---|
| 71 | 565 | Q | IMS | A2 |
| 72 | 566 | I | MSD | A2 |
| 73 | 598 | P | AGV | A2 |
| 74 | 599 | A | GVQ | A2 |
| 75 | 603 | L | EDP | A2 |
| 76 | 616 | S | ING | A2 |
| 77 | 686 | G | LWI | A2 |
| 78 | 713 | K | NTG | A2 |
| 79 | 719 | Y | EDS | A2 |
| 80 | 730 | L | LSK | A2 |
| 81 | 733 | K | NNA | A2 |
| 82 | 745 | N | PPV** | B |
| 83 | 1640 | P | PVL | B |
| 84 | 1652 | R | TTL | B |
| 85 | 1656 | Q | SDQ | A3 |
| 86 | 1685 | N | QSP | A3 |
| 87 | 1711 | M | SSS | A3 |
| 88 | 1713 | S | SPH | A3 |
| 89 | 1720 | N | RAQ | A3 |
| 90 | 1724 | S | GSV | A3 |
| 91 | 1725 | G | SVP | A3 |
| 92 | 1726 | S | VPQ | A3 |
| 93 | 1741 | G | SFT | A3 |
| 94 | 1744 | T | QPL | A3 |
| 95 | 1749 | R | GEL | A3 |
| 96 | 1773 | V | TFR | A3 |
| 97 | 1792 | Y | EED | A3 |
| 98 | 1793 | E | EDQ | A3 |
| 99 | 1796 | Q | RQG | A3 |
| 100 | 1798 | Q | GAE | A3 |
| 101 | 1799 | G | AEP | A3 |
| 102 | 1802 | P | RKN | A3 |
| 103 | 1803 | R | KNF | A3 |
| 104 | 1807 | V | KPN | A3 |
| 105 | 1808 | K | PNE | A3 |
| 106 | 1827 | K | DEF | A3 |
| 107 | 1844 | E | KDV | A3 |
| 108 | 1861 | N | TLN | A3 |
| 109 | 1863 | L | NPA | A3 |
| 110 | 1896 | E | RNC | A3 |
| 111 | 1900 | R | APC | A3 |
| 112 | 1904 | N | IQM | A3 |
| 113 | 1905 | I | QME | A3 |
| 114 | 1910 | P | TFK | A3 |
| 115 | 1920 | A | ING | A3 |
| 116 | 1937 | D | QRI | A3 |
| 117 | 1981 | G | VFE | A3 |
| 118 | 2019 | N | KCQ | A3 |
| 119 | 2020 | K | CQT | C1 |
| 120 | 2044 | G | QWA | C1 |
| 121 | 2068 | F | SWI | C1 |
| 122 | 2073 | V | DLL | C1 |
| 123 | 2090 | R | QKF | C1 |
| 124 | 2092 | K | FSS | C1 |
| 125 | 2093 | F | SSL | C1 |
| 126 | 2111 | K | WQT | C1 |
| 127 | 2115 | Y | RGN | C1 |
| 128 | 2120 | T | GTL | C1 |
| 129 | 2125 | V | FFG | C1 |
| 130 | 2171 | L | NSC | C1 |
| 131 | 2173 | S | CSM | C2 |
| 132 | 2188 | A | QIT | C2 |
| 133 | 2223 | V | NNP | C2 |

TABLE 9-continued

| Exemplary XTEN Insertion Sites | | | | |
|---|---|---|---|---|
| No. | XTEN Insertion Point* | Insertion Residue | FVIII BDD Downstream Sequence | FVIII Domain |
| 134 | 2224 | N | NPK | C2 |
| 135 | 2227 | K | EWL | C2 |
| 136 | 2268 | G | HQW | C2 |
| 137 | 2277 | N | GKV | C2 |
| 138 | 2278 | G | KVK | C2 |
| 139 | 2290 | F | TPV | C2 |
| 140 | 2332 | Y | C terminus of FVIII | CT |

*Indicates an insertion point for XTEN based on the amino acid number of mature full-length human FVIII, wherein the insertion could be either on the N- or C-terminal side of the indicated amino acid.

In some embodiments, one or more XTEN sequences are inserted within about six amino acids up or down from amino acids 32, 220, 224, 336, 339, 399, 416, 603, 1656, 1711, 1725, 1905, or 1910, corresponding to SEQ ID NO: 4 or any combinations thereof.

TABLE 10

| Exemplary XTEN Insertion Ranges | | | | |
|---|---|---|---|---|
| No. | XTEN Insertion Point | Insertion Residue | FVIII BDD Downstream Sequence | FVIII Domain | Distance from insertion residue* |
| 9 | 32 | P | RVP | A1 | −3, +6 |
| 31 | 220 | R | DAA | A1 | — |
| 34 | 224 | S | ARA | A1 | +5 |
| 43 | 336 | R | MKN | a1 | −1, +6 |
| 44 | 339 | N | NEE | a1 | −4, +5 |
| 52 | 399 | V | LAP | A2 | −6, +3 |
| 56 | 416 | P | QRI | A2 | +6 |
| 75 | 603 | L | EDP | A2 | 6, +6 |
| 85 | 1656 | Q | SDQ | B | −3, +6 |
| 87 | 1711 | M | SSS | A3 | −6, +1 |
| 91 | 1725 | G | SVP | A3 | +6 |
| 113 | 1905 | I | QME | A3 | +6 |
| 114 | 1910 | P | TFK | A3 | −5, +6 |

*Distance from insertion residue refers to the relative number of amino acids away from the N-terminus (negative numbers) or C-terminus (positive numbers) of the designated insertion residue (residue "0") where an insertion may be made. The designation "+x" refers to an insertion site which is x amino acids away on the C-terminal side of the designated insertion residue. For example, "−1, 0, +1 or +2" indicates that the insertion is made at the N-terminus or C-terminus of amino acid denoted −1, 0, +1 or +2.

In other embodiments, one or more XTEN sequences are inserted immediately down stream of one or more amino acids corresponding to the full-length mature human FVIII selected from the group consisting of one or more insertion sites in Table 11.

TABLE 11

| Exemplary XTEN Insertion Sites or Ranges | | | |
|---|---|---|---|
| No. | XTEN Insertion Point Range* | First Insertion Residue | FVIII Domain |
| 3 | 18-32 | Q | A1 |
| 8 | 40 | F | A1 |
| 18 | 211-224 | E | A1 |
| 27 | 336-403 | R | A1, A2 |
| 43 | 599 | A | A2 |
| 47 | 745-1640 | N | B |
| 50 | 1656-1728 | Q | B, a3, A3 |
| 57 | 1796-1804 | R | A3 |
| 65 | 1900-1912 | R | A3 |
| 81 | 2171-2332 | L | C1, C2 |

*indicates range of insertion sites numbered relative to the amino acid number of mature human FVIII In yet other embodiments, one or more XTENs are inserted in the B domain of FVIII. In one example, an XTEN is inserted between amino acids 740 and 1640 corresponding to SEQ ID NO: 4, wherein the FVIII sequence between amino acids 740 and 1640 is optionally not present. In another example, an XTEN is inserted between amino acids 741 and 1690 corresponding to SEQ ID NO: 4, wherein the FVIII sequence between amino acids 740 and 1690 is optionally not present. In other examples, an XTEN is inserted between amino acids 741 and 1648 corresponding to SEQ ID NO: 4, wherein the FVIII sequence between amino acids 741 and 1648 is optionally not present. In yet other examples, an XTEN is inserted between amino acids 743 and 1638 corresponding to SEQ ID NO: 4, wherein the FVIII sequence between amino acids 743 and 1638 is optionally not present. In still other examples, an XTEN is inserted between amino acids 745 and 1656 corresponding to SEQ ID NO: 4, wherein the FVIII sequence between amino acids 745 and 1656 is optionally not present. In some examples, an XTEN is inserted between amino acids 745 and 1657 corresponding to SEQ ID NO: 4, wherein the FVIII sequence between amino acids 745 and 1657 is optionally not present. In certain examples, an XTEN is inserted between amino acids 745 and 1667 corresponding to SEQ ID NO: 4, wherein the FVIII sequence between amino acids 745 and 1667 is optionally not present. In still other examples, an XTEN is inserted between amino acids 745 and 1686 corresponding to SEQ ID NO: 4, wherein the FVIII sequence between amino acids 745 and 1686 is optionally not present. In some other examples, an XTEN is inserted between amino acids 747 and 1642 corresponding to SEQ ID NO: 4, wherein the FVIII sequence between amino acids 747 and 1642 is optionally not present. In still other examples, an XTEN is inserted between amino acids 751 and 1667 corresponding to SEQ ID NO: 4, wherein the FVIII sequence between amino acids 751 and 1667 is optionally not present.

In some embodiments, one or more XTENs are inserted in one or more amino acids immediately downstream of an amino acid of an insertion site selected from the group consisting of the amino acid residues in Table 12.

TABLE 12

FVIII XTEN insertion sites and construct designations

| Construct Number | Domain | Up-stream Residue No.* | Down-stream Residue No.* | Up-stream Sequence | Down-stream Sequence |
|---|---|---|---|---|---|
| F8X-1 | A1 | 3 | 4 | ATR | RYY |
| F8X-2 | A1 | 18 | 19 | YMQ | SDL |
| F8X-3 | A1 | 22 | 23 | DLG | ELP |
| F8X-4 | A1 | 26 | 27 | LPV | DAR |
| F8X-5 | A1 | 40 | 41 | FPF | NTS |
| F8X-6 | A1 | 60 | 61 | LFN | IAK |
| F8X-7 | A1 | 116 | 117 | YDD | QTS |
| F8X-8 | A1 | 130 | 131 | VFP | GGS |
| F8X-9 | A1 | 188 | 189 | KEK | TQT |
| F8X-10 | A1 | 216 | 217 | NSL | MQD |
| F8X-11 | A1 | 230 | 231 | WPK | MHT |
| F8X-12 | A1 | 333 | 334 | EEP | QLR |
| F8X-13 | A2 | 375 | 376 | SVA | KKH |
| F8X-14 | A2 | 403 | 404 | APD | DRS |
| F8X-15 | A2 | 442 | 443 | EAI | QHE |
| F8X-16 | A2 | 490 | 491 | RRL | PKG |
| F8X-17 | A2 | 518 | 519 | TVE | DGP |
| F8X-18 | A2 | 599 | 600 | NPA | GVQ |
| F8X-19 | A2 | 713 | 714 | CDK | NTG |
| F8X-20 | BD | 745 | 746 | SQN | PPV |
| F8X-21 | BD | 745 | 746 | SQN | PPV |
| F8X-22 | BD** | 745 | 746 | SQN | PPV |
| F8X-23 | A3 | 1720 | 1721 | APT | KDE |
| F8X-24 | A3 | 1796 | 1797 | EDQ | ROG |
| F8X-25 | A3 | 1802 | 1803 | AEP | RKN |
| F8X-26 | A3 | 1827 | 1828 | PTK | DEF |
| F8X-27 | A3 | 1861 | 1862 | HTN | TLN |
| F8X-28 | A3 | 1896 | 1897 | NME | RNC |
| F8X-29 | A3 | 1900 | 1901 | NCR | APC |
| F8X-30 | A3 | 1904 | 1905 | PCN | IQM |
| F8X-31 | A3 | 1937 | 1938 | AQD | QRI |
| F8X-32 | C1 | 2019 | 2020 | YSN | KCQ |
| F8X-33 | C1 | 2068 | 2069 | EPF | SWI |
| F8X-34 | C1 | 2111 | 2112 | GKK | WQT |
| F8X-35 | C1 | 2120 | 2121 | NST | GTL |
| F8X-36 | C2 | 2171 | 2172 | CDL | NSC |
| F8X-37 | C2 | 2188 | 2189 | SDA | QIT |
| F8X-38 | C2 | 2227 | 2228 | NPK | EWL |
| F8X-39 | C2 | 2277 | 2278 | FON | GKV |
| F8X-40 | CT | 2332 | NA | DLY | NA |
| F8X-41 | CT | 2332 | NA | DLY | NA |
| F8X-42 | A1 | 3 | 4 | ATR | ATR |
| PSD0001 | A2 | 403 | 404 | | |
| pSD0002 | A2 | 599 | 600 | | |
| pSD0021 | N-term | 0 | 1 | | |
| pSD0022 | A1 | 32 | 33 | | |
| pSD0023 | A1 | 65 | 66 | | |
| pSD0024 | A1 | 81 | 82 | | |
| pSD0025 | A1 | 119 | 120 | | |
| pSD0026 | A1 | 211 | 212 | | |
| pSD0027 | A1 | 220 | 221 | | |
| pSD0028 | A1 | 224 | 225 | | |
| pSD0029 | A1 | 336 | 337 | | |
| pSD0030 | A1 | 339 | 340 | | |
| pSD0031 | A2 | 378 | 379 | | |
| pSD0032 | A2 | 399 | 400 | | |
| pSD0033 | A2 | 409 | 410 | | |
| pSD0034 | A2 | 416 | 417 | | |
| pSD0035 | A2 | 487 | 488 | | |
| pSD0036 | A2 | 494 | 495 | | |
| pSD0037 | A2 | 500 | 501 | | |
| pSD0038 | A2 | 603 | 604 | | |
| pSD0039 | A3 | 1656 | 1657 | | |
| pSD0040 | A3 | 1711 | 1712 | | |
| pSD0041 | A3 | 1725 | 1726 | | |
| pSD0042 | A3 | 1749 | 1750 | | |
| pSD0043 | A3 | 1905 | 1906 | | |
| pSD0044 | A3 | 1910 | 1911 | | |
| pDS0062 | A3 | 1900 | 1901 | | |

*Indicates the amino acid number of the mature FVIII protein

In one embodiment, the one or more XTEN insertion sites are located within one or more surface-exposed, flexible loop structure of the FVIII protein (e.g., a permissive loop). For example, at least one XTEN sequence can be inserted in each FVIII "A" domain comprising at least two "permissive loops" into which at least one XTEN polypeptide can be inserted without eliminating procoagulant activity of the recombinant protein, or the ability of the recombinant proteins to be expressed in vivo or in vitro in a host cell. The permissive loops are regions that allow insertion of at least one XTEN sequence with, among other attributes, high surface or solvent exposure and high conformational flexibility. The A1 domain comprises a permissive loop-1 (A1-1) region and a permissive loop-2 (A1-2) region, the A2 domain comprises a permissive loop-1 (A2-1) region and a permissive loop-2 (A2-2) region, the A3 domain comprises a permissive loop-1 (A3-1) region and a permissive loop-2 (A3-2) region.

In one aspect, a first permissive loop in the FVIII A1 domain (A1-1) is located between beta strand 1 and beta strand 2, and a second permissive loop in the FVIII A2 domain (A1-2) is located between beta strand 11 and beta strand 12. A first permissive loop in the FVIII A2 domain (A2-1) is located between beta strand 22 and beta strand 23, and a second permissive loop in the FVIII A2 domain (A2-2) is located between beta strand 32 and beta strand 33. A first permissive loop in the FVIII A3 domain (A3-1) is located between beta strand 38 and beta strand 39, and a second permissive loop in the FVIII A3 (A3-2) is located between beta strand 45 and beta strand 46. In certain aspects, the surface-exposed, flexible loop structure comprising A1-1 corresponds to a region in native mature human FVIII from about amino acid 15 to about amino acid 45 of SEQ ID NO: 4, e.g., from about amino acid 18 to about amino acid 41 of SEQ ID NO: 4. In other aspects, the surface-exposed, flexible loop structure comprising A1-2 corresponds to a region in native mature human FVIII from about amino acid 201 to about amino acid 232 of SEQ ID NO: 4, e.g., from about amino acid 218 to about amino acid 229 of SEQ ID NO: 4. In yet other aspects, the surface-exposed, flexible loop structure comprising A2-1 corresponds to a region in native mature human FVIII from about amino acid 395 to about amino acid 421 of SEQ ID NO: 4, e.g. from about amino acid 397 to about amino acid 418 of SEQ ID NO: 4. In still other embodiments, the surface-exposed, flexible loop structure comprising A2-2 corresponds to a region in native mature human FVIII from about amino acid 577 to about amino acid 635 of SEQ ID NO: 4, e.g., from about amino acid 595 to about amino acid 607 of SEQ ID NO: 4. In certain aspects the surface-exposed, flexible loop structure comprising A3-1 corresponds to a region in native mature human FVIII from about amino acid 1705 to about amino acid 1732 of SEQ ID NO: 4, e.g., from about amino acid 1711 to about amino acid 1725 of SEQ ID NO: 4. In yet other aspects, the surface-exposed, flexible loop structure comprising A3-2 corresponds to a region in native mature human FVIII from about amino acid 1884 to about amino acid 1917 of SEQ ID NO: 4, e.g., from about amino acid 1899 to about amino acid 1911 of SEQ ID NO: 4.

In another embodiment, the one or more amino acids in which at least one XTEN sequence is inserted is located within a3 domain, e.g., amino acids 1649 to 1689, corresponding to full-length mature FVIII polypeptide. In a particular embodiment, an XTEN sequence is inserted between amino acids 1656 and 1657 of SEQ ID NO: 4 (full-length mature FVIII). In a specific embodiment, a FVIII protein comprising an XTEN sequence inserted immediately downstream of amino acid 1656 corresponding to SEQ ID NO: 4 further comprises a deletion from amino acid 745 to amino acid 1656 corresponding to SEQ ID NO: 4.

In some embodiments, the one or more insertion sites for one or more XTEN insertions are immediately downstream of one or more amino acids selected from the group consisting of:

| | |
|---|---|
| (1) | amino acid 3, |
| (2) | amino acid 18, |
| (3) | amino acid 22, |
| (4) | amino acid 26, |
| (5) | amino acid 32, |
| (6) | amino acid 40, |
| (7) | amino acid 60, |
| (8) | amino acid 65, |
| (9) | amino acid 81, |
| (10) | amino acid 116, |
| (11) | amino acid 119, |
| (12) | amino acid 130, |
| (13) | amino acid 188, |
| (14) | amino acid 211, |
| (15) | amino acid 216, |
| (16) | amino acid 220, |
| (17) | amino acid 224, |
| (18) | amino acid 230, |
| (19) | amino acid 333, |
| (20) | amino acid 336, |
| (21) | amino acid 339, |
| (22) | amino acid 375, |
| (23) | amino acid 399, |
| (24) | amino acid 403, |
| (25) | amino acid 409, |
| (26) | amino acid 416, |
| (26) | amino acid 442, |
| (28) | amino acid 487, |
| (29) | amino acid 490, |
| (30) | amino acid 494, |
| (31) | amino acid 500, |
| (32) | amino acid 518, |
| (33) | amino acid 599, |
| (34) | amino acid 603, |
| (35) | amino acid 713, |
| (36) | amino acid 745, |
| (37) | amino acid 1656, |
| (38) | amino acid 1711, |
| (39) | amino acid 1720, |
| (40) | amino acid 1725, |
| (41) | amino acid 1749, |
| (42) | amino acid 1796, |
| (43) | amino acid 1802, |
| (44) | amino acid 1827, |
| (45) | amino acid 1861, |
| (46) | amino acid 1896, |
| (47) | amino acid 1900, |
| (48) | amino acid 1904, |
| (49) | amino acid 1905, |
| (50) | amino acid 1910, |
| (51) | amino acid 1937, |
| (52) | amino acid 2019, |
| (53) | amino acid 2068, |
| (54) | amino acid 2111, |
| (55) | amino acid 2120, |
| (56) | amino acid 2171, |
| (57) | amino acid 2188, |
| (58) | amino acid 2227, |
| (59) | amino acid 2277, and |
| (60) | two or more combinations thereof. |

In one embodiment, a FVIII protein useful for the invention comprises two XTEN sequences, a first XTEN sequence inserted into a first XTEN insertion site and a second XTEN inserted into a second XTEN insertion site. Non-limiting examples of the first XTEN insertion site and the second XTEN insertion site are listed in Table 13.

TABLE 13

| Exemplary Insertion Sites for Two XTENs | | | |
|---|---|---|---|
| Insertion 1 | | Insertion 2 | |
| Insertion Site | Domain | Insertion Site | Domain |
| 745 | B | 2332 | CT |
| 26 | A1 | 403 | A2 |
| 40 | A1 | 403 | A2 |
| 18 | A1 | 403 | A2 |
| 26 | A1 | 599 | A2 |
| 40 | A1 | 599 | A2 |
| 18 | A1 | 599 | A2 |
| 1720 | A3 | 1900 | A3 |
| 1725 | A3 | 1900 | A3 |
| 1711 | A3 | 1905 | A3 |
| 1720 | A3 | 1905 | A3 |
| 1725 | A3 | 1905 | A3 |
| 1656 | A3 | 26 | A1 |
| 1656 | A3 | 18 | A1 |
| 1656 | A3 | 40 | A1 |
| 1656 | A3 | 399 | A2 |
| 1656 | A3 | 403 | A2 |
| 1656 | A3 | 1725 | A3 |
| 1656 | A3 | 1720 | A3 |
| 1900 | A3 | 18 | A1 |
| 1900 | A3 | 26 | A1 |
| 1900 | A3 | 40 | A1 |
| 1905 | A3 | 18 | A1 |
| 1905 | A3 | 40 | A1 |
| 1905 | A3 | 26 | A1 |
| 1910 | A3 | 26 | A1 |
| 18 | A1 | 399 | A2 |
| 26 | A1 | 399 | A2 |
| 40 | A1 | 399 | A2 |
| 18 | A1 | 403 | A2 |
| 1656 | A3 | 1900 | A3 |
| 1656 | A3 | 1905 | A3 |
| 1711 | A3 | 40 | A1 |
| 1711 | A3 | 26 | A1 |
| 1720 | A3 | 26 | A1 |
| 1720 | A3 | 40 | A1 |
| 1720 | A3 | 18 | A1 |
| 1725 | A3 | 26 | A1 |
| 1725 | A3 | 40 | A1 |
| 1725 | A3 | 18 | A1 |
| 1720 | A3 | 403 | A2 |
| 1720 | A3 | 399 | A2 |
| 1711 | A3 | 403 | A2 |
| 1720 | A3 | 403 | A2 |
| 1725 | A3 | 403 | A2 |
| 1725 | A3 | 399 | A2 |
| 1711 | A3 | 403 | A2 |
| 1900 | A3 | 399 | A2 |
| 1900 | A3 | 403 | A2 |
| 1905 | A3 | 403 | A2 |
| 1905 | A3 | 399 | A2 |
| 1910 | A3 | 403 | A2 |

The two XTENs inserted or linked to the FVIII protein can be identical or different. In some embodiments, a FVIII protein useful for the invention comprises two XTEN sequences inserted in the FVIII protein, a first XTEN sequence inserted immediately downstream of amino acid 745 corresponding to SEQ ID NO: 4, and a second XTEN sequence inserted immediately downstream of amino acid 2332 corresponding to SEQ ID NO: 4 (the C-terminus). In other embodiments, the first XTEN sequence is inserted immediately downstream of amino acid 18, 26, 40, 1656, or 1720 corresponding to SEQ ID NO: 4, and a second XTEN sequence inserted immediately downstream of amino acid 403 corresponding to SEQ ID NO: 4. In yet other embodiments, the first XTEN sequence is inserted immediately downstream of amino acid 18, 26, or 40 corresponding to SEQ ID NO: 4, and a second XTEN sequence inserted immediately downstream of amino acid 599 corresponding to SEQ ID NO: 4. In still other embodiments, the first XTEN sequence is inserted immediately downstream of amino acid 1656 corresponding to SEQ ID NO: 4, and a second XTEN sequence inserted immediately downstream of amino acid 18, 26, 40, 399, 403, 1725, 1720, 1900, 1905, or 2332 corresponding to SEQ ID NO: 4. In certain embodiments, the first XTEN sequence is inserted immediately downstream of amino acid 1900 corresponding to SEQ ID NO: 4, and a second XTEN sequence inserted immediately downstream of amino acid 18, 26, or 40 corresponding to SEQ ID NO: 4. In some embodiments, the first XTEN sequence is inserted immediately downstream of amino acid 18, 26, or 40 corresponding to SEQ ID NO: 4, and a second XTEN sequence inserted immediately downstream of amino acid 399 corresponding to SEQ ID NO: 4. In other embodiments, the first XTEN sequence is inserted immediately downstream of amino acid 1720 corresponding to SEQ ID NO: 4, and a second XTEN sequence inserted immediately downstream of amino acid 18, 26, or 40 corresponding to SEQ ID NO: 4. In still other embodiments, the first XTEN sequence is inserted immediately downstream of amino acid 1720 corresponding to SEQ ID NO: 4, and a second XTEN sequence inserted immediately downstream of amino acid 18 corresponding to SEQ ID NO: 4. In a particular embodiment, the FVIII protein comprising two XTEN sequences, a first XTEN sequence inserted immediately downstream of amino acid 745 corresponding to SEQ ID NO: 4 and a second XTEN sequence inserted immediately downstream of amino acid 2332 corresponding to SEQ ID NO: 4, wherein the FVIII protein further has a deletion from amino acid 745 corresponding to SEQ ID NO: 4 to amino acid 1685 corresponding to SEQ ID NO: 4, a mutation or substitution at amino acid 1680 corresponding to SEQ ID NO: 4, e.g., Y1680F, a mutation or substitution at amino acid 1648 corresponding to SEQ ID NO: 4, e.g., R1648A, or at least two mutations or substitutions at amino acid 1648 corresponding to SEQ ID NO: 4, e.g., R1648A, and amino acid 1680 corresponding to SEQ ID NO: 4, e.g., Y1680F. In a specific embodiment, the FVIII protein comprises two XTEN sequences, a first XTEN inserted immediately downstream of amino acid 1656 corresponding to SEQ ID NO: 4 and a second XTEN sequence inserted immediately downstream of amino acid 2332 of SEQ ID NO: 4, wherein the FVIII protein further has a deletion from amino acid 745 to amino acid 1656 corresponding to SEQ ID NO: 4.

In certain embodiments, a FVIII protein comprises three XTEN sequences, a first XTEN sequence inserted into a first XTEN insertion site, a second XTEN sequence inserted into a second XTEN sequence, and a third XTEN sequence inserted into a third XTEN insertion site. The first, second, or third XTEN sequences can be identical or different. The first, second, and third insertion sites can be selected from the group of any one of the insertion sites disclosed herein. In some embodiments, the FVIII protein comprising three XTEN sequences can further comprise a mutation or substitution, e.g., amino acid 1648 corresponding to SEQ ID NO: 4, e.g., R1648A. For example, non-limiting examples of the first, second, and third XTEN insertion sites are listed in Table 14.

TABLE 14

| Exemplary Insertion Sites for Three XTENs | | | | | |
|---|---|---|---|---|---|
| Insertion 1 | | Insertion 2 | | Insertion 3 | |
| Insertion Site | Domain | Insertion Site | Domain | Insertion Site | Domain |
| 26 | A1 | 403 | A2 | 1656 | A3 |
| 26 | A1 | 403 | A2 | 1720 | A3 |
| 26 | A1 | 403 | A2 | 1900 | A3 |
| 26 | A1 | 1656 | A3 | 1720 | A3 |
| 26 | A1 | 1656 | A3 | 1900 | A3 |
| 26 | A1 | 1720 | A3 | 1900 | A3 |
| 403 | A2 | 1656 | A3 | 1720 | A3 |
| 403 | A2 | 1656 | A3 | 1900 | A3 |
| 403 | A2 | 1720 | A3 | 1900 | A3 |
| 1656 | A3 | 1720 | A3 | 1900 | A3 |
| 745 | B | 1900 | | 2332 | |
| 18 | A1 | 745 | B | 2332 | CT |
| 26 | A1 | 745 | B | 2332 | CT |
| 40 | A1 | 745 | B | 2332 | CT |
| 18 | A1 | 745 | B | 2332 | CT |
| 40 | A1 | 745 | B | 2332 | CT |
| 403 | A2 | 745 | B | 2332 | CT |
| 399 | A2 | 745 | B | 2332 | CT |
| 1725 | A3 | 745 | B | 2332 | CT |
| 1720 | A3 | 745 | B | 2332 | CT |
| 1711 | A3 | 745 | B | 2332 | CT |
| 1900 | A3 | 745 | B | 2332 | CT |
| 1905 | A3 | 745 | B | 2332 | CT |
| 1910 | A3 | 745 | B | 2332 | CT |

In some embodiments, a FVIII protein comprises three XTEN sequences, a first XTEN sequence inserted immediately downstream of amino acid 26 corresponding to SEQ ID NO: 4, a second XTEN sequence inserted downstream of amino acid 403 corresponding to SEQ ID NO: 4, and a third XTEN sequence inserted downstream of amino acid 1656, 1720, or 1900 corresponding to SEQ ID NO: 4. In other embodiments, the first XTEN sequence is inserted immediately downstream of amino acid 26 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In yet other embodiments, the first XTEN sequence is inserted immediately downstream of amino acid 26 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In still other embodiments, the first XTEN sequence is inserted immediately downstream of amino acid 403 corresponding to SEQ ID NO: 4, a second XTEN sequence is inserted downstream of amino acid 1656 corresponding to SEQ ID NO: 4, and a third XTEN sequence is inserted downstream of amino acid 1720 or 1900 corresponding to SEQ ID NO: 4. In other embodiments, the first XTEN sequence is inserted immediately downstream of amino acid 403 or 1656 corresponding to SEQ ID NO: 4, a second XTEN sequence is inserted downstream of amino acid 1720 corresponding to SEQ ID NO: 4, and a third XTEN sequence is inserted downstream of amino acid 1900 corresponding to SEQ ID NO: 4. In other embodiments, the first XTEN sequence is inserted immediately downstream of amino acid 18, 26, 40, 399, 403, 1711, 1720, 1725, 1900, 1905, or 1910 corresponding to SEQ ID NO: 4, a second XTEN sequence is inserted downstream of amino acid 745 corresponding to SEQ ID NO: 4, and a third XTEN sequence is inserted downstream of amino acid 2332 corresponding to SEQ ID NO: 4.

In other embodiments, a FVIII protein in the invention comprises four XTEN sequences, a first XTEN sequence inserted into a first insertion site, a second XTEN sequence inserted into a second insertion site, a third XTEN sequence inserted into a third insertion site, and a fourth XTEN sequence inserted into a fourth insertion site. The first, second, third, and fourth XTEN sequences can be identical, different, or combinations thereof. In some embodiments, the FVIII protein comprising four XTEN sequences can further comprise a mutation or substitution, e.g., amino acid 1648 corresponding to SEQ ID NO: 4, e.g., R1648A. Non-limiting examples of the first, second, third, and fourth XTEN insertion sites are listed in Table 15.

TABLE 15

Exemplary Insertion Sites for Four XTENs

| Insertion 1 | | Insertion 2 | | Insertion 3 | | Insertion 4 | |
|---|---|---|---|---|---|---|---|
| Insertion Site | Domain | Insertion Site | Domain | Insertion Site | Domain | Insertion Site | Domain |
| 26 | A1 | 403 | A2 | 1656 | a3 | 1720 | A3 |
| 26 | A1 | 403 | A2 | 1656 | a3 | 1900 | A3 |
| 26 | A1 | 403 | A2 | 1720 | A3 | 1900 | A3 |
| 26 | A1 | 1656 | a3 | 1720 | A3 | 1900 | A3 |
| 403 | A2 | 1656 | a3 | 1720 | A3 | 1900 | A3 |
| 0040 | A1 | 0403 | A2 | 745 | B | 2332 | CT |
| 0040 | A1 | 0403 | A2 | 745 | B | 2332 | CT |
| 0018 | A1 | 0409 | A2 | 745 | B | 2332 | CT |
| 0040 | A1 | 0409 | A2 | 745 | B | 2332 | CT |
| 0040 | A1 | 0409 | A2 | 745 | B | 2332 | CT |
| 0018 | A1 | 0409 | A2 | 745 | B | 2332 | CT |
| 0040 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1900 | A3 | 745 | B | 2332 | CT |
| 0018 | A1 | 1900 | A3 | 745 | B | 2332 | CT |
| 0026 | A1 | 1900 | A3 | 745 | B | 2332 | CT |
| 0040 | A1 | 1900 | A3 | 745 | B | 2332 | CT |
| 0040 | A1 | 1905 | A3 | 745 | B | 2332 | CT |
| 0018 | A1 | 1905 | A3 | 745 | B | 2332 | CT |
| 0040 | A1 | 1905 | A3 | 745 | B | 2332 | CT |
| 0026 | A1 | 1905 | A3 | 745 | B | 2332 | CT |
| 0018 | A1 | 1905 | A3 | 745 | B | 2332 | CT |
| 0018 | A1 | 1905 | A3 | 745 | B | 2332 | CT |
| 0018 | A1 | 1910 | A3 | 745 | B | 2332 | CT |
| 0018 | A1 | 1910 | A3 | 745 | B | 2332 | CT |
| 0040 | A1 | 1910 | A3 | 745 | B | 2332 | CT |
| 0026 | A1 | 1910 | A3 | 745 | B | 2332 | CT |
| 0018 | A1 | 1910 | A3 | 745 | B | 2332 | CT |
| 0026 | A1 | 1910 | A3 | 745 | B | 2332 | CT |
| 0040 | A1 | 1910 | A3 | 745 | B | 2332 | CT |
| 0018 | A1 | 1910 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0403 | A2 | 1720 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0409 | A2 | 1910 | A3 | 745 | B | 2332 | CT |
| 0403 | A2 | 1910 | A3 | 745 | B | 2332 | CT |

TABLE 15-continued

Exemplary Insertion Sites for Four XTENs

| Insertion 1 | | Insertion 2 | | Insertion 3 | | Insertion 4 | |
|---|---|---|---|---|---|---|---|
| Insertion Site | Domain | Insertion Site | Domain | Insertion Site | Domain | Insertion Site | Domain |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 1720 | A3 | 1900 | A3 | 745 | B | 2332 | CT |
| 1720 | A3 | 1905 | A3 | 745 | B | 2332 | CT |
| 1720 | A3 | 1910 | A3 | 745 | B | 2332 | CT |
| 1720 | A3 | 1910 | A3 | 745 | B | 2332 | CT |
| 0403 | A2 | 1656 | a3 | 1720 | A3 | 2332 | CT |
| 0403 | A2 | 1656 | a3 | 1900 | A3 | 2332 | CT |
| 0403 | A2 | 1720 | A3 | 1900 | A3 | 2332 | CT |
| 1656 | a3 | 1720 | A3 | 1900 | A3 | 2332 | CT |
| 0018 | A1 | 0403 | A2 | 1656 | a3 | 2332 | CT |
| 0018 | A1 | 0403 | A2 | 1720 | A3 | 2332 | CT |
| 0018 | A1 | 0403 | A2 | 1900 | A3 | 2332 | CT |
| 0018 | A1 | 1656 | a3 | 1720 | A3 | 2332 | CT |
| 0018 | A1 | 1656 | a3 | 1900 | A3 | 2332 | CT |
| 0018 | A1 | 1720 | A3 | 1900 | A3 | 2332 | CT |
| 0018 | A1 | 0403 | A2 | 0745 | B | 2332 | CT |
| 0018 | A1 | 0745 | B | 1720 | A3 | 2332 | CT |
| 0018 | A1 | 0745 | B | 1900 | A3 | 2332 | CT |
| 0403 | A2 | 0745 | B | 1720 | A3 | 2332 | CT |
| 0403 | A2 | 0745 | B | 1900 | A3 | 2332 | CT |
| 0745 | B | 1720 | A3 | 1900 | A3 | 2332 | CT |
| 0188 | A1 | 1900 | A3 | 0745 | B | 2332 | CT |
| 0599 | | 1900 | A3 | 0745 | B | 2332 | CT |
| 2068 | | 1900 | A3 | 0745 | B | 2332 | CT |
| 2171 | | 1900 | A3 | 0745 | B | 2332 | CT |
| 2227 | | 1900 | A3 | 0745 | B | 2332 | CT |
| 2277 | | 1900 | A3 | 0745 | B | 2332 | CT |

In some embodiments, a FVIII protein comprises five XTEN sequences, a first XTEN sequence inserted into a first insertion site, a second XTEN sequence inserted into a second insertion site, a third XTEN sequence inserted into a third XTEN insertion site, a fourth XTEN sequence inserted into a fourth XTEN insertion site, and a fifth XTEN sequence inserted into a fifth XTEN insertion site. The first, second, third, fourth, of fifth XTEN sequences can be identical, different, or combinations thereof. Non-limiting examples of the first, second, third, fourth, and fifth insertion sites are listed in Table 16.

TABLE 16

Exemplary Insertion Sites for Five XTENs

| XTEN Insertion 1 | XTEN insertion 2 | XTEN Insertion 3 | XTEN Insertion 4 | XTEN Insertion 5 |
|---|---|---|---|---|
| 0403 | 1656 | 1720 | 1900 | 2332 |
| 0018 | 0403 | 1656 | 1720 | 2332 |
| 0018 | 0403 | 1656 | 1900 | 2332 |
| 0018 | 0403 | 1720 | 1900 | 2332 |
| 0018 | 1656 | 1720 | 1900 | 2332 |
| 0018 | 0403 | 0745 | 1720 | 2332 |
| 0018 | 0403 | 0745 | 1900 | 2332 |
| 0018 | 0745 | 1720 | 1900 | 2332 |
| 0403 | 0745 | 1720 | 1900 | 2332 |

In certain embodiments, a FVIII protein comprises six XTEN sequences, a first XTEN sequence inserted into a first XTEN insertion site, a second XTEN sequence inserted into a second XTEN insertion site, a third XTEN sequence inserted into a third XTEN insertion site, a fourth XTEN sequence inserted into a fourth XTEN insertion site, a fifth XTEN sequence inserted into a fifth XTEN insertion site, and a sixth XTEN sequence inserted into a sixth XTEN insertion site. The first, second, third, fourth, fifth, or sixth XTEN sequences can be identical, different, or combinations thereof. Examples of the six XTEN insertion sites include, but are not limited to the insertion sites listed in Table 17.

TABLE 17

| Exemplary XTEN Insertion Sites for Six XTENS | | | | | |
| --- | --- | --- | --- | --- | --- |
| XTEN Insertion 1 | XTEN insertion 2 | XTEN Insertion 3 | XTEN Insertion 4 | XTEN Insertion 5 | XTEN Insertion 5 |
| 0018 | 0403 | 1656 | 1720 | 1900 | 2332 |
| 0018 | 0403 | 0745 | 1720 | 1900 | 2332 |

In a particular example, a first XTEN is inserted between amino acids 26 and 27 corresponding to SEQ ID NO: 4, and a second XTEN is inserted between amino acids 1720 and 1721 corresponding to SEQ ID NO: 4 (full-length mature FVIII). In another example, a first XTEN is inserted between amino acids 403 and 404 corresponding to SEQ ID NO: 4, and a second XTEN is inserted between amino acids 1720 and 1721 corresponding to SEQ ID NO: 4. In some examples, a first XTEN is inserted between amino acids 1656 and 1657 corresponding to SEQ ID NO: 4, and a second XTEN is inserted between amino acids 1720 and 1721 corresponding to SEQ ID NO: 4. In other examples, a first XTEN is inserted between amino acids 26 and 27 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In yet other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In still other embodiments, a first XTEN is inserted between amino acids 403 and 404 corresponding to SEQ ID NO: 4, a second XTEN is inserted between amino acids 1656 and 1657 corresponding to SEQ ID NO: 4, and a third XTEN is inserted between amino acids 1720 and 1721 corresponding to SEQ ID NO: 4. In certain embodiments, a first XTEN is inserted between amino acids 26 and 27 corresponding to SEQ ID NO: 4, a second XTEN is inserted between amino acids 1720 and 1721 corresponding to SEQ ID NO: 4, and a third XTEN is inserted between amino acids 1900 and 1901 corresponding to SEQ ID NO: 4. In some embodiments, a first XTEN is inserted between amino acids 26 and 27 corresponding to SEQ ID NO: 4, a second XTEN is inserted between amino acids 1656 and 1657 corresponding to SEQ ID NO: 4, a third XTEN is inserted between amino acids 1720 and 1721 corresponding to SEQ ID NO: 4, and a fourth XTEN is inserted between 1900 and 1901 corresponding to SEQ ID NO: 4.

In a particular embodiment, an XTEN sequence is inserted between amino acids 745 and 746 of a full-length Factor VIII or the corresponding insertion site of the B-domain deleted Factor VIII.

D) Ig Constant Region or a Portion Thereof

The VWF fragment or the FVIII protein linked to an XTEN sequence in the present invention can further comprise an Ig constant region or a portion thereof. The Ig constant region or a portion thereof can improve pharmacokinetic or pharmacodynamic properties of the VWF fragment or the FVIII protein in combination with the XTEN sequence. In certain embodiments, the Ig constant region or a portion thereof extends a half-life of a molecule fused to the Ig constant region or a portion thereof.

An Ig constant region is comprised of domains denoted CH (constant heavy) domains (CH1, CH2, etc.). Depending on the isotype, (i.e. IgG, IgM, IgA, IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An Ig constant region or a portion thereof for producing the chimeric protein of the present invention may be obtained from a number of different sources. In some embodiments, an Ig constant region or a portion thereof is derived from a human Ig. It is understood, however, that the Ig constant region or a portion thereof may be derived from an Ig of another mammalian species, including for example, a rodent (e.g. a mouse, rat, rabbit, guinea pig) or non-human primate (e.g. chimpanzee, macaque) species. Moreover, the Ig constant region or a portion thereof may be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Ig constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the Ig constant region or a portion thereof can be cloned, e.g., using the polymerase chain reaction and primers which are selected to amplify the domain of interest. To clone a sequence of the Ig constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An Ig constant region used herein can include all domains and the hinge region or portions thereof. In one embodiment, the Ig constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An Ig constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an Ig that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of Igs or Ig fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of Ig constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

Certain of the above mutations may confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the Ig constant region or a portion thereof, e.g, an Fc region, is a polypeptide including the sequence PKNSSMISNTP (SEQ ID NO: 29) and optionally further including a sequence selected from HQSLGTQ (SEQ ID NO: 30), HQNLSDGK (SEQ ID NO: 31), HQNIS-DGK (SEQ ID NO: 32), or VISSHLGQ (SEQ ID NO: 33) (U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The disulfide bond by the immunoglobulin constant region or a portion thereof places the first polypeptide comprising FVIII and the second polypeptide comprising the VWF fragment together so that endogenous VWF does not replace the VWF fragment and does not bind to the FVIII. Therefore, the disulfide bond between the first immunoglobulin constant region or a portion thereof and a second immunoglobulin constant region or a portion thereof prevents interaction between endogenous VWF and the FVIII protein. This inhibition of interaction between the VWF and the FVIII protein allows the half-life of the FVIII protein to go beyond the two fold limit. The hinge region or a portion thereof can further be linked to one or more domains of CH1, CH2, CH3, a fragment thereof, and any combinations thereof. In a particular embodiment, the immunoglobulin constant region or a portion thereof is a hinge region and CH2.

In certain embodiments, the Ig constant region or a portion thereof is hemi-glycosylated. For example, the chimeric protein comprising two Fc regions or FcRn binding partners may contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an Ig constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner used in the invention may also comprise an art recognized amino acid substitution which alters the glycosylation of the chimeric protein. For example, the Fc region or FcRn binding partner of the chimeric protein linked to a VWF fragment or a FVIII protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention may differ in sequence at one or more amino acid positions. For example, at least two of the Fc regions or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

E) Linkers

The chimeric protein of the present invention further comprises one or more linkers. One type of the linkers is a cleavable linker, which can be cleaved by various proteases when administered to a subject in vivo, e.g., at a site of coagulation. In one embodiment, the cleavable linker allows cleavage of moiety, e.g., a VWF fragment, from the chimeric protein at the site of the coagulation cascade, thus allowing activated FVIII (FVIIIa) to have its FVIIIa activity. Another type of the linkers is a processable linker, which contains an intracellular cleavage site and thus can be cleaved by an intracellular processing enzyme in a host cell, allowing convenient expression of a polypeptide and formation of a chimeric protein.

One or more linkers can be present between any two proteins in the chimeric protein. In one embodiment, a chimeric protein comprises (i) a VWF fragment, (ii) an XTEN sequence, and (iii) a FVIII protein, wherein the VWF fragment is linked to the XTEN sequence by a linker, e.g., a cleavable linker, and the XTEN sequence is further linked to the FVIII protein (i.e., V-L-X-FVIII). In another embodiment, a chimeric protein comprises (i) a VWF fragment, (ii) an XTEN sequence, and (iii) a FVIII protein, wherein the VWF fragment is linked to the XTEN sequence, and the XTEN sequence is linked to the FVIII protein by a linker, e.g., a cleavable linker (i.e., V-X-L-FVIII).

In certain embodiments, a chimeric protein comprises (i) a VWF fragment, (ii) an XTEN sequence, (iii) a first Ig constant region or a portion thereof (e.g., a first Fc region), (iv) a FVIII protein, and (v) a second Ig constant region or a portion thereof (e.g., a second Fc region), wherein the VWF fragment is linked to the XTEN sequence by an optional linker, e.g., a cleavable linker. The XTEN sequence can be further linked to the first Ig constant region or a portion thereof by a linker, e.g., a cleavable linker. The FVIII protein (with or without an XTEN sequence) can also be linked to the second Ig constant region or a portion thereof by an optional linker, e.g. a cleavable linker. In certain embodiments, the chimeric protein further comprises one or more linkers, e.g., processable linkers, between the first Ig constant region or a portion thereof (e.g., first Fc region) and the second Ig constant region or a portion thereof (e.g., second Fc region), between the VWF fragment and the second Ig constant region or a portion thereof, or between the FVIII protein and the first Ig constant region or a portion thereof (e.g., first Fc region).

In some embodiments, the present invention includes a chimeric protein comprising (i) a FVIII protein, (ii) an XTEN sequence, (iii) a first Ig constant region or a portion thereof, and (iv) a second Ig constant region or a portion thereof, wherein the first Ig constant region or a portion thereof and the second Ig constant region or a portion thereof are linked by a processable linker.

The linker useful in the present invention can comprise any organic molecule. In one embodiment, the linker comprises a polymer, e.g., polyethylene glycol (PEG) or hydroxyethyl starch (HES). In another embodiment, the linker comprises an amino acids sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids. In one embodiment, the linker comprises an XTEN sequence. Additional examples of XTEN can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2. In another embodiment, the linker is a PAS sequence.

The linker useful in the present invention can comprise any organic molecule. In one embodiment, the linker is a polymer, e.g., polyethylene glycol (PEG) or hydroxyethyl starch (HES). In another embodiment, the linker is an amino acid sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of linkers are well known in the art. In one embodiment, the linker comprises the sequence $G_n$. The linker can comprise the sequence $(GA)_n$. The linker can comprise the sequence $(GGS)_n$. In other embodiments, the linker comprises (GGGS)$_n$ (SEQ ID NO: 34). In still other embodiments, the linker comprises the sequence (GGS)$_n$ (GGGGS)$_n$ (SEQ ID NO: 35). In these instances, n may be an integer from 1-100. In other instances, n may be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 36), GGSGGSGGSGGSGGG (SEQ ID NO: 37), GGSGGSGGGGSGGGGS (SEQ ID NO: 38), GGSGGSGGSGGSGGSGGS (SEQ ID NO: 39), or GGGGSGGGGSGGGGS (SEQ ID NO: 40). The linker does not eliminate or diminish the VWF fragment activity or the clotting activity of Factor VIII. Optionally, the linker enhances the VWF fragment activity or the clotting activity of Factor VIII protein, e.g., by further diminishing the effects of steric hindrance and making the VWF fragment or Factor VIII portion more accessible to its target binding site.

In one embodiment, the linker useful for the chimeric protein is 15-25 amino acids long. In another embodiment, the linker useful for the chimeric protein is 15-20 amino acids long. In some embodiments, the linker for the chimeric protein is 10-25 amino acids long. In other embodiments, the linker for the chimeric protein is 15 amino acids long. In still other embodiments, the linker for the chimeric protein is (GGGGS)$_n$ (SEQ ID NO: 41) where G represents glycine, S represents serine and n is an integer from 1-20.

F) Cleavage Sites

The linker may also incorporate a moiety capable of being cleaved either chemically (e.g., hydrolysis of an ester bond), enzymatically (i.e., incorporation of a protease cleavage sequence), or photolytically (e.g., a chromophore such as 3-amino-3-(2-nitrophenyl) proprionic acid (ANP)) in order to release one molecule from another.

In one embodiment, the linker is a cleavable linker. The cleavable linkers can comprise one or more cleavage sites at the N-terminus or C-terminus or both. In another embodiment, the cleavable linker consists essentially of or consists of one or more cleavable sites. In other embodiments, the cleavable linker comprises heterologous amino acid linker sequences described herein or polymers and one or more cleavable sites.

In certain embodiments, a cleavable linker comprises one or more cleavage sites that can be cleaved in a host cell (i.e., intracellular processing sites). Non limiting examples of the cleavage site include RRRR (SEQ ID NO: 9), RKRRKR (SEQ ID NO: 10), and RRRRS (SEQ ID NO: 11).

In other embodiments, a cleavable linker comprises one or more cleavage sites that are cleaved by a protease after a chimeric protein comprising the cleavable linker is administered to a subject. In one embodiment, the cleavage site is cleaved by a protease selected from the group consisting of factor XIa, factor XIIa, kallikrein, factor VIIa, factor IXa, factor Xa, factor IIa (thrombin), Elastase-2, MMP-12, MMP-13, MMP-17, and MMP-20. In another embodiment, the cleavage site is selected from the group consisting of a FXIa cleavage site (e.g., KLTR↓AET (SEQ ID NO: 42)), a FXIa cleavage site (e.g, DFTR↓VVG (SEQ ID NO: 43)), a FXIIa cleavage site (e.g., TMTR↓IVGG (SEQ ID NO: 44)), a Kallikrein cleavage site (e.g., SPFR↓STGG (SEQ ID NO: 45)), a FVIIa cleavage site (e.g., LQVR↓IVGG (SEQ ID NO: 46)), a FIXa cleavage site (e.g., PLGR↓IVGG (SEQ ID NO: 47)), a FXa cleavage site (e.g., IEGR↓TVGG (SEQ ID NO: 48)), a FIIa (thrombin) cleavage site (e.g, LTPR↓SLLV (SEQ ID NO: 49)), a Elastase-2 cleavage site (e.g, LGPV↓SGVP (SEQ ID NO: 50)), a Granzyme-B cleavage (e.g, VAGD↓SLEE (SEQ ID NO: 51)), a MMP-12 cleavage site (e.g., GPAG↓LGGA (SEQ ID NO: 52)), a MMP-13 cleavage site (e.g., GPAG↓LRGA (SEQ ID NO: 53)), a MMP-17 cleavage site (e.g., APLG↓LRLR (SEQ ID NO: 54)), a MMP-20 cleavage site (e.g., PALP↓LVAQ (SEQ ID NO: 55)), a TEV cleavage site (e.g., ENLYFQ↓G (SEQ ID NO: 56)), a Enterokinase cleavage site (e.g., DDDK↓IVGG (SEQ ID NO: 57)), a Protease 3C (PRESCISSION™) cleavage site (e.g., LEVLFQ↓GP (SEQ ID NO: 58)), and a Sortase A cleavage site (e.g., LPKT↓GSES) (SEQ ID NO: 59). In certain embodiments, the FXIa cleavage sites include, but are not limited to, e.g., TQSFNDFTR (SEQ ID NO: 60) and SVSQTSKLTR (SEQ ID NO: 61). Non-limiting exemplary thrombin cleavage sites include, e.g., DFLAEGGGVR (SEQ ID NO: 62), TTKIKPR (SEQ ID NO: 63), or LVPRG (SEQ ID NO: 64), and a sequence comprising, consisting essentially of, or consisting of ALRPR (SEQ ID NO: 27) (e.g., ALRPRVVGGA (SEQ ID NO: 65)).

In a specific embodiment, the cleavage site is TLDPRSFLLRNPNDKYEPFWEDEEK (SEQ ID NO: 8).

Polynucleotides, Vectors, and Host Cells

Also provided in the invention is a polynucleotide encoding (a) a VWF fragment linked to an XTEN sequence and a FVIII protein, (b) a FVIII protein linked to an XTEN sequence and Fc, or (c) a FVIII protein linked to an XTEN sequence and a VWF fragment described herein. When a chimeric protein is a single polypeptide chain (e.g., F2-L2-X-V-L1-F1-FVIII, wherein FVIII comprises a FVIII protein, F1 comprises a first Ig constant region or a portion thereof, e.g., a first Fc region, L1 comprises a first linker, V comprises a VWF fragment, X comprises an XTEN sequence, L2 comprises a second linker, and F2 comprises a second Ig constant region or a portion thereof, e.g., a second Fc region), the invention is drawn to a single polynucleotide chain encoding the single polypeptide chain. When the chimeric protein comprises a first and a second polypeptide chains (F2-L2-X-V:FVIII-F1), the first polypeptide chain comprising a VWF fragment linked to a XTEN sequence, which is further linked to a first Ig constant region or a portion thereof (e.g., a first Fc region) by a cleavable linker (e.g., F2-L2-X-V) and the second polypeptide chain comprising a FVIII protein and a second Ig constant region or a portion thereof (e.g., a second Fc region) (e.g, FVIII-F1), wherein the first polypeptide chain and the second polypeptide chain are associated with each other, a polynucleotide can comprise the first nucleotide sequence and the second nucleotide sequence. In one embodiment, the first polypeptide chain and the second polypeptide chain can be encoded by a single polynucleotide chain. In another embodiment, the first polypeptide chain and the second polypeptide chain are encoded by two different polynucleotides, i.e., a first nucleotide sequence and a second nucleotide sequence. In another embodiment, the first nucleotide sequence and the second nucleotide sequence are on two different polynucleotides (e.g., different vectors). In certain embodiments, the present invention is directed to a set of polynucleotides comprising a first nucleotide chain and a second nucleotide chain, wherein the first nucleotide chain encodes the VWF fragment of the chimeric protein and the second nucleotide chain encodes the FVIII protein. In some embodiments, a chimeric protein comprising two polypeptide chains or three polypeptide chains can be encoded by a single polynucleotide chain, and then processed into two or three (or more) polypeptide chains. In yet other embodiments, a chimeric protein comprising these polypeptide chains can be encoded by two or three polynucleotide chains.

In other embodiments, the set of the polynucleotides further comprises an additional nucleotide chain (e.g., a second nucleotide chain when the chimeric polypeptide is encoded by a single polynucleotide chain or a third nucleotide chain when the chimeric protein is encoded by two polynucleotide chains) which encodes a protein convertase. The protein convertase can be selected from the group consisting of proprotein convertase subtilisin/kexin type 5 (PCSK5 or PC5), proprotein convertase subtilisin/kexin type 7 (PCSK7 or PC5), a yeast Kex 2, proprotein convertase subtilisin/kexin type 3 (PACE or PCSK3), and two or more combinations thereof. In some embodiments, the protein convertase is PACE, PC5, or PC7. In a specific embodiment, the protein convertase is PC5 or PC7. See International Application no. PCT/US2011/043568.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding the chimeric protein described herein. In one embodiment, one or more of the coding sequences for the VWF fragment and XTEN, the FVIII protein and XTEN, or both are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase the yield of polypeptides driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit easy purification of the recombinantly produced protein. Examples include, but are not limited to, vector pUR278 (Ruther et al. (1983) *EMBO J* 2:1791), in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, VA, and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, VA. (e.g., CHO-KI; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid including a FVIII(X)-Fc fusion coding sequence, a VWF fragment-L-Fc fusion coding sequence, or both and a selectable marker, e.g., zeocin resistance, are transfected into HEK 293 cells, for production of a chimeric protein.

In another embodiment, a plasmid including a FVIII-Fc fusion coding sequence, a VWF fragment-XTEN-L-Fc fusion coding sequence, or both and a selectable marker, e.g., zeocin resistance, are transfected into HEK 293 cells, for production of a chimeric protein.

In other embodiments, a plasmid including a FVIII(X)-Fc fusion coding sequence, a Fc coding sequence, or both and a selectable marker, e.g., zeocin resistance, are transfected into HEK 293 cells, for production of a chimeric protein.

In some embodiments, a first plasmid including a FVIII (X)-Fc fusion coding sequence and a first selectable marker, e.g., a zeocin resistance gene, and a second plasmid including an Fc coding sequence or a VWF fragment-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In still other embodiments, a first plasmid including a FVIII-Fc fusion coding sequence and a first selectable marker, e.g., a zeocin resistance gene, and a second plasmid including a VWF fragment-XTEN-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In yet other embodiments, a first plasmid including a FVIII(X)-Fc fusion coding sequence and a first selectable marker, e.g., a zeocin resistance gene, and a second plasmid including a VWF fragment-XTEN-L-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In certain embodiments, a first plasmid, including a chimeric protein encoding FVIII (with or without XTEN)-F1-L1-V-XTEN-L2-F2 coding sequence and a first selectable marker, e.g., a zeocin resistance gene, and a second plasmid including a protein convertase coding sequence and a second selectable marker, e.g., a hygromycin resistance gene, are cotransfected into HEK 293 cells, for production of the chimeric protein. The promoters for the FVIII(X)-Fc coding sequence and the VWF-XTEN-Fc coding sequence can be different or they can be the same.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CD293 (Invitrogen, Carlsbad, CA.). In another embodiment, the medium is CD17 (Invitrogen, Carlsbad, CA.). Selection of a medium appropriate for the particular cell line used is within the level of those ordinary skilled in the art.

In order to co-express the two polypeptide chains of the chimeric protein, the host cells are cultured under conditions that allow expression of both chains. As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow association of the VWF fragment with the FVIII protein. Conditions that allow expression of the VWF fragment and/or the FVIII protein may include the presence of a source of vitamin K. For example, in one embodiment, stably transfected HEK 293 cells are cultured in CD293 media (Invitrogen, Carlsbad, CA) or OptiCHO media (Invitrogen, Carlsbad, CA) supplemented with 4 mM glutamine.

In one aspect, the present invention is directed to a method of expressing, making, or producing the chimeric protein of the invention comprising a) transfecting a host cell comprising a polynucleotide encoding the chimeric protein and b) culturing the host cell in a culture medium under a condition suitable for expressing the chimeric protein, wherein the chimeric protein is expressed.

In further embodiments, the protein product containing the VWF fragment linked to an XTEN sequence or the FVIII protein linked to an XTEN sequence is secreted into the media. Media is separated from the cells, concentrated, filtered, and then passed over two or three affinity columns, e.g., a protein A column and one or two anion exchange columns.

In certain aspects, the present invention relates to the chimeric protein produced by the methods described herein.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

Pharmaceutical Composition

Compositions containing the chimeric protein of the present invention may contain a suitable pharmaceutically acceptable carrier. For example, they may contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, including, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include antifibrinolytic drugs, e.g., epsilon-amino-caproic acid, tranexamic acid.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a chimeric protein, the polynucleotide encoding the chimeric protein, the vector comprising the polynucleotide, or the host cell comprising the vector, and a pharmaceutically acceptable carrier. The FVIII protein in a chimeric protein has extended half-life compared to wild type FVIII protein or the corresponding FVIII protein without the VWF fragment. In one embodiment, wherein the half-life of the FVIII protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of Factor VIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Gene Therapy

A chimeric protein thereof of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of a suitable chimeric protein-encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal may not be exposed to a nucleic acid encoding a selectable marker gene. In other embodiments, the sequences are incorporated into a non-viral vector known to those skilled in the art.

Methods of Using Chimeric Protein

The present invention is directed to a method of using a chimeric protein described herein to prevent or inhibit endogenous VWF binding to a FVIII protein. The present invention is also directed to a method of using a chimeric protein having a FVIII protein linked to XTEN and an Ig constant region or a portion thereof.

One aspect of the present invention is directed to preventing or inhibiting FVIII interaction with endogenous VWF by blocking or shielding the VWF binding site on the FVIII from endogenous VWF and at the same time extending half-life of the FVIII protein using an XTEN sequence in combination with an Ig constant region or a portion thereof, which can also be a half-life extender. In one embodiment, the invention is directed to a method of constructing a FVIII protein having half-life longer than wild-type FVIII. In one embodiment, an XTEN sequence inhibits or prevents interaction of a FVIII protein in a chimeric protein with endogenous VWF. In another embodiment, an Ig constant region or a portion thereof inhibits or prevents interaction of the FVIII protein with endogenous VWF. The chimeric protein useful in the method includes any one or more chimeric protein described herein.

Another aspect of the invention includes a method of administering to a subject in need thereof a chimeric protein comprising a FVIII protein having half-life longer than wild-type FVIII, wherein the method comprises administering the chimeric protein described herein to the subject.

In one embodiment, the invention is directed to a method of using an XTEN sequence and an Ig constant region or a portion thereof to extend a half-life of a FVIII protein and a VWF fragment to prevent or inhibit endogenous VWF interaction with a FVIII protein. A FVIII protein linked to an XTEN sequence (e.g., FVIII(X)) and then bound to or associated with a VWF fragment is shielded or protected from the clearance pathway of VWF and thus has reduced clearance compared to the FVIII protein not bound to the VWF fragment. The shielded FVIII protein thus has maximum extension of a half-life compared to a FVIII protein not bound to or associated with the XTEN sequence and the VWF fragment. In certain embodiments, the FVIII protein associated with or protected by a VWF fragment and linked to an XTEN sequence is not cleared by a VWF clearance receptor. In other embodiments, the FVIII protein associated with or protected by a VWF fragment and linked to an XTEN sequence is cleared from the system slower than the FVIII protein that is not associated with or protected by the VWF fragment and linked to the XTEN sequence.

In one aspect, the chimeric protein comprising the FVIII protein linked to an XTEN sequence or the FVIII protein bound to or associated with a VWF fragment linked to XTEN has reduced clearance from circulation as the VWF fragment does not contain a VWF clearance receptor binding site. The VWF fragment prevents or inhibits clearance of FVIII bound to or associated with the VWF fragment from the system through the VWF clearance pathway. The VWF fragments useful for the present invention can also provide at least one or more VWF-like FVIII protection properties that are provided by endogenous VWF. In certain embodiments, the VWF fragment or the XTEN sequence can also mask one or more FVIII clearance receptor binding site, thereby preventing clearance of FVIII by its own clearance pathway.

In some embodiments, the prevention or inhibition of a FVIII protein binding to endogenous VWF by the VWF fragment or the XTEN sequence can be in vitro or in vivo.

Also provided is a method of increasing the half-life of a FVIII protein comprising administering the chimeric protein described herein to a subject in need thereof. The half-life of non-activated FVIII bound to or associated with full-length VWF is about 12 to 14 hours in plasma. In VWD type 3, wherein there is almost no VWF in circulation, the half-life of FVIII is only about six hours, leading to symptoms of mild to moderate hemophilia A in such patients due to decreased concentrations of FVIII. The half-life of the FVIII protein linked to or associated with the VWF fragment or the XTEN sequence of the present invention can increase at least about 1.5 times, 1.6 times, 1.7 times, 1.8 times, 1.9 times, 2.0 times, 2.1 times, 2.2 times, 2.3 times, 2.4 times, 2.6 times, 2.7. times, 2.8 times, 2.9 times, 3.0 times, 3.1 times, 3.2 times, 3.3 times, 3.4 times, 3.5 times, 3.6 times, 3.7 times, 3.8 times, 3.9 times, or 4.0 times higher than the half-life of the non-activated FVIII bound to or associated with full-length VWF.

In one embodiment, the half-life of the FVIII protein linked to or associated with the VWF fragment or linked to an Ig constant region or a portion thereof in the chimeric protein comprising an XTEN sequence increases at least about 2 times, 2.5 times, 3.0 times, 3.5 times, 4.0 times, 4.5 times, 5.0 times, 5.5 times, 6.0 times, 7 times, 8 times, 9 times, or 10 times higher than the half-life of the non-activated FVIII bound to or associated with full-length VWF. In another embodiment, the half-life of the FVIII protein linked to or associated with the VWF fragment or an Ig constant region or a portion thereof in the chimeric protein comprising an XTEN sequence increases about 2 to about 5 times, about 3 to about 10 times, about 5 to about 15 times, about 10 to about 20 times, about 15 to about 25 times, about 20 to about 30 times, about 25 to about 35 times, about 30 to about 40 times, about 35 to about 45 times higher than the half-life of the non-activated FVIII bound to or associated with full-length VWF or wild type FVIII. In a specific embodiment, the half-life of the FVIII protein linked to or associated with the VWF fragment or linked to an Ig constant region in the chimeric protein comprising an XTEN sequence increases at least about 30, 31, 32, 33, 34, 35, 36, 37, 38, 39, or 40 times higher than the half-life of the wild type FVIII in a FVIII and VWF double knockout mouse.

In some embodiments, the half-life of the chimeric protein comprising the VWF fragment fused to a first Ig constant region or a portion thereof, e.g., a first Fc region and an XTEN sequence, and a FVIII protein linked to an XTEN sequence and a second Ig constant region or a portion thereof, e.g., a second Fc region, is longer than the half-life of a FVIII associated with endogenous VWF. In other embodiments, the half-life of the chimeric protein is at least about 1.5 times, 2 times, 2.5 times, 3.5 times, 3.6 times, 3.7 times, 3.8 times, 3.9 times, 4.0 times, 4.5 times, or 5.0 times the half-life of wild type FVIII or a FVIII protein associated with endogenous VWF.

In some embodiments, as a result of the invention the half-life of the FVIII protein is extended compared to a FVIII protein without the VWF fragment or wild-type FVIII. The half-life of the chimeric protein of the invention is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a FVIII protein without the VWF fragment or wild-type FVIII. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF fragment. In other embodiments, the half-life of the chimeric protein of the invention is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of the chimeric protein of the invention is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the chimeric protein of the invention per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In addition, the invention provides a method of treating or preventing a bleeding disease or disorder comprising administering an effective amount of a chimeric protein. In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In a specific embodiment, the bleeding disease or disorder is hemophilia A.

The chimeric protein comprising an XTEN sequence and an Ig constant region or a portion thereof in combination with a VWF fragment described herein, that prevents or inhibits interaction of the FVIII protein with endogenous VWF prepared by the invention, has many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of the chimeric protein.

The FVIII protein portion in the chimeric protein treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor VIIIa increases the maximum velocity of Factor X activation by Factor IXa, by approximately 200,000-fold, leading to the large second burst of thrombin generation.

The chimeric protein of the invention can be used to treat any hemostatic disorder. The hemostatic disorders that may be treated by administration of the chimeric protein of the invention include, but are not limited to, hemophilia A, as well as deficiencies or structural abnormalities relating to Factor VIII. In one embodiment, the hemostatic disorder is hemophilia A.

The chimeric protein of the invention can be used prophylactically to treat a subject with a hemostatic disorder. The chimeric protein of the invention can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

The invention also relates to methods of treating a subject that does not have a congenital hemostatic disorder, but has a secondary disease or condition resulting in acquisition of a hemostatic disorder, e.g., due to development of an anti-FVIII antibody or a surgery. The invention thus relates to a method of treating a subject in need of a general hemostatic agent comprising administering a therapeutically effective amount of the chimeric protein prepared by the present methods.

The present invention is also related to methods of reducing immunogenicity of FVIII or inducing less immunogenicity against FVIII comprising administering an effective amount of the chimeric proteins described herein, or the polynucleotides encoding the same.

In one embodiment, the subject in need of a general hemostatic agent is undergoing, or is about to undergo, surgery. The chimeric protein of the invention can be administered prior to, during, or after surgery as a prophylactic regimen. The chimeric protein of the invention can be administered prior to, during, or after surgery to control an acute bleeding episode.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding. Non limiting examples of bleeding episodes include a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, and any combinations thereof.

In prophylactic applications, one or more compositions containing the chimeric protein of the invention or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radio-immuno conjugates and higher doses for cytotoxin-drug modified polypeptides) at relatively short intervals is sometimes required until progression of the disease is reduced or terminated, and until the patient shows partial or complete amelioration of symptoms of disease. Thereafter, the patient can be administered a prophylactic regime.

In some embodiments, a chimeric protein or a composition of the invention is used for on-demand treatment, which includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, the chimeric protein of the present invention is administered intravenously, subcutaneously, intramuscularly, or via any mucosal surface, e.g., orally, sublingually, buccally, nasally, rectally, vaginally or via pulmonary route. The chimeric protein comprising a VWF fragment and a FVIII protein of the present invention can be implanted within or linked to a biopolymer solid support that allows for the slow release of the chimeric protein to the site of bleeding or implanted into bandage/dressing. The dose of the chimeric protein will vary depending on the subject and upon the particular route of administration used. Dosages can range from 0.1 to 100,000 μg/kg body weight. In one embodiment, the dosing range is 0.1-1,000 g/kg. In another embodiment, the dosing range is 0.1-500 g/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay or ROTEM clotting assay. Additionally, effective doses may be extrapolated from dose-response curves obtained from animal models, e.g., a hemophiliac dog (Mount et al. 2002, *Blood* 99(8):2670).

Having now described the present invention in detail, the same will be more clearly understood by reference to the following examples, which are included herewith for purposes of illustration only and are not intended to be limiting of the invention. All patents, publications, and articles referred to herein are expressly and specifically incorporated herein by reference.

Examples Throughout the examples, the following materials and methods were used unless otherwise stated.

Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1

To engineer long-acting recombinant factor VIII (rFVIII) molecules with greater half-life extension than those currently being assessed in clinical trials, we have incorporated three structural elements into FVIII: the D'D3 fragment of von Willebrand factor (VWF) to decouple the clearance of FVIII from that of VWF (Chhabra S E et al., ISTH, 2013), the Fc domain of IgG1 to enable neonatal Fc receptor (FcRn) mediated half-life extension, and XTEN, an unstructured hydrophilic polypeptide that increases the hydrodynamic radius of a payload molecule to prolong its half-life in circulation (Schellenberger V et al., *Nature Biotechnology*, 2009). Members of this new class of heterodimeric FVIII proteins have achieved an approximately 4-fold increase in circulating half-life in Hemophilia A mice (Liu T et al., ISTH, 2013). Here we report two methods for purifying members of this class of FVIII molecules that enable purification with sufficient quality and quantity for biochemical and pharmacological assessment.

The purification of rFVIII is challenging due to its characteristically low expression level in transiently transfected mammalian cells and its sensitivity to modest changes in pH and temperature. For rFVIII and recombinant factor VIII Fc fusion protein (rFVIIIFc) variants, we previously developed a 2-step method that employs a VIIISelect (GE Healthcare) affinity capture step followed by an anion exchange (AEX) polishing step to produce milligram quantities of rFVIII and rFVIIIFc variants with >98% purity. When applied to members of this new class of FVIII-Fc/VWF$_{D'D3}$-Fc heterodimers, however, VIIISelect capture did not achieve comparable target recovery and purity. To address this issue, we developed an alternative method consisting of an AEX capture step followed by an FcRn affinity step. Proteins purified by this method were >90% homogenous, as indicated by SDS-PAGE and size exclusion chromatography (SEC) and retained full activity, with specific activities determined by a FVIII-specific chromogenic assay, comparable to those of rFVIII and rFVIIIFc. Western blotting with antibodies against VWF, FVIII, and Fc confirmed the presence of each element in purified proteins. The apparent molecular weight determined by SEC-HPLC was greater than 900 kDa, a significant increase over that predicted from amino acid sequence (~300 kDa), which is consistent with the demonstrated ability of XTEN to significantly increase the hydrodynamic radius of payload molecules.

We additionally developed an alternative purification method to address the previously noted limitations of the VIIISelect capture step for purification of FVIII-Fc/VWF$_{D'D3}$-Fc heterodimers. This second method employed three sequential steps: 1) concentration of conditioned medium by tangential flow filtration (TFF), 2) VIIISelect affinity chromatography, and 3) AEX chromatography. We observed that both the TFF step and controlling the ionic strength at both the loading and washing steps are critical for efficient recovery of FVIII-Fc/VWF$_{D'D3}$-Fc heterodimers by VIIISelect. This 3-step method has been employed successfully to purify multiple molecules of this class, including those with two and three XTEN insertions. Typically, these constructs can be purified to >80% homogeneity as determined by SDS-PAGE and SEC-HPLC. Several proteins purified by this process showed specific activities, as determined by chromogenic assay, which were comparable to that of rFVIII.

In summary, certain members of a novel class of FVIII-Fc/VWF$_{D'D3}$-Fc heterodimeric molecules have achieved an approximately 4-fold increase in half live relative to rFVIII. The common architecture of members of this class of proteins has necessitated the development of suitable purification methods. Here we describe two such methods, and demonstrate their utility for the biochemical characterization of FVIII-Fc/VWF$_{D'D3}$-Fc heterodimers, including those with one or more XTEN insertions.

Example 2

The FVIII-169/VWF-57 chimeric protein was expressed in host cells in 20 L of medium. The conditioned medium, comprising the FVIII-169/VWF-57 chimeric protein, was then collected and concentrated by tangential flow filtration (TFF) to a final volume of 2 L. One liter of the concentrated conditioned media was then loaded over a 21 mL DEAE column (1.7671×12 cm, OMNIFIT®), which was pre-equilibrated with DEAE running buffer (pH 7.2, 10 mM HEPES+100 mM NaCl, 5 mM CaCl$_2$, 0.01% T-80 (polysorbate 80)). The loaded column was then washed with 10 column volumes of DEAE running buffer. Bound proteins were then eluted using a gradient of 0-100% a DEAE AEX chromatography elution buffer (pH 7.2, 10 mM HEPES+0.8M NaCl, 5 mM CaCl$_2$, 0.01% T-80 (polysorbate 80)) applied over 5 column volumes.

Eluted proteins were analyzed by chromatogram, as shown in FIG. 2. In the chromatogram, UV280 indicates the protein concentration in the collected fractions. Protein was detected at a high concentration from about fraction 1.A.3 through about 1.B.3 (FIG. 2). The eluted proteins were then analyzed by 4-20% SDS PAGE on a Criterion Stain-Free gel, under reducing and non-reducing conditions, as shown in FIG. 3. A chromogenic assay was then performed, and the results are shown in FIG. 4.

The DEAE proved to be less effective than desired for capture of FVIII-169/VWF-57 heterodimer from crude conditioned medium. As shown by the FVIII chromogenic assay (FIG. 4), most of the FVIII activity was observed in the flow-through fraction with a minimal amount observed in the elution peak. Further, SDS PAGE analysis (FIG. 3) shows that the application of crude conditioned medium to DEAE resulted in the capture of most medium-derived contaminants.

Example 3

In order to improve the purification methods discussed above, a multi-step, combined method was developed. The FVIII-169/VWF-57 chimeric protein was expressed in host cells in 20 L of medium. The conditioned medium, comprising the FVIII-169/VWF-57 chimeric protein, was then collected and concentrated by tangential flow filtration (TFF) to a final volume of 2 L. One liter of the concentrated conditioned medium was then loaded over a 7.5 mL VIIISelect column (a factor VIII-specific affinity chromatography matrix comprising a camelid nanobody ligand that binds factor VIII). The VIIISelect column was previously equilibrated with an equilibration buffer (pH 7.4, 10 mM HEPES, 100 mM NaCl, 0.01% TWEEN-20® (polysorbate 20), 5 mM CaCl$_2$). The column was then washed with 5 column volumes of the equilibration buffer, followed by 10 column volumes of a wash buffer (pH 7.2, 0.8M NaCl, 0.2M CaCl$_2$, 10 mM HEPES, 0.01% TWEEN-20® (polysorbate 20)), followed by 10 column volumes of the equilibration buffer. Protein was then eluted using 20 column volumes of an elution buffer (pH 7.2, 50 mM histidine, 0.9M arginine-HCl, 50 mM CaCl$_2$, 45% propylene glycol, 0.05% TWEEN-20® (polysorbate 20)), and 3.5 mL fractions were collected. A chromatogram showing the protein concentration of each fraction is shown in FIG. 5.

Following elution from the VIIISelect column, fractions under the peak (1B2-1B5) as shown in FIG. 5, were pooled, buffer exchanged in DEAE running buffer (pH 7.2, 10 mM HEPES+100 mM NaCl, 5 mM CaCl$_2$, 0.01% T-80 (polysorbate 80)), and loaded over an 8 mL DEAE column. The column was then washed with DEAE running buffer. Proteins were eluted with a gradient of 0-100% DEAE AEX chromatography elution buffer (pH 7.2, 10 mM HEPES+0.8M NaCl, 5 mM CaCl$_2$, 0.01% T-80 (polysorbate 80)) applied over 10 column volumes. Eluted proteins were analyzed by chromatogram, as shown in FIG. 7. In the chromatogram, UV280 indicates the protein concentration of the collected fractions. Protein was detected from about fraction 1.C.1 through about 1.C.5 (FIG. 7). Eluted proteins were then analyzed by 4-20% SDS PAGE on a Criterion Stain-Free gel, under reducing and non-reducing conditions, as shown in FIG. 8, which shows increased purity relative to that shown in FIG. 3. A chromogenic assay was then performed, and the results are shown in FIG. 9. The VIIISelect step proved to be effective for capture of FVIII-169/VWF-57 heterodimer from crude conditioned medium. As seen in FIG. 6, most of the activity was observed in the elution peak (FIG. 5), with a minimal amount of activity observed in the flow-through fraction. The DEAE ion exchange polishing step proved to be effective for capture of FVIII-169/VWF-57 heterodimer post-VIIISelect affinity chromatography. As shown by SDS PAGE (FIG. 8), as well as by the FVIII chromogenic assay (FIG. 9), most of the FVIII activity was observed in the elution peak following the DEAE polishing step.

```
Sequences:
pSYN VWF057 nucleotide sequence (VWF D'D3-Fc with LVPR
thrombin site in the linker)
                                        (SEQ ID NO: 66)
    1   ATGATTCCTG CCAGATTTGC CGGGGTGCTG CTTGCTCTGG CCCTCATTTT

51   GCCAGGGACC CTTTGTGCAG AAGGAACTCG CGGCAGGTCA TCCACGGCCC
```

-continued

```
 101   GATGCAGCCT TTTCGGAAGT GACTTCGTCA ACACCTTTGA TGGGAGCATG

181   TACAGCTTTG CGGGATACTG CAGTTACCTC CTGGCAGGGG GCTGCCAGAA

201   ACGCTCCTTC TCGATTATTG GGGACTTCCA GAATGGCAAG AGAGTGAGCC

251   TCTCCGTGTA TCTTGGGGAA TTTTTTGACA TCCATTTGTT TGTCAATGGT

301   ACCGTGACAC AGGGGGACCA AAGAGTCTCC ATGCCCTATG CCTCCAAAGG

351   GCTGTATCTA GAAACTGAGG CTGGGTACTA CAAGCTGTCC GGTGAGGCCT

401   ATGGCTTTGT GGCCAGGATC GATGGCAGCG GCAACTTTCA AGTCCTGCTG

451   TCAGACAGAT ACTTCAACAA GACCTGCGGG CTGTGTGGCA ACTTTAACAT

091   CTTTGCTGAA GATGACTTTA TGACCCAAGA AGGGACCTTG ACCTCGGACC

551   CTTATGACTT TGCCAACTCA TGGGCTCTGA GCAGTGGAGA ACAGTGGTGT

601   GAACGGGCAT CTCCTCCCAG CAGCTCATGC AACATCTCCT CTGGGGAAAT

651   GCAGAAGGGC CTGTGGGAGC AGTGCCAGCT TCTGAAGAGC ACCTCGGTGT

701   TCGCCCGCTG CCACCCTCTG GTGGACCCCG AGCCTTTTGT GGCCCTGTGT

751   GAGAAGACTT TGTGTGAGTG TGCTGGGGGG CTGGAGTGCG CCTGCCCTGC

801   CCTCCTGGAG TACGCCCGGA CCTGTGCCCA GGAGGGAATG GTGCTGTACG

851   GCTGGACCGA CCACAGCGCG TGCAGCCCAG TGTGCCCTGC TGGTATGGAG

901   TATAGGCAGT GTGTGTCCCC TTGCGCCAGG ACCTGCCAGA GCCTGCACAT

951   CAATGAAATG TGTCAGGAGC GATGCGTGGA TGGCTGCAGC TGCCCTGAGG

1001   GACAGCTCCT GGATGAAGGC CTCTGCGTGG AGAGCACCGA GTGTCCCTGC

1051   GTGCATTCCG GAAAGCGCTA CCCTCCCGGC ACCTCCCTCT CTCGAGACTG

1101   CAACACCTGC ATTTGCCGAA ACAGCCAGTG GATCTGCAGC AATGAAGAAT

1151   GTCCAGGGGA GTGCCTTGTC ACTGGTCAAT CCCACTTCAA GAGCTTTGAC

1201   AACAGATACT TCACCTTCAG TGGGATCTGC CAGTACCTGC TGGCCCGGGA

1251   TTGCCAGGAC CACTCCTTCT CCATTGTCAT TGAGACTGTC CAGTGTGCTG

1301   ATGACCGCGA CGCTGTGTGC ACCCGCTCCG TCACCGTCCG GCTGCCTGGC

1351   CTGCACAACA GCCTTGTGAA ACTGAAGCAT GGGGCAGGAG TTGCCATGGA

1401   TGGCCAGGAC ATCCAGCTCC CCCTCCTGAA AGGTGACCTC CGCATCCAGC

1451   ATACAGTGAC GGCCTCCGTG CGCCTCAGCT ACGGGGAGGA CCTGCAGATG

1501   GACTGGGATG GCCGCGGGAG GCTGCTGGTG AAGCTGTCCC CCGTCTATGC

1551   CGGGAAGACC TGCGGCCTGT GTGGGAATTA CAATGGCAAC CAGGGCGACG

1601   ACTTCCTTAC CCCCTCTGGG CTGGCGGAGC CCCGGGTGGA GGACTTCGGG

1651   AACGCCTGGA AGCTGCACGG GGACTGCCAG GACCTGCAGA AGCAGCACAG

1701   CGATCCCTGC GCCCTCAACC CGCGCATGAC CAGGTTCTCC GAGGAGGCGT

1751   GCGCGGTCCT GACGTCCCCC ACATTCGAGG CCTGCCATCG TGCCGTCAGC

1801   CCGCTGCCCT ACCTGCGGAA CTGCCGCTAC GACGTGTGCT CCTGCTCGGA

1851   CGGCCGCGAG TGCCTGTGCG GCGCCCTGGC CAGCTATGCC GCGGCCTGCG

1901   CGGGGAGAGG CGTGCGCGTC GCGTGGCGCG AGCCAGGCCG CTGTGAGCTG

1951   AACTGCCCGA AAGGCCAGGT GTACCTGCAG TGCGGGACCC CCTGCAACCT

2001   GACCTGCCGC TCTCTCTCTT ACCCGGATGA GGAATGCAAT GAGGCCTGCC

2051   TGGAGGGCTG CTTCTGCCCC CCAGGGCTCT ACATGGATGA GAGGGGGGAC

2101   TGCGTGCCCA AGGCCCAGTG CCCCTGTTAC TATGACGGTG AGATCTTCCA
```

-continued

```
2151  GCCAGAAGAC ATCTTCTCAG ACCATCACAC CATGTGCTAC TGTGAGGATG

2201  GCTTCATGCA CTGTACCATG AGTGGAGTCC CCGGAAGCTT GCTGCCTGAC

2251  GCTGTCCTCA GCAGTCCCCT GTCTCATCGC AGCAAAAGGA GCCTATCCTG

2301  TCGGCCCCCC ATGGTCAAGC TGGTGTGTCC CGCTGACAAC CTGCGGGCTG

2351  AAGGGCTCGA GTGTACCAAA ACGTGCCAGA ACTATGACCT GGAGTGCATG

2401  AGCATGGGCT GTGTCTCTGG CTGCCTCTGC CCCCCGGGCA TGGTCCGGCA

2451  TGAGAACAGA TGTGTGGCCC TGGAAAGGTG TCCCTGCTTC CATCAGGGCA

2501  AGGAGTATGC CCCTGGAGAA ACAGTGAAGA TTGGCTGCAA CACTTGTGTC

2551  TGTCGGGACC GGAAGTGGAA CTGCACAGAC CATGTGTGTG ATGCCACGTG

2601  CTCCACGATC GGCATGGCCC ACTACCTCAC CTTCGACGGG CTCAAATACC

2651  TGTTCCCCGG GGAGTGCCAG TACGTTCTGG TGCAGGATTA CTGCGGCAGT

2701  AACCCTGGGA CCTTTCGGAT CCTAGTGGGG AATAAGGGAT GCAGCCACCC

2751  CTCAGTGAAA TGCAAGAAAC GGGTCACGAT CCTGGTGGAG GGAGGAGAGA

2801  TTGAGCTGTT TGACGGGGAG GTGAATGTGA AGAGGCCCAT GAAGGATGAG

2851  ACTCACTTTG AGGTGGTGGA GTCTGGCCGG TACATCATTC TGCTGCTGGG

2901  CAAAGCCCTC TCCGTGGTCT GGGACCGCCA CCTGAGCATC TCCGTGGTCC

2951  TGAAGCAGAC ATACCAGGAG AAAGTGTGTG GCCTGTGTGG GAATTTTGAT

3001  GGCATCCAGA ACAATGACCT CACCAGCAGC AACCTCCAAG TGGAGGAAGA

3051  CCCTGTGGAC TTTGGGAACT CCTGGAAAGT GAGCTCGCAG TGTGCTGACA

3101  CCAGAAAAGT GCCTCTGGAC TCATCCCCTG CCACCTGCCA TAACAACATC

3151  ATGAAGCAGA CGATGGTGGA TTCCTCCTGT AGAATCCTTA CCAGTGACGT

3201  CTTCCAGGAC TGCAACAAGC TGGTGGACCC CGAGCCATAT CTGGATGTCT

3251  GCATTTACGA CACCTGCTCC TGTGAGTCCA TTGGGGACTG CGCCGCATTC

3301  TGCGACACCA TTGCTGCCTA TGCCCACGTG TGTGCCCAGC ATGGCAAGGT

3351  GGTGACCTGG AGGACGGCCA CATTGTGCCC CCAGAGCTGC GAGGAGAGGA

3401  ATCTCCGGGA GAACGGGTAT GAGGCTGAGT GGCGCTATAA CAGCTGTGCA

3451  CCTGCCTGTC AAGTCACGTG TCAGCACCCT GAGCCACTGG CCTGCCCTGT

3501  GCAGTGTGTG GAGGGCTGCC ATGCCCACTG CCCTCCAGGG AAAATCCTGG

3551  ATGAGCTTTT GCAGACCTGC GTTGACCCTG AAGACTGTCC AGTGTGTGAG

3601  GTGGCTGGCC GGCGTTTTGC CTCAGGAAAG AAAGTCACCT TGAATCCCAG

3651  TGACCCTGAG CACTGCCAGA TTTGCCACTG TGATGTTGTC AACCTCACCT

3701  GTGAAGCCTG CCAGGAGCCG ATATCGGGCG CGCCAACATC AGAGAGCGCC

3751  ACCCCTGAAA GTGGTCCCGG GAGCGAGCCA GCCACATCTG GGTCGGAAAC

3801  GCCAGGCACA AGTGAGTCTG CAACTCCCGA GTCCGGACCT GGCTCCGAGC

3851  CTGCCACTAG CGGCTCCGAG ACTCCGGGAA CTTCCGAGAG CGCTACACCA

3901  GAAAGCGGAC CCGGAACCAG TACCGAACCT AGCGAGGGCT CTGCTCCGGG

3951  CAGCCCAGCC GGCTCTCCTA CATCCACGGA GGAGGGCACT TCCGAATCCG

4001  CCACCCCGGA GTCAGGGCCA GGATCTGAAC CCGCTACCTC AGGCAGTGAG

4051  ACGCCAGGAA CGAGCGAGTC CGCTACACCG GAGAGTGGGC CAGGGAGCCC

4101  TGCTGGATCT CCTACGTCCA CTGAGGAAGG GTCACCAGCG GGCTCGCCCA
```

-continued

```
4151   CCAGCACTGA AGAAGGTGCC TCGAGCGGCG GTGGAGGATC CGGTGGCGGG

4201   GGATCCGGTG GCGGGGGATC CGGTGGCGGG GGATCCGGTG GCGGGGGATC

4251   CGGTGGCGGG GGATCCCTGG TCCCCCGGGG CAGCGGAGGC GACAAAACTC

4301   ACACATGCCC ACCGTGCCCA GCTCCAGAAC TCCTGGGCGG ACCGTCAGTC

4351   TTCCTCTTCC CCCCAAAACC CAAGGACACC CTCATGATCT CCCGGACCCC

4401   TGAGGTCACA TGCGTGGTGG TGGACGTGAG CCACGAAGAC CCTGAGGTCA

4451   AGTTCAACTG GTACGTGGAC GGCGTGGAGG TGCATAATGC CAAGACAAAG

4501   CCGCGGGAGG AGCAGTACAA CAGCACGTAC CGTGTGGTCA GCGTCCTCAC

4551   CGTCCTGCAC CAGGACTGGC TGAATGGCAA GGAGTACAAG TGCAAGGTCT

4601   CCAACAAAGC CCTCCCAGCC CCCATCGAGA AAACCATCTC CAAAGCCAAA

4851   GGGCAGCCCC GAGAACCACA GGTGTACACC CTGCCCCCAT CCCGGGATGA

4701   GCTGACCAAG AACCAGGTCA GCCTGACCTG CCTGGTCAAA GGCTTCTATC

4751   CCAGCGACAT CGCCGTGGAG TGGGAGAGCA ATGGGCAGCC GGAGAACAAC

4801   TACAAGACCA CGCCTCCCGT GTTGGACTCC GACGGCTCCT TCTTCCTCTA

4851   CAGCAAGCTC ACCGTGGACA AGAGCAGGTG GCAGCAGGGG AACGTCTTCT

4901   CATGCTCCGT GATGCATGAG GCTCTGCACA ACCACTACAC GCAGAAGAGC

4951   CTCTCCCTGT CTCCGGGTAA ATGA
```

FVIII 169 nucleotide secuence (SEQ ID NO: 67)

```
   1   ATGCA AATAG AGCTC TCCAC CTGCT TCTTT CTGTG CCTTT TGCGA TTCTG

51   CTTTA GTGCC ACCAG AAGAT ACTAC CTGGG TGCAG TGGAA CTGTC ATGGG

101   ACTAT ATGCA AAGTG ATCTC GGTGA GCTGC CTGTG GACGC AAGAT TTCCT

151   CCTAG AGTGC CAAAA TCTTT TCCAT TCAAC ACCTC AGTCG TGTAC AAAAA

201   GACTC TGTTT GTAGA ATTCA CGGAT CACCT TTTCA ACATC GCTAA GCCAA

251   GGCCA CCCTG GATGG GTCTG CTAGG TCCTA CCATC CAGGC TGAGG TTTAT

301   GATAC AGTGG TCATT ACACT TAAGA ACATG GCTTC CCATC CTGTC AGTCT

351   TCATG CTGTT GGTGT ATCCT ACTGG AAAGC TTCTG AGGGA GCTGA ATATG

401   ATGAT CAGAC CAGTC AAAGG GAGAA AGAAG ATGAT AAAGT CTTCC CTGGT

451   GGAAG CCATA CATAT GTCTG GCAGG TCCTG AAAGA GAATG GTCCA ATGGC

501   CTCTG ACCCA CTGTG CCTTA CCTAC TCATA TCTTT CTCAT GTGGA CCTGG

551   TAAAA GACTT GAATT CAGGC CTCAT GGAG CCCTA CTAGT ATGTA GAGAA

801   GGGAG TCTGG CCAAG GAAAA GACAC AGACC TTGCA CAAAT TTATA CTACT

851   TTTTG CTGTA TTTGA TGAAG GGAAA AGTTG GCACT CAGAA ACAAA GAACT

701   CCTTG ATGCA GGATA GGGAT GCTGC ATCTG CTCGG GCCTG GCCTA AAATG

751   CACAC AGTCA ATGGT TATGT AAACA GGTCT CTGCC AGGTC TGATT GGATG

801   CCACA GGAAA TCAGT CTATT GGCAT GTGAT GGAA TGGGC ACCAC TCCTG

851   AAGTG CACTC AATAT CCTC GAAGG TCACA CATTT CTTGT GAGGA ACCAT

901   CGCCA GGCTA GCTTG GAAAT CTCGC CAATA ACTTT CCTTA CTGCT CAAAC

951   ACTCT TGATG GACCT TGGAC AGTTT CTACT GTTTT GTCAT ATCTC TTCCC

1001   ACCAA CATGA TGGCA TGGAA GCTTA TGTCA AAGTA GACAG CTGTC CAGAG

1051   GAACC CCAAC TACGA ATGAA AAATA TGAA GAAGC GGAAG ACTAT GATGA

1101   TGATC TTACT GATTC TGAAA TGGAT GTGGT CAGGT TTGAT GATGA CAACT
```

-continued

```
1151   CTCCT TCCTT TATCC AAATT CGCTC AGTTG CCAAG AAGCA TCCTA AAACT

1201   TGGGT ACATT ACATT GCTGC TGAAG AGGAG GACTG GGACT ATGCT CCCTT

1251   AGTCC TCGCC CCCGA TGACA GAAGT TATAA AAGTC AATAT TTGAA CAATG

1301   GCCCT CAGCG GATTG GTAGG AAGTA CAAAA AAGTC CGATT TATGG CATAC

1351   ACAGA TGAAA CCTTT AAGAC TCGTG AAGCT ATTCA GCATG AATCA GGAAT

1401   CTTGG GACCT TTACT TTATG GGGAA GTTGG AGACA CACTG TTGAT TATAT

1451   TTAAG AATCA AGCAA GCAGA CCATA TAACA TCTAC CCTCA CGGAA TCACT

1501   GATGT CCGTC CTTTG TATTC AAGGA GATTA CCAAA AGGTG TAAAA CATTT

1551   GAAGG ATTTT CCAAT TCTGC CAGGA GAAAT ATTCA AATAT AAATG GACAG

1601   TGACT GTAGA AGATG GGCCA ACTAA ATCAG ATCCT CGGTG CCTGA CCCGC

1651   TATTA CTCTA GTTTC GTTAA TATGG AGAGA GATCT AGCTT CAGGA CTCAT

1701   TGGCC CTCTC CTCAT CTGCT ACAAA GAATC TGTAG ATCAA AGAGG AAACC

1751   AGATA ATGTC AGACA AGAGG AATGT CATCC TGTTT TCTGT ATTTG ATGAG

1801   AACCG AAGCT GGTAC CTCAC AGAGA ATATA CAACG CTTTC TCCCC AATCC

1851   AGCTG GAGTG CAGCT TGAGG ATCCA GAGTT CCAAG CCTCC AACAT CATGC

1901   ACAGC ATCAA TGGCT ATGTT TTTGA TAGTT TGCAG TTGTC AGTTT GTTTG

1951   CATGA GGTGG CATAC TGGTA CATTC TAAGC ATTGG AGCAC AGACT GACTT

2001   CCTTT CTGTC TTCTT CTCTG GATAT ACCTT CAAAC ACAAA ATGGT CTATG

2051   AAGAC ACACT CACCC TATTC CCATT CTCAG GAGAA ACTGT CTTCA TGTCG

2101   ATGGA AAACC CAGGT CTATG GATTC TGGGG TGCCA CAACT CAGAC TTTCG

2151   GAACA GAGGC ATGAC CGCCT TACTG AAGGT TTCTA GTTGT GACAA GAACA

2201   CTGGT GATTA TTACG AGGAC AGTTA TGAAG ATATT TCAGC ATACT TGCTG

2251   AGTAA AAACA ATGCC ATTGA ACCAA GAAGC TTCTC TCAAA ACGGC GCGCC

2301   AGGTA CCTCA GAGTC TGCTA CCCCC GAGTC AGGGC CAGGA TCAGA GCCAG

2351   CCACC TCCGG GTCTG AGACA CCCGG GACTT CCGAG AGTGC CACCC CTGAG

2401   TCCGG ACCCG GTCCG AGCCG CGCCA CTTCC GGCTC CGAAA CTCCC GGCAC

2451   AAGCG AGAGC GCTAC CCCAG AGTCA GGACC AGGAA CATCT ACAGA GCCCT

2501   CTGAA GGCTC CGCTC CAGGG TCCCC AGCCG GCAGT CCCAC TAGCA CCGAG

2551   GAGGG AACCT CTGAA AGCGC CACAC CCGAA TCAGG GCCAG GGTCT GAGCC

2601   TGCTA CCAGC GGCAG CGAGA CACCA GGCAC TCTGT AGTCC GCCAC ACCAG

2651   AGTCC GGACC CGGAT CTCCC GCTGG GAGCC CCACC TCCAC TGAGG AGGGA

2701   TCTCC TGCTG GCTCT CCAAC ATCTA CTGAG GAAGG TACCT CAACC GAGCC

2751   ATCCG AGGGA TCAGC TCCCG GCACC TCAGA GTCGG CAACC CCGGA GTCTG

2801   GACCC GGAAC TTCCG AAAGT GCCAC ACCAG AGTCC GGTCC CGGGA CTTCA

2851   GAATC AGCAA CACCC GAGTC CGGCC CTGGG TCTGA ACCCG CCACA AGTGG

2901   TAGTG AGACA CCAGG ATCAG AACCT GCTAC CTCAG GGTCA GAGAC ACCCG

2951   GATCT CCGGC AGGCT CACCA ACCTC CACTG AGGAG GGCAC CAGCA CAGAA

3001   CCAAG CGAGG GCTCC GCACC CGGAA CAAGC ACTGA ACCCA GTGAG GGTTC

3051   AGCAC CCGGC TCTGA GCCGG CCACA AGTGG CAGTG AGACA CCCGG CACTT

3101   CAGAG AGTGC CACCC CCGAG AGTGG CCCAG GCACT AGTAC CGAGC CCTCT
```

-continued

```
3151  GAAGG CAGTG CGCCA GCCTC GAGCC CACCA GTCTT GAAAC GCCAT CAAGC

3201  TGAAA TAACT CGTAC TACTC TTCAG TCAGA TCAAG AGGAA ATCGA TTATG

3251  ATGAT ACCAT ATCAG TTGAA ATGAA GAAGG AAGAT TTTGA CATTT ATGAT

3301  GAGGA TGAAA TCAG AGCCC CCGCA GCTTT CAAAA GAAAA CACGA CACTA

3351  TTTTA TTGCT GCAGT GGAGA GGCTC TGGGA TTATG GGATG AGTAG CTCCC

3401  CACAT GTTCT AAGAA ACAGG GCTCA GAGTG GCAGT GTCCC TCAGT TCAAG

3451  AAAGT TGTTT CCAG GAATT TACTG ATGGC TCCTT TACTC AGCCC TTATA

3501  CCGTG GAGAA CTAAA TGAAC ATTTG GGACT CCTGG GGCCA TATAT AAGAG

3551  CAGAA GTTGA AGATA ATATC ATGGT AACTT TCAGA AATCA GGCCT CTCCT

3601  CCCTA TTCCT TCTAT TCTAG CCTTA TTTCT TATGA GGAAG ATCAG AGGCA

3651  AGGAG CAGAA CCTAG AAAAA ACTTT GTCAA GCCTA ATGAA ACCAA AACTT

3701  ACTTT TGGAA AGTGC AACAT CATAT GGCAC CCACT AAAGA TGAGT TTGAC

3751  TGCAA AGCCT GGGCT TATTT CTCTG ATGTT GACCT GGAAA AAGAT GTGCA

3801  CTCAG GCCTG ATTGG ACCCC TTCTG GTCTG CCACA CTAAC ACACT GAACC

3851  CTGCT CATGG GAGAC AAGTG AAAGT ACAGG AATTT GCTCT GTTTT TCACC

3901  ATCTT TGATG AGACC AAAAG CTGGT ACTTC ACTGA AAATA TGGAA AGAAA

3951  CTGCA GGGCT CCCTG CAATA TCCAG ATGGA AGATC CCACT TTTAA AGAGA

4001  ATTAT CGCTT CCATG CAATC AATGG CTACA TAATG GATAC ACTAC CTGGC

4051  TTAGT AATGG CTCAG GATCA AAGGA TTCGA TGGTA TCTGC TCAGC ATGGG

4101  CAGCA ATGAA AACAT CCATT CTATT CATTT CAGTG GACAT GTGTT CACTG

4151  TACGA AAAAA AGAGG AGTAT AAAAT GGCAC TGTAC AATCT CTATC CAGGT

4201  GTTTT TGAGA CAGTG GAAAT GTTAC CATCC AAAGC TGGAA TTTGG CGGGT

4251  GGAAT GCCTT ATTGG CGAGC ATCTA CATGC TGGGA TGAGC ACACT TTTTC

4301  TGGTG TACAG CAATA AGTGT CAGAC TCCCC TGGGA ATGGC TTCTG GACAC

4351  ATTAG AGATT TTCAG ATTAC AGCTT CAGGA CAATA TGGAC AGTGG GCCCC

4401  AAAGC TGGCC AGACT TCATT ATTCC GGATC AATCA ATGCC TGGAG CACCA

4451  AGGAG CCCTT TTCTT GGATC AAGGT GGATC TGTTG GCACC AATGA TTATT

4501  CACGG CATCA AGACC CAGGG TGCCC GTCAG AAGTT CTCCA GCCTC TACAT

4551  CTCTC AGTTT ATCAT CATGT ATAGT CTTGA TGGGA AGAAG TGGCA GACTT

4601  ATCGA GGAAA TTCCA CTGGA ACCTT AATGG TCTTC TTTGG CAATG TGGAT

4651  TCATC TGGGA TAAAA CACAA TATTT TTAAC CCTCC AATTA′TTCCT CGATA

4701  CATCC GTTTG CACCC AACTC ATTAT AGCAT CGCA GCACT CTTCG CATGG

4751  AGTTG ATGGG CTGTG ATTTA AATAG TTGCA GCATG CCATT GGGAA TGGAG

4801  AGTAA AGCAA TATCA GATGC ACAGA TTACT GCTTC ATCCT ACTTT ACCAA

4851  TATGT TTGCC ACCTG GTCTC CTTCA AAAGC TCGAC TTCAC CTCCA AGGGA

4901  GGAGT AATGC CTGGA GACCT CAGGT GAATA ATCCA AAAGA GTGGC TGCAA

4951  GTGGA CTTCC AGAAG ACAAT GAAAG TCACA GGAGT AACTA CTCAG GGAGT

5001  AAAAT CTCTG CTTAC CAGCA TGTAT GTGAA GGAGT TCCTC ATCTC CAGCA

5051  GTCAA GATGG CCATC AGTGG ACTCT CTTTT TTCAG AATGG CAAAG TAAAG

5101  GTTTT TCAGG GAAAT CAAGA CTCCT TCACA CCTGT GGTGA ACTCT CTAGA

5151  CCCAC CGTTA CTGAC TCGCT ACCTT CGAAT TCACC CCCAG AGTTG GGTGC
```

-continued

```
5201  ACCAG ATTGC CCTGA GGATG GAGGT TCTGG GCTGC GAGGC ACAGG ACCTC

5251  TACGA CAAAA CTCAC ACATG CCCAC CGTGC CCAGC TCCAG AACTC CTGGG

5301  CGGAC CGTCA GTCTT CCTCT TCCCC CCAAA ACCCA AGGAC ACCCT CATGA

5351  TCTCC CGGAC CCCTG AGGTC ACATG CGTGG TGGTG GACGT GAGCC ACGAA

5401  GACCC TGAGG TCAAG TTCAA CTGGT ACGTG GACGG CGTGG AGGTG CATAA

5451  TGCCA AGACA AAGCC GCGGG AGGAG CAGTA CAACA GCACG TACCG TGTGG

5501  TCAGC GTCCT CACCG TCCTG CACCA GGACT GGCTG AATGG CAAGG AGTAC

5551  AAGTG CAAGG TCTCC AACAA AGCCC TCCCA GCCCC CATCG AGAAA ACCAT

5601  CTCCA AAGCC AAAGG GCAGC CCCGA GAACC ACAGG TGTAC ACCCT GCCCC

5651  CATCC CGGGA TGAGC TGACC AAGAA CCAGG TCAGC CTGAC CTGCC TGGTC

5701  AAAGG CTTCT ATCCC AGCGA CATCG CCGTG GAGTG GGAGA GCAAT GGGCA

5751  GCCGG AGAAC AACTA CAAGA CCACG CCTCC CGTGT TGGAC TCCGA CGGCT

5801  CCTTC TTCCT CTACA GCAAG CTCAC CGTGG ACAAG AGCAG GTGGC AGCAG

5851  GGGAA CGTCT TCTCA TGCTC CGTGA TGCAT GAGGC TCTGC ACAAC CACTA

5901  CACGC AGAAG AGCCT CTCCC TGTCT CCGGG TAAAT GA
```

WIII 169 protein seqence (SEQ ID NO: 68)

```
   1  MQIELSTCFF LCLLFFCFSA TRRYYLGAVE LSWDYMQSDL GELPVDARFP

51  PRVPKSFPFN TSVVYKKTLF VEFTDHLFNI AKPRPPWMGL LGPTIQAEVY

101  DTVVITLKNM ASHPVSLHAV GVSYWKASEG AEYDDQTSQR EKEDDKVFPG

151  GSHTYVWQVL KENGPMASDP LCLTYSYLSH VDLVKDLNSG LIGALLVCRE

201  GSLAKEKTQT LHKFILLFAV FDEGKSWHSE TKNSLMQDRD AASARAWPKM

251  HTVNGYVNRS LPGLIGCHRK SVYWHVIGMG TTPEVHSIFL EGHTFLVRNH

301  RQNSLEISPI TFLTAQTLLM DLGQFLLFCH ISSHQHDGME AYVKVDSCPE

351  EPQLRMKNNE EAEDYDDDLT DSEMDVVRFD DDNSPSFIQI RSVAKKHPKT

401  WVHYIAAEEE DWDYAPLVLA PDDRSYKSQY LNNGPQRIGR KYKKVRFMAY

451  TDETFKTREA IQHESGILGP LLYGEVGDTL LIIFKNQASR PYNIYPHGIT

501  DVRPLYSRRL PKGVKHLKDF PILPGEIFKY KWTVTVEDGP TKSDPRCLTR

551  YYSSFVNMER DLASGLIGPL LICYKESVDQ RGNQIMSDKR NVILFSVFDE

601  NRSWYLTENI QRFLPNPAGV QLEDPEFQAS NIMHSINGYV FDSLQLSVCL

651  HEVAYWYILS IGAQTDFLSV FFSGYTFKHK MVYEDTLTLF PFSGETVFMS

701  MENPGLWILG CHNSDFRNRG MTALLKVSSC DKNTGDYYED SYEDISAYLL

751  SKNNAIEPRS FSQNGAPGTS ESATPESGPG SEPATSGSET PGTSESATPE

801  SGPGSEPATS GSETPGTSES ATPESGPGTS TEPSEGSAPG SPAGSPTSTE

851  EGTSESATPE SGPGSEPATS GSETPGTSES ATPESGPGSP AGSPTSTEEG

901  SPAGSPTSTE EGTSTEPSEG SAPGTSESAT PESGPGTSES ATPESGPGTS

951  ESATPESGPG SEPATSGSET PGSEPATSGS ETPGSPAGSP TSTEEGTSTE

1001  PSEGSAPGTS TEPSEGSAPG SEPATSGSET PGTSESATPE SGPGTSTEPS

1051  EGSAPASSPP VLKRHQAEIT RTTLQSDQEE IDYDDTISVE MKKEDFDIYD

1101  EDENQSPRSF QKKTRHYFIA AVERLWDYGM SSSPHVLRNR AQSGSVPQFK

1151  KVVFQEFTDG SFTQPLYRGE LNEHLGLLGP YIRAEVEDNI MVTFRNQASR
```

-continued

```
1201    PYSFYSSLIS  YEEDQRQGAE  PRKNFVKPNE  TKTYFWKVQH  HMAPTKDEFD

1251    CKAWAYFSDV  DLEKDVHSGL  IGPLLVCHTN  TLNPAHGRQV  TVQEFALFFT

1301    IFDETKSWYF  TENMERNCRA  PCNIQMEDPT  FKENYRFHAI  NGYIMDTLPG

1351    LVMAQDQRIR  WYLLSMGSNE  NIHSIHFSGH  VFTVRKKEEY  KMALYNLYPG

1401    VFETVEMLPS  KAGIWRVECL  IGEHLHAGMS  TLFLVYSNKC  QTPLGMASGH

1451    IRDFQITASG  QYGQWAPKLA  RLHYSGSINA  WSTKEPFSWI  KVDLLAPMII

1501    HGIKTQGARQ  KFSSLYISQF  IIMYSLDGKK  WQTYRGNSTG  TLMVFFGNVD

1551    SSGIKHNIFN  PPIIARYIRL  HPTHYSIRST  LRMELMGCDL  NSCSMPLGME

1601    SKAISDAQIT  ASSYFTNMFA  TWSPSKARLH  LQGRSNAWRP  QVNNPKEWLQ

1651    VDFQKTMKVT  GVTTQGVKSL  LTSMYVKEFL  ISSSQDGHQW  TLFFQNGKVK

1701    VFQGNQDSFT  PVVNSLDPPL  LTRYLRIHPQ  SWVHQIALRM  EVLGCEAQDL

1751    YDKTHTCPPC  PAPELLGGPS  VFLFPPKPKD  TLMISRTPEV  TCVVVDVSHE

1801    DPEVKFNWYV  DGVEVHNAKT  KPREEQYNST  YRVVSVLTVL  HQDWLNGKEY

1851    KCKVSNKALP  APIEKTISKA  KGQPREPQVY  TLPPSRDELT  KNQVSLTCLV

1901    KGFYPSDIAV  EWESNGQPEN  NYKTTPPVLD  SDGSFFLYSK  LTVDKSRWQQ

1951    GNVFSCSVMH  EALHNHYTQK  SLSLSPGK*
```

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

What is claimed:

1. A method of purifying a chimeric protein comprising a factor VIII (FVIII) protein and a von Willebrand Factor (VWF) protein or a VWF fragment, the method comprising:
   (i) subjecting the chimeric protein to a FVIII-specific affinity chromatography column,
   (ii) eluting the chimeric protein with a FVIII-specific affinity chromatography elution buffer,
   (iii) subjecting the chimeric protein to an anion exchange (AEX) chromatography column, wherein the AEX chromatography column comprises an anion exchange resin comprising one or more quaternary amino groups, and
   (iv) eluting the chimeric protein with an AEX chromatography elution buffer, the AEX chromatography elution buffer comprising:
      about 1 mM to about 1M N-2-hydroxyethylpiperazine-N'-2-ethanesulfonic acid (HEPES),
      at least 400 mM sodium chloride, and
   wherein the AEX chromatography elution buffer has a pH from about 6.0 to about 8.0, thereby providing the purified chimeric protein.

2. The method of claim 1, wherein the FVIII-specific affinity chromatography elution buffer has a pH of about 7.4.

3. The method of claim 1, wherein the AEX chromatography elution buffer comprises about 10 mM HEPES.

4. The method of claim 1, wherein the AEX chromatography elution buffer has a pH of about 7.8.

5. The method of claim 1, wherein the FVIII-specific affinity chromatography elution buffer comprises histidine, calcium chloride, arginine, and propylene glycol.

6. The method of claim 5, wherein the FVIII-specific affinity chromatography elution buffer comprises from about 30 mM to about 100 mM histidine.

7. The method of claim 6, wherein the FVIII-specific affinity chromatography elution buffer comprises about 50 mM histidine.

8. The method of claim 5, wherein the FVIII-specific affinity chromatography elution buffer comprises about 50 mM calcium chloride.

9. The method of claim 5, wherein the FVIII-specific affinity chromatography elution buffer comprises about 900 mM arginine.

10. The method of claim 5, wherein the FVIII-specific affinity chromatography elution buffer comprises from about 30% to about 60% propylene glycol.

11. The method of claim 10, wherein the FVIII-specific affinity chromatography elution buffer comprises about 45% propylene glycol.

12. The method of claim 1, wherein the FVIII-specific affinity chromatography elution buffer has a pH from about 6.0 to about 8.0.

13. The method of claim 1, wherein the method further comprises subjecting the chimeric protein to one or more additional purification and/or separation steps.

14. The method of claim 1, further comprising subjecting the chimeric protein to a tangential flow filtration step prior to step (i).

15. The method of claim 1, wherein the AEX chromatography elution buffer does not comprise calcium chloride.

16. The method of claim 1, wherein the method further comprises subjecting the eluted chimeric protein resulting from step (iv) to one or more additional purification and/or separation steps.

17. The method of claim 16, wherein the one or more additional purification and/or separation steps are selected from cation exchange chromatography, hydrophobic interaction chromatography, size-exclusion chromatography, multimodal chromatography, reversed phase chromatography, chromatofocusing, filtration, viral inactivation, and precipitation.

18. The method of claim 1, wherein the chimeric protein comprises the FVIII protein and a VWF fragment.

19. The method of claim 18, wherein the FVIII protein comprises a full or partial deletion of the B domain.

20. The method of claim 19, wherein the VWF fragment prevents or inhibits binding of endogenous VWF to the FVIII protein.

21. The method of claim 19, wherein the FVIII protein is linked to a first Fc region, the VWF fragment comprises a D' domain and a D3 domain of VWF and is linked to a second Fc region, and the first Fc region and the second Fc region form a disulfide bond.

22. The method of claim 21, wherein the chimeric protein further comprises an XTEN sequence that consists of 4 to 6 types of amino acids selected from the group consisting of glycine (G), alanine (A), serine (S), threonine (T), glutamate (E), and proline (P).

23. The method of claim 22, wherein the XTEN sequence is inserted into the FVIII protein.

24. The method of claim 23, wherein the XTEN sequence is inserted into the FVIII protein immediately downstream of residue 745 of the FVIII polypeptide.

25. A method of purifying a chimeric protein comprising a factor VIII (FVIII) protein and a von Willebrand Factor (VWF) protein or a VWF fragment, comprising:

(i) subjecting the chimeric protein to a FVIII-specific affinity chromatography column, (ii) eluting the chimeric protein with a FVIII-specific affinity chromatography elution buffer, the FVIII-specific affinity chromatography elution buffer comprising:

50 mM histidine, 50 mM calcium chloride, 900 mM arginine-HCl,

45% propylene glycol, and wherein the FVIII-specific affinity chromatography elution buffer has a pH of about 7.4;

(iii) subjecting the chimeric protein to an anion exchange (AEX) chromatography column, wherein the AEX chromatography column comprises an anion exchange resin comprising one or more quaternary amino groups;

(iv) eluting the chimeric protein with an AEX chromatography elution buffer, the AEX chromatography elution buffer comprising:

10 mM HEPES, and at least 400 mM sodium chloride, and wherein the AEX chromatography elution buffer has a pH of about 7.8 thereby providing the purified chimeric protein.

26. The method of claim 25, further comprising subjecting the chimeric protein to a tangential flow filtration step prior to step (i).

27. The method of claim 25, wherein the factor VIII-specific affinity chromatography elution buffer comprises a detergent, wherein the detergent is selected from the group consisting of polysorbate 20, polysorbate 80, polyethylene glycol, p-(1,1,3,3-tetramethylbutyl)-phenyl ether, octylphenoxypolyethoxyethanol, 3-((3-cholamidopropyl) dimethylammonio)-1-propanesulfonate (CHAPS), and 3-[(3-Cholamidopropyl)dimethylammonio]-2-hydroxypropanesulfonate (CHAPSO).

28. The method of claim 25, further comprising washing chimeric protein bound to the affinity chromatography column with a FVIII-specific affinity chromatography wash buffer.

29. The method of claim 25, wherein the AEX chromatography elution buffer further comprises tris-(hydroxymethyl)aminoethane.

30. The method of claim 25, wherein the AEX chromatography elution buffer comprises a detergent, wherein the detergent is selected from the group consisting of polysorbate 20, polysorbate 80, polyethylene glycol, p-(1,1,3,3-tetramethylbutyl)-phenyl ether, octylphenoxypolyethoxyethanol, 3-((3-cholamidopropyl) dimethylammonio)-1-propanesulfonate (CHAPS), and 3-[(3-Cholamidopropyl) dimethylammonio]-2-hydroxypropanesulfonate (CHAPSO).

31. The method of claim 25, further comprising: subjecting the eluted chimeric protein to one or more additional purification and/or separation steps, wherein the one or more additional purification and/or separation are selected from cation exchange chromatography, hydrophobic interaction chromatography, size-exclusion chromatography, multimodal chromatography, reversed phase chromatography, chromatofocusing, filtration, viral inactivation, and precipitation.

32. The method of claim 25, wherein the AEX chromatography elution buffer does not comprise calcium chloride.

33. The method of claim 25, wherein the anion exchange resin is strong quaternary ammonium (Q) anion exchanger.

34. The method of claim 25, wherein the chimeric protein comprises the FVIII protein and a VWF fragment.

35. The method of claim 34, wherein the FVIII protein is linked to a first Fc region, the VWF fragment comprises a D' domain and a D3 domain of VWF and is linked to a second Fc region, and the first Fc region and the second Fc region form a disulfide bond.

36. The method of claim 35, wherein the VWF fragment prevents or inhibits binding of endogenous VWF to the FVIII protein.

37. The method of claim 35, wherein the chimeric protein further comprises an XTEN sequence that consists of 4 to 6 types of amino acids selected from the group consisting of glycine (G), alanine (A), serine (S), threonine (T), glutamate (E), and proline (P).

* * * * *

SEQUENCE LISTING

```
<160> NUMBER OF SEQ ID NOS: 98

<210> SEQ ID NO 1
<211> LENGTH: 8442
<212> TYPE: DNA
<213> ORGANISM: Homo sapiens

<400> SEQUENCE: 1
atgattcctg ccagatttgc cggggtgctg cttgctctgg ccctcatttt gccagggacc          60
ctttgtgcag aaggaactcg cggcaggtca tccacggccc gatgcagcct tttcggaagt         120
gacttcgtca acacctttga tgggagcatg tacagctttg cgggatactg cagttacctc         180
ctggcagggg gctgccagaa acgctccttc tcgattattg gggacttcca gaatggcaag         240
agagtgagcc tctccgtgta tcttggggaa tttttttgaca tccatttgtt tgtcaatggt        300
accgtgacac aggggggacca aagagtctcc atgccctatg cctccaaagg gctgtatcta        360
gaaactgagg ctgggtacta caagctgtcc ggtgaggcct atggctttgt ggccaggatc        420
gatggcagcg gcaactttca agtcctgctg tcagacagat acttcaacaa gacctgcggg        480
ctgtgtggca cttttaacat ctttgctgaa gatgacttta tgacccaaga agggaccttg        540
acctcggacc cttatgactt tgccaactca tgggctctga gcagtggaga acagtggtgt        600
```

-continued

```
gaacgggcat ctcctcccag cagctcatgc aacatctcct ctggggaaat gcagaagggc    660
ctgtgggagc agtgccagct tctgaagagc acctcggtgt ttgcccgctg ccaccctctg    720 gtggacccg  agccttttgt ggccctgtgt gagaagactt tgtgtgagtg tgctgggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct ggatgaaggc    1020 ctctgcgtgg agagcaccga gtgtccctgc gtgcattccg gaaagcgcta ccctcccggc    1080
acctccctct ctcgagactg caacacctgc atttgccgaa acagccagtg gatctgcagc    1140
aatgaagaat gtccagggga gtgccttgtc actggtcaat cccacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac atccagctcc ccctcctgaa aggtgacctc    1440
cgcatccagc atacagtgac ggcctccgtg cgcctcagct acgggaggga cctgcagatg    1500
gactgggatg gccgcgggag gctgctggtg aagctgtccc ccgtctatgc cgggaagacc    1560
tgcggcctgt gtgggaatta caatggcaac cagggcgacg acttccttac cccctctggg    1620
ctggcrgagc cccgggtgga ggacttcggg aacgcctgga agctgcacgg ggactgccag    1680
gacctgcaga agcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aaggccaggt gtacctgcag    1980
tgcgggaccc cctgcaacct gacctgccgc tctctctctt acccggatga ggaatgcaat    2040
gaggcctgcc tggagggctg cttctgcccc ccagggctct acatggatga gaggggggac    2100
tgcgtgccca aggcccagtg cccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggccccc  atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg gggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
```

-continued

```
tccgtggtcc tgaagcagac ataccaggag aaagtgtgtg gcctgtgtgg gaattttgat      3000
ggcatccaga acaatgacct caccagcagc aacctccaag tggaggaaga ccctgtggac      3060
tttgggaact cctggaaagt gagctcgcag tgtgctgaca ccagaaaagt gcctctggac      3120
tcatcccctg ccacctgcca taacaacatc atgaagcaga cgatggtgga ttcctcctgt      3180
agaatcctta ccagtgacgt cttccaggac tgcaacaagc tggtggaccc cgagccatat      3240
ctggatgtct gcatttacga cacctgctcc tgtgagtcca ttggggactg cgcctgcttc      3300
tgcgacacca ttgctgccta tgcccacgtg tgtgcccagc atggcaaggt ggtgacctgg      3360
aggacggcca cattgtgccc ccagagctgc gaggagagga atctccggga gaacgggtat      3420
gagtgtgagt ggcgctataa cagctgtgca cctgcctgtc aagtcacgtg tcagcaccct      3480
gagccactgg cctgccctgt gcagtgtgtg gagggctgcc atgcccactg ccctccaggg      3540
aaaatcctgg atgagctttt gcagacctgc gttgaccctg aagactgtcc agtgtgtgag      3600
gtggctggcc ggcgttttgc ctcaggaaag aaagtcacct tgaatcccag tgaccctgag      3660
cactgccaga tttgccactg tgatgttgtc aacctcacct gtgaagcctg ccaggagccg      3720
ggaggcctgg tggtgcctcc cacagatgcc ccggtgagcc ccaccactct gtatgtggag      3780
gacatctcgg aaccgccgtt gcacgatttc tactgcagca ggctactgga cctggtcttc      3840
ctgctggatg gctcctccag gctgtccgag gctgagtttg aagtgctgaa ggcctttgtg      3900
gtggacatga tggagcggct gcgcatctcc cagaagtggg tccgcgtggc cgtggtggag      3960
taccacgacg gctcccacgc ctacatcggg ctcaaggacc ggaagcgacc gtcagagctg      4020
cggcgcattg ccagccaggt gaagtatgcg ggcagccagg tggcctccac cagcgaggtc      4080
ttgaaataca cactgttcca aatcttcagc aagatcgacc gccctgaagc ctcccgcatc      4140
gccctgctcc tgatggccag ccaggagccc caacggatgt cccggaactt tgtccgctac      4200
gtccagggcc tgaagaagaa gaaggtcatt gtgatcccgg tgggcattgg gccccatgcc      4260
aacctcaagc agatccgcct catcgagaag caggcccctg agaacaaggc cttcgtgctg      4320
agcagtgtgg atgagctgga gcagcaaagg gacgagatcg ttagctacct ctgtgacctt      4380
gcccctgaag cccctcctcc tactctgccc cccgacatgg cacaagtcac tgtgggcccg      4440
gggctcttgg gggtttcgac cctggggccc aagaggaact ccatggttct ggatgtggcg      4500
ttcgtcctgg aaggatcgga caaaattggt gaagccgact tcaacaggag caaggagttc      4560
atggaggagg tgattcagcg gatggatgtg ggccaggaca gcatccacgt cacggtgctg      4620
cagtactcct acatggtgac cgtggagtac cccttcagcg aggcacagtc caaaggggac      4680
atcctgcagc gggtgcgaga gatccgctac cagggcggca acaggaccaa cactgggctg      4740
gccctgcggt acctctctga ccacagcttc ttggtcagcc agggtgaccg ggagcaggcg      4800
cccaacctgg tctacatggt caccggaaat cctgcctctg atgagatcaa gaggctgcct      4860
ggagacatcc aggtggtgcc cattggagtg ggccctaatg ccaacgtgca ggagctggag      4920
aggattggct ggcccaatgc ccctatcctc atccaggact ttgagacgct cccccgagag      4980
gctcctgacc tggtgctgca gaggtgctgc tccggagagg ggctgcagat cccacccctc      5040
tcccctgcac ctgactgcag ccagccctg gacgtgatcc ttctcctgga tggctcctcc      5100
agtttcccag cttcttattt tgatgaaatg aagagtttcg ccaaggcttt catttcaaaa      5160
gccaatatag ggcctcgtct cactcaggtg tcagtgctgc agtatggaag catcaccacc      5220
attgacgtgc catggaacgt ggtcccggag aaagcccatt tgctgagcct tgtggacgtc      5280
atgcagcggg agggaggccc cagccaaatc ggggatgcct tgggctttgc tgtgcgatac      5340
```

-continued

```
ttgacttcag aaatgcatgg tgccaggccg ggagcctcaa aggcggtggt catcctggtc     5400
acggacgtct ctgtggattc agtggatgca gcagctgatg ccgccaggtc caacagagtg     5460
acagtgttcc ctattggaat tggagatcgc tacgatgcag cccagctacg gatcttggca     5520
ggcccagcag gcgactccaa cgtggtgaag ctccagcgaa tcgaagacct ccctaccatg     5580
gtcaccttgg gcaattcctt cctccacaaa ctgtgctctg gatttgttag gatttgcatg     5640
gatgaggatg ggaatgagaa gaggcccggg gacgtctgga ccttgccaga ccagtgccac     5700
accgtgactt gccagccaga tggccagacc ttgctgaaga gtcatcgggt caactgtgac     5760
cgggggctga ggccttcgtg ccctaacagc cagtccctg ttaaagtgga agagacctgt     5820
ggctgccgct ggacctgccc ctgygtgtgc acaggcagct ccactcggca catcgtgacc     5880
tttgatgggc agaatttcaa gctgactggc agctgttctt atgtcctatt tcaaaacaag     5940
gagcaggacc tggaggtgat tctccataat ggtgcctgca gccctggagc aaggcagggc     6000
tgcatgaaat ccatcgaggt gaagcacagt gccctctccg tcgagstgca cagtgacatg     6060
gaggtgacgg tgaatgggag actggtctct gttccttacg tgggtgggaa catggaagtc     6120
aacgtttatg gtgccatcat gcatgaggtc agattcaatc accttggtca catcttcaca     6180
ttcactccac aaaacaatga gttccaactg cagctcagcc ccaagacttt tgcttcaaag     6240
acgtatggtc tgtgtgggat ctgtgatgag aacggagcca atgacttcat gctgagggat     6300
ggcacagtca ccacagactg gaaaacactt gttcaggaat ggactgtgca gcggccaggg     6360
cagacgtgcc agcccatcct ggaggagcag tgtcttgtcc ccgacagctc ccactgccag     6420
gtcctcctct taccactgtt tgctgaatgc cacaaggtcc tggctccagc cacattctat     6480
gccatctgcc agcaggacag ttgccaccag gagcaagtgt gtgaggtgat cgcctcttat     6540
gcccacctct gtcggaccaa cggggtctgc gttgactgga ggacacctga tttctgtgct     6600
atgtcatgcc caccatctct ggtctacaac cactgtgagc atggctgtcc ccggcactgt     6660
gatggcaacg tgagctcctg tggggaccat ccctccgaag gctgtttctg ccctccagat     6720
aaagtcatgt tggaaggcag ctgtgtccct gaagaggcct gcactcagtg cattggtgag     6780
gatggagtcc agcaccagtt cctggaagcc tgggtcccgg accaccagcc ctgtcagatc     6840
tgcacatgcc tcagcgggcg gaaggtcaac tgcacaacgc agccctgccc cacggccaaa     6900
gctcccacgt gtggctgtg tgaagtagcc cgcctccgcc agaatgcaga ccagtgctgc     6960
cccgagtatg agtgtgtgtg tgacccagtg agctgtgacc tgccccagt gcctcactgt     7020 gaacgtggcc tccagcccac actgaccaac cctggcgagt gcagacccaa cttcacctgc     7080
gcctgcagga aggaggagtg caaaagagtg tccccaccct cctgcccccc gcaccgtttg     7140
cccacccttc ggaagaccca gtgctgtgat gagtatgagt gtgcctgcaa ctgtgtcaac     7200
tccacagtga gctgtccct tgggtacttg gcctcaaccg ccaccaatga ctgtggctgt     7260
accacaacca cctgccttcc cgacaaggtg tgtgtccacc gaagcaccat ctaccctgtg     7320
ggccagttct gggaggaggg ctgcgatgtg tgcacctgca ccgacatgga ggatgccgtg     7380
atgggcctcc gcgtggccca gtgctcccag aagccctgtg aggacagctg tcggtcgggc     7440
ttcacttacg ttctgcatga aggcgagtgc tgtggaaggt gcctgccatc tgcctgtgag     7500
gtggtgactg gctcaccgcg ggggactcc cagtcttcct ggaagagtgt cggctcccag     7560
tgggcctccc cggagaaccc ctgcctcatc aatgagtgtg tccgagtgaa ggaggaggtc     7620
tttatacaac aaaggaacgt ctcctgcccc cagctggagg tccctgtctg cccctcgggc     7680
```

-continued

```
tttcagctga gctgtaagac ctcagcgtgc tgcccaagct gtcgctgtga gcgcatggag      7740
gcctgcatgc tcaatggcac tgtcattggg cccgggaaga ctgtgatgat cgatgtgtgc      7800
acgacctgcc gctgcatggt gcaggtgggg gtcatctctg gattcaagct ggagtgcagg      7860
aagaccacct gcaacccctg cccctgggt  tacaaggaag aaaataacac aggtgaatgt       7920
tgtgggagat gtttgcctac ggcttgcacc attcagctaa gaggaggaca gatcatgaca      7980
ctgaagcgtg atgagacgct ccaggatggc tgtgatactc acttctgcaa ggtcaatgag      8040
agaggagagt acttctggga aagagggtc  acaggctgcc cacccttga  tgaacacaag       8100 tgtcttgctg agggaggtaa aattatgaaa attccaggca cctgctgtga cacatgtgag      8160
gagcctgagt gcaacgacat cactgccagg ctgcagtatg tcaaggtggg aagctgtaag      8220
tctgaagtag aggtggatat ccactactgc cagggcaaat gtgccagcaa agccatgtac      8280
tccattgaca tcaacgatgt gcaggaccag tgctcctgct gctctccgac acggacggag      8340
cccatgcagg tggccctgca ctgcaccaat ggctctgttg tgtaccatga ggttctcaat      8400
gccatggagt gcaaatgctc ccccaggaag tgcagcaagt ga                         8442
```

```
<210> SEQ ID NO 2
<211> LENGTH: 2813
<212> TYPE: PRT
<213> ORGANISM: Homo sapiens
<220> FEATURE:
<221> NAME/KEY: MISC_FEATURE
<222> LOCATION: (2016)..(2016)
<223> OTHER INFORMATION: where Xaa can be any amino acid other than
      cysteine

<400> SEQUENCE: 2

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
```

```
            210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
            290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
            370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
                435                 440                 445

Pro Gly Leu His Asn Ser Leu Val Lys Leu Lys His Gly Ala Gly Val
            450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640
```

-continued

```
Ala Trp Arg Glu Pro Gly Arg Cys Glu Leu Asn Cys Pro Lys Gly Gln
                645             650             655

Val Tyr Leu Gln Cys Gly Thr Pro Cys Asn Leu Thr Cys Arg Ser Leu
            660             665             670

Ser Tyr Pro Asp Glu Glu Cys Asn Glu Ala Cys Leu Glu Gly Cys Phe
            675             680             685

Cys Pro Pro Gly Leu Tyr Met Asp Glu Arg Gly Asp Cys Val Pro Lys
        690             695             700

Ala Gln Cys Pro Cys Tyr Tyr Asp Gly Glu Ile Phe Gln Pro Glu Asp
705             710             715             720

Ile Phe Ser Asp His His Thr Met Cys Tyr Cys Glu Asp Gly Phe Met
            725             730             735

His Cys Thr Met Ser Gly Val Pro Gly Ser Leu Leu Pro Asp Ala Val
            740             745             750

Leu Ser Ser Pro Leu Ser His Arg Ser Lys Arg Ser Leu Ser Cys Arg
            755             760             765

Pro Pro Met Val Lys Leu Val Cys Pro Ala Asp Asn Leu Arg Ala Glu
        770             775             780

Gly Leu Glu Cys Thr Lys Thr Cys Gln Asn Tyr Asp Leu Glu Cys Met
785             790             795             800

Ser Met Gly Cys Val Ser Gly Cys Leu Cys Pro Pro Gly Met Val Arg
            805             810             815

His Glu Asn Arg Cys Val Ala Leu Glu Arg Cys Pro Cys Phe His Gln
            820             825             830

Gly Lys Glu Tyr Ala Pro Gly Glu Thr Val Lys Ile Gly Cys Asn Thr
            835             840             845

Cys Val Cys Arg Asp Arg Lys Trp Asn Cys Thr Asp His Val Cys Asp
        850             855             860

Ala Thr Cys Ser Thr Ile Gly Met Ala His Tyr Leu Thr Phe Asp Gly
865             870             875             880

Leu Lys Tyr Leu Phe Pro Gly Glu Cys Gln Tyr Val Leu Val Gln Asp
            885             890             895

Tyr Cys Gly Ser Asn Pro Gly Thr Phe Arg Ile Leu Val Gly Asn Lys
            900             905             910

Gly Cys Ser His Pro Ser Val Lys Cys Lys Lys Arg Val Thr Ile Leu
            915             920             925

Val Glu Gly Gly Glu Ile Glu Leu Phe Asp Gly Glu Val Asn Val Lys
        930             935             940

Arg Pro Met Lys Asp Glu Thr His Phe Glu Val Val Glu Ser Gly Arg
945             950             955             960

Tyr Ile Ile Leu Leu Leu Gly Lys Ala Leu Ser Val Val Trp Asp Arg
            965             970             975

His Leu Ser Ile Ser Val Val Leu Lys Gln Thr Tyr Gln Glu Lys Val
            980             985             990

Cys Gly Leu Cys Gly Asn Phe Asp  Gly Ile Gln Asn Asn  Asp Leu Thr
            995             1000            1005

Ser Ser  Asn Leu Gln Val Glu  Glu Asp Pro Val Asp  Phe Gly Asn
    1010            1015            1020

Ser Trp  Lys Val Ser Ser Gln  Cys Ala Asp Thr Arg  Lys Val Pro
    1025            1030            1035

Leu Asp  Ser Ser Pro Ala Thr  Cys His Asn Asn Ile  Met Lys Gln
    1040            1045            1050
```

```
Thr Met  Val Asp Ser Ser Cys  Arg Ile Leu Thr Ser  Asp Val Phe
    1055              1060              1065

Gln Asp  Cys Asn Lys Leu Val  Asp Pro Glu Pro Tyr  Leu Asp Val
    1070              1075              1080

Cys Ile  Tyr Asp Thr Cys Ser  Cys Glu Ser Ile Gly  Asp Cys Ala
    1085              1090              1095

Cys Phe  Cys Asp Thr Ile Ala  Ala Tyr Ala His Val  Cys Ala Gln
    1100              1105              1110

His Gly  Lys Val Val Thr Trp  Arg Thr Ala Thr Leu  Cys Pro Gln
    1115              1120              1125

Ser Cys  Glu Glu Arg Asn Leu  Arg Glu Asn Gly Tyr  Glu Cys Glu
    1130              1135              1140

Trp Arg  Tyr Asn Ser Cys Ala  Pro Ala Cys Gln Val  Thr Cys Gln
    1145              1150              1155

His Pro  Glu Pro Leu Ala Cys  Pro Val Gln Cys Val  Glu Gly Cys
    1160              1165              1170

His Ala  His Cys Pro Pro Gly  Lys Ile Leu Asp Glu  Leu Leu Gln
    1175              1180              1185

Thr Cys  Val Asp Pro Glu Asp  Cys Pro Val Cys Glu  Val Ala Gly
    1190              1195              1200

Arg Arg  Phe Ala Ser Gly Lys  Lys Val Thr Leu Asn  Pro Ser Asp
    1205              1210              1215

Pro Glu  His Cys Gln Ile Cys  His Cys Asp Val Val  Asn Leu Thr
    1220              1225              1230

Cys Glu  Ala Cys Gln Glu Pro  Gly Gly Leu Val Val  Pro Pro Thr
    1235              1240              1245

Asp Ala  Pro Val Ser Pro Thr  Thr Leu Tyr Val Glu  Asp Ile Ser
    1250              1255              1260

Glu Pro  Pro Leu His Asp Phe  Tyr Cys Ser Arg Leu  Leu Asp Leu
    1265              1270              1275

Val Phe  Leu Leu Asp Gly Ser  Ser Arg Leu Ser Glu  Ala Glu Phe
    1280              1285              1290

Glu Val  Leu Lys Ala Phe Val  Val Asp Met Met Glu  Arg Leu Arg
    1295              1300              1305

Ile Ser  Gln Lys Trp Val Arg  Val Ala Val Val Glu  Tyr His Asp
    1310              1315              1320

Gly Ser  His Ala Tyr Ile Gly  Leu Lys Asp Arg Lys  Arg Pro Ser
    1325              1330              1335

Glu Leu  Arg Arg Ile Ala Ser  Gln Val Lys Tyr Ala  Gly Ser Gln
    1340              1345              1350

Val Ala  Ser Thr Ser Glu Val  Leu Lys Tyr Thr Leu  Phe Gln Ile
    1355              1360              1365

Phe Ser  Lys Ile Asp Arg Pro  Glu Ala Ser Arg Ile  Ala Leu Leu
    1370              1375              1380

Leu Met  Ala Ser Gln Glu Pro  Gln Arg Met Ser Arg  Asn Phe Val
    1385              1390              1395

Arg Tyr  Val Gln Gly Leu Lys  Lys Lys Lys Val Ile  Val Ile Pro
    1400              1405              1410

Val Gly  Ile Gly Pro His Ala  Asn Leu Lys Gln Ile  Arg Leu Ile
    1415              1420              1425

Glu Lys  Gln Ala Pro Glu Asn  Lys Ala Phe Val Leu  Ser Ser Val
    1430              1435              1440

Asp Glu  Leu Glu Gln Gln Arg  Asp Glu Ile Val Ser  Tyr Leu Cys
```

-continued

```
        1445                1450                1455

Asp Leu  Ala Pro Glu Ala Pro  Pro Pro Thr Leu Pro  Pro Asp Met
    1460                1465                1470

Ala Gln  Val Thr Val Gly Pro  Gly Leu Leu Gly Val  Ser Thr Leu
    1475                1480                1485

Gly Pro  Lys Arg Asn Ser Met  Val Leu Asp Val Ala  Phe Val Leu
    1490                1495                1500

Glu Gly  Ser Asp Lys Ile Gly  Glu Ala Asp Phe Asn  Arg Ser Lys
    1505                1510                1515

Glu Phe  Met Glu Glu Val Ile  Gln Arg Met Asp Val  Gly Gln Asp
    1520                1525                1530

Ser Ile  His Val Thr Val Leu  Gln Tyr Ser Tyr Met  Val Thr Val
    1535                1540                1545

Glu Tyr  Pro Phe Ser Glu Ala  Gln Ser Lys Gly Asp  Ile Leu Gln
    1550                1555                1560

Arg Val  Arg Glu Ile Arg Tyr  Gln Gly Gly Asn Arg  Thr Asn Thr
    1565                1570                1575

Gly Leu  Ala Leu Arg Tyr Leu  Ser Asp His Ser Phe  Leu Val Ser
    1580                1585                1590

Gln Gly  Asp Arg Glu Gln Ala  Pro Asn Leu Val Tyr  Met Val Thr
    1595                1600                1605

Gly Asn  Pro Ala Ser Asp Glu  Ile Lys Arg Leu Pro  Gly Asp Ile
    1610                1615                1620

Gln Val  Val Pro Ile Gly Val  Gly Pro Asn Ala Asn  Val Gln Glu
    1625                1630                1635

Leu Glu  Arg Ile Gly Trp Pro  Asn Ala Pro Ile Leu  Ile Gln Asp
    1640                1645                1650

Phe Glu  Thr Leu Pro Arg Glu  Ala Pro Asp Leu Val  Leu Gln Arg
    1655                1660                1665

Cys Cys  Ser Gly Glu Gly Leu  Gln Ile Pro Thr Leu  Ser Pro Ala
    1670                1675                1680

Pro Asp  Cys Ser Gln Pro Leu  Asp Val Ile Leu Leu  Leu Asp Gly
    1685                1690                1695

Ser Ser  Ser Phe Pro Ala Ser  Tyr Phe Asp Glu Met  Lys Ser Phe
    1700                1705                1710

Ala Lys  Ala Phe Ile Ser Lys  Ala Asn Ile Gly Pro  Arg Leu Thr
    1715                1720                1725

Gln Val  Ser Val Leu Gln Tyr  Gly Ser Ile Thr Thr  Ile Asp Val
    1730                1735                1740

Pro Trp  Asn Val Val Pro Glu  Lys Ala His Leu Leu  Ser Leu Val
    1745                1750                1755

Asp Val  Met Gln Arg Glu Gly  Gly Pro Ser Gln Ile  Gly Asp Ala
    1760                1765                1770

Leu Gly  Phe Ala Val Arg Tyr  Leu Thr Ser Glu Met  His Gly Ala
    1775                1780                1785

Arg Pro  Gly Ala Ser Lys Ala  Val Val Ile Leu Val  Thr Asp Val
    1790                1795                1800

Ser Val  Asp Ser Val Asp Ala  Ala Ala Asp Ala Ala  Arg Ser Asn
    1805                1810                1815

Arg Val  Thr Val Phe Pro Ile  Gly Ile Gly Asp Arg  Tyr Asp Ala
    1820                1825                1830

Ala Gln  Leu Arg Ile Leu Ala  Gly Pro Ala Gly Asp  Ser Asn Val
    1835                1840                1845
```

-continued

```
Val Lys Leu Gln Arg Ile Glu Asp Leu Pro Thr Met Val Thr Leu
    1850            1855            1860

Gly Asn Ser Phe Leu His Lys Leu Cys Ser Gly Phe Val Arg Ile
    1865            1870            1875

Cys Met Asp Glu Asp Gly Asn Glu Lys Arg Pro Gly Asp Val Trp
    1880            1885            1890

Thr Leu Pro Asp Gln Cys His Thr Val Thr Cys Gln Pro Asp Gly
    1895            1900            1905

Gln Thr Leu Leu Lys Ser His Arg Val Asn Cys Asp Arg Gly Leu
    1910            1915            1920

Arg Pro Ser Cys Pro Asn Ser Gln Ser Pro Val Lys Val Glu Glu
    1925            1930            1935

Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

Gln Gly Cys Met Lys Ser Ile Glu Val Lys His Ser Ala Leu Ser
    2000            2005            2010

Val Glu Xaa His Ser Asp Met Glu Val Thr Val Asn Gly Arg Leu
    2015            2020            2025

Val Ser Val Pro Tyr Val Gly Gly Asn Met Glu Val Asn Val Tyr
    2030            2035            2040

Gly Ala Ile Met His Glu Val Arg Phe Asn His Leu Gly His Ile
    2045            2050            2055

Phe Thr Phe Thr Pro Gln Asn Asn Glu Phe Gln Leu Gln Leu Ser
    2060            2065            2070

Pro Lys Thr Phe Ala Ser Lys Thr Tyr Gly Leu Cys Gly Ile Cys
    2075            2080            2085

Asp Glu Asn Gly Ala Asn Asp Phe Met Leu Arg Asp Gly Thr Val
    2090            2095            2100

Thr Thr Asp Trp Lys Thr Leu Val Gln Glu Trp Thr Val Gln Arg
    2105            2110            2115

Pro Gly Gln Thr Cys Gln Pro Ile Leu Glu Glu Gln Cys Leu Val
    2120            2125            2130

Pro Asp Ser Ser His Cys Gln Val Leu Leu Leu Pro Leu Phe Ala
    2135            2140            2145

Glu Cys His Lys Val Leu Ala Pro Ala Thr Phe Tyr Ala Ile Cys
    2150            2155            2160

Gln Gln Asp Ser Cys His Gln Glu Gln Val Cys Glu Val Ile Ala
    2165            2170            2175

Ser Tyr Ala His Leu Cys Arg Thr Asn Gly Val Cys Val Asp Trp
    2180            2185            2190

Arg Thr Pro Asp Phe Cys Ala Met Ser Cys Pro Pro Ser Leu Val
    2195            2200            2205

Tyr Asn His Cys Glu His Gly Cys Pro Arg His Cys Asp Gly Asn
    2210            2215            2220

Val Ser Ser Cys Gly Asp His Pro Ser Glu Gly Cys Phe Cys Pro
    2225            2230            2235
```

161

-continued

```
Pro Asp Lys Val Met Leu Glu  Gly Ser Cys Val Pro  Glu Glu Ala
    2240              2245              2250

Cys Thr Gln Cys Ile Gly Glu  Asp Gly Val Gln His  Gln Phe Leu
    2255              2260              2265

Glu Ala Trp Val Pro Asp His  Gln Pro Cys Gln Ile  Cys Thr Cys
    2270              2275              2280

Leu Ser Gly Arg Lys Val Asn  Cys Thr Thr Gln Pro  Cys Pro Thr
    2285              2290              2295

Ala Lys Ala Pro Thr Cys Gly  Leu Cys Glu Val Ala  Arg Leu Arg
    2300              2305              2310

Gln Asn Ala Asp Gln Cys Cys  Pro Glu Tyr Glu Cys  Val Cys Asp
    2315              2320              2325

Pro Val Ser Cys Asp Leu Pro  Pro Val Pro His Cys  Glu Arg Gly
    2330              2335              2340

Leu Gln Pro Thr Leu Thr Asn  Pro Gly Glu Cys Arg  Pro Asn Phe
    2345              2350              2355

Thr Cys Ala Cys Arg Lys Glu  Glu Cys Lys Arg Val  Ser Pro Pro
    2360              2365              2370

Ser Cys Pro Pro His Arg Leu  Pro Thr Leu Arg Lys  Thr Gln Cys
    2375              2380              2385

Cys Asp Glu Tyr Glu Cys Ala  Cys Asn Cys Val Asn  Ser Thr Val
    2390              2395              2400

Ser Cys Pro Leu Gly Tyr Leu  Ala Ser Thr Ala Thr  Asn Asp Cys
    2405              2410              2415

Gly Cys Thr Thr Thr Thr Cys  Leu Pro Asp Lys Val  Cys Val His
    2420              2425              2430

Arg Ser Thr Ile Tyr Pro Val  Gly Gln Phe Trp Glu  Glu Gly Cys
    2435              2440              2445

Asp Val Cys Thr Cys Thr Asp  Met Glu Asp Ala Val  Met Gly Leu
    2450              2455              2460

Arg Val Ala Gln Cys Ser Gln  Lys Pro Cys Glu Asp  Ser Cys Arg
    2465              2470              2475

Ser Gly Phe Thr Tyr Val Leu  His Glu Gly Glu Cys  Cys Gly Arg
    2480              2485              2490

Cys Leu Pro Ser Ala Cys Glu  Val Val Thr Gly Ser  Pro Arg Gly
    2495              2500              2505

Asp Ser Gln Ser Ser Trp Lys  Ser Val Gly Ser Gln  Trp Ala Ser
    2510              2515              2520

Pro Glu Asn Pro Cys Leu Ile  Asn Glu Cys Val Arg  Val Lys Glu
    2525              2530              2535

Glu Val Phe Ile Gln Gln Arg  Asn Val Ser Cys Pro  Gln Leu Glu
    2540              2545              2550

Val Pro Val Cys Pro Ser Gly  Phe Gln Leu Ser Cys  Lys Thr Ser
    2555              2560              2565

Ala Cys Cys Pro Ser Cys Arg  Cys Glu Arg Met Glu  Ala Cys Met
    2570              2575              2580

Leu Asn Gly Thr Val Ile Gly  Pro Gly Lys Thr Val  Met Ile Asp
    2585              2590              2595

Val Cys Thr Thr Cys Arg Cys  Met Val Gln Val Gly  Val Ile Ser
    2600              2605              2610

Gly Phe Lys Leu Glu Cys Arg  Lys Thr Thr Cys Asn  Pro Cys Pro
    2615              2620              2625

Leu Gly Tyr Lys Glu Glu Asn  Asn Thr Gly Glu Cys  Cys Gly Arg
```

-continued

```
        2630                2635                2640

Cys Leu  Pro Thr Ala Cys Thr  Ile Gln Leu Arg Gly  Gly Gln Ile
    2645                2650                2655

Met Thr  Leu Lys Arg Asp Glu  Thr Leu Gln Asp Gly  Cys Asp Thr
    2660                2665                2670

His Phe  Cys Lys Val Asn Glu  Arg Gly Glu Tyr Phe  Trp Glu Lys
    2675                2680                2685

Arg Val  Thr Gly Cys Pro Pro  Phe Asp Glu His Lys  Cys Leu Ala
    2690                2695                2700

Glu Gly  Gly Lys Ile Met Lys  Ile Pro Gly Thr Cys  Cys Asp Thr
    2705                2710                2715

Cys Glu  Glu Pro Glu Cys Asn  Asp Ile Thr Ala Arg  Leu Gln Tyr
    2720                2725                2730

Val Lys  Val Gly Ser Cys Lys  Ser Glu Val Glu Val  Asp Ile His
    2735                2740                2745

Tyr Cys  Gln Gly Lys Cys Ala  Ser Lys Ala Met Tyr  Ser Ile Asp
    2750                2755                2760

Ile Asn  Asp Val Gln Asp Gln  Cys Ser Cys Cys Ser  Pro Thr Arg
    2765                2770                2775

Thr Glu  Pro Met Gln Val Ala  Leu His Cys Thr Asn  Gly Ser Val
    2780                2785                2790

Val Tyr  His Glu Val Leu Asn  Ala Met Glu Cys Lys  Cys Ser Pro
    2795                2800                2805

Arg Lys  Cys Ser Lys
    2810
```

```
<210> SEQ ID NO 3
<211> LENGTH: 19
<212> TYPE: PRT
<213> ORGANISM: Artificial Sequence
<220> FEATURE:
<223> OTHER INFORMATION: Signal peptide

<400> SEQUENCE: 3

Met Gln Ile Glu Leu Ser Thr Cys Phe Phe Leu Cys Leu Leu Arg Phe
1               5                10                15

Cys Phe Ser

<210> SEQ ID NO 4
<211> LENGTH: 2332
<212> TYPE: PRT
<213> ORGANISM: Homo sapiens

<400> SEQUENCE: 4

Ala Thr Arg Arg Tyr Tyr Leu Gly Ala Val Glu Leu Ser Trp Asp Tyr
1               5                10                15

Met Gln Ser Asp Leu Gly Glu Leu Pro Val Asp Ala Arg Phe Pro Pro
                20                25                30

Arg Val Pro Lys Ser Phe Pro Phe Asn Thr Ser Val Val Tyr Lys Lys
            35                40                45

Thr Leu Phe Val Glu Phe Thr Asp His Leu Phe Asn Ile Ala Lys Pro
        50                55                60

Arg Pro Pro Trp Met Gly Leu Leu Gly Pro Thr Ile Gln Ala Glu Val
65                70                75                80

Tyr Asp Thr Val Val Ile Thr Leu Lys Asn Met Ala Ser His Pro Val
                85                90                95
```

-continued

```
Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
```

```
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
    930                 935                 940
```

Ser Lys Leu Leu Glu Ser Gly Leu Met Asn Ser Gln Glu Ser Ser Trp
945                    950                    955                    960

Gly Lys Asn Val Ser Ser Thr Glu Ser Gly Arg Leu Phe Lys Gly Lys
                       965                    970                    975

Arg Ala His Gly Pro Ala Leu Leu Thr Lys Asp Asn Ala Leu Phe Lys
                 980                    985                    990

Val Ser Ile Ser Leu Leu Lys Thr  Asn Lys Thr Ser Asn  Asn Ser Ala
          995                    1000                   1005

Thr Asn  Arg Lys Thr His Ile  Asp Gly Pro Ser Leu  Leu Ile Glu
     1010                   1015                   1020

Asn Ser  Pro Ser Val Trp Gln  Asn Ile Leu Glu Ser  Asp Thr Glu
     1025                   1030                   1035

Phe Lys  Lys Val Thr Pro Leu  Ile His Asp Arg Met  Leu Met Asp
     1040                   1045                   1050

Lys Asn  Ala Thr Ala Leu Arg  Leu Asn His Met Ser  Asn Lys Thr
     1055                   1060                   1065

Thr Ser  Ser Lys Asn Met Glu  Met Val Gln Gln Lys  Lys Glu Gly
     1070                   1075                   1080

Pro Ile  Pro Pro Asp Ala Gln  Asn Pro Asp Met Ser  Phe Phe Lys
     1085                   1090                   1095

Met Leu  Phe Leu Pro Glu Ser  Ala Arg Trp Ile Gln  Arg Thr His
     1100                   1105                   1110

Gly Lys  Asn Ser Leu Asn Ser  Gly Gln Gly Pro Ser  Pro Lys Gln
     1115                   1120                   1125

Leu Val  Ser Leu Gly Pro Glu  Lys Ser Val Glu Gly  Gln Asn Phe
     1130                   1135                   1140

Leu Ser  Glu Lys Asn Lys Val  Val Val Gly Lys Gly  Glu Phe Thr
     1145                   1150                   1155

Lys Asp  Val Gly Leu Lys Glu  Met Val Phe Pro Ser  Ser Arg Asn
     1160                   1165                   1170

Leu Phe  Leu Thr Asn Leu Asp  Asn Leu His Glu Asn  Asn Thr His
     1175                   1180                   1185

Asn Gln  Glu Lys Lys Ile Gln  Glu Glu Ile Glu Lys  Lys Glu Thr
     1190                   1195                   1200

Leu Ile  Gln Glu Asn Val Val  Leu Pro Gln Ile His  Thr Val Thr
     1205                   1210                   1215

Gly Thr  Lys Asn Phe Met Lys  Asn Leu Phe Leu Leu  Ser Thr Arg
     1220                   1225                   1230

Gln Asn  Val Glu Gly Ser Tyr  Asp Gly Ala Tyr Ala  Pro Val Leu
     1235                   1240                   1245

Gln Asp  Phe Arg Ser Leu Asn  Asp Ser Thr Asn Arg  Thr Lys Lys
     1250                   1255                   1260

His Thr  Ala His Phe Ser Lys  Lys Gly Glu Glu Glu  Asn Leu Glu
     1265                   1270                   1275

Gly Leu  Gly Asn Gln Thr Lys  Gln Ile Val Glu Lys  Tyr Ala Cys
     1280                   1285                   1290

Thr Thr  Arg Ile Ser Pro Asn  Thr Ser Gln Gln Asn  Phe Val Thr
     1295                   1300                   1305

Gln Arg  Ser Lys Arg Ala Leu  Lys Gln Phe Arg Leu  Pro Leu Glu
     1310                   1315                   1320

Glu Thr  Glu Leu Glu Lys Arg  Ile Ile Val Asp Asp  Thr Ser Thr
     1325                   1330                   1335

-continued

```
Gln Trp  Ser Lys Asn Met Lys  His Leu Thr Pro Ser  Thr Leu Thr
    1340              1345              1350

Gln Ile  Asp Tyr Asn Glu Lys  Glu Lys Gly Ala Ile  Thr Gln Ser
    1355              1360              1365

Pro Leu  Ser Asp Cys Leu Thr  Arg Ser His Ser Ile  Pro Gln Ala
    1370              1375              1380

Asn Arg  Ser Pro Leu Pro Ile  Ala Lys Val Ser Ser  Phe Pro Ser
    1385              1390              1395

Ile Arg  Pro Ile Tyr Leu Thr  Arg Val Leu Phe Gln  Asp Asn Ser
    1400              1405              1410

Ser His  Leu Pro Ala Ala Ser  Tyr Arg Lys Lys Asp  Ser Gly Val
    1415              1420              1425

Gln Glu  Ser Ser His Phe Leu  Gln Gly Ala Lys Lys  Asn Asn Leu
    1430              1435              1440

Ser Leu  Ala Ile Leu Thr Leu  Glu Met Thr Gly Asp  Gln Arg Glu
    1445              1450              1455

Val Gly  Ser Leu Gly Thr Ser  Ala Thr Asn Ser Val  Thr Tyr Lys
    1460              1465              1470

Lys Val  Glu Asn Thr Val Leu  Pro Lys Pro Asp Leu  Pro Lys Thr
    1475              1480              1485

Ser Gly  Lys Val Glu Leu Leu  Pro Lys Val His Ile  Tyr Gln Lys
    1490              1495              1500

Asp Leu  Phe Pro Thr Glu Thr  Ser Asn Gly Ser Pro  Gly His Leu
    1505              1510              1515

Asp Leu  Val Glu Gly Ser Leu  Leu Gln Gly Thr Glu  Gly Ala Ile
    1520              1525              1530

Lys Trp  Asn Glu Ala Asn Arg  Pro Gly Lys Val Pro  Phe Leu Arg
    1535              1540              1545

Val Ala  Thr Glu Ser Ser Ala  Lys Thr Pro Ser Lys  Leu Leu Asp
    1550              1555              1560

Pro Leu  Ala Trp Asp Asn His  Tyr Gly Thr Gln Ile  Pro Lys Glu
    1565              1570              1575

Glu Trp  Lys Ser Gln Glu Lys  Ser Pro Glu Lys Thr  Ala Phe Lys
    1580              1585              1590

Lys Lys  Asp Thr Ile Leu Ser  Leu Asn Ala Cys Glu  Ser Asn His
    1595              1600              1605

Ala Ile  Ala Ala Ile Asn Glu  Gly Gln Asn Lys Pro  Glu Ile Glu
    1610              1615              1620

Val Thr  Trp Ala Lys Gln Gly  Arg Thr Glu Arg Leu  Cys Ser Gln
    1625              1630              1635

Asn Pro  Pro Val Leu Lys Arg  His Gln Arg Glu Ile  Thr Arg Thr
    1640              1645              1650

Thr Leu  Gln Ser Asp Gln Glu  Glu Ile Asp Tyr Asp  Asp Thr Ile
    1655              1660              1665

Ser Val  Glu Met Lys Lys Glu  Asp Phe Asp Ile Tyr  Asp Glu Asp
    1670              1675              1680

Glu Asn  Gln Ser Pro Arg Ser  Phe Gln Lys Lys Thr  Arg His Tyr
    1685              1690              1695

Phe Ile  Ala Ala Val Glu Arg  Leu Trp Asp Tyr Gly  Met Ser Ser
    1700              1705              1710

Ser Pro  His Val Leu Arg Asn  Arg Ala Gln Ser Gly  Ser Val Pro
    1715              1720              1725

Gln Phe  Lys Lys Val Val Phe  Gln Glu Phe Thr Asp  Gly Ser Phe
```

-continued

```
       1730              1735              1740

Thr Gln  Pro Leu Tyr Arg Gly  Glu Leu Asn Glu His  Leu Gly Leu
   1745              1750              1755

Leu Gly  Pro Tyr Ile Arg Ala  Glu Val Glu Asp Asn  Ile Met Val
   1760              1765              1770

Thr Phe  Arg Asn Gln Ala Ser  Arg Pro Tyr Ser Phe  Tyr Ser Ser
   1775              1780              1785

Leu Ile  Ser Tyr Glu Glu Asp  Gln Arg Gln Gly Ala  Glu Pro Arg
   1790              1795              1800

Lys Asn  Phe Val Lys Pro Asn  Glu Thr Lys Thr Tyr  Phe Trp Lys
   1805              1810              1815

Val Gln  His His Met Ala Pro  Thr Lys Asp Glu Phe  Asp Cys Lys
   1820              1825              1830

Ala Trp  Ala Tyr Phe Ser Asp  Val Asp Leu Glu Lys  Asp Val His
   1835              1840              1845

Ser Gly  Leu Ile Gly Pro Leu  Leu Val Cys His Thr  Asn Thr Leu
   1850              1855              1860

Asn Pro  Ala His Gly Arg Gln  Val Thr Val Gln Glu  Phe Ala Leu
   1865              1870              1875

Phe Phe  Thr Ile Phe Asp Glu  Thr Lys Ser Trp Tyr  Phe Thr Glu
   1880              1885              1890

Asn Met  Glu Arg Asn Cys Arg  Ala Pro Cys Asn Ile  Gln Met Glu
   1895              1900              1905

Asp Pro  Thr Phe Lys Glu Asn  Tyr Arg Phe His Ala  Ile Asn Gly
   1910              1915              1920

Tyr Ile  Met Asp Thr Leu Pro  Gly Leu Val Met Ala  Gln Asp Gln
   1925              1930              1935

Arg Ile  Arg Trp Tyr Leu Leu  Ser Met Gly Ser Asn  Glu Asn Ile
   1940              1945              1950

His Ser  Ile His Phe Ser Gly  His Val Phe Thr Val  Arg Lys Lys
   1955              1960              1965

Glu Glu  Tyr Lys Met Ala Leu  Tyr Asn Leu Tyr Pro  Gly Val Phe
   1970              1975              1980

Glu Thr  Val Glu Met Leu Pro  Ser Lys Ala Gly Ile  Trp Arg Val
   1985              1990              1995

Glu Cys  Leu Ile Gly Glu His  Leu His Ala Gly Met  Ser Thr Leu
   2000              2005              2010

Phe Leu  Val Tyr Ser Asn Lys  Cys Gln Thr Pro Leu  Gly Met Ala
   2015              2020              2025

Ser Gly  His Ile Arg Asp Phe  Gln Ile Thr Ala Ser  Gly Gln Tyr
   2030              2035              2040

Gly Gln  Trp Ala Pro Lys Leu  Ala Arg Leu His Tyr  Ser Gly Ser
   2045              2050              2055

Ile Asn  Ala Trp Ser Thr Lys  Glu Pro Phe Ser Trp  Ile Lys Val
   2060              2065              2070

Asp Leu  Leu Ala Pro Met Ile  Ile His Gly Ile Lys  Thr Gln Gly
   2075              2080              2085

Ala Arg  Gln Lys Phe Ser Ser  Leu Tyr Ile Ser Gln  Phe Ile Ile
   2090              2095              2100

Met Tyr  Ser Leu Asp Gly Lys  Lys Trp Gln Thr Tyr  Arg Gly Asn
   2105              2110              2115

Ser Thr  Gly Thr Leu Met Val  Phe Phe Gly Asn Val  Asp Ser Ser
   2120              2125              2130
```

```
Gly Ile Lys His Asn Ile Phe  Asn Pro Pro Ile  Ile  Ala Arg Tyr
    2135              2140              2145

Ile Arg Leu His Pro Thr His  Tyr Ser Ile Arg Ser  Thr Leu Arg
    2150              2155              2160

Met Glu Leu Met Gly Cys Asp  Leu Asn Ser Cys Ser  Met Pro Leu
    2165              2170              2175

Gly Met Glu Ser Lys Ala Ile  Ser Asp Ala Gln Ile  Thr Ala Ser
    2180              2185              2190

Ser Tyr Phe Thr Asn Met Phe  Ala Thr Trp Ser Pro  Ser Lys Ala
    2195              2200              2205

Arg Leu His Leu Gln Gly Arg  Ser Asn Ala Trp Arg  Pro Gln Val
    2210              2215              2220

Asn Asn Pro Lys Glu Trp Leu  Gln Val Asp Phe Gln  Lys Thr Met
    2225              2230              2235

Lys Val Thr Gly Val Thr Thr  Gln Gly Val Lys Ser  Leu Leu Thr
    2240              2245              2250

Ser Met Tyr Val Lys Glu Phe  Leu Ile Ser Ser Ser  Gln Asp Gly
    2255              2260              2265

His Gln Trp Thr Leu Phe Phe  Gln Asn Gly Lys Val  Lys Val Phe
    2270              2275              2280

Gln Gly Asn Gln Asp Ser Phe  Thr Pro Val Val Asn  Ser Leu Asp
    2285              2290              2295

Pro Pro Leu Leu Thr Arg Tyr  Leu Arg Ile His Pro  Gln Ser Trp
    2300              2305              2310

Val His Gln Ile Ala Leu Arg  Met Glu Val Leu Gly  Cys Glu Ala
    2315              2320              2325

Gln Asp Leu Tyr
    2330
```

```
<210> SEQ ID NO 5
<211> LENGTH: 7053
<212> TYPE: DNA
<213> ORGANISM: Homo sapiens

<400> SEQUENCE: 5
atgcaaatag agctctccac ctgcttcttt ctgtgccttt tgcgattctg ctttagtgcc    60
accagaagat actacctggg tgcagtggaa ctgtcatggg actatatgca aagtgatctc   120
ggtgagctgc ctgtggacgc aagatttcct cctagagtgc aaaatctttt ccattcaac    180 acctcagtcg tgtacaaaaa gactctgttt gtagaattca cggatcacct tttcaacatc   240
gctaagccaa ggccaccctg gatgggtctg ctaggtccta ccatccaggc tgaggtttat   300
gatacagtgg tcattacact taagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catatgtctg gcaggtcctg   480
aaagagaatg gtccaatggc ctctgaccca ctgtgcctta cctactcata tctttctcat   540
gtggacctgg taaaagactt gaattcaggc ctcattggag ccctactagt atgtagagaa   600
gggagtctgg ccaaggaaaa gacacagacc ttgcacaaat ttatactact ttttgctgta   660
tttgatgaag ggaaaagttg gcactcagaa acaaagaact ccttgatgca ggatagggat   720
gctgcatctg ctcgggcctg gcctaaaatg cacacagtca atggttatgt aaacaggtct   780
ctgccaggtc tgattggatg ccacaggaaa tcagtctatt ggcatgtgat tggaatgggc   840
```

-continued

```
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca aagtagacag ctgtccagag gaaccccaac tacgaatgaa aaataatgaa     1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctccctt agtcctcgcc     1260
cccgatgaca gaagttataa aagtcaatat ttgaacaatg ccctcagcg gattggtagg     1320 aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg gatatacctt caaacacaaa     2040
atggtctatg aagacacact caccctattc ccattctcag gagaaactgt cttcatgtcg     2100
atggaaaacc caggtctatg gattctgggg tgccacaact cagactttcg gaacagaggc     2160
atgaccgcct tactgaaggt ttctagttgt gacaagaaca ctggtgatta ttacgaggac     2220
agttatgaag atatttcagc atacttgctg agtaaaaaca atgccattga accaagaagc     2280
ttctcccaga attcaagaca ccctagcact aggcaaaagc aatttaatgc caccacaatt     2340
ccagaaaatg acatagagaa gactgaccct tggtttgcac acagaacacc tatgcctaaa     2400
atacaaaatg tctcctctag tgatttgttg atgctcttgc gacagagtcc tactccacat     2460
gggctatcct tatctgatct ccaagaagcc aaatatgaga cttttctga tgatccatca      2520 cctggagcaa tagacagtaa taacagcctg tctgaaatga cacacttcag gccacagctc     2580
catcacagtg gggacatggt atttaccccct gagtcaggcc tccaattaag attaaatgag     2640
aaactgggga caactgcagc aacagagttg aagaaacttg atttcaaagt ttctagtaca     2700
tcaaataatc tgatttcaac aattccatca gacaatttgg cagcaggtac tgataataca     2760
agttccttag acccccaag tatgccagtt cattatgata gtcaattaga taccactcta      2820
tttggcaaaa agtcatctcc ccttactgag tctggtggac ctctgagctt gagtgaagaa     2880
aataatgatt caaagttgtt agaatcaggt ttaatgaata gccaagaaag ttcatgggga     2940
aaaaatgtat cgtcaacaga gagtggtagg ttatttaaag ggaaaagagc tcatggacct     3000
gctttgttga ctaaagataa tgccttattc aaagttagca tctctttgtt aaagacaaac     3060
aaaacttcca ataattcagc aactaataga aagactcaca ttgatggccc atcattatta     3120
attgagaata gtccatcagt ctggcaaaat atattagaaa gtgacactga gtttaaaaaa     3180
gtgacacctt tgattcatga cagaatgctt atggacaaaa atgctacagc tttgaggcta     3240
```

-continued

```
aatcatatgt caaataaaac tacttcatca aaaaacatgg aaatggtcca acagaaaaaa      3300
gagggcccca ttccaccaga tgcacaaaat ccagatatgt cgttctttaa gatgctattc      3360
ttgccagaat cagcaaggtg gatacaaagg actcatggaa agaactctct gaactctggg      3420
caaggcccca gtccaaagca attagtatcc ttaggaccag aaaaatctgt ggaaggtcag      3480
aatttcttgt ctgagaaaaa caaagtggta gtaggaaagg gtgaatttac aaaggacgta      3540
ggactcaaag agatggtttt tccaagcagc agaaacctat ttcttactaa cttggataat      3600
ttacatgaaa ataatacaca caatcaagaa aaaaaaattc aggaagaaat agaaaagaag      3660
gaaacattaa tccaagagaa tgtagttttg cctcagatac atacagtgac tggcactaag      3720
aatttcatga agaacctttt cttactgagc actaggcaaa atgtagaagg ttcatatgac      3780
ggggcatatg ctccagtact tcaagatttt aggtcattaa atgattcaac aaatagaaca      3840
aagaaacaca cagctcattt ctcaaaaaaa ggggaggaag aaaacttgga aggcttggga      3900
aatcaaacca agcaaattgt agagaaatat gcatgcacca caaggatatc tcctaataca      3960
agccagcaga attttgtcac gcaacgtagt aagagagctt tgaaacaatt cagactccca      4020
ctagaagaaa cagaacttga aaaaaggata attgtggatg acacctcaac ccagtggtcc      4080
aaaaacatga aacatttgac cccgagcacc ctcacacaga tagactacaa tgagaaggag      4140
aaaggggcca ttactcagtc tcccttatca gattgcctta cgaggagtca tagcatccct      4200
caagcaaata gatctccatt acccattgca aaggtatcat catttccatc tattagacct      4260
atatatctga ccagggtcct attccaagac aactcttctc atcttccagc agcatcttat      4320
agaaagaaag attctggggt ccaagaaagc agtcatttct tacaaggagc caaaaaaaat      4380
aacctttctt tagccattct aaccttggag atgactggtg atcaaagaga ggttggctcc      4440
ctggggacaa gtgccacaaa ttcagtcaca tacaagaaag ttgagaacac tgttctcccg      4500
aaaccagact tgcccaaaac atctggcaaa gttgaattgc ttccaaaagt tcacatttat      4560
cagaaggacc tattccctac ggaaactagc aatgggtctc ctggccatct ggatctcgtg      4620
gaagggagcc ttcttcaggg aacagaggga gcgattaagt ggaatgaagc aaacagacct      4680
ggaaaagttc cctttctgag agtagcaaca gaaagctctg caaagactcc ctccaagcta      4740
ttggatcctc ttgcttggga taaccactat ggtactcaga taccaaaaga agagtggaaa      4800
tcccaagaga agtcaccaga aaaaacagct tttaagaaaa aggataccat tttgtccctg      4860
aacgcttgtg aaagcaatca tgcaatagca gcaataaatg agggacaaaa taagcccgaa      4920
atagaagtca cctgggcaaa gcaaggtagg actgaaaggc tgtgctctca aaacccacca      4980
gtcttgaaac gccatcaacg ggaaataact cgtactactc ttcagtcaga tcaagaggaa      5040
attgactatg atgataccat atcagttgaa atgaagaagg aagattttga catttatgat      5100
gaggatgaaa atcagagccc ccgcagcttt caaaagaaaa cacgacacta ttttattgct      5160
gcagtggaga ggctctggga ttatgggatg agtagctccc cacatgttct aagaaacagg      5220
gctcagagtg gcagtgtccc tcagttcaag aaagttgttt tccaggaatt tactgatggc      5280
tcctttactc agcccttata ccgtggagaa ctaaatgaac atttgggact cctggggcca      5340
tatataagag cagaagttga agataatatc atggtaactt tcagaaatca ggcctctcgt      5400
ccctattcct tctattctag ccttatttct tatgaggaag atcagaggca aggagcagaa      5460
cctagaaaaa actttgtcaa gcctaatgaa accaaaactt acttttggaa agtgcaacat      5520
catatggcac ccactaaaga tgagtttgac tgcaaagcct gggcttattt ctctgatgtt      5580
```

-continued

```
gacctggaaa aagatgtgca ctcaggcctg attggacccc ttctggtctg ccacactaac      5640
acactgaacc ctgctcatgg gagacaagtg acagtacagg aatttgctct gttttttcacc     5700 atctttgatg agaccaaaag ctggtacttc actgaaaata tggaaagaaa ctgcagggct      5760
ccctgcaata tccagatgga agatcccact tttaaagaga attatcgctt ccatgcaatc      5820
aatggctaca taatggatac actacctggc ttagtaatgg ctcaggatca aaggattcga      5880
tggtatctgc tcagcatggg cagcaatgaa aacatccatt ctattcattt cagtggacat      5940
gtgttcactg tacgaaaaaa agaggagtat aaaatggcac tgtacaatct ctatccaggt      6000
gtttttgaga cagtggaaat gttaccatcc aaagctggaa tttggcgggt ggaatgcctt      6060
attggcgagc atctacatgc tgggatgagc acactttttc tggtgtacag caataagtgt      6120
cagactcccc tgggaatggc ttctggacac attagagatt ttcagattac agcttcagga      6180
caatatggac agtgggcccc aaagctggcc agacttcatt attccggatc aatcaatgcc      6240
tggagcacca aggagccctt ttcttggatc aaggtggatc tgttggcacc aatgattatt      6300
cacggcatca gacccaggg tgcccgtcag aagttctcca gcctctacat ctctcagttt       6360
atcatcatgt atagtcttga tgggaagaag tggcagactt atcgaggaaa ttccactgga      6420
accttaatgg tcttctttgg caatgtggat tcatctggga taaaacacaa tatttttaac      6480
cctccaatta ttgctcgata catccgtttg cacccaactc attatagcat tcgcagcact      6540
cttcgcatgg agttgatggg ctgtgattta aatagttgca gcatgccatt gggaatggag      6600
agtaaagcaa tatcagatgc acagattact gcttcatcct actttaccaa tatgtttgcc      6660
acctggtctc cttcaaaagc tcgacttcac ctccaaggga ggagtaatgc ctggagacct      6720
caggtgaata atccaaaaga gtggctgcaa gtggacttcc agaagacaat gaaagtcaca      6780
ggagtaacta ctcaggggagt aaaatctctg cttaccagct gtatgtgaa ggagttcctc      6840 atctccagca gtcaagatgg ccatcagtgg actctctttt ttcagaatgg caaagtaaag      6900
gtttttcagg gaaatcaaga ctccttcaca cctgtggtga actctctaga cccaccgtta      6960
ctgactcgct accttcgaat tcacccccag agttgggtgc accagattgc cctgaggatg      7020
gaggttctgg gctgcgaggc acaggacctc tac                                  7053
```

<210> SEQ ID NO 6
<211> LENGTH: 1438
<212> TYPE: PRT
<213> ORGANISM: Artificial Sequence
<220> FEATURE:
<223> OTHER INFORMATION: BDD FVIII

<400> SEQUENCE: 6

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
```

```
            100                 105                 110
Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525
```

```
Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
    930                 935                 940
```

-continued

```
Ser Asp Val Asp Leu Glu Lys Asp Val His Ser Gly Leu Ile Gly Pro
945             950             955             960

Leu Leu Val Cys His Thr Asn Thr Leu Asn Pro Ala His Gly Arg Gln
        965             970             975

Val Thr Val Gln Glu Phe Ala Leu Phe Phe Thr Ile Phe Asp Glu Thr
        980             985             990

Lys Ser Trp Tyr Phe Thr Glu Asn  Met Glu Arg Asn Cys  Arg Ala Pro
    995             1000                1005

Cys Asn  Ile Gln Met Glu Asp  Pro Thr Phe Lys Glu  Asn Tyr Arg
    1010            1015                1020

Phe His  Ala Ile Asn Gly Tyr  Ile Met Asp Thr Leu  Pro Gly Leu
    1025            1030                1035

Val Met  Ala Gln Asp Gln Arg  Ile Arg Trp Tyr Leu  Leu Ser Met
    1040            1045                1050

Gly Ser  Asn Glu Asn Ile His  Ser Ile His Phe Ser  Gly His Val
    1055            1060                1065

Phe Thr  Val Arg Lys Lys Glu  Glu Tyr Lys Met Ala  Leu Tyr Asn
    1070            1075                1080

Leu Tyr  Pro Gly Val Phe Glu  Thr Val Glu Met Leu  Pro Ser Lys
    1085            1090                1095

Ala Gly  Ile Trp Arg Val Glu  Cys Leu Ile Gly Glu  His Leu His
    1100            1105                1110

Ala Gly  Met Ser Thr Leu Phe  Leu Val Tyr Ser Asn  Lys Cys Gln
    1115            1120                1125

Thr Pro  Leu Gly Met Ala Ser  Gly His Ile Arg Asp  Phe Gln Ile
    1130            1135                1140

Thr Ala  Ser Gly Gln Tyr Gly  Gln Trp Ala Pro Lys  Leu Ala Arg
    1145            1150                1155

Leu His  Tyr Ser Gly Ser Ile  Asn Ala Trp Ser Thr  Lys Glu Pro
    1160            1165                1170

Phe Ser  Trp Ile Lys Val Asp  Leu Leu Ala Pro Met  Ile Ile His
    1175            1180                1185

Gly Ile  Lys Thr Gln Gly Ala  Arg Gln Lys Phe Ser  Ser Leu Tyr
    1190            1195                1200

Ile Ser  Gln Phe Ile Ile Met  Tyr Ser Leu Asp Gly  Lys Lys Trp
    1205            1210                1215

Gln Thr  Tyr Arg Gly Asn Ser  Thr Gly Thr Leu Met  Val Phe Phe
    1220            1225                1230

Gly Asn  Val Asp Ser Ser Gly  Ile Lys His Asn Ile  Phe Asn Pro
    1235            1240                1245

Pro Ile  Ile Ala Arg Tyr Ile  Arg Leu His Pro Thr  His Tyr Ser
    1250            1255                1260

Ile Arg  Ser Thr Leu Arg Met  Glu Leu Met Gly Cys  Asp Leu Asn
    1265            1270                1275

Ser Cys  Ser Met Pro Leu Gly  Met Glu Ser Lys Ala  Ile Ser Asp
    1280            1285                1290

Ala Gln  Ile Thr Ala Ser Ser  Tyr Phe Thr Asn Met  Phe Ala Thr
    1295            1300                1305

Trp Ser  Pro Ser Lys Ala Arg  Leu His Leu Gln Gly  Arg Ser Asn
    1310            1315                1320

Ala Trp  Arg Pro Gln Val Asn  Asn Pro Lys Glu Trp  Leu Gln Val
    1325            1330                1335

Asp Phe  Gln Lys Thr Met Lys  Val Thr Gly Val Thr  Thr Gln Gly
```

-continued

```
        1340                1345                1350

Val Lys  Ser Leu Leu Thr Ser  Met Tyr Val Lys Glu  Phe Leu Ile
    1355             1360              1365

Ser Ser  Ser Gln Asp Gly His  Gln Trp Thr Leu Phe  Phe Gln Asn
    1370             1375              1380

Gly Lys  Val Lys Val Phe Gln  Gly Asn Gln Asp Ser  Phe Thr Pro
    1385             1390              1395

Val Val  Asn Ser Leu Asp Pro  Pro Leu Leu Thr Arg  Tyr Leu Arg
    1400             1405              1410

Ile His  Pro Gln Ser Trp Val  His Gln Ile Ala Leu  Arg Met Glu
    1415             1420              1425

Val Leu  Gly Cys Glu Ala Gln  Asp Leu Tyr
    1430             1435
```

<210> SEQ ID NO 7
<211> LENGTH: 4371
<212> TYPE: DNA
<213> ORGANISM: Artificial Sequence
<220> FEATURE:
<223> OTHER INFORMATION: BDD FVIII

<400> SEQUENCE: 7

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaatctttt ccattcaac      180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggataggggat     720 gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca gaagttataa aagtcaatat ttgaacaatg ccctcagcg gattggtagg     1320 aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
```

```
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata ttttttaaccc tccaattatt gctcgataca tccgtttgca cccaactcat   3840
```

-continued

```
tatagcattc gcagcactct tcgcatggag ttgatgggct gtgatttaaa tagttgcagc        3900
atgccattgg gaatggagag taaagcaata tcagatgcac agattactgc ttcatcctac        3960
tttaccaata tgtttgccac ctggtctcct tcaaaagctc gacttcacct ccaagggagg        4020
agtaatgcct ggagacctca ggtgaataat ccaaaagagt ggctgcaagt ggacttccag        4080
aagacaatga aagtcacagg agtaactact cagggagtaa aatctctgct taccagcatg        4140
tatgtgaagg agttcctcat ctccagcagt caagatggcc atcagtggac tctctttttt        4200
cagaatggca aagtaaaggt ttttcaggga aatcaagact ccttcacacc tgtggtgaac        4260
tctctagacc caccgttact gactcgctac cttcgaattc accccagag ttgggtgcac        4320 cagattgccc tgaggatgga ggttctgggc tgcgaggcac aggacctcta c                4371
```

```
<210> SEQ ID NO 8
<211> LENGTH: 25
<212> TYPE: PRT
<213> ORGANISM: Artificial Sequence
<220> FEATURE:
<223> OTHER INFORMATION: Cleavage site

<400> SEQUENCE: 8

Thr Leu Asp Pro Arg Ser Phe Leu Leu Arg Asn Pro Asn Asp Lys Tyr
1               5                   10                  15

Glu Pro Phe Trp Glu Asp Glu Glu Lys
            20                  25

<210> SEQ ID NO 9
<211> LENGTH: 4
<212> TYPE: PRT
<213> ORGANISM: Artificial Sequence
<220> FEATURE:
<223> OTHER INFORMATION: Cleavage site

<400> SEQUENCE: 9

Arg Arg Arg Arg
1

<210> SEQ ID NO 10
<211> LENGTH: 6
<212> TYPE: PRT
<213> ORGANISM: Artificial Sequence
<220> FEATURE:
<223> OTHER INFORMATION: Cleavage site

<400> SEQUENCE: 10

Arg Lys Arg Arg Lys Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Cleavage site

<400> SEQUENCE: 11

Arg Arg Arg Arg Ser
1               5

<210> SEQ ID NO 12
<211> LENGTH: 42
<212> TYPE: PRT
<213> ORGANISM: Artificial Sequence
<220> FEATURE:
```

<223> OTHER INFORMATION: XTEN AE42

<400> SEQUENCE: 12

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 13
<211> LENGTH: 78
<212> TYPE: PRT
<213> ORGANISM: Artificial Sequence
<220> FEATURE:
<223> OTHER INFORMATION: XTEN AE72

<400> SEQUENCE: 13

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
            20                  25                  30

Thr Pro Glu Ser Gly Pro Gly Ser Glu Pro Ala Thr Ser Gly Ser Glu
        35                  40                  45

Thr Pro Gly Thr Ser Glu Ser Ala Thr Pro Glu Ser Gly Pro Gly Thr
    50                  55                  60

Ser Thr Glu Pro Ser Glu Gly Ser Ala Pro Gly Ala Ser Ser
65                  70                  75

<210> SEQ ID NO 14
<211> LENGTH: 143
<212> TYPE: PRT
<213> ORGANISM: Artificial Sequence
<220> FEATURE:
<223> OTHER INFORMATION: XTEN AE144

<400> SEQUENCE: 14

Gly Ser Glu Pro Ala Thr Ser Gly Ser Glu Thr Pro Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Ser Pro Ala Gly Ser Pro Thr Ser Thr Glu Glu
        35                  40                  45

Gly Thr Ser Thr Glu Pro Ser Glu Gly Ser Ala Pro Gly Ser Glu Pro
    50                  55                  60

Ala Thr Ser Gly Ser Glu Thr Pro Gly Ser Glu Pro Ala Thr Ser Gly
65                  70                  75                  80

Ser Glu Thr Pro Gly Ser Glu Pro Ala Thr Ser Gly Ser Glu Thr Pro
                85                  90                  95

Gly Thr Ser Thr Glu Pro Ser Glu Gly Ser Ala Pro Gly Thr Ser Glu
            100                 105                 110

Ser Ala Pro Glu Ser Gly Pro Gly Ser Glu Pro Ala Thr Ser Gly Ser
        115                 120                 125

Glu Thr Pro Gly Thr Ser Thr Glu Pro Ser Glu Gly Ser Ala Pro
    130                 135                 140

<210> SEQ ID NO 15
<211> LENGTH: 144
<212> TYPE: PRT

```
<213> ORGANISM: Artificial Sequence
<220> FEATURE:
<223> OTHER INFORMATION: XTEN AG144

<400> SEQUENCE: 15

Gly Thr Pro Gly Ser Gly Thr Ala Ser Ser Ser Pro Gly Ser Ser Thr
1               5                   10                  15

Pro Ser Gly Ala Thr Gly Ser Pro Gly Ser Ser Pro Ser Ala Ser Thr
                20                  25                  30

Gly Thr Gly Pro Gly Ser Ser Pro Ser Ala Ser Thr Gly Thr Gly Pro
            35                  40                  45

Gly Ala Ser Pro Gly Thr Ser Ser Thr Gly Ser Pro Gly Ala Ser Pro
        50                  55                  60

Gly Thr Ser Ser Thr Gly Ser Pro Gly Ser Ser Thr Pro Ser Gly Ala
65                  70                  75                  80

Thr Gly Ser Pro Gly Ser Ser Pro Ser Ala Ser Thr Gly Thr Gly Pro
                85                  90                  95

Gly Ala Ser Pro Gly Thr Ser Ser Thr Gly Ser Pro Gly Ser Ser Pro
            100                 105                 110

Ser Ala Ser Thr Gly Thr Gly Pro Gly Thr Pro Gly Ser Gly Thr Ala
        115                 120                 125

Ser Ser Ser Pro Gly Ser Ser Thr Pro Ser Gly Ala Thr Gly Ser Pro
        130                 135                 140

<210> SEQ ID NO 16
<211> LENGTH: 288
<212> TYPE: PRT
<213> ORGANISM: Artificial Sequence
<220> FEATURE:
<223> OTHER INFORMATION: XTEN AE288

<400> SEQUENCE: 16

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
                20                  25                  30

Glu Ser Gly Pro Gly Ser Glu Pro Ala Thr Ser Gly Ser Glu Thr Pro
            35                  40                  45

Gly Thr Ser Glu Ser Ala Thr Pro Glu Ser Gly Pro Gly Thr Ser Thr
        50                  55                  60

Glu Pro Ser Glu Gly Ser Ala Pro Gly Ser Pro Ala Gly Ser Pro Thr
65                  70                  75                  80

Ser Thr Glu Glu Gly Thr Ser Glu Ser Ala Thr Pro Glu Ser Gly Pro
                85                  90                  95

Gly Ser Glu Pro Ala Thr Ser Gly Ser Glu Thr Pro Gly Thr Ser Glu
            100                 105                 110

Ser Ala Thr Pro Glu Ser Gly Pro Gly Ser Pro Ala Gly Ser Pro Thr
        115                 120                 125

Ser Thr Glu Glu Gly Ser Pro Ala Gly Ser Pro Thr Ser Thr Glu Glu
        130                 135                 140

Gly Thr Ser Thr Glu Pro Ser Glu Gly Ser Ala Pro Gly Thr Ser Glu
145                 150                 155                 160

Ser Ala Thr Pro Glu Ser Gly Pro Gly Thr Ser Glu Ser Ala Thr Pro
                165                 170                 175

Glu Ser Gly Pro Gly Thr Ser Glu Ser Ala Thr Pro Glu Ser Gly Pro
            180                 185                 190
```

```
Gly Ser Glu Pro Ala Thr Ser Gly Ser Glu Thr Pro Gly Ser Glu Pro
        195                 200                 205

Ala Thr Ser Gly Ser Glu Thr Pro Gly Ser Pro Ala Gly Ser Pro Thr
        210                 215                 220

Ser Thr Glu Glu Gly Thr Ser Thr Glu Pro Ser Glu Gly Ser Ala Pro
225                 230                 235                 240

Gly Thr Ser Thr Glu Pro Ser Glu Gly Ser Ala Pro Gly Ser Glu Pro
                245                 250                 255

Ala Thr Ser Gly Ser Glu Thr Pro Gly Thr Ser Glu Ser Ala Thr Pro
                260                 265                 270

Glu Ser Gly Pro Gly Thr Ser Thr Glu Pro Ser Glu Gly Ser Ala Pro
                275                 280                 285
```

```
<210> SEQ ID NO 17
<211> LENGTH: 288
<212> TYPE: PRT
<213> ORGANISM: Artificial Sequence
<220> FEATURE:
<223> OTHER INFORMATION: XTEN AG288

<400> SEQUENCE: 17
```

```
Pro Gly Ala Ser Pro Gly Thr Ser Ser Thr Gly Ser Pro Gly Ala Ser
1               5                   10                  15

Pro Gly Thr Ser Ser Thr Gly Ser Pro Gly Thr Pro Gly Ser Gly Thr
        20                  25                  30

Ala Ser Ser Ser Pro Gly Ser Ser Thr Pro Ser Gly Ala Thr Gly Ser
        35                  40                  45

Pro Gly Thr Pro Gly Ser Gly Thr Ala Ser Ser Ser Pro Gly Ser Ser
    50                  55                  60

Thr Pro Ser Gly Ala Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Ser Ser Thr Pro Ser Gly Ala Thr Gly Ser Pro Gly Ser Ser
        100                 105                 110

Pro Ser Ala Ser Thr Gly Thr Gly Pro Gly Ser Ser Pro Ser Ala Ser
        115                 120                 125

Thr Gly Thr Gly Pro Gly Ala Ser Pro Gly Thr Ser Ser Thr Gly Ser
    130                 135                 140

Pro Gly Thr Pro Gly Ser Gly Thr Ala Ser Ser Ser Pro Gly Ser Ser
145                 150                 155                 160

Thr Pro Ser Gly Ala Thr Gly Ser Pro Gly Ser Ser Pro Ser Ala Ser
                165                 170                 175

Thr Gly Thr Gly Pro Gly Ser Ser Pro Ser Ala Ser Thr Gly Thr Gly
            180                 185                 190

Pro Gly Ala Ser Pro Gly Thr Ser Ser Thr Gly Ser Pro Gly Ala Ser
            195                 200                 205

Pro Gly Thr Ser Ser Thr Gly Ser Pro Gly Ser Ser Thr Pro Ser Gly
        210                 215                 220

Ala Thr Gly Ser Pro Gly Ser Ser Pro Ser Ala Ser Thr Gly Thr Gly
225                 230                 235                 240

Pro Gly Ala Ser Pro Gly Thr Ser Ser Thr Gly Ser Pro Gly Ser Ser
            245                 250                 255

Pro Ser Ala Ser Thr Gly Thr Gly Pro Gly Thr Pro Gly Ser Gly Thr
        260                 265                 270
```

-continued

```
Ala Ser Ser Ser Pro Gly Ser Ser Thr Pro Ser Gly Ala Thr Gly Ser
        275                 280                 285

<210> SEQ ID NO 18
<211> LENGTH: 576
<212> TYPE: PRT
<213> ORGANISM: Artificial Sequence
<220> FEATURE:
<223> OTHER INFORMATION: XTEN AE576

<400> SEQUENCE: 18

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
            35                  40                  45

Gly Thr Ser Thr Glu Pro Ser Glu Gly Ser Ala Pro Gly Thr Ser Thr
        50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
            85                  90                  95

Gly Ser Glu Pro Ala Thr Ser Gly Ser Glu Thr Pro Gly Ser Pro Ala
            100                 105                 110

Gly Ser Pro Thr Ser Thr Glu Glu Gly Thr Ser Glu Ser Ala Thr Pro
        115                 120                 125

Glu Ser Gly Pro Gly Thr Ser Thr Glu Pro Ser Glu Gly Ser Ala Pro
        130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
            165                 170                 175

Gly Ser Ala Pro Gly Thr Ser Thr Glu Pro Ser Glu Gly Ser Ala Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
            245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
        275                 280                 285

Gly Ser Pro Ala Gly Ser Pro Thr Ser Thr Glu Glu Gly Thr Ser Glu
        290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
            325                 330                 335

Gly Thr Ser Thr Glu Pro Ser Glu Gly Ser Ala Pro Gly Thr Ser Thr
        340                 345                 350
```

-continued

```
Glu Pro Ser Glu Gly Ser Ala Pro Gly Thr Ser Thr Glu Pro Ser Glu
        355                 360             365

Gly Ser Ala Pro Gly Thr Ser Thr Glu Pro Ser Glu Gly Ser Ala Pro
    370             375             380

Gly Thr Ser Thr Glu Pro Ser Glu Gly Ser Ala Pro Gly Thr Ser Thr
385                 390             395             400

Glu Pro Ser Glu Gly Ser Ala Pro Gly Ser Pro Ala Gly Ser Pro Thr
            405             410             415

Ser Thr Glu Glu Gly Thr Ser Thr Glu Pro Ser Glu Gly Ser Ala Pro
        420             425             430

Gly Thr Ser Glu Ser Ala Thr Pro Glu Ser Gly Pro Gly Ser Glu Pro
        435             440             445

Ala Thr Ser Gly Ser Glu Thr Pro Gly Thr Ser Glu Ser Ala Thr Pro
    450             455             460

Glu Ser Gly Pro Gly Ser Glu Pro Ala Thr Ser Gly Ser Glu Thr Pro
465             470             475             480

Gly Thr Ser Glu Ser Ala Thr Pro Glu Ser Gly Pro Gly Thr Ser Thr
            485             490             495

Glu Pro Ser Glu Gly Ser Ala Pro Gly Thr Ser Glu Ser Ala Thr Pro
        500             505             510

Glu Ser Gly Pro Gly Ser Pro Ala Gly Ser Pro Thr Ser Thr Glu Glu
        515             520             525

Gly Ser Pro Ala Gly Ser Pro Thr Ser Thr Glu Glu Gly Ser Pro Ala
    530             535             540

Gly Ser Pro Thr Ser Thr Glu Glu Gly Thr Ser Glu Ser Ala Thr Pro
545             550             555             560

Glu Ser Gly Pro Gly Thr Ser Thr Glu Pro Ser Glu Gly Ser Ala Pro
            565             570             575
```

```
<210> SEQ ID NO 19
<211> LENGTH: 576
<212> TYPE: PRT
<213> ORGANISM: Artificial Sequence
<220> FEATURE:
<223> OTHER INFORMATION: XTEN AG576

<400> SEQUENCE: 19

Pro Gly Thr Pro Gly Ser Gly Thr Ala Ser Ser Ser Pro Gly Ser Ser
1               5                   10                  15

Thr Pro Ser Gly Ala Thr Gly Ser Pro Gly Ser Ser Pro Ser Ala Ser
            20                  25                  30

Thr Gly Thr Gly Pro Gly Ser Ser Pro Ser Ala Ser Thr Gly Thr Gly
        35                  40                  45

Pro Gly Ser Ser Thr Pro Ser Gly Ala Thr Gly Ser Pro Gly Ser Ser
    50                  55                  60

Thr Pro Ser Gly Ala Thr Gly Ser Pro Gly Ala Ser Pro Gly Thr Ser
65                  70                  75                  80

Ser Thr Gly Ser Pro Gly Ala Ser Pro Gly Thr Ser Ser Thr Gly Ser
            85                  90                  95

Pro Gly Ala Ser Pro Gly Thr Ser Ser Thr Gly Ser Pro Gly Thr Pro
            100                 105                 110

Gly Ser Gly Thr Ala Ser Ser Ser Pro Gly Ala Ser Pro Gly Thr Ser
        115                 120                 125

Ser Thr Gly Ser Pro Gly Ala Ser Pro Gly Thr Ser Ser Thr Gly Ser
    130                 135                 140
```

-continued

```
Pro Gly Ala Ser Pro Gly Thr Ser Ser Thr Gly Ser Pro Gly Ser Ser
145             150                 155                 160

Pro Ser Ala Ser Thr Gly Thr Gly Pro Gly Thr Pro Gly Ser Gly Thr
                165             170             175

Ala Ser Ser Ser Pro Gly Ala Ser Pro Gly Thr Ser Ser Thr Gly Ser
                180             185             190

Pro Gly Ala Ser Pro Gly Thr Ser Ser Thr Gly Ser Pro Gly Ala Ser
            195             200             205

Pro Gly Thr Ser Ser Thr Gly Ser Pro Gly Ser Ser Thr Pro Ser Gly
            210             215             220

Ala Thr Gly Ser Pro Gly Ser Ser Thr Pro Ser Gly Ala Thr Gly Ser
225             230             235             240

Pro Gly Ala Ser Pro Gly Thr Ser Ser Thr Gly Ser Pro Gly Thr Pro
            245             250             255

Gly Ser Gly Thr Ala Ser Ser Ser Pro Gly Ser Ser Thr Pro Ser Gly
            260             265             270

Ala Thr Gly Ser Pro Gly Ser Ser Thr Pro Ser Gly Ala Thr Gly Ser
            275             280             285

Pro Gly Ser Ser Thr Pro Ser Gly Ala Thr Gly Ser Pro Gly Ser Ser
            290             295             300

Pro Ser Ala Ser Thr Gly Thr Gly Pro Gly Ala Ser Pro Gly Thr Ser
305             310             315             320

Ser Thr Gly Ser Pro Gly Ala Ser Pro Gly Thr Ser Ser Thr Gly Ser
                325             330             335

Pro Gly Thr Pro Gly Ser Gly Thr Ala Ser Ser Ser Pro Gly Ala Ser
            340             345             350

Pro Gly Thr Ser Ser Thr Gly Ser Pro Gly Ala Ser Pro Gly Thr Ser
            355             360             365

Ser Thr Gly Ser Pro Gly Ala Ser Pro Gly Thr Ser Ser Thr Gly Ser
            370             375             380

Pro Gly Ala Ser Pro Gly Thr Ser Ser Thr Gly Ser Pro Gly Thr Pro
385             390             395             400

Gly Ser Gly Thr Ala Ser Ser Ser Pro Gly Ser Ser Thr Pro Ser Gly
                405             410             415

Ala Thr Gly Ser Pro Gly Thr Pro Gly Ser Gly Thr Ala Ser Ser Ser
                420             425             430

Pro Gly Ser Ser Thr Pro Ser Gly Ala Thr Gly Ser Pro Gly Thr Pro
            435             440             445

Gly Ser Gly Thr Ala Ser Ser Ser Pro Gly Ser Ser Thr Pro Ser Gly
            450             455             460

Ala Thr Gly Ser Pro Gly Ser Ser Thr Pro Ser Gly Ala Thr Gly Ser
465             470             475             480

Pro Gly Ser Ser Pro Ser Ala Ser Thr Gly Thr Gly Pro Gly Ser Ser
            485             490             495

Pro Ser Ala Ser Thr Gly Thr Gly Pro Gly Ala Ser Pro Gly Thr Ser
            500             505             510

Ser Thr Gly Ser Pro Gly Thr Pro Gly Ser Gly Thr Ala Ser Ser Ser
            515             520             525

Pro Gly Ser Ser Thr Pro Ser Gly Ala Thr Gly Ser Pro Gly Ser Ser
            530             535             540

Pro Ser Ala Ser Thr Gly Thr Gly Pro Gly Ser Ser Pro Ser Ala Ser
545             550             555             560

Thr Gly Thr Gly Pro Gly Ala Ser Pro Gly Thr Ser Ser Thr Gly Ser
```

-continued

```
                565                 570                 575

<210> SEQ ID NO 20
<211> LENGTH: 864
<212> TYPE: PRT
<213> ORGANISM: Artificial Sequence
<220> FEATURE:
<223> OTHER INFORMATION: XTEN AE864

<400> SEQUENCE: 20

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
            100                 105                 110

Gly Ser Pro Thr Ser Thr Glu Glu Gly Thr Ser Glu Ser Ala Thr Pro
        115                 120                 125

Glu Ser Gly Pro Gly Thr Ser Thr Glu Pro Ser Glu Gly Ser Ala Pro
    130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
            165                 170                 175

Gly Ser Ala Pro Gly Thr Ser Thr Glu Pro Ser Glu Gly Ser Ala Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
        275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
            325                 330                 335

Gly Thr Ser Thr Glu Pro Ser Glu Gly Ser Ala Pro Gly Thr Ser Thr
        340                 345                 350

Glu Pro Ser Glu Gly Ser Ala Pro Gly Thr Ser Thr Glu Pro Ser Glu
```

-continued

```
              355                 360                 365

Gly Ser Ala Pro Gly Thr Ser Thr Glu Pro Ser Glu Gly Ser Ala Pro
    370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
                420                 425                 430

Gly Thr Ser Glu Ser Ala Thr Pro Glu Ser Gly Pro Gly Ser Glu Pro
                435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
                500                 505                 510

Glu Ser Gly Pro Gly Ser Pro Ala Gly Ser Pro Thr Ser Thr Glu Glu
                515                 520                 525

Gly Ser Pro Ala Gly Ser Pro Thr Ser Thr Glu Glu Gly Ser Pro Ala
    530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

Gly Thr Ser Glu Ser Ala Thr Pro Glu Ser Gly Pro Gly Ser Glu Pro
                580                 585                 590

Ala Thr Ser Gly Ser Glu Thr Pro Gly Thr Ser Glu Ser Ala Thr Pro
    595                 600                 605

Glu Ser Gly Pro Gly Ser Glu Pro Ala Thr Ser Gly Ser Glu Thr Pro
    610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
                645                 650                 655

Ser Thr Glu Glu Gly Thr Ser Glu Ser Ala Thr Pro Glu Ser Gly Pro
                660                 665                 670

Gly Ser Glu Pro Ala Thr Ser Gly Ser Glu Thr Pro Gly Thr Ser Glu
    675                 680                 685

Ser Ala Thr Pro Glu Ser Gly Pro Gly Ser Pro Ala Gly Ser Pro Thr
    690                 695                 700

Ser Thr Glu Glu Gly Ser Pro Ala Gly Ser Pro Thr Ser Thr Glu Glu
705                 710                 715                 720

Gly Thr Ser Thr Glu Pro Ser Glu Gly Ser Ala Pro Gly Thr Ser Glu
                725                 730                 735

Ser Ala Thr Pro Glu Ser Gly Pro Gly Thr Ser Glu Ser Ala Thr Pro
                740                 745                 750

Glu Ser Gly Pro Gly Thr Ser Glu Ser Ala Thr Pro Glu Ser Gly Pro
                755                 760                 765

Gly Ser Glu Pro Ala Thr Ser Gly Ser Glu Thr Pro Gly Ser Glu Pro
    770                 775                 780
```

```
Ala Thr Ser Gly Ser Glu Thr Pro Gly Ser Pro Ala Gly Ser Pro Thr
785                 790                 795                 800

Ser Thr Glu Glu Gly Thr Ser Thr Glu Pro Ser Glu Gly Ser Ala Pro
                805                 810                 815

Gly Thr Ser Thr Glu Pro Ser Glu Gly Ser Ala Pro Gly Ser Glu Pro
                820                 825                 830

Ala Thr Ser Gly Ser Glu Thr Pro Gly Thr Ser Glu Ser Ala Thr Pro
                835                 840                 845

Glu Ser Gly Pro Gly Thr Ser Thr Glu Pro Ser Glu Gly Ser Ala Pro
        850                 855                 860

<210> SEQ ID NO 21
<211> LENGTH: 864
<212> TYPE: PRT
<213> ORGANISM: Artificial Sequence
<220> FEATURE:
<223> OTHER INFORMATION: XTEN AG864

<400> SEQUENCE: 21

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
                20                  25                  30

Gly Thr Gly Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

Gly Thr Pro Gly Ser Gly Thr Ala Ser Ser Ser Pro Gly Ser Ser Thr
145                 150                 155                 160

Pro Ser Gly Ala Thr Gly Ser Pro Gly Ala Ser Pro Gly Thr Ser Ser
                165                 170                 175

Thr Gly Ser Pro Gly Thr Pro Gly Ser Gly Thr Ala Ser Ser Ser Pro
            180                 185                 190

Gly Ser Ser Thr Pro Ser Gly Ala Thr Gly Ser Pro Gly Ser Ser Pro
        195                 200                 205

Ser Ala Ser Thr Gly Thr Gly Pro Gly Ser Ser Pro Ser Ala Ser Thr
    210                 215                 220

Gly Thr Gly Pro Gly Ser Ser Thr Pro Ser Gly Ala Thr Gly Ser Pro
225                 230                 235                 240

Gly Ser Ser Thr Pro Ser Gly Ala Thr Gly Ser Pro Gly Ala Ser Pro
                245                 250                 255

Gly Thr Ser Ser Thr Gly Ser Pro Gly Ala Ser Pro Gly Thr Ser Ser
            260                 265                 270

Thr Gly Ser Pro Gly Ala Ser Pro Gly Thr Ser Ser Thr Gly Ser Pro
    275                 280                 285
```

```
Gly Thr Pro Gly Ser Gly Thr Ala Ser Ser Ser Pro Gly Ala Ser Pro
    290                 295                 300

Gly Thr Ser Ser Thr Gly Ser Pro Gly Ala Ser Pro Gly Thr Ser Ser
305                 310                 315                 320

Thr Gly Ser Pro Gly Ala Ser Pro Gly Thr Ser Ser Thr Gly Ser Pro
                325                 330                 335

Gly Ser Ser Pro Ser Ala Ser Thr Gly Thr Gly Pro Gly Thr Pro Gly
            340                 345                 350

Ser Gly Thr Ala Ser Ser Ser Pro Gly Ala Ser Pro Gly Thr Ser Ser
        355                 360                 365

Thr Gly Ser Pro Gly Ala Ser Pro Gly Thr Ser Ser Thr Gly Ser Pro
    370                 375                 380

Gly Ala Ser Pro Gly Thr Ser Ser Thr Gly Ser Pro Gly Ser Ser Thr
385                 390                 395                 400

Pro Ser Gly Ala Thr Gly Ser Pro Gly Ser Ser Thr Pro Ser Gly Ala
                405                 410                 415

Thr Gly Ser Pro Gly Ala Ser Pro Gly Thr Ser Ser Thr Gly Ser Pro
                420                 425                 430

Gly Thr Pro Gly Ser Gly Thr Ala Ser Ser Ser Pro Gly Ser Ser Thr
            435                 440                 445

Pro Ser Gly Ala Thr Gly Ser Pro Gly Ser Ser Thr Pro Ser Gly Ala
    450                 455                 460

Thr Gly Ser Pro Gly Ser Ser Thr Pro Ser Gly Ala Thr Gly Ser Pro
465                 470                 475                 480

Gly Ser Ser Pro Ser Ala Ser Thr Gly Thr Gly Pro Gly Ala Ser Pro
                485                 490                 495

Gly Thr Ser Ser Thr Gly Ser Pro Gly Ala Ser Pro Gly Thr Ser Ser
            500                 505                 510

Thr Gly Ser Pro Gly Thr Pro Gly Ser Gly Thr Ala Ser Ser Ser Pro
            515                 520                 525

Gly Ala Ser Pro Gly Thr Ser Ser Thr Gly Ser Pro Gly Ala Ser Pro
    530                 535                 540

Gly Thr Ser Ser Thr Gly Ser Pro Gly Ala Ser Pro Gly Thr Ser Ser
545                 550                 555                 560

Thr Gly Ser Pro Gly Ala Ser Pro Gly Thr Ser Ser Thr Gly Ser Pro
                565                 570                 575

Gly Thr Pro Gly Ser Gly Thr Ala Ser Ser Ser Pro Gly Ser Ser Thr
            580                 585                 590

Pro Ser Gly Ala Thr Gly Ser Pro Gly Thr Pro Gly Ser Gly Thr Ala
            595                 600                 605

Ser Ser Ser Pro Gly Ser Ser Thr Pro Ser Gly Ala Thr Gly Ser Pro
    610                 615                 620

Gly Thr Pro Gly Ser Gly Thr Ala Ser Ser Ser Pro Gly Ser Ser Thr
625                 630                 635                 640

Pro Ser Gly Ala Thr Gly Ser Pro Gly Ser Ser Thr Pro Ser Gly Ala
                645                 650                 655

Thr Gly Ser Pro Gly Ser Ser Pro Ser Ala Ser Thr Gly Thr Gly Pro
            660                 665                 670

Gly Ser Ser Pro Ser Ala Ser Thr Gly Thr Gly Pro Gly Ala Ser Pro
        675                 680                 685

Gly Thr Ser Ser Thr Gly Ser Pro Gly Thr Pro Gly Ser Gly Thr Ala
    690                 695                 700
```

```
Ser Ser Ser Pro Gly Ser Ser Thr Pro Ser Gly Ala Thr Gly Ser Pro
705             710             715             720

Gly Ser Ser Pro Ser Ala Ser Thr Gly Thr Gly Pro Gly Ser Ser Pro
                725             730             735

Ser Ala Ser Thr Gly Thr Gly Pro Gly Ala Ser Pro Gly Thr Ser Ser
            740             745             750

Thr Gly Ser Pro Gly Ala Ser Pro Gly Thr Ser Ser Thr Gly Ser Pro
        755             760             765

Gly Ser Ser Thr Pro Ser Gly Ala Thr Gly Ser Pro Gly Ser Ser Pro
    770             775             780

Ser Ala Ser Thr Gly Thr Gly Pro Gly Ala Ser Pro Gly Thr Ser Ser
785             790             795             800

Thr Gly Ser Pro Gly Ser Ser Pro Ser Ala Ser Thr Gly Thr Gly Pro
            805             810             815

Gly Thr Pro Gly Ser Gly Thr Ala Ser Ser Ser Pro Gly Ser Ser Thr
        820             825             830

Pro Ser Gly Ala Thr Gly Ser Pro Gly Ser Ser Thr Pro Ser Gly Ala
        835             840             845

Thr Gly Ser Pro Gly Ala Ser Pro Gly Thr Ser Ser Thr Gly Ser Pro
    850             855             860
```

```
<210> SEQ ID NO 22
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 22

Thr Gln Ser Phe Asn Asp Phe Thr Arg
1               5
```

```
<210> SEQ ID NO 23
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 23

Ser Val Ser Gln Thr Ser Lys Leu Thr Arg
1               5               10
```

```
<210> SEQ ID NO 24
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 24

Asp Phe Leu Ala Glu Gly Gly Gly Val Arg
1               5               10
```

```
<210> SEQ ID NO 25
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 25
```

-continued

```
Thr Thr Lys Ile Lys Pro Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 26

Leu Val Pro Arg Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 27

Ala Leu Arg Pro Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Recognition signal motif
<220> FEATURE:
<221> NAME/KEY: MISC_FEATURE
<222> LOCATION: (3)..(3)
<223> OTHER INFORMATION: Any naturally occurring amino acid

<400> SEQUENCE: 28

Leu Pro Xaa Thr Gly
1               5

<210> SEQ ID NO 29
<211> LENGTH: 11
<212> TYPE: PRT
<213> ORGANISM: Artificial Sequence
<220> FEATURE:
<223> OTHER INFORMATION: Ig constant region

<400> SEQUENCE: 29

Pro Lys Asn Ser Ser Met Ile Ser Asn Thr Pro
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Ig constant region

<400> SEQUENCE: 30

His Gln Ser Leu Gly Thr Gln
1               5

<210> SEQ ID NO 31
<211> LENGTH: 8
<212> TYPE: PRT
<213> ORGANISM: Artificial Sequence
<220> FEATURE:
<223> OTHER INFORMATION: Ig constant region
```

-continued

<400> SEQUENCE: 31

His Gln Asn Leu Ser Asp Gly Lys
1               5

<210> SEQ ID NO 32
<211> LENGTH: 8
<212> TYPE: PRT
<213> ORGANISM: Artificial Sequence
<220> FEATURE:
<223> OTHER INFORMATION: Ig constant region

<400> SEQUENCE: 32

His Gln Asn Ile Ser Asp Gly Lys
1               5

<210> SEQ ID NO 33
<211> LENGTH: 8
<212> TYPE: PRT
<213> ORGANISM: Artificial Sequence
<220> FEATURE:
<223> OTHER INFORMATION: Ig constant region

<400> SEQUENCE: 33

Val Ile Ser Ser His Leu Gly Gln
1               5

<210> SEQ ID NO 34
<211> LENGTH: 400
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(400)
<223> OTHER INFORMATION: Some of these amino acids may be absent

<400> SEQUENCE: 34

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
        50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
            85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
        130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
            165                 170                 175

-continued

```
Gly Gly Gly Ser Gly Gly Gly Ser Gly Gly Ser Gly Gly Gly Ser
            180                 185                 190

Gly Gly Gly Ser Gly Gly Gly Ser Gly Gly Gly Ser Gly Gly Gly Ser
            195                 200                 205

Gly Gly Gly Ser Gly Gly Gly Ser Gly Gly Gly Ser Gly Gly Gly Ser
        210                 215                 220

Gly Gly Gly Ser Gly Gly Gly Ser Gly Gly Gly Ser Gly Gly Gly Ser
    225                 230                 235                 240

Gly Gly Gly Ser Gly Gly Gly Ser Gly Gly Gly Ser Gly Gly Gly Ser
                245                 250                 255

Gly Gly Gly Ser Gly Gly Gly Ser Gly Gly Gly Ser Gly Gly Gly Ser
            260                 265                 270

Gly Gly Gly Ser Gly Gly Gly Ser Gly Gly Gly Ser Gly Gly Gly Ser
            275                 280                 285

Gly Gly Gly Ser Gly Gly Gly Ser Gly Gly Gly Ser Gly Gly Gly Ser
        290                 295                 300

Gly Gly Gly Ser Gly Gly Gly Ser Gly Gly Gly Ser Gly Gly Gly Ser
    305                 310                 315                 320

Gly Gly Gly Ser Gly Gly Gly Ser Gly Gly Gly Ser Gly Gly Gly Ser
                325                 330                 335

Gly Gly Gly Ser Gly Gly Gly Ser Gly Gly Gly Ser Gly Gly Gly Ser
            340                 345                 350

Gly Gly Gly Ser Gly Gly Gly Ser Gly Gly Gly Ser Gly Gly Gly Ser
            355                 360                 365

Gly Gly Gly Ser Gly Gly Gly Ser Gly Gly Gly Ser Gly Gly Gly Ser
        370                 375                 380

Gly Gly Gly Ser Gly Gly Gly Ser Gly Gly Gly Ser Gly Gly Gly Ser
    385                 390                 395                 400

<210> SEQ ID NO 35
<211> LENGTH: 800
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(800)
<223> OTHER INFORMATION: Some of the amino acids may be absent

<400> SEQUENCE: 35

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
            35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125
```

-continued

```
Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
                165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
        195                 200                 205

Gly Ser Gly Gly Ser Gly Gly Ser Gly Gly Ser Gly Gly Ser Gly Gly
    210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
            245                 250                 255

Gly Ser Gly Gly Ser Gly Gly Ser Gly Gly Ser Gly Gly Ser Gly Gly
            260                 265                 270

Ser Gly Gly Ser Gly Gly Ser Gly Gly Ser Gly Gly Ser Gly Gly Ser
        275                 280                 285

Gly Gly Ser Gly Gly Ser Gly Gly Ser Gly Gly Ser Gly Gly Gly Gly
    290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
            325                 330                 335

Gly Gly Gly Ser Gly Gly Gly Gly Ser Gly Gly Gly Gly Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gly Gly Gly Gly
    370                 375                 380

Ser Gly Gly Gly Gly Ser Gly Gly Gly Gly Ser Gly Gly Gly Gly Ser
385                 390                 395                 400

Gly Gly Gly Gly Ser Gly Gly Gly Gly Ser Gly Gly Gly Gly Ser Gly
            405                 410                 415

Gly Gly Gly Ser Gly Gly Gly Gly Ser Gly Gly Gly Gly Ser Gly Gly
            420                 425                 430

Gly Gly Ser Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Gly Gly Gly Gly Ser Gly Gly Gly Gly Ser Gly
            485                 490                 495

Gly Gly Gly Ser Gly Gly Gly Gly Ser Gly Gly Gly Gly Ser Gly Gly
            500                 505                 510

Gly Gly Ser Gly Gly Gly Gly Ser Gly Gly Gly Gly Ser Gly Gly Gly
        515                 520                 525

Gly Ser Gly Gly Gly Gly Ser Gly Gly Gly Gly Ser Gly Gly Gly Gly
    530                 535                 540
```

-continued

```
Ser Gly Gly Gly Gly Ser Gly Gly Gly Gly Ser Gly Gly Gly Ser
545                 550                 555                 560

Gly Gly Gly Gly Ser Gly Gly Gly Gly Ser Gly Gly Gly Gly Ser Gly
                565                 570                 575

Gly Gly Gly Ser Gly Gly Gly Gly Ser Gly Gly Gly Gly Ser Gly Gly
                580                 585                 590

Gly Gly Ser Gly Gly Gly Gly Ser Gly Gly Gly Gly Ser Gly Gly Gly
            595                 600                 605

Gly Ser Gly Gly Gly Gly Ser Gly Gly Gly Gly Ser Gly Gly Gly Gly
        610                 615                 620

Ser Gly Gly Gly Gly Ser Gly Gly Gly Gly Ser Gly Gly Gly Gly Ser
625                 630                 635                 640

Gly Gly Gly Gly Ser Gly Gly Gly Gly Ser Gly Gly Gly Gly Ser Gly
                645                 650                 655

Gly Gly Gly Ser Gly Gly Gly Gly Ser Gly Gly Gly Gly Ser Gly Gly
                660                 665                 670

Gly Gly Ser Gly Gly Gly Gly Ser Gly Gly Gly Gly Ser Gly Gly Gly
            675                 680                 685

Gly Ser Gly Gly Gly Gly Ser Gly Gly Gly Gly Ser Gly Gly Gly Gly
        690                 695                 700

Ser Gly Gly Gly Gly Ser Gly Gly Gly Gly Ser Gly Gly Gly Gly Ser
705                 710                 715                 720

Gly Gly Gly Gly Ser Gly Gly Gly Gly Ser Gly Gly Gly Gly Ser Gly
                725                 730                 735

Gly Gly Gly Ser Gly Gly Gly Gly Ser Gly Gly Gly Gly Ser Gly Gly
                740                 745                 750

Gly Gly Ser Gly Gly Gly Gly Ser Gly Gly Gly Gly Ser Gly Gly Gly
            755                 760                 765

Gly Ser Gly Gly Gly Gly Ser Gly Gly Gly Gly Ser Gly Gly Gly Gly
        770                 775                 780

Ser Gly Gly Gly Gly Ser Gly Gly Gly Gly Ser Gly Gly Gly Gly Ser
785                 790                 795                 800

<210> SEQ ID NO 36
<211> LENGTH: 7
<212> TYPE: PRT
<213> ORGANISM: Artificial Sequence
<220> FEATURE:
<223> OTHER INFORMATION: Gly/Ser linker

<400> SEQUENCE: 36

Ser Gly Gly Ser Gly Gly Ser
1               5

<210> SEQ ID NO 37
<211> LENGTH: 15
<212> TYPE: PRT
<213> ORGANISM: Artificial Sequence
<220> FEATURE:
<223> OTHER INFORMATION: Gly/Ser linker

<400> SEQUENCE: 37

Gly Gly Ser Gly Gly Ser Gly Gly Ser Gly Gly Ser Gly Gly Gly
1               5                   10                  15

<210> SEQ ID NO 38
<211> LENGTH: 16
<212> TYPE: PRT
<213> ORGANISM: Artificial Sequence
```

-continued

```
<220> FEATURE:
<223> OTHER INFORMATION: Gly/Ser linker

<400> SEQUENCE: 38

Gly Gly Ser Gly Gly Ser Gly Gly Gly Gly Ser Gly Gly Gly Gly Ser
1               5                   10                  15

<210> SEQ ID NO 39
<211> LENGTH: 18
<212> TYPE: PRT
<213> ORGANISM: Artificial Sequence
<220> FEATURE:
<223> OTHER INFORMATION: Gly/Ser linker

<400> SEQUENCE: 39

Gly Gly Ser Gly Gly Ser Gly Gly Ser Gly Gly Ser Gly Gly Ser Gly
1               5                   10                  15

Gly Ser

<210> SEQ ID NO 40
<211> LENGTH: 15
<212> TYPE: PRT
<213> ORGANISM: Artificial Sequence
<220> FEATURE:
<223> OTHER INFORMATION: Gly/Ser linker

<400> SEQUENCE: 40

Gly Gly Gly Gly Ser Gly Gly Gly Gly Ser Gly Gly Gly Gly Ser
1               5                   10                  15

<210> SEQ ID NO 41
<211> LENGTH: 100
<212> TYPE: PRT
<213> ORGANISM: Artificial Sequence
<220> FEATURE:
<223> OTHER INFORMATION: Gly/Ser linker
<220> FEATURE:
<221> NAME/KEY: MISC_FEATURE
<222> LOCATION: (1)..(100)
<223> OTHER INFORMATION: Some of these amino acids may be absent

<400> SEQUENCE: 41

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 42
<211> LENGTH: 7
<212> TYPE: PRT
<213> ORGANISM: Artificial Sequence
<220> FEATURE:
<223> OTHER INFORMATION: FXIa cleavage site
```

<400> SEQUENCE: 42

Lys Leu Thr Arg Ala Glu Thr
1               5

<210> SEQ ID NO 43
<211> LENGTH: 7
<212> TYPE: PRT
<213> ORGANISM: Artificial Sequence
<220> FEATURE:
<223> OTHER INFORMATION: FXIa cleavage site

<400> SEQUENCE: 43

Asp Phe Thr Arg Val Val Gly
1               5

<210> SEQ ID NO 44
<211> LENGTH: 8
<212> TYPE: PRT
<213> ORGANISM: Artificial Sequence
<220> FEATURE:
<223> OTHER INFORMATION: FXIa cleavage site

<400> SEQUENCE: 44

Thr Met Thr Arg Ile Val Gly Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Kallikrein cleavage site

<400> SEQUENCE: 45

Ser Pro Phe Arg Ser Thr Gly Gly
1               5

<210> SEQ ID NO 46
<211> LENGTH: 8
<212> TYPE: PRT
<213> ORGANISM: Artificial Sequence
<220> FEATURE:
<223> OTHER INFORMATION: FVIIa cleavage site

<400> SEQUENCE: 46

Leu Gln Val Arg Ile Val Gly Gly
1               5

<210> SEQ ID NO 47
<211> LENGTH: 8
<212> TYPE: PRT
<213> ORGANISM: Artificial Sequence
<220> FEATURE:
<223> OTHER INFORMATION: FIXa cleavage site

<400> SEQUENCE: 47

Pro Leu Gly Arg Ile Val Gly Gly
1               5

<210> SEQ ID NO 48
<211> LENGTH: 8
<212> TYPE: PRT
<213> ORGANISM: Artificial Sequence
<220> FEATURE:
<223> OTHER INFORMATION: FXa cleavage site

<400> SEQUENCE: 48

Ile Glu Gly Arg Thr Val Gly Gly
1                5

<210> SEQ ID NO 49
<211> LENGTH: 8
<212> TYPE: PRT
<213> ORGANISM: Artificial Sequence
<220> FEATURE:
<223> OTHER INFORMATION: FIIa (thrombin) cleavage site

<400> SEQUENCE: 49

Leu Thr Pro Arg Ser Leu Leu Val
1                5

<210> SEQ ID NO 50
<211> LENGTH: 8
<212> TYPE: PRT
<213> ORGANISM: Artificial Sequence
<220> FEATURE:
<223> OTHER INFORMATION: Elastase-2 cleavage site

<400> SEQUENCE: 50

Leu Gly Pro Val Ser Gly Val Pro
1                5

<210> SEQ ID NO 51
<211> LENGTH: 8
<212> TYPE: PRT
<213> ORGANISM: Artificial Sequence
<220> FEATURE:
<223> OTHER INFORMATION: Granzyme-B cleavage site

<400> SEQUENCE: 51

Val Ala Gly Asp Ser Leu Glu Glu
1                5

<210> SEQ ID NO 52
<211> LENGTH: 8
<212> TYPE: PRT
<213> ORGANISM: Artificial Sequence
<220> FEATURE:
<223> OTHER INFORMATION: MMP-12 cleavage site

<400> SEQUENCE: 52

Gly Pro Ala Gly Leu Gly Gly Ala
1                5

<210> SEQ ID NO 53
<211> LENGTH: 8
<212> TYPE: PRT
<213> ORGANISM: Artificial Sequence
<220> FEATURE:
<223> OTHER INFORMATION: MMP-13 cleavage site

<400> SEQUENCE: 53

Gly Pro Ala Gly Leu Arg Gly Ala
1                5

<210> SEQ ID NO 54
<211> LENGTH: 8
<212> TYPE: PRT
<213> ORGANISM: Artificial Sequence
<220> FEATURE:
<223> OTHER INFORMATION: MMP-17 cleavage site

<400> SEQUENCE: 54

-continued

```
Ala Pro Leu Gly Leu Arg Leu Arg
1               5

<210> SEQ ID NO 55
<211> LENGTH: 8
<212> TYPE: PRT
<213> ORGANISM: Artificial Sequence
<220> FEATURE:
<223> OTHER INFORMATION: MMP-20 cleavage site

<400> SEQUENCE: 55

Pro Ala Leu Pro Leu Val Ala Gln
1               5

<210> SEQ ID NO 56
<211> LENGTH: 7
<212> TYPE: PRT
<213> ORGANISM: Artificial Sequence
<220> FEATURE:
<223> OTHER INFORMATION: TEV cleavage site

<400> SEQUENCE: 56

Glu Asn Leu Tyr Phe Gln Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Enterokinase cleavage site

<400> SEQUENCE: 57

Asp Asp Asp Lys Ile Val Gly Gly
1               5

<210> SEQ ID NO 58
<211> LENGTH: 8
<212> TYPE: PRT
<213> ORGANISM: Artificial Sequence
<220> FEATURE:
<223> OTHER INFORMATION: Protease 3C (PRESCISSION) cleavage site

<400> SEQUENCE: 58

Leu Glu Val Leu Phe Gln Gly Pro
1               5

<210> SEQ ID NO 59
<211> LENGTH: 8
<212> TYPE: PRT
<213> ORGANISM: Artificial Sequence
<220> FEATURE:
<223> OTHER INFORMATION: Sortase A cleavage site

<400> SEQUENCE: 59

Leu Pro Lys Thr Gly Ser Glu Ser
1               5

<210> SEQ ID NO 60
<211> LENGTH: 9
<212> TYPE: PRT
<213> ORGANISM: Artificial Sequence
<220> FEATURE:
<223> OTHER INFORMATION: FXIa cleavage site

<400> SEQUENCE: 60

Thr Gln Ser Phe Asn Asp Phe Thr Arg
```

-continued

```
1               5

<210> SEQ ID NO 61
<211> LENGTH: 10
<212> TYPE: PRT
<213> ORGANISM: Artificial Sequence
<220> FEATURE:
<223> OTHER INFORMATION: FXIa cleavage site

<400> SEQUENCE: 61

Ser Val Ser Gln Thr Ser Lys Leu Thr Arg
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 62

Asp Phe Leu Ala Glu Gly Gly Gly Val Arg
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Thrombin cleavage site

<400> SEQUENCE: 63

Thr Thr Lys Ile Lys Pro Arg
1               5

<210> SEQ ID NO 64
<211> LENGTH: 5
<212> TYPE: PRT
<213> ORGANISM: Artificial Sequence
<220> FEATURE:
<223> OTHER INFORMATION: Thrombin cleavage site

<400> SEQUENCE: 64

Leu Val Pro Arg Gly
1               5

<210> SEQ ID NO 65
<211> LENGTH: 10
<212> TYPE: PRT
<213> ORGANISM: Artificial Sequence
<220> FEATURE:
<223> OTHER INFORMATION: Thrombin cleavage site

<400> SEQUENCE: 65

Ala Leu Arg Pro Arg Val Val Gly Gly Ala
1               5                   10

<210> SEQ ID NO 66
<211> LENGTH: 4974
<212> TYPE: DNA
<213> ORGANISM: Artificial Sequence
<220> FEATURE:
<223> OTHER INFORMATION: VWF D'D3-Fc with LVPR thrombin site in the
      linker

<400> SEQUENCE: 66
atgattcctg ccagatttgc cggggtgctg cttgctctgg ccctcatttt gccagggacc     60
```

```
ctttgtgcag aaggaactcg cggcaggtca tccacggccc gatgcagcct tttcggaagt      120
gacttcgtca acacctttga tgggagcatg tacagctttg cgggatactg cagttacctc      180
ctggcagggg gctgccagaa acgctccttc tcgattattg gggacttcca gaatggcaag      240
agagtgagcc tctccgtgta tcttggggaa ttttttgaca tccatttgtt tgtcaatggt      300
accgtgacac aggggggacca aagagtctcc atgccctatg cctccaaagg gctgtatcta      360
gaaactgagg ctgggtacta caagctgtcc ggtgaggcct atggctttgt ggccaggatc      420
gatggcagcg gcaactttca agtcctgctg tcagacagat acttcaacaa gacctgcggg      480
ctgtgtggca actttaacat ctttgctgaa gatgacttta tgacccaaga agggaccttg      540
acctcggacc cttatgactt tgccaactca tgggctctga gcagtggaga acagtggtgt      600
gaacgggcat ctcctcccag cagctcatgc aacatctcct ctgggaaat gcagaagggc      660 ctgtgggagc agtgccagct tctgaagagc acctcggtgt ttgcccgctg ccaccctctg      720
gtggaccccg agccttttgt ggccctgtgt gagaagactt tgtgtgagtg tgctggggggg      780 ctggagtgcg cctgccctgc cctcctggag tacgcccgga cctgtgccca ggagggaatg      840
gtgctgtacg gctggaccga ccacagcgcg tgcagcccag tgtgccctgc tggtatggag      900
tataggcagt gtgtgtcccc ttgcgccagg acctgccaga gcctgcacat caatgaaatg      960
tgtcaggagc gatgcgtgga tggctgcagc tgccctgagg gacagctcct ggatgaaggc      1020
ctctgcgtgg agagcaccga gtgtccctgc gtgcattccg gaaagcgcta ccctccgggc      1080
acctccctct ctcgagactg caacacctgc atttgccgaa acagccagtg gatctgcagc      1140
aatgaagaat gtccagggga gtgccttgtc actggtcaat cccacttcaa gagctttgac      1200
aacagatact tcaccttcag tgggatctgc cagtacctgc tggcccggga ttgccaggac      1260
cactccttct ccattgtcat tgagactgtc cagtgtgctg atgaccgcga cgctgtgtgc      1320
acccgctccg tcaccgtccg gctgcctggc ctgcacaaca gccttgtgaa actgaagcat      1380
ggggcaggag ttgccatgga tggccaggac atccagctcc ccctcctgaa aggtgacctc      1440
cgcatccagc atacagtgac ggcctccgtc cgcctcagct acggggagga cctgcagatg      1500
gactgggatg gccgcgggag gctgctggtg aagctgtccc ccgtctatgc cgggaagacc      1560
tgcggcctgt gtgggaatta caatggcaac cagggcgacg acttccttac ccctctgggg      1620
ctggcggagc cccgggtgga ggacttcggg aacgcctgga agctgcacgg ggactgccag      1680
gacctgcaga agcagcacag cgatccctgc gccctcaacc cgcgcatgac caggttctcc      1740
gaggaggcgt gcgcggtcct gacgtccccc acattcgagg cctgccatcg tgccgtcagc      1800
ccgctgccct acctgcggaa ctgccgctac gacgtgtgct cctgctcgga cggccgcgag      1860
tgcctgtgcg gcgccctggc cagctatgcc gcggcctgcg cggggagagg cgtgcgcgtc      1920
gcgtggcgcg agccaggccg ctgtgagctg aactgcccga aaggccaggt gtacctgcag      1980
tgcgggaccc cctgcaacct gacctgccgc tctctctctt acccggatga ggaatgcaat      2040
gaggcctgcc tggagggctg cttctgcccc ccagggctct acatggatga gaggggggac      2100
tgcgtgccca aggcccagtg cccctgttac tatgacggtg agatcttcca gccagaagac      2160
atcttctcag accatcacac catgtgctac tgtgaggatg gcttcatgca ctgtaccatg      2220
agtggagtcc ccggaagctt gctgcctgac gctgtcctca gcagtcccct gtctcatcgc      2280
agcaaaagga gcctatcctg tcggcccccc atggtcaagc tggtgtgtcc cgctgacaac      2340
ctgcgggctg aagggctcga gtgtaccaaa acgtgccaga actatgacct ggagtgcatg      2400
```

-continued

```
agcatgggct gtgtctctgg ctgcctctgc cccccgggca tggtccggca tgagaacaga   2460
tgtgtggccc tggaaaggtg tccctgcttc catcagggca aggagtatgc ccctggagaa   2520
acagtgaaga ttggctgcaa cacttgtgtc tgtcgggacc ggaagtggaa ctgcacagac   2580
catgtgtgtg atgccacgtg ctccacgatc ggcatggccc actacctcac cttcgacggg   2640
ctcaaatacc tgttccccgg ggagtgccag tacgttctgg tgcaggatta ctgcggcagt   2700
aaccctggga cctttcggat cctagtgggg aataagggat gcagccaccc ctcagtgaaa   2760
tgcaagaaac gggtcaccat cctggtggag ggaggagaga ttgagctgtt tgacgggggag   2820 gtgaatgtga agaggcccat gaaggatgag actcactttg aggtggtgga gtctggccgg   2880
tacatcattc tgctgctggg caaagccctc tccgtggtct gggaccgcca cctgagcatc   2940
tccgtggtcc tgaagcagac ataccaggag aaagtgtgtg gcctgtgtgg gaattttgat   3000
ggcatccaga acaatgacct caccagcagc aacctccaag tggaggaaga ccctgtggac   3060
tttgggaact cctggaaagt gagctcgcag tgtgctgaca ccagaaaagt gcctctggac   3120
tcatcccctg ccacctgcca taacaacatc atgaagcaga cgatggtgga ttcctcctgt   3180
agaatcctta ccagtgacgt cttccaggac tgcaacaagc tggtggaccc cgagccatat   3240
ctggatgtct gcatttacga cacctgctcc tgtgagtcca ttggggactg cgccgcattc   3300
tgcgacacca ttgctgccta tgcccacgtg tgtgcccagc atggcaaggt ggtgacctgg   3360
aggacggcca cattgtgccc ccagagctgc gaggagagga atctccggga gaacgggtat   3420
gaggctgagt ggcgctataa cagctgtgca cctgcctgtc aagtcacgtg tcagcaccct   3480
gagccactgg cctgccctgt gcagtgtgtg gagggctgcc atgcccactg ccctccaggg   3540
aaaatcctgg atgagctttt gcagacctgc gttgaccctg aagactgtcc agtgtgtgag   3600
gtggctggcc ggcgtttgc ctcaggaaag aaagtcacct tgaatcccag tgaccctgag   3660
cactgccaga tttgccactg tgatgttgtc aacctcacct gtgaagcctg ccaggagccg   3720
atatcgggcg cgccaacatc agagagcgcc acccctgaaa gtggtcccgg gagcgagcca   3780
gccacatctg ggtcggaaac gccaggcaca agtgagtctg caactcccga gtccggacct   3840
ggctccgagc ctgccactag cggctccgag actccgggaa cttccgagag cgctacacca   3900
gaaagcggac ccggaaccag taccgaacct agcgagggct ctgctccggg cagcccagcc   3960
ggctctccta catccacgga ggagggcact tccgaatccg ccaccccgga gtcagggcca   4020
ggatctgaac ccgctacctc aggcagtgag acgccaggaa cgagcgagtc cgctacaccg   4080
gagagtgggc cagggagccc tgctggatct cctacgtcca ctgaggaagg gtcaccagcg   4140
ggctcgccca ccagcactga agaaggtgcc tcgagcggcg gtggaggatc cggtggcggg   4200
ggatccggtg gcgggggatc cggtggcggg ggatccggtg gcgggggatc cggtggcggg   4260
ggatccctgg tccccgggg cagcggaggc gacaaaactc acacatgccc accgtgccca   4320
gctccagaac tcctgggcgg accgtcagtc ttcctcttcc ccccaaaacc caaggacacc   4380
ctcatgatct cccggacccc tgaggtcaca tgcgtggtgg tggacgtgag ccacgaagac   4440
cctgaggtca agttcaactg gtacgtggac ggcgtggagg tgcataatgc caagacaaag   4500
ccgcgggagg agcagtacaa cagcacgtac cgtgtggtca gcgtcctcac cgtcctgcac   4560
caggactggc tgaatggcaa ggagtacaag tgcaaggtct ccaacaaagc cctcccagcc   4620
cccatcgaga aaaccatctc caaagccaaa gggcagcccc gagaaccaca ggtgtacacc   4680
ctgcccccat cccgggatga gctgaccaag aaccaggtca gcctgacctg cctggtcaaa   4740
ggcttctatc ccagcgacat cgccgtggag tgggagagca atgggcagcc ggagaacaac   4800
```

-continued

```
tacaagacca cgcctcccgt gttggactcc gacggctcct tcttcctcta cagcaagctc    4860
accgtggaca agagcaggtg gcagcagggg aacgtcttct catgctccgt gatgcatgag    4920
gctctgcaca accactacac gcagaagagc ctctccctgt ctccgggtaa atga         4974

<210> SEQ ID NO 67
<211> LENGTH: 5937
<212> TYPE: DNA
<213> ORGANISM: Artificial Sequence
<220> FEATURE:
<223> OTHER INFORMATION: FVIII 169

<400> SEQUENCE: 67
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcta gcttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca aagttataaa aagtcaatat ttgaacaatg ccctcagcg gattggtagg   1320 aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat ggccctctc ctcatctgct acaaagaatc tgtagatcaa   1740
agaggaaacc agataatgtc agacaagagg aatgtcatcc tgtttctgt atttgatgag   1800 aaccgaagct ggtacctcac agagaatata caacgctttc tccccaatcc agctggagtg   1860
```

-continued

```
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acggcgcgcc aggtacctca gagtctgcta cccccgagtc agggccagga    2340
tcagagccag ccacctccgg gtctgagaca cccgggactt ccgagagtgc cacccctgag    2400
tccggacccg ggtccgagcc cgccacttcc ggctccgaaa ctcccggcac aagcgagagc    2460
gctaccccag agtcaggacc aggaacatct acagagccct ctgaaggctc cgctccaggg    2520
tccccagccg gcagtcccac tagcaccgag gagggaacct ctgaaagcgc cacacccgaa    2580
tcagggccag ggtctgagcc tgctaccagc ggcagcgaga caccaggcac ctctgagtcc    2640
gccacaccag agtccggacc cggatctccc gctgggagcc ccacctccac tgaggaggga    2700
tctcctgctg gctctccaac atctactgag gaaggtacct caaccgagcc atccgaggga    2760
tcagctcccg gcacctcaga gtcggcaacc ccggagtctg acccggaac ttccgaaagt    2820 gccacaccag agtccggtcc cgggacttca gaatcagcaa cacccgagtc cggccctggg    2880
tctgaacccg ccacaagtgg tagtgagaca ccaggatcag aacctgctac ctcagggtca    2940
gagacacccg gatctccggc aggctcacca acctccactg aggagggcac cagcacagaa    3000
ccaagcgagg gctccgcacc cggaacaagc actgaaccca gtgagggttc agcacccggc    3060
tctgagccgg ccacaagtgg cagtgagaca cccggcactt cagagagtgc cacccccgag    3120
agtggcccag gcactagtac cgagccctct gaaggcagtg cgccagcctc gagcccacca    3180
gtcttgaaac gccatcaagc tgaaataact cgtactactc ttcagtcaga tcaagaggaa    3240
atcgattatg atgataccat atcagttgaa atgaagaagg aagattttga catttatgat    3300
gaggatgaaa atcagagccc ccgcagcttt caaaagaaaa cacgacacta ttttattgct    3360
gcagtggaga ggctctggga ttatgggatg agtagctccc cacatgttct aagaaacagg    3420
gctcagagtg gcagtgtccc tcagttcaag aaagttgttt tccaggaatt tactgatggc    3480
tcctttactc agcccttata ccgtggagaa ctaaatgaac atttgggact cctggggcca    3540
tatataagag cagaagttga agataatatc atggtaactt tcagaaatca ggcctctcgt    3600
ccctattcct tctattctag ccttatttct tatgaggaag atcagaggca aggagcagaa    3660
cctagaaaaa actttgtcaa gcctaatgaa accaaaactt acttttggaa agtgcaacat    3720
catatggcac ccactaaaga tgagtttgac tgcaaagcct gggcttattt ctctgatgtt    3780
gacctggaaa aagatgtgca ctcaggcctg attggacccc ttctggtctg ccacactaac    3840
acactgaacc ctgctcatgg gagacaagtg acagtacagg aatttgctct gtttttcacc    3900
atctttgatg agaccaaaag ctggtacttc actgaaaata tggaaagaaa ctgcagggct    3960
ccctgcaata tccagatgga agatcccact tttaaagaga attatcgctt ccatgcaatc    4020
aatggctaca taatggatac actacctggc ttagtaatgg ctcaggatca aaggattcga    4080
tggtatctgc tcagcatggg cagcaatgaa aacatccatt ctattcattt cagtggacat    4140
gtgttcactg tacgaaaaaa agaggagtat aaaatggcac tgtacaatct ctatccaggt    4200 gttttttgaga cagtggaaat gttaccatcc aaagctggaa tttggcgggt ggaatgcctt    4260
```

-continued

```
attggcgagc atctacatgc tgggatgagc acactttttc tggtgtacag caataagtgt     4320
cagactcccc tgggaatggc ttctggacac attagagatt ttcagattac agcttcagga     4380
caatatggac agtgggcccc aaagctggcc agacttcatt attccggatc aatcaatgcc     4440
tggagcacca aggagccctt ttcttggatc aaggtggatc tgttggcacc aatgattatt     4500
cacggcatca agacccaggg tgcccgtcag aagttctcca gcctctacat ctctcagttt     4560
atcatcatgt atagtcttga tgggaagaag tggcagactt atcgaggaaa ttccactgga     4620
accttaatgg tcttctttgg caatgtggat tcatctggga taaaacacaa tattttaac     4680 cctccaatta ttgctcgata catccgtttg cacccaactc attatagcat tcgcagcact     4740
cttcgcatgg agttgatggg ctgtgattta aatagttgca gcatgccatt gggaatggag     4800
agtaaagcaa tatcagatgc acagattact gcttcatcct actttaccaa tatgtttgcc     4860
acctggtctc cttcaaaagc tcgacttcac ctccaaggga ggagtaatgc ctggagacct     4920
caggtgaata atccaaaaga gtggctgcaa gtggacttcc agaagacaat gaaagtcaca     4980
ggagtaacta ctcagggagt aaaatctctg cttaccagca tgtatgtgaa ggagttcctc     5040
atctccagca gtcaagatgg ccatcagtgg actctctttt ttcagaatgg caaagtaaag     5100 gttttcagg gaaatcaaga ctccttcaca cctgtggtga actctctaga cccaccgtta     5160
ctgactcgct accttcgaat tcacccccag agttgggtgc accagattgc cctgaggatg     5220
gaggttctgg gctgcgaggc acaggacctc tacgacaaaa ctcacacatg cccaccgtgc     5280
ccagctccag aactcctggg cggaccgtca gtcttcctct tccccccaaa acccaaggac     5340
accctcatga tctcccggac ccctgaggtc acatgcgtgg tggtggacgt gagccacgaa     5400
gaccctgagg tcaagttcaa ctggtacgtg gacggcgtgg aggtgcataa tgccaagaca     5460
aagccgcggg aggagcagta caacagcacg taccgtgtgg tcagcgtcct caccgtcctg     5520
caccaggact ggctgaatgg caaggagtac aagtgcaagg tctccaacaa agccctccca     5580
gcccccatcg agaaaaccat ctccaaagcc aaagggcagc cccgagaacc acaggtgtac     5640
accctgcccc catcccggga tgagctgacc aagaaccagg tcagcctgac ctgcctggtc     5700
aaaggcttct atcccagcga catcgccgtg gagtgggaga gcaatgggca gccggagaac     5760
aactacaaga ccacgcctcc cgtgttggac tccgacggct ccttcttcct ctacagcaag     5820
ctcaccgtgg acaagagcag gtggcagcag gggaacgtct tctcatgctc cgtgatgcat     5880
gaggctctgc acaaccacta cacgcagaag agcctctccc tgtctccggg taaatga     5937
```

<210> SEQ ID NO 68
<211> LENGTH: 1978
<212> TYPE: PRT
<213> ORGANISM: Artificial Sequence
<220> FEATURE:
<223> OTHER INFORMATION: FVIII 169

<400> SEQUENCE: 68

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

-continued

```
Tyr Lys Lys Thr Leu Phe Val Glu Phe Thr Asp His Leu Phe Asn Ile
65              70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
```

```
                        485               490               495

His Gly Ile Thr Asp Val Arg Pro Leu Tyr Ser Arg Arg Leu Pro Lys
            500               505               510

Gly Val Lys His Leu Lys Asp Phe Pro Ile Leu Pro Gly Glu Ile Phe
            515               520               525

Lys Tyr Lys Trp Thr Val Thr Val Glu Asp Gly Pro Thr Lys Ser Asp
    530               535               540

Pro Arg Cys Leu Thr Arg Tyr Tyr Ser Ser Phe Val Asn Met Glu Arg
545               550               555               560

Asp Leu Ala Ser Gly Leu Ile Gly Pro Leu Leu Ile Cys Tyr Lys Glu
            565               570               575

Ser Val Asp Gln Arg Gly Asn Gln Ile Met Ser Asp Lys Arg Asn Val
            580               585               590

Ile Leu Phe Ser Val Phe Asp Glu Asn Arg Ser Trp Tyr Leu Thr Glu
            595               600               605

Asn Ile Gln Arg Phe Leu Pro Asn Pro Ala Gly Val Gln Leu Glu Asp
    610               615               620

Pro Glu Phe Gln Ala Ser Asn Ile Met His Ser Ile Asn Gly Tyr Val
625               630               635               640

Phe Asp Ser Leu Gln Leu Ser Val Cys Leu His Glu Val Ala Tyr Trp
            645               650               655

Tyr Ile Leu Ser Ile Gly Ala Gln Thr Asp Phe Leu Ser Val Phe Phe
            660               665               670

Ser Gly Tyr Thr Phe Lys His Lys Met Val Tyr Glu Asp Thr Leu Thr
            675               680               685

Leu Phe Pro Phe Ser Gly Glu Thr Val Phe Met Ser Met Glu Asn Pro
    690               695               700

Gly Leu Trp Ile Leu Gly Cys His Asn Ser Asp Phe Arg Asn Arg Gly
705               710               715               720

Met Thr Ala Leu Leu Lys Val Ser Ser Cys Asp Lys Asn Thr Gly Asp
            725               730               735

Tyr Tyr Glu Asp Ser Tyr Glu Asp Ile Ser Ala Tyr Leu Leu Ser Lys
            740               745               750

Asn Asn Ala Ile Glu Pro Arg Ser Phe Ser Gln Asn Gly Ala Pro Gly
            755               760               765

Thr Ser Glu Ser Ala Thr Pro Glu Ser Gly Pro Gly Ser Glu Pro Ala
    770               775               780

Thr Ser Gly Ser Glu Thr Pro Gly Thr Ser Glu Ser Ala Thr Pro Glu
785               790               795               800

Ser Gly Pro Gly Ser Glu Pro Ala Thr Ser Gly Ser Glu Thr Pro Gly
            805               810               815

Thr Ser Glu Ser Ala Thr Pro Glu Ser Gly Pro Gly Thr Ser Thr Glu
            820               825               830

Pro Ser Glu Gly Ser Ala Pro Gly Ser Pro Ala Gly Ser Pro Thr Ser
            835               840               845

Thr Glu Glu Gly Thr Ser Glu Ser Ala Thr Pro Glu Ser Gly Pro Gly
    850               855               860

Ser Glu Pro Ala Thr Ser Gly Ser Glu Thr Pro Gly Thr Ser Glu Ser
865               870               875               880

Ala Thr Pro Glu Ser Gly Pro Gly Ser Pro Ala Gly Ser Pro Thr Ser
            885               890               895

Thr Glu Glu Gly Ser Pro Ala Gly Ser Pro Thr Ser Thr Glu Glu Gly
            900               905               910
```

-continued

```
Thr Ser Thr Glu Pro Ser Glu Gly Ser Ala Pro Gly Thr Ser Glu Ser
        915                 920                 925

Ala Thr Pro Glu Ser Gly Pro Gly Thr Ser Glu Ser Ala Thr Pro Glu
    930                 935                 940

Ser Gly Pro Gly Thr Ser Glu Ser Ala Thr Pro Glu Ser Gly Pro Gly
945                 950                 955                 960

Ser Glu Pro Ala Thr Ser Gly Ser Glu Thr Pro Gly Ser Glu Pro Ala
                965                 970                 975

Thr Ser Gly Ser Glu Thr Pro Gly Ser Pro Ala Gly Ser Pro Thr Ser
            980                 985                 990

Thr Glu Glu Gly Thr Ser Thr Glu  Pro Ser Glu Gly Ser  Ala Pro Gly
        995                 1000                1005

Thr Ser  Thr Glu Pro Ser Glu  Gly Ser Ala Pro Gly  Ser Glu Pro
    1010                1015                1020

Ala Thr  Ser Gly Ser Glu Thr  Pro Gly Thr Ser Glu  Ser Ala Thr
    1025                1030                1035

Pro Glu  Ser Gly Pro Gly Thr  Ser Thr Glu Pro Ser  Glu Gly Ser
    1040                1045                1050

Ala Pro  Ala Ser Ser Pro Pro  Val Leu Lys Arg His  Gln Ala Glu
    1055                1060                1065

Ile Thr  Arg Thr Thr Leu Gln  Ser Asp Gln Glu Glu  Ile Asp Tyr
    1070                1075                1080

Asp Asp  Thr Ile Ser Val Glu  Met Lys Lys Glu Asp  Phe Asp Ile
    1085                1090                1095

Tyr Asp  Glu Asp Glu Asn Gln  Ser Pro Arg Ser Phe  Gln Lys Lys
    1100                1105                1110

Thr Arg  His Tyr Phe Ile Ala  Ala Val Glu Arg Leu  Trp Asp Tyr
    1115                1120                1125

Gly Met  Ser Ser Ser Pro His  Val Leu Arg Asn Arg  Ala Gln Ser
    1130                1135                1140

Gly Ser  Val Pro Gln Phe Lys  Lys Val Val Phe Gln  Glu Phe Thr
    1145                1150                1155

Asp Gly  Ser Phe Thr Gln Pro  Leu Tyr Arg Gly Glu  Leu Asn Glu
    1160                1165                1170

His Leu  Gly Leu Leu Gly Pro  Tyr Ile Arg Ala Glu  Val Glu Asp
    1175                1180                1185

Asn Ile  Met Val Thr Phe Arg  Asn Gln Ala Ser Arg  Pro Tyr Ser
    1190                1195                1200

Phe Tyr  Ser Ser Leu Ile Ser  Tyr Glu Glu Asp Gln  Arg Gln Gly
    1205                1210                1215

Ala Glu  Pro Arg Lys Asn Phe  Val Lys Pro Asn Glu  Thr Lys Thr
    1220                1225                1230

Tyr Phe  Trp Lys Val Gln His  His Met Ala Pro Thr  Lys Asp Glu
    1235                1240                1245

Phe Asp  Cys Lys Ala Trp Ala  Tyr Phe Ser Asp Val  Asp Leu Glu
    1250                1255                1260

Lys Asp  Val His Ser Gly Leu  Ile Gly Pro Leu Leu  Val Cys His
    1265                1270                1275

Thr Asn  Thr Leu Asn Pro Ala  His Gly Arg Gln Val  Thr Val Gln
    1280                1285                1290

Glu Phe  Ala Leu Phe Phe Thr  Ile Phe Asp Glu Thr  Lys Ser Trp
    1295                1300                1305
```

___

Tyr Phe Thr Glu Asn Met Glu Arg Asn Cys Arg Ala Pro Cys Asn
    1310                1315                1320

Ile Gln Met Glu Asp Pro Thr Phe Lys Glu Asn Tyr Arg Phe His
    1325                1330                1335

Ala Ile Asn Gly Tyr Ile Met Asp Thr Leu Pro Gly Leu Val Met
    1340                1345                1350

Ala Gln Asp Gln Arg Ile Arg Trp Tyr Leu Leu Ser Met Gly Ser
    1355                1360                1365

Asn Glu Asn Ile His Ser Ile His Phe Ser Gly His Val Phe Thr
    1370                1375                1380

Val Arg Lys Lys Glu Glu Tyr Lys Met Ala Leu Tyr Asn Leu Tyr
    1385                1390                1395

Pro Gly Val Phe Glu Thr Val Glu Met Leu Pro Ser Lys Ala Gly
    1400                1405                1410

Ile Trp Arg Val Glu Cys Leu Ile Gly Glu His Leu His Ala Gly
    1415                1420                1425

Met Ser Thr Leu Phe Leu Val Tyr Ser Asn Lys Cys Gln Thr Pro
    1430                1435                1440

Leu Gly Met Ala Ser Gly His Ile Arg Asp Phe Gln Ile Thr Ala
    1445                1450                1455

Ser Gly Gln Tyr Gly Gln Trp Ala Pro Lys Leu Ala Arg Leu His
    1460                1465                1470

Tyr Ser Gly Ser Ile Asn Ala Trp Ser Thr Lys Glu Pro Phe Ser
    1475                1480                1485

Trp Ile Lys Val Asp Leu Leu Ala Pro Met Ile Ile His Gly Ile
    1490                1495                1500

Lys Thr Gln Gly Ala Arg Gln Lys Phe Ser Ser Leu Tyr Ile Ser
    1505                1510                1515

Gln Phe Ile Ile Met Tyr Ser Leu Asp Gly Lys Lys Trp Gln Thr
    1520                1525                1530

Tyr Arg Gly Asn Ser Thr Gly Thr Leu Met Val Phe Phe Gly Asn
    1535                1540                1545

Val Asp Ser Ser Gly Ile Lys His Asn Ile Phe Asn Pro Pro Ile
    1550                1555                1560

Ile Ala Arg Tyr Ile Arg Leu His Pro Thr His Tyr Ser Ile Arg
    1565                1570                1575

Ser Thr Leu Arg Met Glu Leu Met Gly Cys Asp Leu Asn Ser Cys
    1580                1585                1590

Ser Met Pro Leu Gly Met Glu Ser Lys Ala Ile Ser Asp Ala Gln
    1595                1600                1605

Ile Thr Ala Ser Ser Tyr Phe Thr Asn Met Phe Ala Thr Trp Ser
    1610                1615                1620

Pro Ser Lys Ala Arg Leu His Leu Gln Gly Arg Ser Asn Ala Trp
    1625                1630                1635

Arg Pro Gln Val Asn Asn Pro Lys Glu Trp Leu Gln Val Asp Phe
    1640                1645                1650

Gln Lys Thr Met Lys Val Thr Gly Val Thr Thr Gln Gly Val Lys
    1655                1660                1665

Ser Leu Leu Thr Ser Met Tyr Val Lys Glu Phe Leu Ile Ser Ser
    1670                1675                1680

Ser Gln Asp Gly His Gln Trp Thr Leu Phe Phe Gln Asn Gly Lys
    1685                1690                1695

Val Lys Val Phe Gln Gly Asn Gln Asp Ser Phe Thr Pro Val Val

-continued

```
             1700              1705             1710

Asn Ser  Leu Asp Pro Pro Leu  Leu Thr Arg Tyr Leu  Arg Ile His
    1715             1720             1725

Pro Gln  Ser Trp Val His Gln  Ile Ala Leu Arg Met  Glu Val Leu
    1730             1735             1740

Gly Cys  Glu Ala Gln Asp Leu  Tyr Asp Lys Thr His  Thr Cys Pro
    1745             1750             1755

Pro Cys  Pro Ala Pro Glu Leu  Leu Gly Gly Pro Ser  Val Phe Leu
    1760             1765             1770

Phe Pro  Pro Lys Pro Lys Asp  Thr Leu Met Ile Ser  Arg Thr Pro
    1775             1780             1785

Glu Val  Thr Cys Val Val Val  Asp Val Ser His Glu  Asp Pro Glu
    1790             1795             1800

Val Lys  Phe Asn Trp Tyr Val  Asp Gly Val Glu Val  His Asn Ala
    1805             1810             1815

Lys Thr  Lys Pro Arg Glu Glu  Gln Tyr Asn Ser Thr  Tyr Arg Val
    1820             1825             1830

Val Ser  Val Leu Thr Val Leu  His Gln Asp Trp Leu  Asn Gly Lys
    1835             1840             1845

Glu Tyr  Lys Cys Lys Val Ser  Asn Lys Ala Leu Pro  Ala Pro Ile
    1850             1855             1860

Glu Lys  Thr Ile Ser Lys Ala  Lys Gly Gln Pro Arg  Glu Pro Gln
    1865             1870             1875

Val Tyr  Thr Leu Pro Pro Ser  Arg Asp Glu Leu Thr  Lys Asn Gln
    1880             1885             1890

Val Ser  Leu Thr Cys Leu Val  Lys Gly Phe Tyr Pro  Ser Asp Ile
    1895             1900             1905

Ala Val  Glu Trp Glu Ser Asn  Gly Gln Pro Glu Asn  Asn Tyr Lys
    1910             1915             1920

Thr Thr  Pro Pro Val Leu Asp  Ser Asp Gly Ser Phe  Phe Leu Tyr
    1925             1930             1935

Ser Lys  Leu Thr Val Asp Lys  Ser Arg Trp Gln Gln  Gly Asn Val
    1940             1945             1950

Phe Ser  Cys Ser Val Met His  Glu Ala Leu His Asn  His Tyr Thr
    1955             1960             1965

Gln Lys  Ser Leu Ser Leu Ser  Pro Gly Lys
    1970             1975
```

```
<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Gly Glu Ser Pro Gly Gly Ser Ser Gly Ser Glu Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70
```

```
Gly Ser Glu Gly Ser Ser Gly Pro Gly Glu Ser Ser
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Gly Ser Ser Glu Ser Gly Ser Ser Glu Gly Gly Pro
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Gly Ser Gly Gly Glu Pro Ser Glu Ser Gly Ser Ser
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic

<400> SEQUENCE: 73

Gly Ser Pro Ala Gly Ser Pro Thr Ser Thr Glu Glu
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic

<400> SEQUENCE: 74

Gly Ser Glu Pro Ala Thr Ser Gly Ser Glu Thr Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic

<400> SEQUENCE: 75

Gly Thr Ser Glu Ser Ala Thr Pro Glu Ser Gly Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Gly Thr Ser Thr Glu Pro Ser Glu Gly Ser Ala Pro
```

-continued

```
1               5                    10

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

Gly Ser Thr Ser Glu Ser Pro Ser Gly Thr Ala Pro
1               5                    10

<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

Gly Thr Ser Thr Pro Glu Ser Gly Ser Ala Ser Pro
1               5                    10

<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

Gly Thr Ser Pro Ser Gly Glu Ser Ser Thr Ala Pro
1               5                    10

<210> SEQ ID NO 80
<211> LENGTH: 12
<212> TYPE: PRT
<213> ORGANISM: Artificial Sequence
<220> FEATURE:
<223> OTHER INFORMATION: Synthetic

<400> SEQUENCE: 80

Gly Ser Thr Ser Ser Thr Ala Glu Ser Pro Gly Pro
1               5                    10

<210> SEQ ID NO 81
<211> LENGTH: 12
<212> TYPE: PRT
<213> ORGANISM: Artificial Sequence
<220> FEATURE:
<223> OTHER INFORMATION: Synthetic

<400> SEQUENCE: 81

Gly Thr Pro Gly Ser Gly Thr Ala Ser Ser Ser Pro
1               5                    10

<210> SEQ ID NO 82
<211> LENGTH: 12
<212> TYPE: PRT
<213> ORGANISM: Artificial Sequence
<220> FEATURE:
<223> OTHER INFORMATION: Synthetic

<400> SEQUENCE: 82

Gly Ser Ser Thr Pro Ser Gly Ala Thr Gly Ser Pro
1               5                    10
```

-continued

```
<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Gly Ser Ser Pro Ser Ala Ser Thr Gly Thr Gly Pro
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Gly Ala Ser Pro Gly Thr Ser Ser Thr Gly Ser Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic

<400> SEQUENCE: 85

Gly Glu Pro Ala Gly Ser Pro Thr Ser Thr Ser Glu
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

Gly Thr Gly Glu Pro Ser Ser Thr Pro Ala Ser Glu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic

<400> SEQUENCE: 87

Gly Ser Gly Pro Ser Thr Glu Ser Ala Pro Thr Glu
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Gly Ser Glu Thr Pro Ser Gly Pro Ser Glu Thr Ala
1               5                   10
```

-continued

```
<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Gly Pro Ser Glu Thr Ser Thr Ser Glu Pro Gly Ala
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Gly Ser Pro Ser Glu Pro Thr Glu Gly Thr Ser Ala
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic

<400> SEQUENCE: 91

Gly Ser Gly Ala Ser Glu Pro Thr Ser Thr Glu Pro
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

Gly Ser Glu Pro Ala Thr Ser Gly Thr Glu Pro Ser
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic

<400> SEQUENCE: 93

Gly Thr Ser Glu Pro Ser Thr Ser Glu Pro Gly Ala
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic

<400> SEQUENCE: 94

Gly Thr Ser Thr Glu Pro Ser Glu Pro Gly Ser Ala
1               5                   10
```

```
<210> SEQ ID NO 95
<211> LENGTH: 12
<212> TYPE: PRT
<213> ORGANISM: Artificial Sequence
<220> FEATURE:
<223> OTHER INFORMATION: Synthetic

<400> SEQUENCE: 95

Gly Ser Thr Ala Gly Ser Glu Thr Ser Thr Glu Ala
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic

<400> SEQUENCE: 96

Gly Ser Glu Thr Ala Thr Ser Gly Ser Glu Thr Ala
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Gly Thr Ser Glu Ser Ala Thr Ser Glu Ser Gly Ala
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic

<400> SEQUENCE: 98

Gly Thr Ser Thr Glu Ala Ser Glu Gly Ser Ala Ser
1               5                   10
```